US008101608B2

(12) United States Patent
Wan et al.

(10) Patent No.: US 8,101,608 B2
(45) Date of Patent: Jan. 24, 2012

(54) COMPOUNDS AND COMPOSITIONS AS PROTEIN KINASE INHIBITORS

(75) Inventors: Yongqin Wan, Irvine, CA (US); Yuan Mi, San Diego, CA (US); Yi Fan, Poway, CA (US); Dai Cheng, San Diego, CA (US); Yi Liu, San Diego, CA (US); Nathanael S. Gray, Boston, MA (US); Pamela Albaugh, Carlsbad, CA (US)

(73) Assignee: IRM LLC, a Delware Limited Corporation, Hamilton (BM)

( * ) Notice: Subject to any disclaimer, the term of this patent is extended or adjusted under 35 U.S.C. 154(b) by 1159 days.

(21) Appl. No.: 11/718,886

(22) PCT Filed: Nov. 7, 2005

(86) PCT No.: PCT/US2005/040372
§ 371 (c)(1),
(2), (4) Date: May 8, 2007

(87) PCT Pub. No.: WO2006/052936
PCT Pub. Date: May 18, 2006

(65) Prior Publication Data
US 2008/0221192 A1    Sep. 11, 2008

Related U.S. Application Data

(60) Provisional application No. 60/626,785, filed on Nov. 9, 2004, provisional application No. 60/709,648, filed on Aug. 19, 2005.

(51) Int. Cl.
| | |
|---|---|
| *A61K 31/404* | (2006.01) |
| *A61K 31/4025* | (2006.01) |
| *A61K 31/4178* | (2006.01) |
| *A61K 31/4245* | (2006.01) |
| *A61K 31/454* | (2006.01) |
| *A61K 31/5377* | (2006.01) |
| *A61K 31/496* | (2006.01) |
| *C07D 401/14* | (2006.01) |
| *C07D 403/14* | (2006.01) |
| *C07D 405/06* | (2006.01) |
| *C07D 405/14* | (2006.01) |
| *C07D 413/06* | (2006.01) |
| *C07D 413/14* | (2006.01) |
| *C07D 471/04* | (2006.01) |

(52) U.S. Cl. .............. 514/235.2; 514/339; 514/397; 514/254.09; 514/364; 514/414; 548/468; 548/312.1; 548/266.4; 546/201; 544/373; 544/144

(58) Field of Classification Search .............. None
See application file for complete search history.

(56) References Cited

U.S. PATENT DOCUMENTS

| | | | | |
|---|---|---|---|---|
| 6,369,086 B1 * | 4/2002 | Davis et al. | ............. | 514/338 |
| 6,387,919 B1 | 5/2002 | Davis | | |

FOREIGN PATENT DOCUMENTS

| | | |
|---|---|---|
| RU | 2165925 | 9/1998 |
| WO | WO9915500 | 4/1999 |
| WO | WO9948868 | 9/1999 |
| WO | WO 99/61422 | 12/1999 |
| WO | WO9961421 | 12/1999 |
| WO | WO0008202 | 2/2000 |
| WO | WO 00/35909 | 6/2000 |
| WO | WO0056710 | 9/2000 |
| WO | WO0160814 | 8/2001 |
| WO | WO0194312 | 12/2001 |
| WO | WO03051838 | 6/2003 |
| WO | WO 03/055492 | 7/2003 |
| WO | WO 2004/050681 | 6/2004 |

OTHER PUBLICATIONS

Byrn et al., Solid-State Chemistry of Drugs, 2d, Chapter 11 Hydrates and Solvates, 233-247 (1999).*
Morissette et al., Adv. Drug Delivery Rev., 56:275 (2004).*
A.M. Rouhi, Chem. & Eng. News, 81:32 (Feb. 24, 2003).*
Sun, Li, Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases, J. Med. Chem. 1999, 42, 5120-5130.
Sun, Li, Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Râ Tyrosine Kinases, J. Med. Chem. 2000, 43, 2655-2663.
Tominaga, Y., General Model for Estimation of the Inhibition of Protein Kinases Using Monte Carlo Simulations, J. Med. Chem. 2004, 47, 2534-2549. Boschelli, et al., "Synthesis and Src Kinase Inhibitory Activity of a Series of 4-Phenylamino-3-quinolinecarbonitriles", J. Med. Chem., 2001, pp. 822-833, vol. 44, No. 5, American Chemical Society, US.
Manley et al "Anthranilic Acid Amides: A Novel Class of Antiangiogenic VEGF Receptor Kinase Inhibitors", J. Med. Chem., 2002, pp. 5687-5693, vol. 45, No. 26, American Chemical Society, US.
Ple, et al., "Discovery of a New Class of Anilinoquinazoline Inhibitors with High Affinity and Specificity for the Tyrosine Kinase Domain of c-Src", J. Med. Chem., 2004, pp. 871-887, vol. 47, No. 4, American Chemical Society, US.

* cited by examiner

*Primary Examiner* — Yong Chu
*Assistant Examiner* — Michael Barker
(74) *Attorney, Agent, or Firm* — Genomics Institute of the Novartis Research Foundation; Chihang Amy Smith

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, Bcr-Abl, cSrc, TPR-Met, Tie2, MET, FGFR3, Aurora, Axl, Bmx, BTK, c-kit, CHK2, Flt3, MST2, p70S6K, PDGFR, PKB, PKC, Raf, ROCK-II, Rsk1, SGK, TrkA, TrkB and TrkC kinases.

10 Claims, No Drawings

COMPOUNDS AND COMPOSITIONS AS PROTEIN KINASE INHIBITORS

CROSS-REFERENCE TO RELATED APPLICATIONS

This application is a 371 U.S. national phase application of international application number PCT/US2005/040372 filed 07 Nov. 2005, which application claims priority to U.S. Provisional Patent Application No. 60/626,785, filed 9 Nov. 2004 and U.S. Provisional Patent Application No. 60/709,648, filed 19 Aug. 2005. The full disclosure of these applications is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, Bcr-Abl, cSrc, TPR-Met, Tie2, MET, FGFR3, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and TrkC kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the nerve growth factor receptor, Trk-A, -B and -C, and the fibroblast growth factor receptor, FGFR3; non-receptor tyrosine kinases such Abl and the fusion kinase BCR-Abl, Lck, Csk, Fes, BTK, Bmx and c-src; and serine/threonine kinases such as Aurora, c-RAF, SGK, MAP kinases (e.g., MKK4, MKK6, etc.) and SAPK2α and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

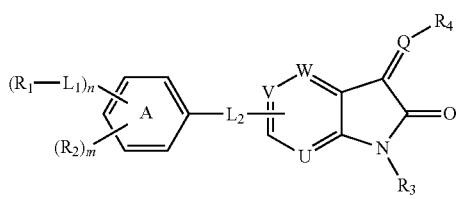

in which:
U, V and W are independently selected from $CR_5$ and N; wherein $R_5$ is selected from hydrogen and $C_{1-6}$alkyl;

Q is selected from $NR_5$ and $CR_5$; wherein $R_5$ is selected from hydrogen and $C_{1-6}$alkyl;

$L_1$ is selected from —$NR_5C(O)$—, —$NR_5C(O)NR_5$—, —$C(O)NR_5$— and —$NR_5$—; wherein $R_5$ is selected from hydrogen and $C_{1-6}$alkyl;

$L_2$ is selected from a bond, —O—, —$NR_5C(O)$—, —$NR_5C(O)NR_5$—, —$C(O)NR_5$— and —$NR_5$—; wherein $R_5$ is selected from hydrogen and $C_{1-6}$alkyl;

n is selected from 0 and 1;

m is selected from 0, 1, 2, 3 and 4;

$R_1$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of $R_1$ is optionally substituted by one to three radicals independently selected from halo, amino, nitro, cyano, $C_{1-6}$alkyl, $C_{1-6}$alkoxy, halo-substituted-$C_{1-6}$alkyl, halo-substituted $C_{1-6}$alkoxy, $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein a methylene of any alkyl group can be optionally replaced by oxygen;

wherein any aryl, heteroaryl, cycloalkyl or heterocycloalkyl substituent of $R_1$ can be optionally substituted by 1 to 3 radicals independently selected from $C_{1-6}$alkyl, $C_{1-6}$alkoxy, halo-substituted-$C_{1-6}$alkyl, halo-substituted $C_{1-6}$alkoxy and hydroxy-substituted-$C_{1-6}$alkyl;

$R_2$ is selected from halo, amino, nitro, cyano, $C_{1-6}$alkyl, $C_{1-6}$alkoxy, halo-substituted-$C_{1-6}$alkyl, halo-substituted $C_{1-6}$alkoxy, $C_{6-10}$aryl-$C_{0-4}$alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$alkyl; wherein any aryl, heteroaryl, cycloalkyl or heterocycloalkyl of $R_2$ is optionally substituted by one to three radicals independently selected from halo, amino, nitro, cyano, $C_{1-6}$alkyl, $C_{1-6}$alkoxy, halo-substituted-$C_{1-6}$alkyl and halo-substituted $C_{1-6}$alkoxy;

$R_3$ is selected from hydrogen and $C_{1-6}$alkyl; and $R_4$ is selected from hydrogen, —$XR_6$, —$XNR_5XR_6$, —$XOXR_6$ and —$XNR_5XNR_5R_6$; wherein each X is independently selected from a bond, $C_{1-4}$alkylene and $C_{2-4}$alkenylene wherein any alkylene or alkenylene of X can be optionally substituted with hydroxy; $R_5$ is selected from hydrogen and $C_{1-6}$alkyl; $R_6$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of $R_6$ can be optionally substituted with 1 to 3 radicals independently selected from $C_{1-6}$alkyl, hydroxy, cyano, —$NR_5S(O)_{0-2}R_5$, —$S(O)_{0-2}NR_5R_5$, —$NR_5S(O)_{0-2}NR_5R_5$, —$C(O)NR_5XNR_5R_5$, —$C(O)NR_5XOR_5$, —$C(O)NR_5R_5$, —$C(O)NR_5XR_7$ and —$XC(O)OR_5$; wherein each X is independently selected from a bond, $C_{1-4}$alkylene and $C_{2-4}$alkenylene wherein any alkylene or alkenylene of X can be optionally substituted with hydroxy; wherein each $R_5$ is independently selected from hydrogen and $C_{1-6}$alkyl; and $R_7$ is selected from $C_{5-10}$heteroaryl-$C_{0-4}$alkyl and $C_{3-10}$heterocycloalkyl-$C_{0-4}$alkyl; wherein any heteroaryl or heterocycloalkyl of $R_7$ is optionally substituted with a radical selected from the group consisting of $C_{1-6}$alkyl, halo-substituted-$C_{1-6}$alkyl and —$C(O)OR_5$; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof, or a pharmaceutically acceptable salt thereof, in admixture with one or more suitable excipients.

In a third aspect, the present invention provides a method of treating a disease in an animal in which inhibition of kinase activity, particularly Abl, Bcr-Abl, cSrc, TPR-Met, Tie2, MET, FGFR3, Aurora, Axl, Bmx, BTK, c-kit, CBK2, Flt3, MST2, p70S6K, PDGFR, PKB, PKCα, Raf, ROCK-II, Rsk1, SGK, TrkA, TrkB and/or TrkC (NTRK3) activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, Bcr-Abl, cSrc, TPR-Met, Tie2, MET, FGFR3, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and/or TrkC (NTRK3) activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like "Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example heteroaryl includes pyridyl, indolyl, indazolyl, quinoxalinyl, quinolinyl, benzofuranyl, benzopyranyl, benzothiopyranyl, benzo[1,3] dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Mutant forms of BCR-Abl" means single or multiple amino acid changes from the wild-type sequence. Over 22 mutations have been reported to date with the most common being G250E, E255V, T315I, F317L and M351T.

"NTKR1" is the gene name equivalent to TrkA protein; "NTKR2" is the gene name equivalent to TrkB protein; and "NTKR3" is the gene name equivalent to TrkC protein.

"Treat", "treating" and "treatment" refer to a method of alleviating or abating a disease and/or its attendant symptoms.

Description of the Preferred Embodiments

The present invention provides compounds, compositions and methods for the treatment of kinase related disease, particularly Abl, Bcr-Abl, cSrc, TPR-Met, Tie2, MET, FGFR3, Aurora, Axl, Bmx, BTK, c-kit, CHK, Flt3, MST2, p70S6K, PDGFR, PKB, PKCα, Raf, ROCK-II, Rsk1, SGK, TrkA, TrkB and TrkC(NTRK3) kinase related diseases. For example, leukemia and other proliferation disorders related to BCR-Abl can be treated through the inhibition of wild type and mutant forms of Bcr-Abl.

In one embodiment, with reference to compounds of Formula I:

W is CH;

$L_1$ is selected from —NR$_5$C(O)—, —C(O)NR$_5$— and $C_{5-10}$heteroaryl; wherein R$_5$ is selected from hydrogen and $C_{1-6}$alkyl;

$L_2$ is selected from a bond, —O—, —NR$_5$C(O), —NR$_5$C(O)NR$_5$—, —C(O)NR$_5$— and —NR$_5$—; wherein R$_5$ is selected from hydrogen and $C_{1-6}$alkyl;

n is selected from 0 and 1;

m is selected from 0, 1, 2 and 3;

$R_1$ is selected from $C_{6-10}$aryl and $C_{5-10}$heteroaryl; wherein any aryl or heteroaryl is optionally substituted by one to three radicals independently selected from halo, $C_{1-6}$alkyl, halo-substituted-$C_{1-6}$alkyl, $C_{5-10}$heteroaryl-$C_{0-4}$alkyl and $C_{3-8}$heterocycloalkyl-$C_{0-4}$alkyl; wherein a methylene of any alkyl group can be optionally replaced by oxygen;

wherein any heteroaryl or heterocycloalkyl substituent of $R_1$ can be optionally substituted by 1 to 3 radicals independently selected from $C_{1-6}$alkyl and hydroxy-substituted-$C_{1-6}$ alkyl;

$R_2$ is selected from $C_{1-6}$alkyl, $C_{1-6}$alkoxy, halo-substituted-$C_{1-6}$alkyl and $C_{3-8}$heterocycloalkyl-$C_{0-4}$alkyl optionally substituted by 1 to 3 $C_{1-6}$alkyl radicals;

$R_3$ is selected from hydrogen and $C_{1-6}$alkyl; and

R is selected from hydrogen, —XR$_6$, —XNR$_5$XR$_6$, —XOXR$_6$ and —XNR$_5$XNR$_5$R$_6$; wherein each X is independently selected from a bond and $C_{1-4}$alkylene; wherein any alkylene of X can be optionally substituted with hydroxy; R$_6$ is selected from $C_{6-10}$aryl, $C_{5-10}$heteroaryl, $C_{3-12}$cycloalkyl and $C_{3-8}$heterocycloalkyl; wherein any heteroaryl, heterocycloalkyl or cycloalkyl of R$_6$ is optionally substituted with 1 to 3 radicals independently selected from hydroxy, $C_{1-6}$alkyl, cyano, —C(O)NR$_5$R$_5$, —C(O)NR$_5$XNR$_5$R$_5$, —XNR$_5$XNR$_5$R$_5$, —C(O)R$_7$, —C(O)NR$_5$XOR$_5$, —S(O)$_{0-2}$NR$_5$R$_5$, C(O)NR$_5$XR$_7$ and —XC(O)OR$_5$; wherein each X is independently selected from a bond and $C_{1-4}$alkylene; wherein any alkylene of X can be optionally substituted with hydroxy; wherein each R$_5$ is independently selected from hydrogen and $C_{1-6}$alkyl; and R$_7$ is $C_{3-10}$heterocycloalkyl-$C_{0-4}$ alkyl optionally substituted with a radical selected from dimethylamino, pyrimidinyl, pyrazinyl, diethylamino-ethyl, amino and methyl.

In another embodiment, $L_1$ is selected from —NHC(O)—, —C(O)NH— and [1,2,4]oxadiazole; $L_2$ is selected from a bond, —O—, —NHC(O), —NHC(O)NH—, —C(O)NH— and —NH—; n is selected from 0 and 1; and m is selected from 0, 1 and 2.

In another embodiment, $R_1$ is selected from phenyl, indolyl and pyrazolyl; wherein any phenyl, indolyl or pyrazolyl is optionally substituted by one to three radicals independently selected from halo, methyl, trifluoromethyl, tert-butyl, morpholino, piperazinyl, piperazinyl-oxy, piperazinyl-methyl, piperidinyl, piperidinyl-oxy and imidazolyl; wherein any heteroaryl or heterocycloalkyl substituent of $R_1$ can be optionally substituted by 1 to 3 radicals independently selected from methyl, ethyl, hydroxy and hydroxy-ethyl.

In a further embodiment, $R_2$ is selected from methyl, methoxy, trifluoromethyl and imidazolyl optionally substituted by methyl.

In a further embodiment, $R_4$ is selected from hydrogen, $-XR_6$, $-XNR_5XR_6$, $-XOXR_6$ and $-XNR_5XNR_5R_6$; wherein each X is independently selected from a bond and $C_{1-4}$alkylene; wherein any alkylene of X can be optionally substituted with hydroxy; $R_6$ is pyrrolyl, imidazolyl, indolyl, furanyl, phenyl, thiazolyl, pyridinyl and cyclopentyl; wherein each $R_6$ can be optionally substituted with 1 to 3 radicals independently selected from methyl, ethyl, hydroxy, cyano, $-C(O)NR_5R_5$, $-C(O)NR_5XNR_5R_5$, $-XNR_5XNR_5R_5$, $-C(O)R_7$, $-C(O)NR_5XOR_5$, $-S(O)_{0-2}NR_5R_5$, $-C(O)NR_5XR_7$ and $-XC(O)OR_5$; wherein each X is independently selected from a bond and $C_{1-4}$alkylene; wherein any alkylene of X can be optionally substituted with hydroxy; wherein each $R_5$ is independently selected from hydrogen, methyl and ethyl; and $R_7$ is selected from piperazinyl, pyrrolidinyl and morpholino; wherein each $R_7$ is optionally substituted with a radical selected from dimethylamino, pyrimidinyl, pyrazinyl, diethylamino-ethyl, amino and methyl.

Preferred compounds of the invention are detailed in the Examples and Table I, infra.

Further preferred compounds are selected from: 3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide; N-[2-Oxo-3-(1H-pyrrol-2-ylmethylene)-2,3-dihydro-1H-indol-6-yl]-benzamide; 5-(6-Benzoylamino-2-oxo-1,2-dihydro-indol-3-ylidenemethyl)-2,4-dimethyl-1H-pyrrole-3-carboxylic acid (2-diethylamino-ethyl)-amide; 3-(4-Methyl-imidazol-1-yl)-N-(3-{3-[2-oxo-3-(1H-pyrrol-2-ylmethylene)-2,3-dihydro-1H-indol-6-yl]-ureido}-phenyl)-5-trifluoromethyl-benzamide; 2-Oxo-3-(1H-pyrrol-2-ylmethylene)-2,3-dihydro-1H-indole-6-carboxylic acid (3-benzoylamino-phenyl)-amide; 6-(3-Amino-phenylamino)-3-(1H-pyrrol-2-ylmethylene)-1,3-dihydro-indol-2-one; 4-(4-Methyl-piperazin-1-ylmethyl)-N-{3-[2-oxo-3-(1H-pyrrol-2-ylmethylene)-2,3-dihydro-1H-indol-7-ylamino]-phenyl}-benzamide; 4-(4-Methyl-piperazin-1-ylmethyl)-N-{3-[2-oxo-3-(1H-pyrrol-2-ylmethylene)-2,3-dihydro-1H-indol-5-ylamino]-phenyl}-benzamide; 4-(4-Ethyl-piperazin-1-ylmethyl)-N-{3-[2-oxo-3-(1H-pyrrol-2-ylmethylene)-2,3-dihydro-1H-indol-6-ylamino]-phenyl}-3-trifluoromethyl-benzamide; 3-(4-Methyl-piperazin-1-yl)-N-{3-[2-oxo-3-(1H-pyrrol-2-ylmethylene)-2,3-dihydro-1H-indol-6-yloxy]-phenyl}-5-trifluoromethyl-benzamide; 5-(6-Benzoylamino-2-oxo-1,2-dihydro-indol-3-ylidenemethyl)-2,4-dimethyl-1H-pyrrole-3-carboxylic acid (2-pyrrolidin-1-yl-ethyl)-amide; 5-(6-Benzoylamino-2-oxo-1,2-dihydro-indol-3-ylidenemethyl)-2,4-dimethyl-1H-pyrrole-3-carboxylic acid (2-piperidin-1-yl-ethyl)-amide; 5-(6-Benzoylamino-2-oxo-1,2-dihydro-indol-3-ylidenemethyl)-2,4-dimethyl-1H-pyrrole-3-carboxylic acid (3-pyrrolidin-1-yl-propyl)-amide; N-[2-Oxo-3-(1H-pyrrol-2-ylmethylene)-2,3-dihydro-1H-indol-6-yl]-3-trifluoromethyl-benzamide; 3-{2,4-Dimethyl-5-[2-oxo-6-(3-trifluoromethyl-benzoylamino)-1,2-dihydro-indol-3-ylidenemethyl]-1H-pyrrol-3-yl}-propionic acid; 2,4-Dimethyl-5-[2-oxo-6-(3-trifluoromethyl-benzoylamino)-1,2-dihydro-indol-3-ylidenemethyl]-1H-pyrrole-3-carboxylic acid; 2,4-Dimethyl-5-[2-oxo-6-(3-trifluoromethyl-benzoylamino)-1,2-dihydro-indol-3-ylidenemethyl]-1H-pyrrole-3-carboxylic acid (2-dimethylamino-ethyl)-amide; 2,4-Dimethyl-5-[2-oxo-6-(3-trifluoromethyl-benzoylamino)-1,2-dihydro-indol-3-ylidenemethyl]-1H-pyrrole-3-carboxylic acid (2-pyrrolidin-1-yl-ethyl)-amide; 2,4-Dimethyl-5-[2-oxo-6-(3-trifluoromethyl-benzoylamino)-1,2-dihydro-indol-3-ylidenemethyl]-1H-pyrrole-3-carboxylic acid (2-diethylamino-ethyl)-amide; N-[3-(3,5-Dimethyl-1H-pyrrol-2-ylmethylene)-2-oxo-2,3-dihydro-1H-indol-6-yl]-3-(4-methyl-imidazol-1-yl)-5-trifluoromethyl-benzamide; 3-(4-Methyl-imidazol-1-yl)-N-[2-oxo-3-(1H-pyrrol-2-ylmethylene)-2,3-dihydro-1H-indol-6-yl]-5-trifluoromethyl-benzamide; 2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid; 3-(2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrol-3-yl)-propionic acid; 4-(4-Methyl-piperazin-1-ylmethyl)-N-[2-oxo-3-(1H-pyrrol-2-ylmethylene)-2,3-dihydro-1H-indol-6-yl]-benzamide; 2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-diethylamino-ethyl)-amide; 2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-diethylamino-ethyl)-amide; 2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-dimethylamino-ethyl)-amide; 2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-pyrrolidin-1-yl-ethyl)-amide; 2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-dimethylamino-ethyl)-amide; 2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-pyrrolidin-1-yl-ethyl)-amide; 3-{2,4-Dimethyl-5-[6-(3-{3-[4-(4-methyl-imidazol-1-yl)-5-trifluoromethyl-benzoylamino]-phenyl}-ureido)-2-oxo-1,2-dihydro-indol-3-ylidenemethyl]-1H-pyrrol-3-yl}-propionic acid; 5-{6-[3-(3-Benzoylamino-phenyl)-ureido]-2-oxo-1,2-dihydro-indol-3-ylidenemethyl}-2,4-dimethyl-1H-pyrrole-3-carboxylic acid (2-pyrrolidin-1-yl-ethyl)-amide; 4-(4-Methyl-piperazin-1-ylmethyl)-N-(3-{3-[2-oxo-3-(1H-pyrrol-2-ylmethylene)-2,3-dihydro-1H-indol-6-yl]-ureido}-phenyl)-benzamide; 2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-diethylamino-ethyl)-amide; 2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-dimethylamino-ethyl)-amide; 2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-diethylamino-ethyl)-amide; 2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-dimethylamino-ethyl)-amide; 5-{6-[3-(3-Benzoylamino-phenyl)-ureido]-2-oxo-1,2-dihydro-indol-3-ylidenemethyl}-2,4-dimethyl-1H- pyrrole-3-carboxylic acid (2-diethylamino-ethyl)-amide; 2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-pyrrolidin-1-yl-ethyl)-amide; 2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-pyrrolidin-1-yl-ethyl)-amide; 3-(4-Methyl-imidazol-1-yl)-N-(4-methyl-3-{3-[2-oxo-3-(1H-pyrrol-2-ylmethylene)-2,3-dihydro-1H-indol-6-yl]-ureido}-phenyl)-5-trifluoromethyl-benzamide; N-(4-Methyl-3-{3-[2-oxo-3-(1H-pyrrol-2-ylmethylene)-2,3-dihydro-1H-indol-6-yl]-ureido}-phenyl)-3-trifluoromethyl-benzamide; 2,4-Dimethyl-5-(6-{3-[2-methyl-5-(3-trifluoromethyl-benzoylamino)-phenyl]-ureido}-2-oxo-1,2-dihydro-indol-3-ylidenemethyl)-1H-pyrrole-3-carboxylic acid (2-pyrrolidin-1-yl-ethyl)-amide; N-(4-Methyl-3-{3-[2-oxo-3-(1H-pyrrol-2-ylmethylene)-2,3-dihydro-1H-indol-6-yl]-ureido}-phenyl)-benzamide; 5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-diethylamino-ethyl)-amide; 5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-dimethylamino-ethyl)-amide; 5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-pyrrolidin-1-yl-ethyl)-amide; N-(4-Methyl-3-{3-[2-oxo-3-(1H-pyrrol-2-ylmethylene)-2,3-dihydro-1H-indol-6-yl]-ureido}-phenyl)-4-(4-methyl-piperazin-1-ylmethyl)-benzamide; 2-Oxo-3-(1H-pyrrol-2-ylmethylene)-2,3-dihydro-1H-indole-6-carboxylic acid {3-[4-(4-methyl-piperazin-1-ylmethyl)-benzoylamino]-phenyl}-amide; 3-[4-(2-Diethylamino-ethylcarbamoyl)-3,5-dimethyl-1H-pyrrol-2-ylmethylene]-2-oxo-2,3-dihydro-1H-indole-6-carboxylic acid (3-benzoylamino-phenyl)-amide; 3-[3,5-Dimethyl-4-(2-pyrrolidin-1-yl-ethylcarbamoyl)-1H-pyrrol-2-ylmethylene]-2-oxo-2,3-dihydro-1H-indole-6-carboxylic acid (3-benzoylamino-phenyl)-amide; 2-Oxo-3-(1H-pyrrol-2-ylmethylene)-2,3-dihydro-1H-indole-6-carboxylic acid (5-benzoylamino-2-methyl-phenyl)-amide; 2-Oxo-3-(1H-pyrrol-2-ylmethylene)-2,3-dihydro-1H-indole-6-carboxylic acid {2-methyl-5-[4-(4-methyl-piperazin-1-ylmethyl)-benzoylamino]-phenyl}-amide; 3-[4-(2-Diethylamino-ethylcarbamoyl)-3,5-dimethyl-1H-pyrrol-2-ylmethylene]-2-oxo-2,3-dihydro-1H-indole-6-carboxylic acid (5-benzoylamino-2-methyl-phenyl)-amide; 3-[3,5-Dimethyl-4-(2-pyrrolidin-1-yl-ethylcarbamoyl)-1H-pyrrol-2-ylmethylene]-2-oxo-2,3-dihydro-1H-indole-6-carboxylic acid (5-benzoylamino-2-methyl-phenyl)-amide; N-{3-[2-Oxo-3-(1H-pyrrol-2-ylmethylene)-2,3-dihydro-1H-indol-6-ylamino]-phenyl}-benzamide; N-{3-[2-Oxo-3-(1H-pyrrol-2-ylmethylene)-2,3-dihydro-1H-indol-6-ylamino]-phenyl}-3-trifluoromethyl-benzamide; 4-(4-Methyl-piperazin-1-ylmethyl)-N-{3-[2-oxo-3-(1H-pyrrol-2-ylmethylene)-2,3-dihydro-1H-indol-6-ylamino]-phenyl}-benzamide; N-{4-Methyl-3-[2-oxo-3-(1H-pyrrol-2-ylmethylene)-2,3-dihydro-1H-indol-6-ylamino]-phenyl}-benzamide; N-{4-Methyl-3-[2-oxo-3-(1H-pyrrol-2-ylmethylene)-2,3-dihydro-1H-indol-6-ylamino]-phenyl}-3-trifluoromethyl-benzamide; N-{4-Methyl-3-[2-oxo-3-(1H-pyrrol-2-ylmethylene)-2,3-dihydro-1H-indol-6-ylamino]-phenyl}-4-(4-methyl-piperazin-1-ylmethyl)-benzamide; 5-[6-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide; 5-[6-(3-Benzoylamino-phenylamino)-2-oxo-1,2-dihydro-indol-3-ylidenemethyl]-2,4-dimethyl-1H-pyrrole-3-carboxylic acid (2-dimethylamino-ethyl)-amide; 5-[6-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; 5-[6-(3-Benzoylamino-phenylamino)-2-oxo-1,2-dihydro-indol-3-ylidenemethyl]-2,4-dimethyl-1H-pyrrole-3-carboxylic acid (2-piperidin-1-yl-ethyl)-amide; 5-[6-(3-Benzoylamino-phenylamino)-2-oxo-1,2-dihydro-indol-3-ylidenemethyl]-2,4-dimethyl-1H-pyrrole-3-carboxylic acid (3-pyrrolidin-1-yl-propyl)-amide; 2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid (2-dimethylamino-ethyl)-amide; 2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid (2-diethylamino-ethyl)-amide; 2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid (2-pyrrolidin-1-yl-ethyl)-amide; 2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid (2-piperidin-1-yl-ethyl)-amide; 2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid (3-pyrrolidin-1-yl-propyl)-amide; 5-[6-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide; 5-[6-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; 2,4-Dimethyl-5-{6-[2-methyl-5-(3-trifluoromethyl-benzoylamino)-phenylamino]-2-oxo-1,2-dihydro-indol-3-ylidenemethyl}-1H-pyrrole-3-carboxylic acid (2-diethylamino-ethyl)-amide; N-{3-[2-Oxo-3-(1H-pyrrol-2-ylmethylene)-2,3-dihydro-1H-indol-7-ylamino]-phenyl}-benzamide; 5-[7-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide; 5-[7-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; 2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-diethylamino-ethyl)-amide, 2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-dimethylamino-ethyl)-amide; 2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-pyrrolidin-1-yl-ethyl)-amide; N-{4-Methyl-3-[2-oxo-3-(1H-pyrrol-2-ylmethylene)-2,3-dihydro-1H-indol-7-ylamino]-phenyl}-benzamide; N-{4-Methyl-3-[2-oxo-3-(1H-pyrrol-2-ylmethylene)-2,3-dihydro-1H-indol-7-ylamino]-phenyl}-4-(4-methyl-piperazin-1-ylmethyl)-benzamide; 5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide; 5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-dimethylamino-ethyl)-amide; 5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; 5-(3-Amino-phenylamino)-3-(1H-pyrrol-2-ylmethylene)-1,3-dihydro-indol-2-one; N-{3-[2-Oxo-3-(1H-pyrrol-2- ylmethylene)-2,3-dihydro-1H-indol-5-ylamino]-phenyl}benzamide; N-{3-[2-Oxo-3-(1H-pyrrol-2-ylmethylene)-2,3-dihydro-1H-indol-5-ylamino]-phenyl}-3-trifluoromethyl-benzamide; 3-(4-Methyl-imidazol-1-yl)-N-{3-[2-oxo-3-(1H-pyrrol-2-ylmethylene)-2,3-dihydro-1H-indol-5-ylamino]-phenyl}-5-trifluoromethyl-benzamide; 5-[5-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide; 5-[5-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; N-{4-Methyl-3-[2-oxo-3-(1H-pyrrol-2-ylmethylene)-2,3-dihydro-1H-indol-5-ylamino]-phenyl}-benzamide; N-{4-Methyl-3-[2-oxo-3-(1H-pyrrol-2-ylmethylene)-2,3-dihydro-1H-indol-5-ylamino]-phenyl}-4-(4-methyl-piperazin-1-ylmethyl)-benzamide; 5-[5-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide; 5-[5-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide; 3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide; 3-(4-Methyl-imidazol-1-yl)-N-{3-[6-oxo-5-(1H-pyrrol-2-ylmethylene)-6,7-dihydro-5H-pyrrolo[2,3-d]pyrimidin-2-ylamino]-phenyl}-5-trifluoromethyl-benzamide; 3-(4-Ethyl-piperazin-1-yl)-N-{3-[3-(3H-imidazol-4-ylmethylene)-2-oxo-2,3-dihydro-1H-indol-6-ylamino]-phenyl}-5-trifluoromethyl-benzamide; 2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid (2-diethylamino-ethyl)-amide; 2,4-Dimethyl-5-(6-{3-[3-(1-methyl-piperidin-4-yloxy)-5-trifluoromethyl-benzoylamino]-phenylamino}-2-oxo-1,2-dihydro-indol-3-ylidenemethyl)-1H-pyrrole-3-carboxylic acid; 3-(1-Methyl-piperidin-4-yloxy)-N-{3-[2-oxo-3-(1H-pyrrol-2-ylmethylene)-2,3-dihydro-1H-indol-6-ylamino]-phenyl}-5-trifluoromethyl-benzamide; N-{3-[3-(4-Cyano-1H-pyrrol-2-ylmethylene)-2-oxo-2,3-dihydro-1H-indol-6-ylamino]-5-methoxy-phenyl}-3-(1-methyl-piperidin-4-yloxy)-5-trifluoromethyl-benzamide; N-{3-[3-(5-Methyl-3H-imidazol-4-ylmethylene)-2-oxo-2,3-dihydro-1H-indol-6-ylamino]-phenyl}-3-(1-methyl-piperidin-4-yloxy)-5-trifluoromethyl-benzamide; 3-[4-(2-Hydroxy-ethyl)-piperazin-1-yl]-N-{3-[2-oxo-3-(1H-pyrrol-2-ylmethylene)-2,3-dihydro-1H-indol-6-ylamino]-phenyl}-5-trifluoromethyl-benzamide; 4-Morpholin-4-yl-N-{3-[2-oxo-3-(1H-pyrrol-2-ylmethylene)-2,3-dihydro-1H-indol-6-ylamino]-phenyl}-3-trifluoromethyl-benzamide; 4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide; 4-(4-Ethyl-piperazin-1-ylmethyl)-N-{3-[3-(5-methyl-3H-imidazol-4-ylmethylene)-2-oxo-2,3-dihydro-1H-indol-6-ylamino]-phenyl}-3-trifluoromethyl-benzamide; 4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide; 5-(6-{3-[4-(4-Ethyl-piperazin-1-ylmethyl)-3-trifluoromethyl-benzoylamino]-phenylamino}-2-oxo-1,2-dihydro-indol-3-ylidenemethyl)-2,4-dimethyl-1H-pyrrole-3-carboxylic acid; 4-(4-Ethyl-piperazin-1-ylmethyl)-N-{3-[3-(5-methyl-2H-pyrazol-3-ylmethylene)-2-oxo-2,3-dihydro-1H-indol-6-ylamino]-phenyl}-3-trifluoromethyl-benzamide; 4-(4-Ethyl-piperazin-1-ylmethyl)-N-{3-[3-(4-methyl-1H-imidazol-2-ylmethylene)-2-oxo-2,3-dihydro-1H-indol-6-ylamino]-phenyl}-3-trifluoromethyl-benzamide; 3-Chloro-4-(4-ethyl-piperazin-1-ylmethyl)-N-{3-[3-(3H-imidazol-4-ylmethylene)-2-oxo-2,3-dihydro-1H-indol-6-ylamino]-phenyl}-benzamide; 3-Chloro-4-(4-ethyl-piperazin-1-ylmethyl)-N-{3-[3-(5-methyl-3H-imidazol-4-ylmethylene)-2-oxo-2,3-dihydro-1H-indol-6-ylamino]-phenyl}-benzamide; 5-(6-{3-[3-Chloro-4-(4-ethyl-piperazin-1-ylmethyl)-benzoylamino]-phenylamino}-2-oxo-1,2-dihydro-indol-3-ylidenemethyl)-2,4-dimethyl-1H-pyrrole-3-carboxylic acid; N-{3-[3-(2-Ethyl-5-methyl-3H-imidazol-4-ylmethylene)-2-oxo-2,3-dihydro-(H-indol-6-ylamino]-phenyl}-3-(4-methyl-imidazol-1-yl)-5-trifluoromethyl-benzamide; N-{3-[3-(1H-Indol-3-ylmethylene)-2-oxo-2,3-dihydro-1H-indol-6-ylamino]-phenyl}-3-(4-methyl-imidazol-1-yl)-5-trifluoromethyl-benzamide; N-[3-(3-Furan-3-ylmethylene-2-oxo-2,3-dihydro-1H-indol-6-ylamino)-phenyl]-3-(4-methyl-imidazol-1-yl)-5-trifluoromethyl-benzamide; 3-(4-Methyl-imidazol-1-yl)-N-{3-[3-(5-methyl-3H-imidazol-4-ylmethylene)-2-oxo-2,3-dihydro-1H-indol-6-ylamino]-phenyl}-5-trifluoromethyl-benzamide; 3-(4-Methyl-imidazol-1-yl)-N-{3-[3-(4-methyl-1H-imidazol-2-ylmethylene)-2-oxo-2,3-dihydro-1H-indol-6-ylamino]-phenyl}-5-trifluoromethyl-benzamide; N-{3-[3-(3H-Imidazol-4-ylmethylene)-2-oxo-2,3-dihydro-1H-indol-6-ylamino]-phenyl}-3-(4-methyl-imidazol-1-yl)-5-trifluoromethyl-benzamide; 2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid; N-{3-[3-(4-Cyano-1H-pyrrol-2-ylmethylene)-2-oxo-2,3-dihydro-1H-indol-6-ylamino]-phenyl}-3-(4-methyl-imidazol-1-yl)-5-trifluoromethyl-benzamide; N-{3-[3-(1H-Indol-2-ylmethylene)-2-oxo-2,3-dihydro-1H-indol-6-ylamino]-phenyl}-3-(4-methyl-imidazol-1-yl)-5-trifluoromethyl-benzamide; N-{3-[3-(2-Ethyl-5-methyl-3H-imidazol-4-ylmethylene)-2-oxo-2,3-dihydro-1H-indol-6-ylamino]-4-methyl-phenyl}-3-(4-methyl-imidazol-1-yl)-5-trifluoromethyl-benzamide; 5-(6-{3-[3-(4-Methyl-imidazol-1-yl)-5-trifluoromethyl-benzoylamino]-phenylamino}-2-oxo-1,2-dihydro-indol-3-ylidenemethyl)-1H-pyrrole-3-carboxylic acid amide; 4-(6-{3-[3-(4-Methyl-imidazol-1-yl)-5-trifluoromethyl-benzoylamino]-phenylamino}-2-oxo-1,2-dihydro-indol-3-ylidenemethyl)-1H-pyrrole-2-carboxylic acid methyl ester; 3-(4-Methyl-imidazol-1-yl)-N-(3-{3-[(4-methylsulfamoyl-phenylamino)-methylene]-2-oxo-2,3-dihydro-1H-indol-6-ylamino}-phenyl)-5-trifluoromethyl-benzamide; 2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid (2,3-dihydroxy-propyl)-amide; N-[3-(3-{4-[(2-Diethylamino-ethylamino)-methyl]-1H-pyrrol-2-ylmethylene}-2-oxo-2,3-dihydro-1H-indol-6-ylamino)-phenyl]-3-trifluoromethyl-benzamide; 2,4-Dimethyl-5-(6-{3-[3-(4-methyl-piperazin-1-yl)-5-trifluoromethyl-benzoylamino]-phenylamino}-2-oxo-1,2-dihydro-indol-3-ylidenemethyl)-1H-pyrrole-3-carboxylic acid; N-{3-[3-(5-Methyl-3H-imidazol-4-ylmethylene)-2-oxo-2,3-dihydro-1H-indol-6-ylamino]-phenyl}-3-(4-methyl-piperazin-1-yl)-5-trifluoromethyl-benzamide; 3-(4-Methyl-piperazin-1-yl)-N-{3-[2-oxo-3-(1H-pyrrol-2-ylmethylene)-2,3-dihydro-1H-indol-6-ylamino]-phenyl}-5-trifluoromethyl-benzamide; 3-(4-Methyl-piperazin-1-yl)-N-{3-[2-oxo-3-(1H-pyrrol-2-ylmethylene)-2,3-dihydro-1H-indol-6-yloxy]-phenyl}-5-trifluoromethyl-benzamide; 3-(4-Methyl-piperazin-1-yl)-N-{3-[2-oxo-3-(1H-pyrrol-2-ylmethylene)-2,3-dihydro-1H-indol-6-yl]-phenyl}-5- trifluoromethyl-benzamide; 3-(4-Methyl-piperazin-1-yl)-N-(3-{2-oxo-3-[(4-sulfamoyl-phenyl)-hydrazono]-2,3-dihydro-1H-indol-6-ylamino}-phenyl)-5-trifluoromethyl-benzamide; N-{3-[3-(4-Cyano-1H-pyrrol-2-ylmethylene)-2-oxo-2,3-dihydro-1H-indol-6-ylamino]-phenyl}-3-(4-methyl-piperazin-1-yl)-5-trifluoromethyl-benzamide; N-{3-Methoxy-5-[2-oxo-3-(1H-pyrrol-2-ylmethylene)-2,3-dihydro-1H-indol-6-ylamino]-phenyl}-3-(4-methyl-piperazin-1-yl)-5-trifluoromethyl-benzamide; 5-(6-{3-[3-(4-Methyl-piperazin-1-yl)-5-trifluoromethyl-benzoylamino]-phenylamino}-2-oxo-1,2-dihydro-indol-3-ylidenemethyl)-1H-pyrrole-3-carboxylic acid amide; N-{3-[3-(4-Cyano-1H-pyrrol-2-ylmethylene)-2-oxo-2,3-dihydro-1H-indol-6-ylamino]-5-methoxy-phenyl}-3-(4-methyl-piperazin-1-yl)-5-trifluoromethyl-benzamide; N-{4-Methyl-3-[2-oxo-3-(1H-pyrrol-2-ylmethylene)-2,3-dihydro-1H-indol-6-ylamino]-phenyl}-3-(4-Methyl-piperazin-1-yl)-5-trifluoromethyl-benzamide; N-{3-[3-(4-Cyano-1H-pyrrol-2-ylmethylene)-2-oxo-2,3-dihydro-1H-indol-6-ylamino]-phenyl}-3-(4-hydroxy-piperidin-1-yl)-5-trifluoromethyl-benzamide; 3-(4-Hydroxy-piperidin-1-yl)-N-{3-[2-oxo-3-(1H-pyrrol-2-ylmethylene)-2,3-dihydro-1H-indol-6-ylamino]-phenyl}-5-trifluoromethyl-benzamide; 5-(6-{3-[4-(4-Methyl-piperazin-1-yl)-3-trifluoromethyl-benzoylamino]-phenylamino}-2-oxo-1,2-dihydro-indol-3-ylidenemethyl)-1H-pyrrole-3-carboxylic acid amide; 3-Methyl-N-{3-[3-(5-methyl-3H-imidazol-4-ylmethylene)-2-oxo-2,3-dihydro-1H-indol-6-ylamino]-phenyl}-benzamide; N-{3-[3-(5-Methyl-3H-imidazol-4-ylmethylene)-2-oxo-2,3-dihydro-1H-indol-6-ylamino]-phenyl}-3-trifluoromethyl-benzamide; N-{3-[3-(4-Cyano-1H-pyrrol-2-ylmethylene)-2-oxo-2,3-dihydro-1H-indol-6-ylamino]-4-methyl-phenyl}-3-(4-methyl-piperazin-1-yl)-5-trifluoromethyl-benzamide; 5-{6-[3-(3-Methyl-benzoylamino)-phenylamino]-2-oxo-1,2-dihydro-indol-3-ylidenemethyl}-1H-pyrrole-3-carboxylic acid amide; 2,4-Dimethyl-5-(6-{3-[3-(4-methyl-piperazin-1-yl)-5-trifluoromethyl-benzoylamino]-phenylamino}-2-oxo-1,2-dihydro-indol-3-ylidenemethyl)-1H-pyrrole-3-carboxylic acid (3-dimethylamino-propyl)-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid (2-dimethylamino-ethyl)-methyl-amide; N-(3-{3-[3,5-Dimethyl-4-(4-methyl-piperazine-1-carbonyl)-1H-pyrrol-2-ylmethylene]-2-oxo-2,3-dihydro-1H-indol-6-yloxy}-phenyl)-3-trifluoromethyl-benzamide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid (3-dimethylamino-propyl)-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid (pyrrolidin-1-yl-propyl)-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid methyl-(3-methylamino-propyl)-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid (2-morpholin-4-yl-ethyl)-amide; N-(3-{3-[4-(3-Dimethylamino-pyrrolidine-1-carbonyl)-3,5-dimethyl-1H-pyrrol-2-ylmethylene]-2-oxo-2,3-dihydro-1H-indol-6-yloxy}-phenyl)-3-trifluoromethyl-benzamide; N-[3-(3-{4-[4-(2-Diethylamino-ethyl)-piperazine-1-carbonyl]-3,5-dimethyl-1H-pyrrol-2-ylmethylene}-2-oxo-2,3-dihydro-1H-indol-6-yloxy)-phenyl]-3-trifluoromethyl-benzamide; 5-{2-Oxo-6-[3-(3-trifluoromethyl-benzoylamino)-phenoxy]-1,2-dihydro-indol-3-ylidenemethyl}-1H-pyrrole-3-carboxylic acid methyl-(3-methylamino-propyl)-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid ethoxy-amide; 2,4-Dimethyl-5-{2-oxo-6-[3-(3-trifluoromethyl-benzoylamino)-phenoxy]-1,2-dihydro-indol-3-ylidenemethyl}-1H-pyrrole-3-carboxylic acid (4-methyl-piperazin-1-yl)-amide; 5-{2-Oxo-6-[3-(3-trifluoromethyl-benzoylamino)-phenoxy]-1,2-dihydro-indol-3-ylidenemethyl}-1H-pyrrole-3-carboxylic acid; 5-{2-Oxo-6-[3-(3-trifluoromethyl-benzoylamino)-phenoxy]-1,2-dihydro-indol-3-ylidenemethyl}-1H-pyrrole-3-carboxylic acid (3-dimethylamino-propyl)-amide; N-(3-{3-[4-(4-Methyl-piperazine-1-carbonyl)-1H-pyrrol-2-ylmethylene]-2-oxo-2,3-dihydro-1H-indol-6-yloxy}-phenyl)-3-trifluoromethyl-benzamide; 5-{2-Oxo-6-[3-(3-trifluoromethyl-benzoylamino)-phenoxy]-1,2-dihydro-indol-3-ylidenemethyl}-1H-pyrrole-3-carboxylic acid (2-dimethylamino-ethyl)-methyl-amide; N-(3-{3-{4-[4-(2-Diethylamino-ethyl)-piperazine-1-carbonyl]-1H-pyrrol-2-ylmethylene}-2-oxo-2,3-dihydro-1H-indol-6-yloxy)-phenyl]-3-trifluoromethyl-benzamide; 2,4-Dimethyl-5-{6-[3-(3-methyl-benzoylamino)-phenoxy]-2-oxo-1,2-dihydro-indol-3-ylidenemethyl}-1H-pyrrole-3-carboxylic acid; N-(3-{3-[3,5-Dimethyl-4-(4-methyl-piperazine-1-carbonyl)-1H-pyrrol-2-ylmethylene]-2-oxo-2,3-dihydro-1H-indol-6-yloxy}-phenyl)-3-methyl-benzamide; 2,4-Dimethyl-5-{6-[3-(3-methyl-benzoylamino)-phenoxy]-2-oxo-1,2-dihydro-indol-3-ylidenemethyl}-1H-pyrrole-3-carboxylic acid (2-morpholin-4-yl-ethyl)-amide; 5-{6-[3-(3-Methyl-benzoylamino)-phenoxy]-2-oxo-1,2-dihydro-indol-3-ylidenemethyl}-1H-pyrrole-3-carboxylic acid (3-pyrrolidin-1-yl-propyl)-amide; 5-{6-[3-(3-Methyl-benzoylamino)-phenoxy]-2-oxo-1,2-dihydro-indol-3-ylidenemethyl}-1H-pyrrole-3-carboxylic acid; 5-{6-[3-(3-Methyl-benzoylamino)-phenoxy]-2-oxo-1,2-dihydro-indol-3-ylidenemethyl}-1H-pyrrole-3-carboxylic acid (3-dimethylamino-propyl)-amide; 5-{6-[3-(3-Methyl-benzoylamino)-phenoxy]-2-oxo-1,2-dihydro-indol-3-ylidenemethyl}-1H-pyrrole-3-carboxylic acid (2-morpholin-4-yl-ethyl)-amide; 5-{6-[3-(3-Methyl-benzoylamino)-phenoxy]-2-oxo-1,2-dihydro-indol-3-ylidenemethyl}-1H-pyrrole-3-carboxylic acid (2-dimethylamino-ethyl)-methyl-amide; 3-Methyl-N-(3-{3-[4-(4-methyl-piperazine-1-carbonyl)-1H-pyrrol-2-ylmethylene]-2-oxo-2,3-dihydro-1H-indol-6-yloxy}-phenyl)-benzamide; 5-{6-[3-(3-Methyl-benzoylamino)-phenoxy]-2-oxo-1,2-dihydro-indol-3-ylidenemethyl}-1H-pyrrole-3-carboxylic acid (4-methyl-piperazin-1-yl)-amide; N-[3-(3-{4-[4-(2-Diethylamino-ethyl)-piperazine-1-carbonyl]-1H-pyrrol-2-ylmethylene}-2-oxo-2,3-dihydro-1H-indol-6-yloxy)-phenyl]-3-methyl-benzamide; N-(3-{3-[3,5-Dimethyl-4-(4-pyrimidin-2-yl-piperazine-1-carbonyl)-1H-pyrrol-2-ylmethylene]-2-oxo-2,3-dihydro-1H-indol-6-yloxy}-phenyl)-3-trifluoromethyl-benzamide; N-(3-{3-[3,5-Dimethyl-4-(2,3,5,6-tetrahydro-[1,2']bipyrazinyl-4-carbonyl)-1H-pyrrol-2-ylmethylene]-2-oxo-2,3-dihydro-1H-indol-6-yloxy}-phenyl)-3-trifluoromethyl-benzamide; 2,4-Dimethyl-5-{6-[3-(3-methyl-benzoylamino)-phenoxy]-2-oxo-1,2-dihydro-indol-3-ylidenemethyl}-1H-pyrrole-3-carboxylic acid (2-dimethylamino-ethyl)-methyl-amide; N-[4-(4-Methyl-piperazin-1-ylmethyl)-3-trifluoromethyl-phenyl]-3-[2-oxo-3-(1H-pyrrol-2-ylmethylene)-2,3-dihydro-1H-pyrrolo[2,3-b]pyridin-6-ylamino]-benzamide; 4-Trifluoromethyl-1H-indole-6-carboxylic acid {3-methoxy-5-[2-oxo-3-(1H-pyrrol-2-ylmethylene)-2,3-dihydro-1H-indol-6-ylamino]-phenyl}-amide; N-[3-(3-Benzyloxyimino-2-oxo-2,3-dihydro-1H-indol-6-ylamino)-phenyl]-3-(4-methylpiperazin-1-yl)-5-trifluoromethyl-benzamide; 3-[2-Oxo-3-(1H-pyrrol-2-ylmethylene)-2,3-dihydro-1H-pyrrolo[2,3-b]pyridin-6-yloxy]-N-(3-trifluoromethyl-phenyl)-benzamide; 5-(6-Benzoylamino-2-oxo-1,2-dihydro-indol-3-ylidenemethyl)-2,4-dimethyl-1H-pyrrole-3-carboxylic acid (2-dimethylamino-ethyl)-amide; and 3-(1H-Pyrrol-2-ylmethylene)-6-{3-[3-(3-trifluoromethyl-phenyl)-[1,2,4]oxadiazol-5-yl]-phenylamino}-1,3-dihydro-indol-2-one.

Pharmacology and Utility

Compounds of the invention modulate the activity of kinases and, as such, are useful for treating diseases or disorders in which kinases, contribute to the pathology and/or symptomology of the disease. Examples of kinases that are inhibited by the compounds and compositions described herein and against which the methods described herein are useful include, but are not limited to, Abl, Bcr-Abl, cSrc, TPR-Met, Tie2, MET, FGFR3, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and TrkC(NTRK3) kinases.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The trk family of neurotrophin receptors (trkA or "NTKR1", trkB or "NTKR2", trkC or "NTKR3") are able to control tumor cell growth and survival as well as differentiation, migration and metastasis.

NTKR2 (TrkB) protein is expressed in neuroendocrine-type cells in the small intestine and colon, in the alpha cells of the pancreas, in the monocytes and macrophages of the lymph nodes and of the spleen, and in the granular layers of the epidermis. Expression of the TrkB protein has been associated with an unfavorable progression of Wilms tumors and of neuroblastomas. TkrB is, moreover, expressed in cancerous prostate cells but not in normal cells.

NTRK3 (TrkC) and its closely related family members NTRK1 (TrkA) and NTRK2 (TrkB) are implicated in the development and progression of cancer, possibly by upregulation of either the receptor, their ligand (Nerve Growth Factor, Brain Derived Neurotrophic Factor, Neurotrophins) or both (Rubin and Segal, 2003, Nakagawara, 2001). High expression of NTRK2 and/or its ligand BDNF has been shown in pancreatic and prostate carcinomas, Wilm's tumors and neuroblastomas. In addition, high expression of NTRK3 is a hallmark of Melanoma, especially in cases with brain metastasis. In many cases high Trk expression is associated with aggressive tumor behavior, poor prognosis and metastasis.

NTRK2 is a potent inhibitor of anoikis, defined as apoptosis induced by loss of attachment of a cell to its matrix. By activating the Phosphatidylinositol-3-kinase/Protein Kinase B signaling axis, NTRK2 was shown to promote the survival of non-transformed epithelial cells in 3-dimensional cultures and to induce tumor formation and metastasis of those cells in immuno-compromised mice.

Genetic abnormalities, i.e. point mutations and chromosomal rearrangements involving both NTRK2 and NTRK3 have been found in a variety of cancer types. In a kinome-wide approach to identify point mutants in tyrosine kinases both NTRK2 and NTRK3 mutations were found in cell lines and primary samples from patients with colorectal cancer (Manning et al., 2002, Bardelli et al., 2003). Although no further validation of the various mutants was presented in this analysis, the implication of Trk family members in regulating metastasis suggests a functional relevance of this observation in colorectal cancer.

In addition, chromosomal translocations involving both NTRK1 and NTRK3 have been found in several different types of tumors. Gene rearrangements involving NTRK1 and a set of different fusion partners (TPM3, TPR, TFG) are a hallmark of a subset of papillary thyroid cancers (PTC) (Tallini, 2002). Moreover, secretary breast cancer, infant fibrosarcoma and congenital mesoblastic nephroma have been shown to be associated with a chromosomal rearrangement t(12; 15) generating a ETV6-NTRK3 fusion gene that was shown to have constitutive kinase activity and transforming potential in several different cell lines including fibroblasts, hematopoietic cells and breast epithelial cells (Euhus et al., 2002, Tognon et al., 2002, Knezevich et al., 1998b, Knezevich et al., 1998a).

The signaling pathway downstream of the trk receptors involves the cascade of MAPK activation through the Shc, activated Ras, ERK-1 and ERK-2 genes, and the PLC-gammal transduction pathway (Sugimoto et al., 2001).

The Tec family kinase, Bmx, a non-receptor protein-tyrosine kinase, controls the proliferation of mammary epithelial cancer cells.

The activity of serum and glucocorticoid-regulated kinase (SGK), is correlated to perturbed ion-channel activities, in particular, those of sodium and/or potassium channels and compounds of the invention can be useful for treating hypertension.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November; 267 (21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4):447-51) and cell growth (Prog. Nucleic Acid Res. Mol. Biol., 2000; 65:101-27), and hence, may be important in tumor metastasis, the immune response and tissue repair as well as other disease conditions.

Flt3 is a member of the type III receptor tyrosine kinase (RTK) family. Flt3 (fms-like tyrosine kinase) is also known as FLk-2 (fetal liver kinase 2). Aberrant expression of the Flt3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). Activating mutations of the Flt3 receptor have been found in about 35% of patients with acute myeloblastic leukemia (AML), and are associated with a poor prognosis. The most common mutation involves in-frame duplication within the juxtamembrane domain, with an additional 5-10% of patients having a point mutation at asparagine 835. Both of these mutations are associated with constitutive activation of the tyrosine kinase activity of Flt3, and result in proliferation and viability signals in the absence of ligand. Patients expressing the mutant form of the receptor have been shown to have a decreased chance for cure. Thus, there is accumulating evidence for a role for hyper-activated (mutated) Flt3 kinase activity in human leukemias and myelodysplastic syndrome.

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

Aurora-2 is a serine/threonine protein kinase that has been implicated in human cancer, such as colon, breast and other solid tumors. This kinase is believed to be involved in protein phosphorylation events that regulate the cell cycle. Specifically, Aurora-2 may play a role in controlling the accurate segregation of chromosomes during mitosis. Misregulation of the cell cycle can lead to cellular proliferation and other abnormalities. In human colon cancer tissue, the aurora-2 protein has been found to be overexpressed.

The Aurora family of serine/threonine kinases [Aurora-A ("1" f), B ("2") and C ("3")] is essential for cell proliferation. These proteins are responsible for chromosome segregation, mitotic spindle function and cytokinesis and are linked to tumorigenesis. Elevated levels of all Aurora family members are observed in a wide variety of tumour cell lines. Aurora kinases are over-expressed in many human tumors and this is reported to be associated with chromosomal instability in mammary tumors. For example, aberrant activity of aurora A kinase has been implicated in colorectal, gastric, human bladder and ovarian cancers and high levels of Aurora-A have also been reported in renal, cervical, neuroblastoma, melanoma, lymphoma, pancreatic and prostate tumour cell lines. Aurora-B is also highly expressed in multiple human tumour cell lines, for example, leukemic cells and colorectal cancers. Aurora-C, which is normally only found in germ cells, is also over-expressed in a high percentage of primary colorectal cancers and in a variety of tumour cell lines including cervical adenocarcinoma and breast carcinoma cells. Based on the known function of the Aurora kinases, inhibition of their activity should disrupt mitosis leading to cell cycle arrest. In vivo, an Aurora inhibitor therefore slows tumor growth and induces regression.

The inactivation of Chk1 and Chk2 abrogates the G2/M arrest which is induced by damaged DNA and sensitizes the resulting checkpoint deficient cells to the killing by DNA damaging events. As cancer cells are more sensitive towards the abrogation of the G2/M checkpoint than normal cells there is great interest in compounds, which inhibit Chk1, Chk2 or Chk1 and Chk2, as a result abrogate the G2/M checkpoint and improve the killing of cancer cells by DNA damaging events.

It is believed that a wide variety of disease states and conditions can be mediated by modulating the activity of Mammalian Sterile 20-like Kinase, "Mst 1" and "Mst 2" or combinations thereof, to treat or prevent diseases which include osteoporosis, osteopenia, Paget's disease, vascular restenosis, diabetic retinopathy, macular degeneration, angiogenesis, atherosclerosis, inflammation and tumor growth.

The kinases known as PKA or cyclic AMP-dependent protein kinase, PKB or Akt, and PKC, all play key roles in signal transduction pathways responsible for oncogenesis. Compounds capable of inhibiting the activity of these kinases can be useful in the treatment of diseases characterized by abnormal cellular proliferation, such as cancer.

Rho kinase (Rock-II) participates in vasoconstriction, platelet aggregation, bronchial smooth muscle constriction, vascular smooth muscle proliferation, endothelial proliferation, stress fiber formation, cardiac hypertrophy, Na/H exchange transport system activation, adducing activation, ocular hypertension, erectile dysfunction, premature birth, retinopathy, inflammation, immune diseases, AIDS, fertilization and implantation of fertilized ovum, osteoporosis, brain functional disorder, infection of digestive tracts with bacteria, and the like.

Axl is a receptor tyrosine kinase associated with a number of disease states such as leukemia and various other cancers including gastric cancer.

Bruton's tyrosine kinase (Btk) is important for B lymphocyte development. The Btk family of non-receptor tyrosine kinases includes Btk/Atk, Itk/Emt/Tsk, Bmx/Etk, and Tec. Btk family kinases play central but diverse modulatory roles in various cellular processes. They participate in signal transduction in response to extracellular stimuli resulting in cell growth, differentiation and apoptosis. The aberrant activity of this family of kinases is linked to immunodeficiency diseases and various cancers.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, wherein $R_4$ is a 2-vinyl-1H-pyrrolyl derivative, can be prepared by proceeding as in the following Reaction Scheme I:

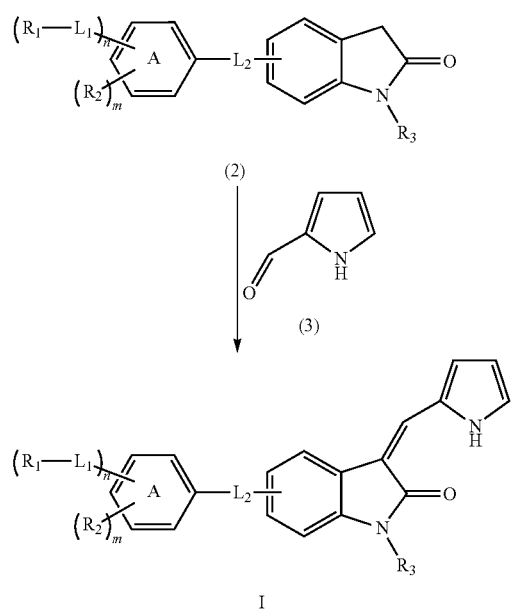

Reactions Scheme I in which $L_1$, $L_2$, m, n, $R_1$, $R_2$ and $R_3$ are as defined for Formula I in the Summary of the Invention. Pyrrolyl can be further substituted according to the definition of $R_4$ in the Summary of the Invention—not shown in reaction scheme I. A compound of Formula I can be prepared by reacting a compound of formula 2 with a compound of formula 3 in the presence of a suitable base (e.g., piperidine, or the like) and a suitable solvent (e.g., ethanol, or the like). The reaction proceeds in a temperature range of about 50 to about 120° C. and can take up to about 10 hours to complete.

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

3-(4-Methyl-imidazol-1-yl-N-{3-[2-oxo-3-(1H-pyrrol-2-ylmethylene)-2,3-dihydro-1 H-indol-6-ylamino]phenyl}-5-trifluoromethyl-benzamide

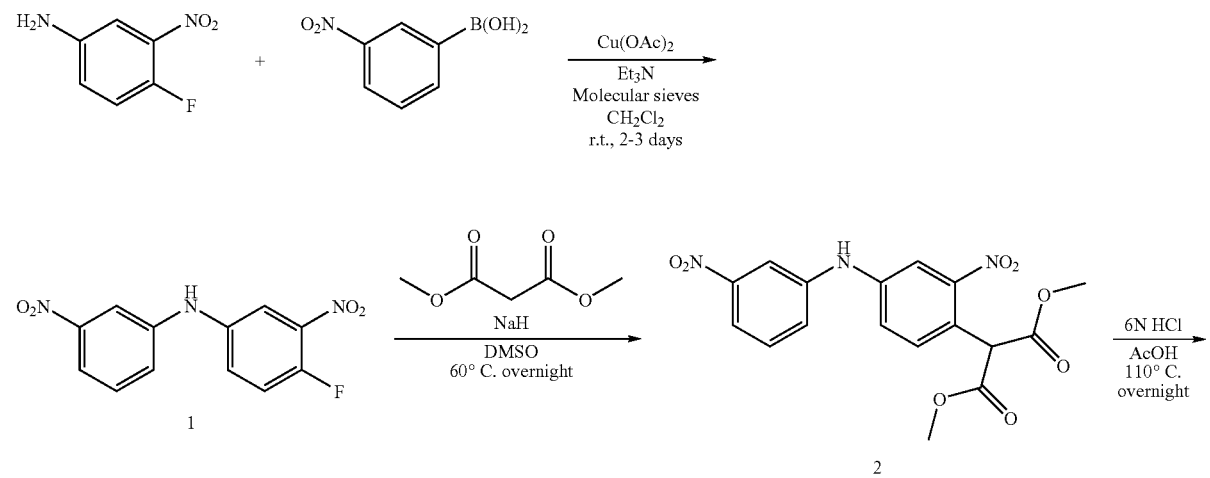

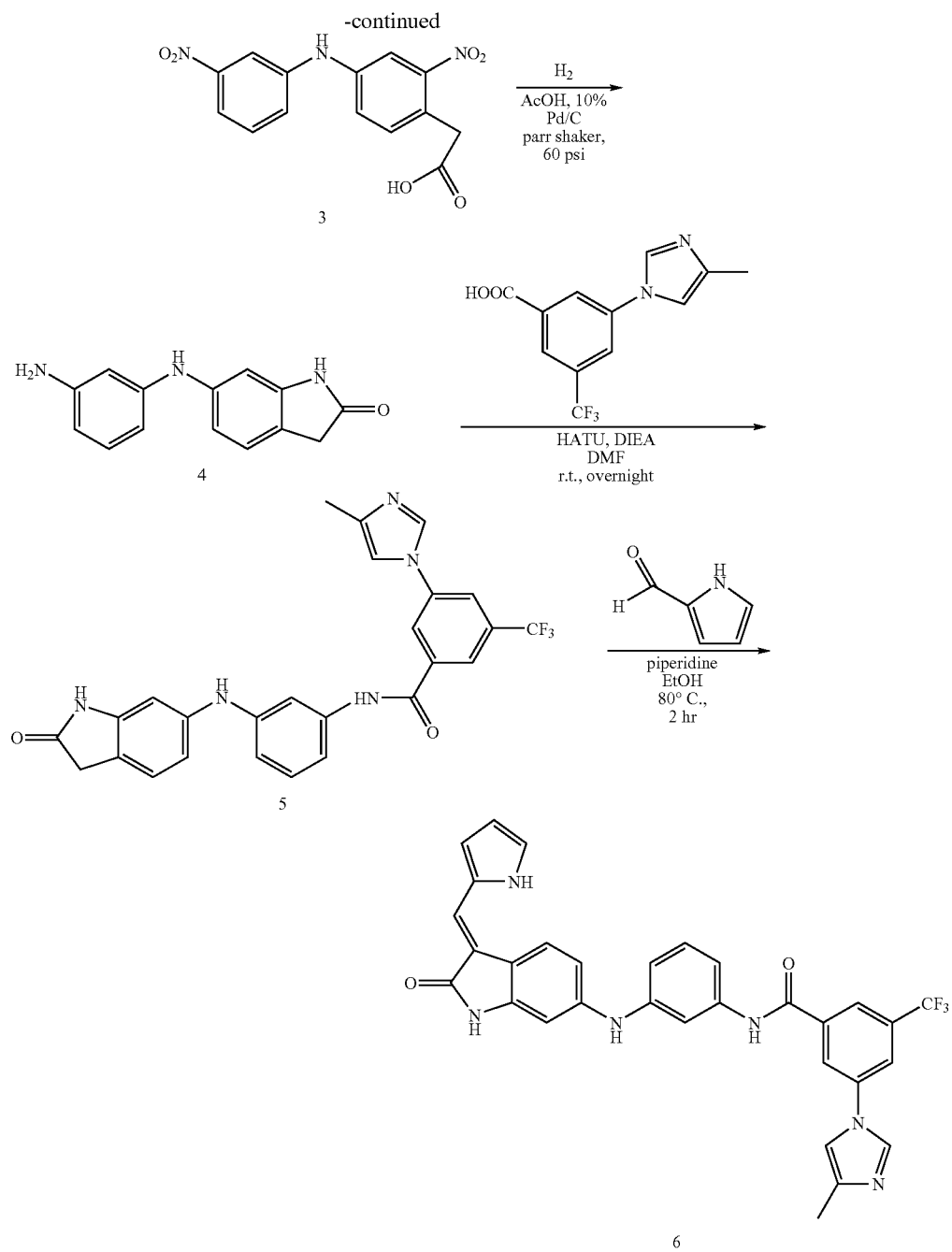

Synthesis of (4-fluoro-3-nitro-phenyl)-(3-nitro-phenyl)-amine (1)

A round bottom flask is charged with 3-nitrophenylboronic acid (4.2 g, 25 mmol), dry molecular sieves (5 g), copper acetate (1.95 g, 12.5 mmol) and dry dichloromethane (150 mL). Triethylamine (8.7 mL, 62.5 mmol) is added followed by the addition of 4-fluoro-3-nitroaniline (2.27 g, 12.5 mmol). The resulting mixture is stirred at ambient temperature for three days. The mixture is filtered through celite and washed with EtOAc. The filtrate is concentrated and purified by column chromatography (EtOAc/Hexane=1:3) to give the desired product: $^1$H NMR (400 MHz, DMSO) δ 9.12 (s, 1 H), 7.82 (m, 1 H), 7.79-7.37 (m, 1 H), 7.73-7.70 (m, 1 H), 7.56-7.49 (m, 4 H); LC-MS: 278.3 (MH$^+$).

Synthesis of 2-[2-nitro-4-(3-nitro-phenylamino)-phenyl]-malonic acid dimethyl ester (2)

To a suspension of 60% of NaH in mineral oil (300 mg, 7.41 mmol) in DMSO (2.5 mL) is added dimethyl malonate (851 μL, 7.41 mmol). The mixture is heated to 60° C. for 10 minutes and then cooled to ambient temperature before (4-fluoro-3-nitro-phenyl)-(3-nitro-phenyl)-amine (686 mg, 2.47 mmol) is added. The resulting mixture is heated to 60° C. for 3 hours and quenched with saturated aqueous NH$_4$Cl solution. The mixture is extracted with EtOAc, washed with brine, dried over MgSO₄, and concentrated. The crude product is purified by column chromatography (EtOAc/Hexane, gradient) to give the desired product: ¹H NMR (400 MHz, CDCl₃) δ. 7.94 (s, 1 H), 7.88 (d, 1 H), 7.70 (d, 1 H), 7.51-7.47 (m, 1 H), 7.44-7.40 (m, 2 H); 7.32-7.28 (m, 1H), 5.27 (s, 1H), 3.83 (s, 6H); LC-MS: 390.3 (MH⁺).

Synthesis of 2-nitro-4-(3-nitro-phenylamino)-phenyl]-acetic acid (3)

To a suspension of 2-[2-nitro-4-(3-nitro-phenylamino)-phenyl]-malonic acid dimethyl ester (800 mg, 2.05 mmol) in acetic acid (2.5 mL) is added 6N HCl (2.6 mL, 15.6 mmol). The mixture is heated to 110° C. overnight (about 15 hours). All the solvent is evaporated to dryness. The crude product is used in the next step without further purification: LC-MS: 318.3 (MH⁺), 340.3 (MNa⁺).

Synthesis of 6-(3-amino-phenylamino)-1,3-dihydro-indol-2-one (4)

To a solution of 2-nitro-4-(3-nitro-phenylamino)-phenyl]-acetic acid (317 mg, 1 mmol) in acetic acid (5 mL) is added 10% Pd/C (48 mg). The mixture is put on a Parr shaker (60 psi) overnight. The catalyst is filtered and the solvent is evaporated to dryness. The crude product is purified by column chromatography (EtOAc/Hexane=9:1) to give the desired product: ¹H NMR (400 MHz, CD3OD) δ 6.90 (s, 1 H), 6.92 (t, 1 H), 6.65-6.60 (m, 2 H), 6.45 (s, 1 H), 6.4 (d, 1 H); 6.23 (d, 1H), 3.37 (s, 2H); LC-MS: 240.4 (MH⁺).

Synthesis of 3-(4-methyl-imidazol-1-yl)-N-[3-(2-oxo-2,3-dihydro-1H-indol-6-ylamino)-phenyl]-5-trifluoromethyl-benzamide (5)

To a solution of 6-(3-Amino-phenylamino)-1,3-dihydroindol-2-one (36 mg, 0.15 mmol) and 3-(4-methyl-imidazol-1-yl)-5-trifluoromethyl-benzoic acid (53 mg, 0.195 mmol) in DMF (1.5 mL) is added N,N-diisopropylethylamine (78 μL, 0.45 mmol) followed by addition of HATU (63 mg, 0.165 mmol). The mixture is stirred at ambient temperature overnight. The mixture is diluted with EtOAc and washed with 10% Na₂S₂O₃ aqueous solution and brine. The organic layer is separated, dried over MgSO₄, and concentrated. The crude product is used in the next step without further purification: LC-MS: 492.1 (MH⁺).

Synthesis of 3-(4-methyl-4-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide (6)

To a suspension of 3-(4-methyl-imidazol-1-yl)-N-[3-(2-oxo-2,3-dihydro-1H-1-indol-6-ylamino)-phenyl]-5-trifluoromethyl-benzamide (100 mg, crude, 0.2 mmol) in EtOH (5 mL) is added pyrrole-2-carboxaldehyde (23 mg, 0.24 mmol) and piperidine (40 mL, 0.4 mmol). The mixture is heated to 80° C. for 2 hours. All the solvent is evaporated to dryness. The crude product is purified by prep-LC/MS to give the desired product in TFA salt form: ¹H NMR (400 MHz, DMSO) δ 10.78 (s, 1 H), 10.52 (s, 1H), 9.58 (s, 1H), 8.57 (s, 1 H), 8.43 (s, 3 H); 8.16 (s, 1 H), 7.69 (s, 1 H), 7.51-7.47 (m, 2 H), 7.29-7.24 (m, 3 H), 6.89-6.85 (m, 1 H), 6.77 (dd, 1 H), 6.73-6.70 (m, 1 H), 6.67 (d, 1 H), 6.32-6.29 (m, 1 H), 2.35 (s, 3 H); LC-MS: 569.3 (MH⁺).

Example 2

N-[2-Oxo-3-(1H-pyrrol-2-ylmethylene)-2,3-dihydro-1H-indol-6-yl]-benzamide

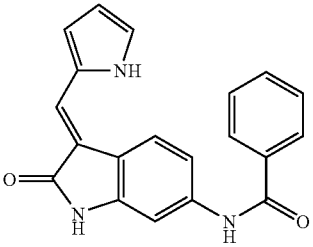

To a solution of 6-amino-1,3-dihydro-indol-2-one (0.15 g, 1.0 mmol) in 2:1 CH₂Cl₂-1,4-dioxane mixture (30 ml) is added triethylamine (0.30 g, 3.0 mmol) and benzoyl chloride (0.14 g, 1.0 mmol). The reaction is stirred for 2 hours at room temperature, and then a saturated aqueous solution of NH₄Cl is added. The precipitate is collected and washed with water to give crude N-(2-oxo-2,3-dihydro-1H-indol-6-yl)-benzamide. To a solution of this benzamide (20 mg, 0.079 mmol) and 1H-pyrrole-2-carbaldehyde (7.6 mg, 0.079 mmol) in ethanol (2 ml) is added 2 drops of piperidine. It is stirred at 80° C. for 4 hours and then cooled to room temperature. The precipitate is collected by vacuum filtration, washed with a small amount of cold ethanol and purified by HPLC(C₁₈ column, eluted with CH₃CN—H₂O containing 0.05% TFA) to give the desired compound as an orange solid: ¹H NMR (DMSO-d₆) δ 6.34 (s, 1H), 6.80 (s, 1H), 7.33 (s, 1H), 7.39 (d, 1H, J=8.4 Hz), 7.53 (t, 2H, J=7.8 Hz), 7.57 (s, 1H), 7.59 (s, 1H), 7.61 (s, 1H), 7.64 (s, 1H), 7.96 (d, 2H, J=7.8 Hz), 10.29 (s, 1H), 10.94 (s, 1H), 13.23 (s, 1H); LC-MS: 330.1 (MH⁺).

Example 3

5-(6-Benzoylamino-2-oxo-1,2-dihydro-indol-3-ylidenemethyl)-2,4-dimethyl-1H-pyrrole-3-carboxylic acid (2-diethylamino-ethyl)-amide

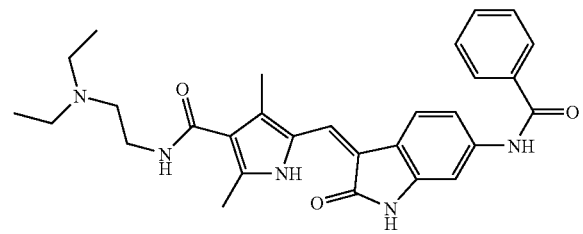

To a solution of N-(2-oxo-2,3-dihydro-1H-indol-6-yl)-benzamide (80 mg, 0.32 mmol) and 5-formyl-2,4-dimethyl-1H-pyrrole-3-carboxylic acid (53 mg, 0.32 mmol) in ethanol (8 ml) is added 4 drops of piperidine. It is stirred at 80° C. for 20 hours and then cooled to room temperature. The precipitate is collected by vacuum filtration, washed with a small amount of cold ethanol to give crude 5-(6-benzoylamino-2-oxo-1,2-dihydro-indol-3-ylidenemethyl)-2,4-dimethyl-1H-pyrrole-3-carboxylic acid. This carboxylic acid (20 mg, 0.050 mmol) is then dissolved in DMF (1 ml). To this reaction is also added N, N-diethylethylenediamine (17 mg, 0.15 mmol), N,N-diisopropylethylamine (19 mg, 0.15 mmol) and HATU (23 mg, 0.061 mmol). It is stirred for 2 hours and concentrated. The desired compound is obtained after HPLC purification: $^1$H NMR (DMSO-$d_6$) δ 1.24 (t, 6H, J=7.2 Hz), 2.43 (s, 3H), 2.47 (s, 3H), 3.20-3.24 (m, 6H), 3.57 (q, 2H, J=5.4 Hz), 7.38 (d, 1H, J=6.6 Hz), 7.53 (t, 2H, J=7.2 Hz), 7.56 (s, 1H), 7.58-7.61 (m, 2H), 7.73-7.77 (m, 2H), 7.96 (d, 2H, J=7.8 Hz), 9.32 (s, 1H), 10.27 (s, 1H), 10.97 (s, 1H), 13.60 (s, 1H); LC-MS: 500.2 (MH$^+$).

Example 4

3-(4-Methyl-imidazol-1-yl)-N-(3-{3-[2-oxo-3-(1H-pyrrol-2-ylmethylene)-2,3-dihydro-1H indol-6-yl]-ureido}-phenyl)-5-trifluoromethyl-benzamide

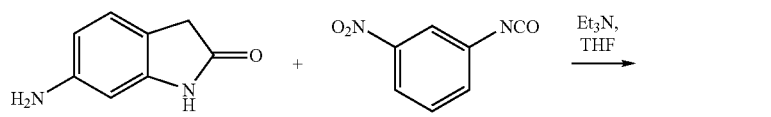

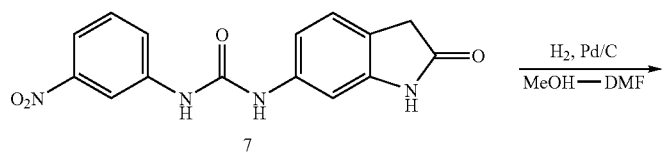

7

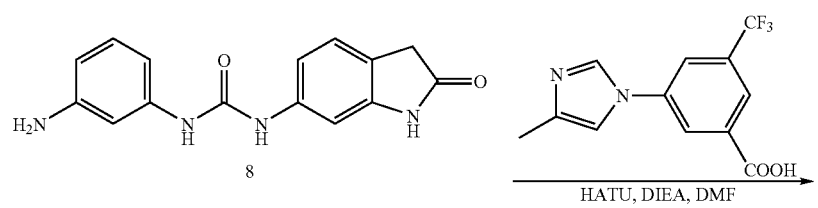

8

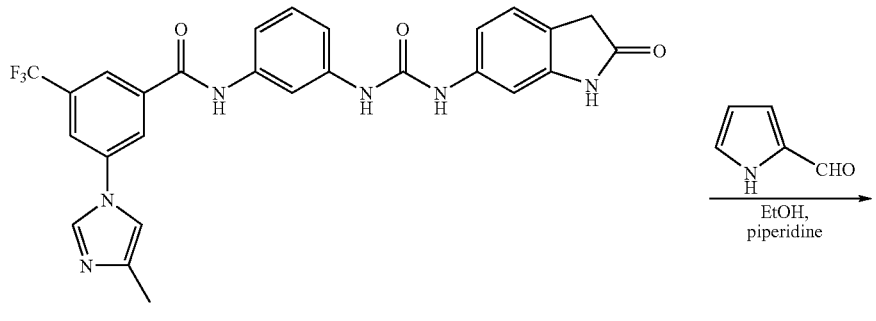

9

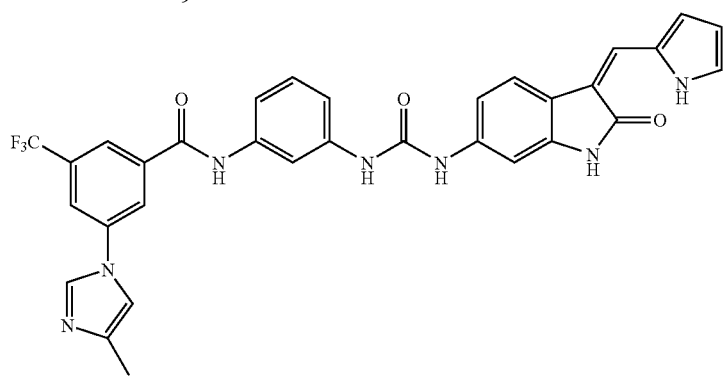

10

Synthesis of 1-(3-nitro-phenyl)-3-(2-oxo-2,3-dihydro-1H-indol-6-yl)-urea (7)

To a solution of 6-amino-1,3-dihydro-indol-2-one (0.15 g, 1.0 mmol) and triethylamine (0.30 g, 3.0 mmol) in THF (10 ml) is added 1-isocyanato-3-nitro-benzene (0.16 g, 1.0 mmol). The reaction is stirred at room temperature for 1 hour and the precipitate is collected by vacuum filtration and washed with ethanol to give the desired compound as a light yellow solid. LC-MS: 313.1 (MH$^+$).

Synthesis of 1-(3-amino-phenyl)-3-(2-oxo-2,3-dihydro-1H-indol-6-yl)-urea (8)

1-(3-nitro-phenyl)-3-(2-oxo-2,3-dihydro-1H-indol-6-yl)-urea (0.23 g, 0.74 mmol) is dissolved in a mixture of DMF-MeOH. To this solution is added Pd/C (10%, wet, 0.10 g). The reaction is placed under a hydrogen balloon and stirred for 20 hours at room temperature. The catalyst is removed and the solvent is evaporated to give 1-(3-amino-phenyl)-3-(2-oxo-2,3-dihydro-1H-indol-6-yl)-urea. LC-MS: 283.1 (MH$^+$).

Synthesis of 3-(4-methyl-imidazol-1-yl)-N-{3-[3-(2-oxo-2,3-dihydro-1H-indol-6-yl)-ureido]-phenyl}-5-trifluoromethyl-benzamide (9)

1-(3-amino-phenyl)-3-(2-oxo-2,3-dihydro-1H-indol-6-yl)-urea (75 mg, 0.27 mmol) is dissolved in DMF (5 ml). To this solution is added 3-(4-methyl-imidazol-1-yl)-5-trifluoromethyl-benzoic acid (73 mg, 0.27 mmol), N,N-diisopropylethylamine (105 mg, 0.81 mmol) and HATU (0.10 g, 0.26 mmol). It is stirred for 24 hours and then concentrated. 3-(4-methyl-imidazol-1-yl)-N-{3-[3-(2-oxo-2,3-dihydro-1H-indol-6-yl)-ureido]-phenyl}-5-trifluoromethyl-benzamide is obtained after HPLC purification. LC-MS: 535.2 (MH$^+$).

Synthesis of 3-(4-methyl-imidazol-1-yl)-N-(3-{3-[2-oxo-3-(1H-pyrrol-2-ylmethylene)-2,3-dihydro-1H-indol-6-yl]-ureido}-phenyl)-5-trifluoromethyl-benzamide (10)

The above obtained benzamide (25 mg, 0.047 mmol) is reacted with 1H-pyrrole-3-carboxylic acid (48 mg, 0.29 mmol) in ethanol (2 ml) in the presence of 2 drops of piperidine at 80° C. for 12 hours. It is concentrated and the desired compound is obtained after HPLC purification: $^1$H NMR (DMSO-d$_6$) 2.20 (s, 3H), 6.32 (q, 1H, J=2.4 Hz), 6.76 (s, 1H), 6.88 (dd, 1H, J=9.0 Hz, J$_2$=2.4 Hz), 7.22 (d, 1H, J=8.4 Hz), 7.28-7.31 (m, 2H), 7.38 (d, 1H, J=2.4 Hz), 7.42 (d, 1H, J=7.8 Hz), 7.51 (d, 1H, J=9.0 Hz), 7.57 (s, 1H), 7.72 (s, 1H), 8.05 (s, 1H), 8.18 (s, 1H), 8.24 (s, 1H), 8.41 (s, 1H), 8.46 (s, 1H), 8.75 (s, 1H), 8.77 (s, 1H), 10.49 (s, 1H), 10.87 (s, 1H), 13.21 (s, 1H); LC-MS: 612.1 (MH$^+$).

Example 5

2-Oxo-3-(1H-pyrrol-2-ylmethylene)-2,3-dihydro-1H-indole-6-carboxylic acid (3-benzoylamino-phenyl)-amide

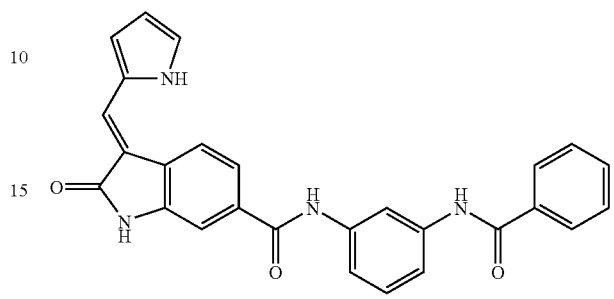

To a solution of 2-oxo-2,3-dihydro-1H-indole-6-carboxylic acid (0.20 g, 1.1 mmol) in DMF (1 ml) is added N-(3-amino-phenyl)-benzamide (0.26 g, 1.2 mmol), N,N-diisopropylethylamine (0.44 g, 3.4 mmol) and HATU (0.47 g, 1.24 mmol). The reaction is stirred for 20 hours and concentrated. The residue is purified by HPLC (C$_{18}$ column, eluted with CH$_3$CN—H$_2$O containing 0.05% TFA) to give 2-oxo-2,3-dihydro-1H-indole-6-carboxylic acid (3-benzoylamino-phenyl)-amide as off-white solid. This amide (15 mg, 0.04 mmol) is then heated with 1H-pyrrole-2-carbaldehyde (6.0 mg, 0.06 mmol) in ethanol (2 ml) in the presence of 2 drops of piperidine at 80° C. for 20 hours. The mixture is concentrated and the desired compound is obtained after HPLC purification: $^1$H NMR (DMSO-d$_6$) δ 6.41 (s, 1H), 6.93 (s, 1H), 7.31 (t, 1H, J=7.8 Hz), 7.44 (s, 1H), 7.48-7.51 (m, 3H), 7.54 (t, 2H, J=7.2 Hz), 7.59 (d, 1H, J=6.6 Hz), 7.70 (d, 1H, J=8.4 Hz), 7.78 (d, 1H, J=8.4 Hz), 7.92 (s, 1H), 7.98 (d, 2H, J=7.2 Hz), 8.33 (s, 1H), 10.27 (s, 1H), 10.31 (s, 1H), 11.13 (s, 1H), 13.38 (s, 1H); LC-MS: 449.1 (MH$^+$).

Example 6

6-(3-Amino-phenylamino)-3-(1H-pyrrol-2-ylmethylene)-1,3-dihydro-indol-2-one

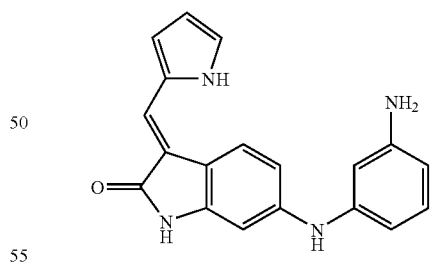

A suspension of 6-bromo-3-(1H-pyrrol-2-ylmethylene)-1,3-dihydro-indol-2-one (10 mg, 0.035 mmol), 1,3-diaminophenylene (4.5 mg, 0.042 mmol), Pd$_2$(dba)$_3$ (1.6 mg, 0.0017 mmol), biphenyl-2-yl-di-tert-butyl-phosphane (2.1 mg, 0.007 mmol) and K$_3$PO$_4$ (37 mg, 0.17 mmol) in ethylene glycol dimethyl ether (1 ml) is heated in a sealed vessel at 85° C. for 20 hours. After cooling and diluting with ethyl acetate, the organic layer is washed with saturated NH$_4$Cl solution, dried and the solvent is removed under vacuum. The residue is purified by HPLC (C$_{18}$ column, eluted with CH$_3$CN—H$_2$O containing 0.05% TFA) to give the desired compound as a red solid: ¹H NMR (DMSO-d₆) δ 5.21 (bs, 2H), 6.14 (d, 1H, J=7.2 Hz), 6.27-6.32 (m, 2H), 6.37-6.40 (m, 1H), 6.61 (s, 1H), 6.65 (d, 1H, J=8.0 Hz), 6.68-6.70 (m, 1H), 6.90 (t, 1H, J=7.2 Hz), 7.22-7.26 (m, 1H), 7.41 (d, 1H, J=8.0 Hz), 7.43 (s, 1H), 8.02 (s, 1H), 10.69 (s, 1H), 13.14 (s, 1H); LC-MS: 317.2 (MH⁺).
Example 7
4-(4-Methyl-piperazin-1-ylmethyl)-N-{3-[2-oxo-3-(1H-pyrrol-2-ylmethylene)-2,3-dihydro-1H-indol-7-ylamino]-phenyl}-benzamide
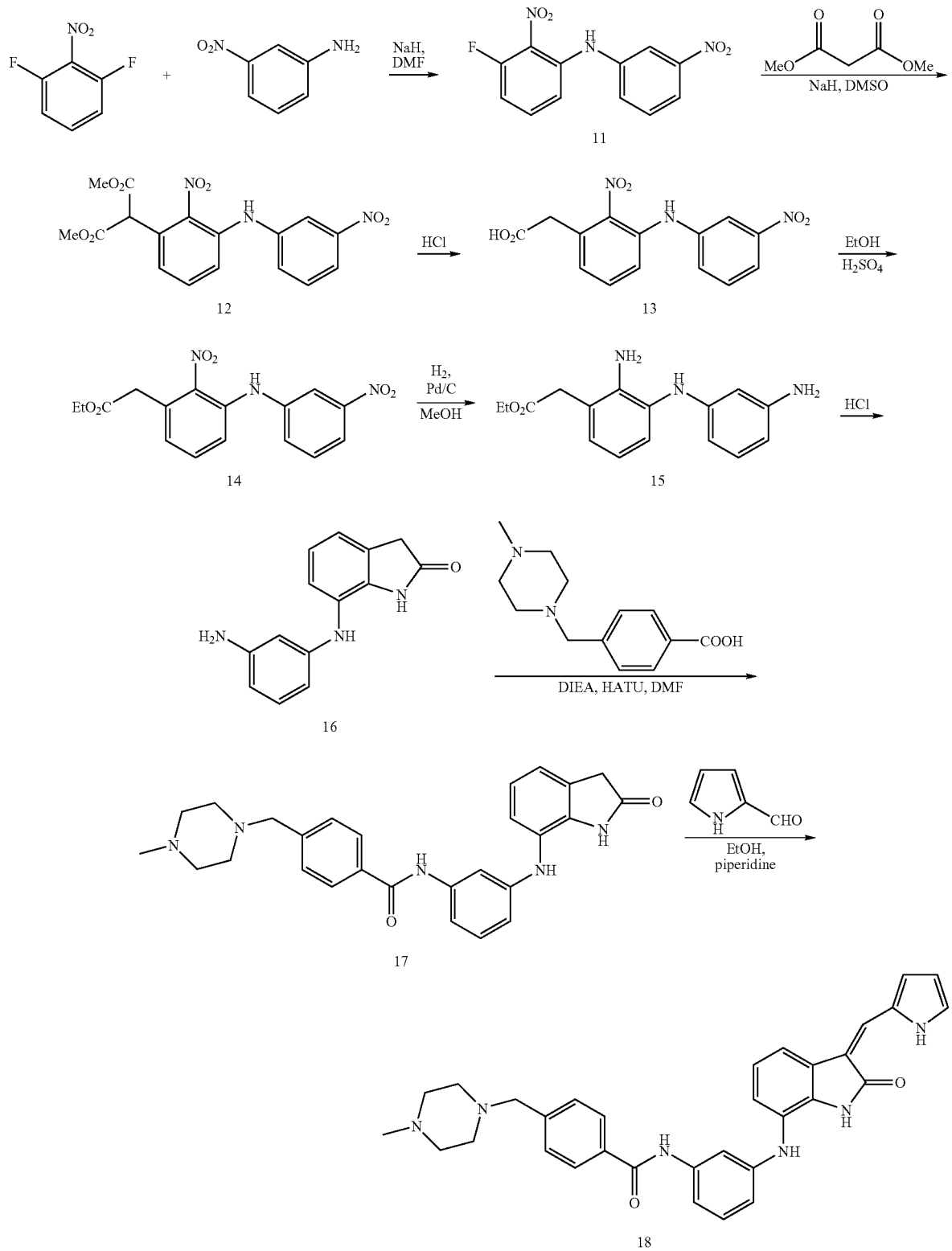

Synthesis of (3-fluoro-2-nitro-phenyl)-(3-nitro-phenyl)-amine (11)

To a solution of 3-nitro-phenylamine (1.82 g, 0.013 mol) in DMF (8 ml) at 0° C. is added NaH (60% dispersion in mineral oil, 0.53 g, 0.013 mol). The reaction is stirred at this temperature for 15 min. Subsequently, a solution of 1,3-difluoro-2-nitro-benzene (0.70 g, 4.4 mmol) in DMF (2 ml) is added slowly. After stirring for additional 30 min, it is poured into a saturated aqueous solution of $NH_4Cl$. The precipitate therefore formed is collected by vacuum filtration. The desired compound is obtained after flash column chromatography purification of the precipitate (silica gel, eluted by hexanes-ethyl acetate). $^1H$ NMR ($CDCl_3$) δ 6.77 (dd, 1H, J=10 Hz, $J_2$=10.6 Hz), 7.11 (d, 1H, J=8.8 Hz), 7.35-7.41 (m, 1H), 7.49-7.59 (m, 2H), 7.99 (dt, 1H, $J_1$=8.0 Hz, $J_2$-2.0 Hz), 8.09 (t, 1H, J=2.0 Hz), 8.35 (bs, 1H); LC-MS: 278.0 ($MH^+$).

Synthesis of 2-[2-nitro-3-(3-nitro-phenylamino)-phenyl]-malonic acid dimethyl ester (12)

To a suspension of NaH (60% dispersion in mineral oil, 0.26 g, 11 mmol) in DMSO (30 ml) is added dimethyl malonate (1.43 g, 11 mmol) slowly. The reaction is stirred at room temperature for 1 hour. After that, a solution of (3-fluoro-2-nitro-phenyl)-(3-nitro-phenyl)-amine (1.0 g, 3.6 mmol) in DMSO (5 ml) is added. The reaction is brought to 80° C. and stirred for 20 hours. It is poured into saturated $NH_4Cl$ and extracted with ethyl acetate (30 ml×3). The organic layers are combined, washed with water, brine and dried with $Na_2SO_4$. The desired compound is obtained after purification of the residue by flash column chromatography (silica gel, eluted by hexa-nes-ethyl acetate): LC-MS: 390.0 ($MH^+$),

Synthesis of [2-nitro-3-(3-nitro-phenylamino)-phenyl]-acetic acid (13)

2-[2-Nitro-3-(3-nitro-phenylamino)-phenyl]-malonic acid dimethyl ester (1.26 g, 3.24 mmol) is heated in 6 N hydrochloric acid (100 ml) at 110° C. for 10 hours. It is then cooled to room temperature; the precipitate therefore formed is collected by vacuum filtration to give the desired compound: LC-MS: 318.0 ($MH^+$).

Synthesis of [2-nitro-3-(3-nitro-phenylamino)-phenyl]-acetic acid ethyl ester (14)

[2-Nitro-3-(3-nitro-phenylamino)-phenyl]-acetic acid (0.79 g, 2.5 mmol) is refluxed in EtOH (50 ml) in the presence of 0.5 ml concentrated $H_2SO_4$ for 2 hours. It is then concentrated and to the residue is added saturated $NaHCO_3$. The mixture is extracted with ethyl acetate (30 ml×3). The organic layers are combined and dried with $Na_2SO_4$ to give the desired compound after concentration: $^1H$ NMR ($CDCl_3$) δ 1.29 (t, 3H, J=7.2 Hz), 3.92 (s, 2H), 4.20 (q, 2H, J=7.2 Hz), 6.89 (d, 1H, J=6.0 Hz), 7.34-7.41 (m, 2H), 7.44-7.52 (m, 2H), 7.92 (d, 1H, J=7.6 Hz), 8.03 (s, 1H), 8.17 (s, 1H); LC-MS: 346.0 ($MH^+$).

Synthesis of [2-amino-3-(3-amino-phenylamino)-phenyl]-acetic acid ethyl ester (15)

To a solution of [2-nitro-3-(3-nitro-phenylamino)-phenyl]-acetic acid ethyl ester (0.62 g, 1.8 mmol) in ethanol (50 ml) is added Pd/C (10%, wet, 0.50 g). It is placed under a hydrogen balloon and stirred for 20 hours. The catalyst is filtered and the solvent is removed to give the desired compound: LC-MS: 286.1 ($MH^+$).

Synthesis of 7-(3-amino-phenylamino)-1,3-dihydro-indol-2-one (16)

[2-Amino-3-(3-amino-phenylamino)-phenyl]-acetic acid ethyl ester (0.50 g, 1.7 mmol) is refluxed in 1 N hydrochloric acid for 30 minutes. The reaction mixture is cooled to room temperature and basified with saturated $Na_2CO_3$. The mixture is then extracted with ethyl acetate (30 ml×3). The organic layers are combined, dried with $Na_2SO_4$ and concentrated. The residue is purified by flash column chromatography (silica gel, eluted with ethyl acetate-methanol with 0.5% $NH_3$) to give the desired compound. $^1H$ NMR (DMSO-$d_6$) δ 4.93 (s, 2H), 6.06 (d, 1H, J=6.8 Hz), 6.14 (d, 1H, J=8.0 Hz), 6.21 (s, 1H), 6.78 (d, 1H, J=7.2 Hz), 6.85 (t, 2H, J=8.0 Hz), 6.97 (s, 1H), 7.05 (d, 1H, J=8.0 Hz), 9.96 (s, 1H); LC-MS: 240.1 ($MH^+$).

Synthesis of 4-(4-methyl-piperazin-1-ylmethyl)-N-[3-(2-oxo-2,3-dihydro-1H-indol-7-ylamino)-phenyl]-benzamide (17)

To a solution of 7-(3-amino-phenylamino)-1,3-dihydro-indol-2-one (80 mg, 0.33 mmol) in DMF (2 ml) is added 4-(4-methyl-piperazin-1-ylmethyl)-benzoic acid (113 mg, 0.37 mmol), N,N-diisopropylethylamine (0.22 g, 1.67 mmol) and HATU (0.14 g, 0.37 mmol). The reaction is stirred for 12 hours and concentrated. The residue is purified by HPLC to afford the desired compound: LC-MS: 456.2 ($MH^+$).

Synthesis of 4-(4-methyl-piperazin-1-ylmethyl)-N-{3-[2-oxo-3-(1H-pyrrol-2-ylmethylene)-2,3-dihydro-1H-indol-7-ylamino]-phenyl}-benzamide (18)

A solution of 4-(4-methyl-piperazin-1-ylmethyl)-N-[3-(2-oxo-2,3-dihydro-1H-indol-7-ylamino)-phenyl]-benzamide (23 mg, 0.05 mmol) is heated with 1H-pyrrole-2-carbaldehyde (5 mg, 0.05 mmol) in ethanol (2 ml) in the presence of 2 drops of piperidine for 12 hours. It is then concentrated and purified by HPLC to give the desired compound: $^1H$ NMR (DMSO-$d_6$) δ 2.40-2.48 (m, 2H), 2.79 (s, 3H), 2.96-3.08 (m, 4H), 3.36-3.46 (m, 2H), 3.75 (s, 2H), 6.37 (s, 1H), 6.71 (d, 1H, J=7.8 Hz), 6.85 (s, 1H), 6.97 (t, 1H, J=7.8 Hz), 7.11 (d, 1H, J=7.2 Hz), 7.19 (t, 1H, J=7.8 Hz), 7.24 (d, 1H, J=7.8 Hz), 7.30 (t, 1H, J=7.8 Hz), 7.36 (s, 1H), 7.47 (d, 2H, J=7.8 Hz), 7.53 (s, 1H), 7.75 (s, 1H), 7.93 (d, 2H, J=7.8 Hz), 10.13 (s, 1H), 10.60 (s, 1H), 13.36 (s, 1H); LC-MS: 533.2 ($MH^+$).

Example 8
4-(4-Methyl-piperazin-1-ylmethyl)-N-{3-[2-oxo-3-(1H-pyrrol-2-ylmethylene)-2,3-dihydro-1H-indol-5-ylamino]-phenyl}-benzamide
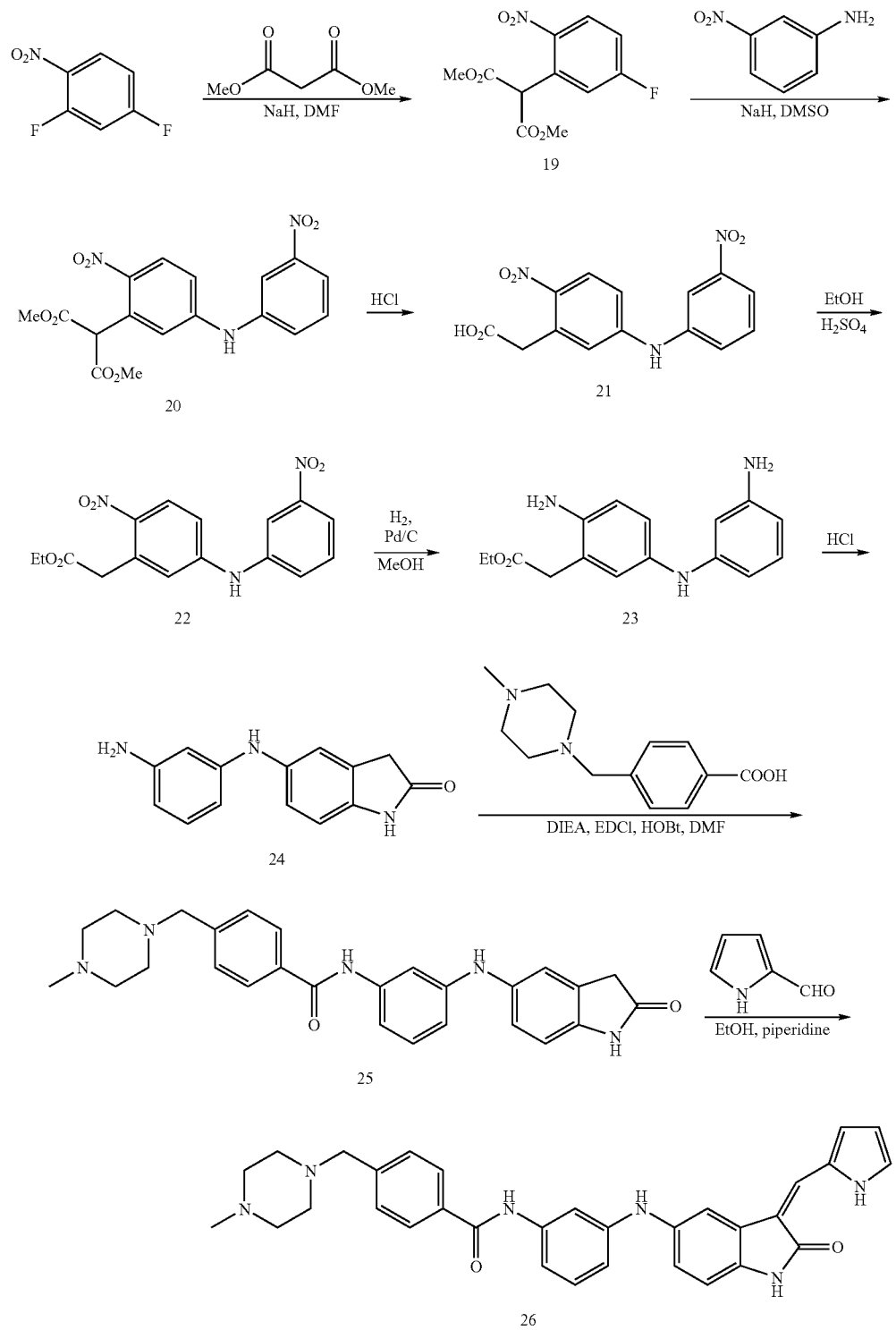

Synthesis of 2-(5-fluoro-2-nitro-phenyl)-malonic acid dimethyl ester (19)

To a mixture of dimethyl malonate (6.24 g, 46.7 mmol) and potassium carbonate (6.51 g, 47.2 mmol) in DMF (20 ml) is added 2,4-difluoronitrobenzene (5.00 g, 30.8 mmol). The reaction is stirred at room temperature for 1 hour and then is brought to 60° C. After stirring for 1 hour, it is cooled to room temperature and 1 N HCl (100 ml) is added. The mixture is extracted with ethyl acetate (80 ml×2). The organic layers are combined, dried and concentrated. The desired compound is obtained after flash column chromatography purification (silica gel, eluted with hexanes-ethyl acetate): $^1$H NMR (CDCl$_3$) δ 3.82 (s, 6H), 5.40 (s, 1H), 7.18-7.26 (m, 2l), 8.16 (dd, 1H, J$_1$=4.8 Hz, J$_2$=8.8 Hz); LC-MS: 272.1 (MH$^+$).

Synthesis of 2-[2-nitro-5-(3-nitro-phenylamino)-phenyl]-malonic acid dimethyl ester (20)

To a solution of 3-nitro-phenylamine (2.08 g, 15.1 mmol) in DMSO (40 ml) is added NaH (60% dispersion in mineral oil, 0.60 g, 15 mol). The reaction is stirred at this temperature for 30 minutes. After that, a solution of 2-(5-fluoro-2-nitro-phenyl)-malonic acid dimethyl ester (1.36 g, 5.02 mmol) in DMSO (10 ml) is added slowly. The reaction is stirred at 80° C. for 24 hours, and is poured into a saturated solution of NH$_4$Cl (150 ml). The mixture is extracted with ethyl acetate (100 ml×3). The insoluble is filtered off. The organic layers are combined, dried and concentrated. The desired ester is obtained after flash column chromatography purification (silica gel, eluted by hexanes-ethyl acetate): LC-MS: 390.1 (MH$^+$).

Synthesis of [2-nitro-5-(3-nitro-phenylamino)-phenyl]-acetic acid (21)

A solution of 2-[2-nitro-5-(3-nitro-phenylamino)-phenyl]-malonic acid dimethyl ester (0.68 g, 1.7 mmol) in 6 N hydrochloric acid (20 ml) is heated at 110° C. for 10 hours. It is then cooled to room temperature and the mixture is extracted with ethyl acetate (100 ml×3). The organic layers are combined, dried, concentrated to give crude [2-nitro-5-(3-nitro-phenylamino)-phenyl]-acetic acid: LC-MS: 318.0 (MH$^+$).

Synthesis of [2-nitro-5-(3-nitro-phenylamino)-phenyl]-acetic acid ethyl ester (22)

A solution of [2-nitro-5-(3-nitro-phenylamino)-phenyl]-acetic acid (0.49 g, 1.5 mmol) in EtOH (20 ml) is refluxed in the presence of 0.2 ml concentrated H$_2$SO$_4$ for 3 hours before it is concentrated. To the residue is added saturated NaHCO$_3$. The mixture is extracted with ethyl acetate (30 ml×3). The organic layers are combined and dried with Na$_2$SO$_4$ to give [2-nitro-5-(3-nitro-phenylamino)-phenyl]-acetic acid ethyl ester: LC-MS: 346.0 (MH$^+$).

Synthesis of [2-amino-5-(3-amino-phenylamino)-phenyl]-acetic acid ethyl ester (23)

To a solution of [2-nitro-5-(3-nitro-phenylamino)-phenyl]-acetic acid ethyl ester (0.36 g, 1.0 mmol) in methanol (10 ml) is added Pd/C (10%, wet, 0.1 g). The reaction is placed under a hydrogen balloon and stirred for 20 hours. The catalyst is filtered and the solvent is removed to give the desired compound. LC-MS: 286.1 (MH$^+$).

Synthesis of 5-(3-amino-phenylamino)-1,3-dihydro-4-indol-2-one (24)

The above-obtained amine is refluxed in 1 N hydrochloric acid for 30 min. The reaction mixture is cooled to room temperature and basified with saturated Na$_2$CO$_3$. The mixture is then extracted with ethyl acetate (30 ml×3). The organic layers are combined, dried with Na$_s$SO$_4$ and concentrated. The residue is purified by flash column chromatography (silica gel, eluted with ethyl acetate-methanol with 0.5% NH$_3$) to give the desired compound. An analytical sample was purified by HPLC(C$_{18}$ column, eluted with CH$_3$CN—H$_2$O containing 0.05% TFA): $^1$H NMR (DMSO-d$_6$) δ 3.44 (s, 2H), 6.41 (d, 1H, J=8.0 Hz), 6.61 (s, 1H), 6.64 (d, 1H, J$_3$=8.0 Hz), 6.75 (d, 1H, J=8.0 Hz), 6.92 (d, 1H, J=8.8 Hz), 6.99 (s, 1H), 7.10 (t, 2H, 3=8.0 Hz), 7.99 (bs, 1H), 10.3 (s, 1H); LC-MS: 240.1 (MH$^+$).

Synthesis of 4-(4-methyl-piperazin-1-ylmethyl)-N-[3-(2-oxo-2,3-dihydro-1H-indol-5-ylamino)-phenyl]-benzamide (25)

To a solution of 5-(3-amino-phenylamino)-1,3-dihydro-indol-2-one (20 mg, 0.083 mmol) in DMF (2 ml) is added 4-(4-methyl-piperazin-1-ylmethyl)-benzoic acid (31 mg, 0.1 mmol), N,N-diisopropylethylamine (54 mg, 0.42 mmol), EDCI (32 mg, 0.17 mmol) and HOBt (11 mg, 0.083 mmol). The reaction is stirred for 12 hours and concentrated. The residue is purified by HPLC to afford the desired compound: LC-MS: 456.2 (MH$^+$).

Synthesis of 4-(4-methyl-piperazin-1-ylmethyl)-N-{3-[2-oxo-3-(1H-pyrrol-2-ylmethylene)-2,3-dihydro-1H-indol-5-ylamino]-phenyl}-benzamide (26)

To a solution of 4-(4-methyl-piperazin-1-ylmethyl)-N-[3-(2-oxo-2,3-dihydro-1H-indol-5-ylamino)-phenyl]-benzamide (23 mg, 0.05 mmol) in ethanol (2 ml) is added 1H-pyrrole-2-carbaldehyde (16 mg, 0.17 mmol) and 2 drops of piperidine. The reaction is refluxed for 12 hours and then concentrated. The desired compound after HPLC purification: $^1$H NMR (DMSO-d$_6$) δ 2.44-2.52 (m, 2H), 2.79 (s, 3H), 2.98-3.10 (m, 2H), 3.18-3.22 (m, 2H), 3.38-3.42 (m, 2H), 3.77 (s, 2H), 6.32-6.36 (m, 1H), 6.61-6.69 (m, 1l1), 6.81-6.82 (m, 2H), 6.92 (dd, 1H, J=8.8 Hz, J$_2$=1.6 Hz), 7.12-7.18, (m, 2H), 7.34 (s, 1H), 7.46 (dd, 2H, J=4.8 Hz, J$_2$=1.6 Hz), 7.48 (s, 2H), 7.69 (s, 1H), 7.93 (d, 2H, J=8.0 Hz), 8.01 (s, 1H), 10.09 (s, 1H), 10.78 (s, 1H), 13.39 (s, 1H); LC-MS: 533.2 (MH$^+$).

Example 9

4-(4-Ethyl-piperazin-1-ylmethyl)-N-{3-[2-oxo-3-(1H-pyrrol-2-ylmethylene)-2,3-dihydro-1H-indol-6-ylamino]-phenyl}-3-trifluoromethyl-benzamide

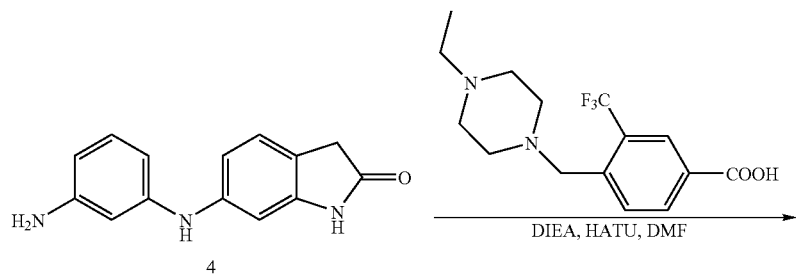

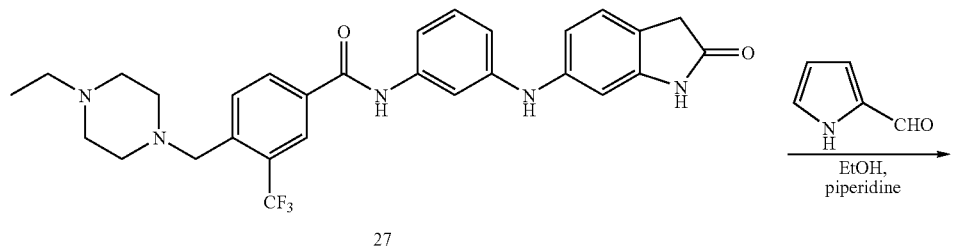

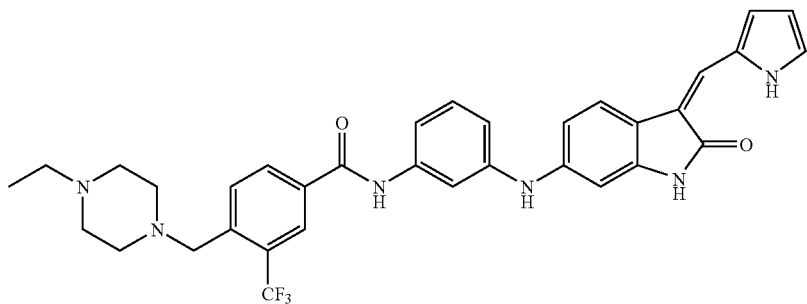

Synthesis of 4-(4-Ethyl-piperazin-1-ylmethyl)-N-[3-(2-oxo-2,3-dihydro-1H-indol-6-ylamino)-phenyl]-3-trifluoromethyl-benzamide (27)

To a solution of 6-(3-amino-phenylamino)-1,3-dihydro-indol-2-one (120 mg, 0.50 mmol, prepared as described in Example 1) and 4-(4-ethyl-piperazin-1-ylmethyl)-3-trifluoromethyl-benzoic acid hydrochloride (213 mg, 0.60 mmol) in DMF (5 mL) is added N,N-diisopropylethylamine (437 µL, 2.5 mmol) followed by addition of HATU (191 mg, 0.50 mmol). The mixture is stirred at ambient temperature overnight. The mixture is diluted with EtOAc and washed with 10% $Na_2S_2O_3$ aqueous solution and brine. The organic layer is separated, dried over $MgSO_4$, and concentrated. The crude is purified by column chromatography ($CH_2Cl_2/CH_3OH$=9:1) to give the desired compound. LC-MS: 538.2 ($MH^+$).

Synthesis of 4-(4-Ethyl-piperazin-1-ylmethyl)-N-{3-[2-oxo-3-(1H-pyrrol-2-ylmethylene)-2,3-dihydro-1H-indol-6-ylamino]-phenyl}-3-trifluoromethyl-benzamide (28)

To a suspension of 4-(4-ethyl-piperazin-1-ylmethyl)-N-[3-(2-oxo-2,3-dihydro-1H-indol-6-ylamino)-phenyl]-3-trifluoromethyl-benzamide (200 mg, 0.372 mmol) in EtOH (10 mL) are added pyrrole-2-carboxaldehyde (42 mg, 0.446 mmol) and piperidine (74 µL, 0.74 mmol). The mixture is heated at 80° C. for 2 hours. All the solvent is evaporated to dryness. The crude is recrystallized in EtOH to give 136 mg of the desired compound: $^1$H NMR (400 MHz, DMSO) δ 10.74 (s, 1 H), 10.34 (s, 1 H), 8.37 (s, 1 H), 8.18-8.24 (m, 2 H), 7.92 (d, 1 H); 7.67 (s, 1 H), 7.46-7.50 (t, 2 H), 7.24-7.28 (m, 3 H), 6.84 (d, 1 H), 6.76 (s, 1 H), 6.72 (m, 1 H), 6.67 (d, 1 H), 6.29-6.31 (m, 1 H), 3.69 (s, 2 H), 3.30 (s, 2 H), 2.30-2.48 (m, 8H), 1.00 (t, 3H); LC-MS: 615.3 ($MH^+$).

Example 10

3-(4-Methyl-piperazin-1-yl)-N-{3-[2-oxo-3-(1H-pyrrol-2-ylmethylene-2,3-dihydro-1H-indol-6-yloxy]-phenyl}-5-trifluoromethyl-benzamide

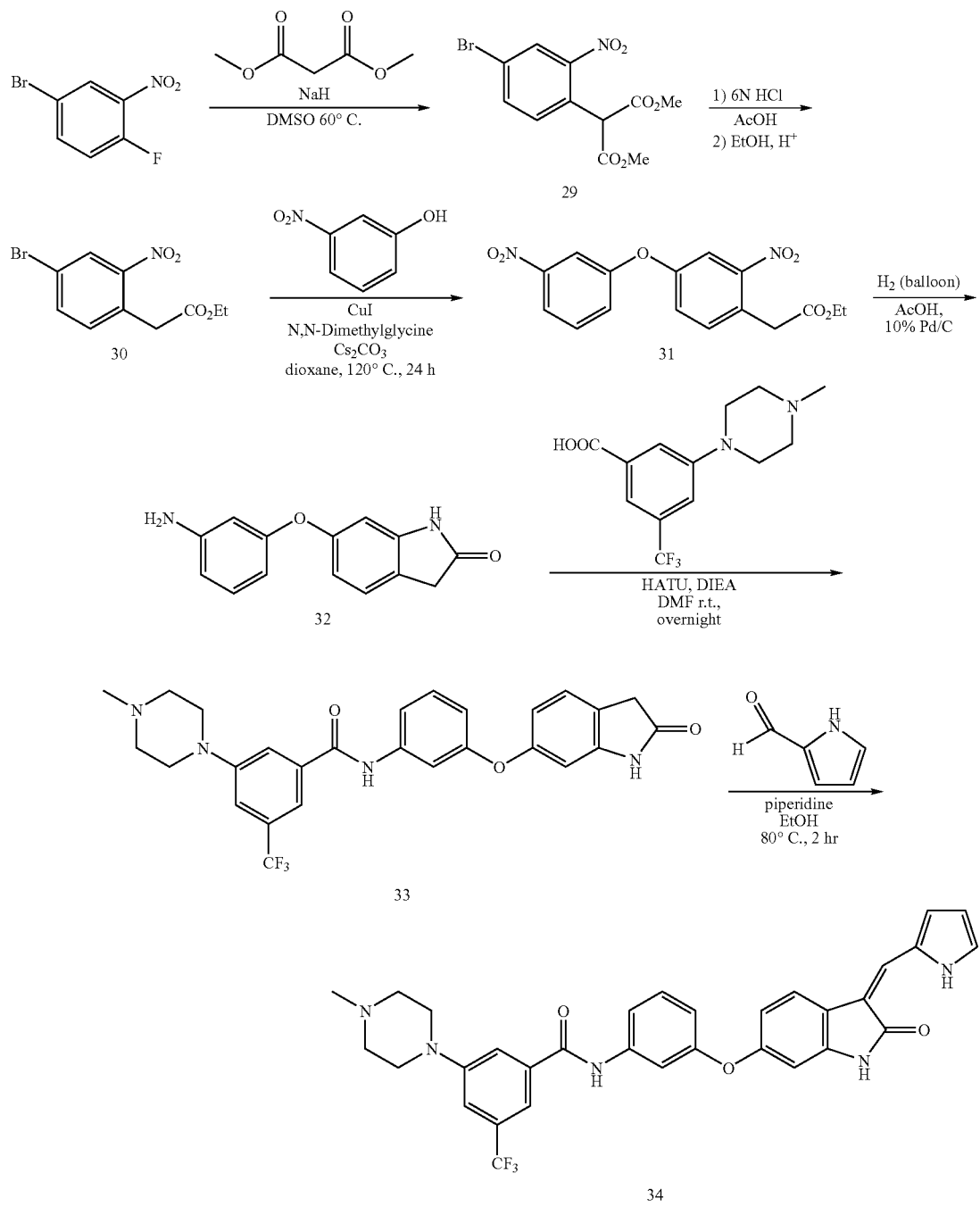

Synthesis of 2-(4-Bromo-2-nitro-phenyl)-malonic acid dimethyl ester (29)

To a suspension of NaH (60% in mineral oil, 972 mg, 24.3 mmol) in DMSO (16 mL) is added dimethyl malonate (2.78 mL, 24.3 mmol). The mixture is heated at 60° C. for 10 min and then is cooled to room temperature before 4-bromo-1-fluoro-2-nitro-benzene (1.0 mL, 8.1 mmol) is added. The resulting mixture is heated at 60° C. for 3 hr and then is quenched with saturated aqueous NH$_4$Cl solution. The mixture is extracted with EtOAc, washed with brine, dried over MgSO$_4$, and concentrated. The crude is used without further purification.

Synthesis of (4-Bromo-2-nitro-phenyl)-acetic acid ethyl ester (30)

To a suspension of 2-(4-bromo-2-nitro-phenyl)-malonic acid dimethyl ester (crude, 8.1 mmol) in acetic acid (10 mL) is added 6N HCl (10 mL). The mixture is heated at 110° C. overnight (about 15 hr). The reaction mixture is evaporated to dryness. The crude is used in the next step without further purification. To a solution of the crude in ethanol (40 mL) is added concentrated $H_2SO_4$ (3 drops) and the resulting reaction mixture is heated at reflux over night. Solvent is removed under reduced pressure. It is purified by flash column chromatography. $^1$H NMR (400 MHz, $CDCl_3$) δ 8.25 (s, 1 H), 7.72-7.7 (m, 1 H), 7.26-7.22 (m, 1 H), 4.23-4.13 (q, 2 H), 3.97 (s, 2 H), 1.29-1.23 (t, 3 H).

Synthesis of [2-Nitro-4-(3-nitro-phenoxy)-phenyl]-acetic acid ethyl ester (31)

To a sealed tube are charged with 3-nitrophenol (83 mg, 0.6 mmol), (4-bromo-2-nitro-phenyl)-acetic acid ethyl ester (180 mg, 0.63 mmol), copper iodide (12 mg, 0.06 mmol), N,N-dimethylglycine (23 mg, 0.2 mmol), $Cs_2CO_3$ (400 mg, 1.2 mmol) in 1,4-dioxane. The resulting mixture is stirred at 120° C. for 24 h. The reaction mixture is diluted with water and extracted with EtOAc. The organic phase is dried, concentrated, and purified by flash column chromatography (DCM/Hexane=9:1) to give 130 mg of the desired product (yield 62%). $^1$H NMR (400 MHz, $CDCl_3$) δ 8.00-7.97 (m, 1 H), 7.82-7.81 (m, 1 H), 7.70-7.69 (m, 1 H), 7.53-7.49 (m, 1 H), 7.34-7.30 (m, 1 H), 7.22-7.19 (m, 1 H), 4.14-4.09 (m, 2 H), 3.94 (s, 2 H), 1.23-1.18 (m, 3 H). LC/MS: 347.2 ($MH^+$).

Synthesis of 6-(3-Amino-phenoxy)-1,3-dihydro-indol-2-one (32)

To a solution of [2-nitro-4-(3-nitro-phenoxy)-phenyl]-acetic acid ethyl ester (496 mg, 1.4 mmol) in acetic acid (5 mL) is added 10% Pd/C (48 mg). The mixture is stirred under hydrogen (balloon) overnight. The catalyst is filtered off and the solvent is evaporated to dryness. The crude product is purified by column chromatography (EtOAc/Hexane=9:1) to give 120 mg of the desired product (yield 50%). LC/MS: 242.2 ($MH^+$).

Synthesis of 3-(4-methyl-imidazol-1-yl)-N-[3-(2-oxo-2,3-dihydro-1H-indol-6-ylamino)-phenyl]-5-trifluoromethyl-benzamide (33)

To a solution of 6-(3-amino-phenoxy)-1,3-dihydro-indol-2-one (200 mg, 0.83 mmol) and 3-(4-methyl-piperazin-1-yl)-5-trifluoromethyl-benzoic acid hydrochloride (291 mg, 0.89 mmol) in DMF (10 mL) is added N,N-diisopropylethylamine (164 μL, 1 mmol) followed by addition of HATU (380 mg, 1 mmol). The mixture is stirred at ambient temperature overnight. The mixture is diluted with EtOAc and washed with 10% aq $Na_2S_2O_3$ solution and brine. The organic layer is separated, dried over $MgSO_4$, and concentrated. The crude (310 mg) was used in the next step without further purification. LC/MS: 511.2 ($MH^+$).

Synthesis of 3-(4-Methyl-piperazin-1-yl)-N-{3-[2-oxo-3-(1H-pyrrol-2-ylmethylene)-2,3-dihydro-1H-indol-6-yloxy]-phenyl}-5-trifluoromethyl-benzamide (34)

To a suspension of 3-(4-methyl-imidazol-1-yl)-N-[3-(2-oxo-2,3-dihydro-1H-indol-6-ylamino)-phenyl]-5-trifluoromethyl-benzamide (306 mg, crude, 0.6 mmol) in EtOH (20 mL) are added pyrrole-2-carboxaldehyde (69 mg, 0.72 mmol) and piperidine (120 μL, 1.2 mmol). The mixture is heated at 80° C. for 2 hours. All the solvent is evaporated to dryness. The crude is purified by prep-LC/MS to give 200 mg of the desired product in TFA salt form. The TFA salt is then converted to HCl salt. $^1$H NMR (400 MHz, DMSO) δ 10.90 (s, 1 H), 10.38 (s, 1 H), 7.72-7.70 (m, 1 H), 7.66-7.64 (m, 2 H), 7.59-7.57 (m, 2 H); 7.52-7.51 (m, 1 H), 7.41-7.33 (m, 3 H), 6.82-6.81 (m, 2 H), 6.71 (dd, 1 H), 6.51 (d, 1 H), 6.36-6.34 (m, 1 H), 3.33-3.30 (m, 4 H), 2.48-2.44 (m, 4 H), 2.28 (s, 3 H). LC/MS: 588.2 ($MH^+$).

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (DMSO-$d_6$) and/or MS(m/z) |
|---|---|---|
| 11 | (structure) | $^1$H NMR (DMSO-$d_6$) δ 1.86-1.92 (m, 2H), 2.00-2.08 (m, 2H), 2.44 (s, 3H), 2.48 (s, 3H), 3.04-3.12 (m, 2H), 3.33 (q, 2H, J = 6.6 Hz), 3.56 (q, 2H, J = 6.6 Hz), 3.64-3.69 (m, 2H), 7.38 (6, 1H, J = 7.8 Hz), 7.53 (t, 2H, J = 7.8 Hz), 7.57 (s, 1H), 7.58-7.60 (m, 2H), 7.72 (t, 1H, J = 5.4 Hz), 7.74 (d, 1H, J = 8.4 Hz), 7.95 (d, 2H, J = 7.8 Hz), 9.62 (s, 1H), 10.27 (s, 1H), 10.96 (s, 1H), 13.60 (s, 1H); m/z [$M^+$ + 1] 498.2. |

TABLE 1-continued

| Compound Number | Structure | Physical Data $^1$H NMR 400 MHz (DMSO-$d_6$) and/or MS(m/z) |
|---|---|---|
| 12 | 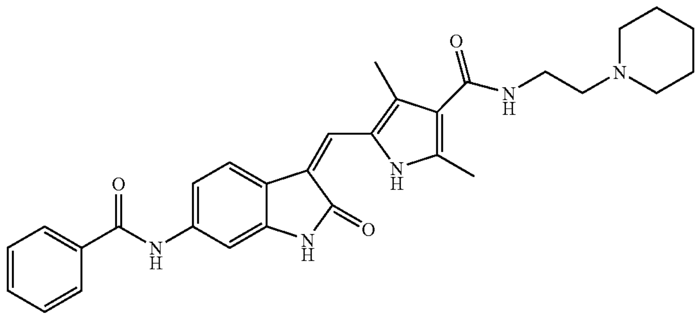 | $^1$H NMR (DMSO-$d_6$) δ 1.38-1.44 (m, 1H), 1.62-1.72 (m, 3H), 1.82-1.88 (m, 2H), 2.43 (s, 3H), 2.47 (s, 3H), 2.92-3.00 (m, 2H), 3.20-3.24 (m, 2H), 3.52-3.58 (m, 2H), 3.59 (q, 2H, J = 6.6 Hz), 7.38 (d, 1H, J = 9.0 Hz), 7.53 (t, 2H, J = 6.6 Hz), 7.56 (s, 1H), 7.58-7.60 (m, 2H), 7.74 (d, 1H, J = 9.0 Hz), 7.76 (t, 1H, J = 5.4 Hz), 7.96 (d, 2H, J = 6.6 Hz), 9.26 (s, 1H), 10.27 (s, 1H), 10.96 (s, 1H), 13.59 (s, 1H); m/z [M$^+$ + 1] 512.2. |
| 13 | 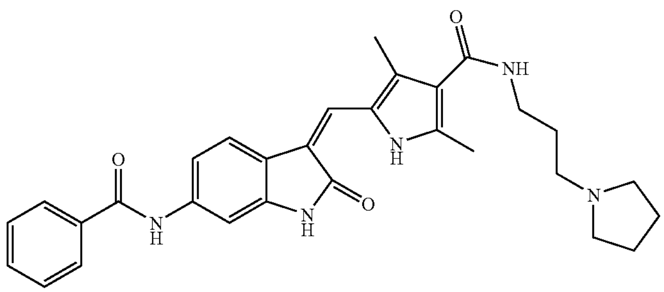 | $^1$H NMR (DMSO-$d_6$) δ 1.84-1.92 (m, 4H), 1.98-2.04 (m, 2H), 2.41 (s, 3H), 2.45 (s, 3H), 2.98-3.04 (m, 2H), 3.16-3.20 (m, 2H), 3.31 (q, 2H, J = 5.4 Hz), 3.56-3.60 (m, 2H), 7.38 (d, 1H, J = 7.8 Hz), 7.53 (t, 2H, J = 7.2 Hz), 7.56 (s, 1H), 7.59 (d, 1H, J = 7.8 Hz), 7.60 (s, 1H), 7.71-7.75 (m, 2H), 7.95 (d, 2H, J = 7.8 Hz), 9.61 (s, 1H), 10.27 (s, 1H), 10.95 (s, 1H), 13.56 (s, 1H); m/z [M$^+$ + 1] 512.2. |
| 14 | 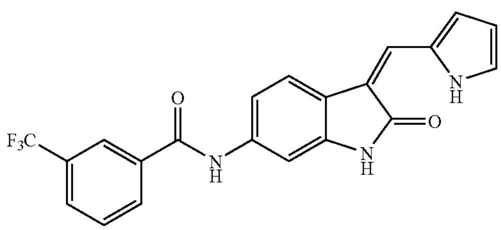 | $^1$H NMR (DMSO-$d_6$) δ 6.34 (q, 1H, J = 1.6 Hz), 6.80 (s, 1H), 7.34 (s, 1H), 7.37 (dd, 1H, J$_1$ = 8.0 Hz, J$_2$ = 1.6 Hz), 7.59 (d, 1H, J = 1.6 Hz), 7.61 (d, 1H, J = 8.4 Hz), 7.66 (s, 1H), 7.79 (t, 1H, J = 8.0 Hz), 7.97 (d, 1H, J = 8.0 Hz), 8.26 (d, 1H, J = 8.4 Hz), 8.29 (s, 1H), 10.50 (s, 1H), 10.98 (s, 1H), 13.26 (s, 1H); m/z [M$^+$ + 1] 398.0. |
| 15 | 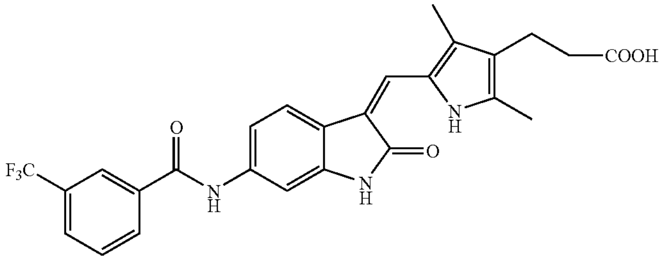 | $^1$H NMR (DMSO-$d_6$) δ 2.24 (s, 3H), 2.29 (s, 3H), 2.61 (t, 2H, J = 8.0 Hz), 2.76-2.82 (m, 2H), 7.33 (dd, 1H, J$_1$ = 8.0 Hz, J$_2$ = 1.2 Hz), 7.49 (s, 1H), 7.57 (d, 1H, J = 1.2 Hz), 7.69 (d, 1H, J = 8.0 Hz), 7.78 (t, 1H, J = 8.0 Hz), 7.96 (d, 1H, J = 8.0 Hz), 8.27 (d, 1H, J = 8.4 Hz), 8.30 (s, 1H), 10.47 (s, 1H), 10.84 (s, 1H), 13.27 (s, 1H); m/z [M$^+$ + 1] 498.1. |
| 16 | 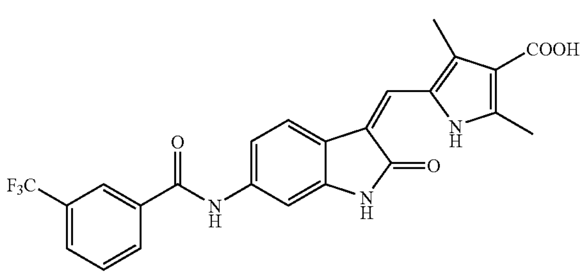 | $^1$H NMR (DMSO-$d_6$) δ 2.49 (s, 3H), 2.53 (s, 3H), 7.37 (dd, 1H, J$_1$ = 8.0 Hz, J$_2$ = 1.2 Hz), 7.60 (s, 2H), 7.78 (d, 1H, J = 8.0 Hz), 7.79 (t, 1H, J = 7.2 Hz), 7.97 (d, 1H, J = 8.0 Hz), 8.26 (d, 1H, J = 8.0 Hz), 8.29 (s, 1H), 10.51 (s, 1H), 11.03 (s, 1H), 13.72 (s, 1H); m/z [M$^+$ + 1] 470.0. |

TABLE 1-continued

| Compound Number | Structure | Physical Data ¹H NMR 400 MHz (DMSO-$d_6$) and/or MS(m/z) |
|---|---|---|
| 17 | 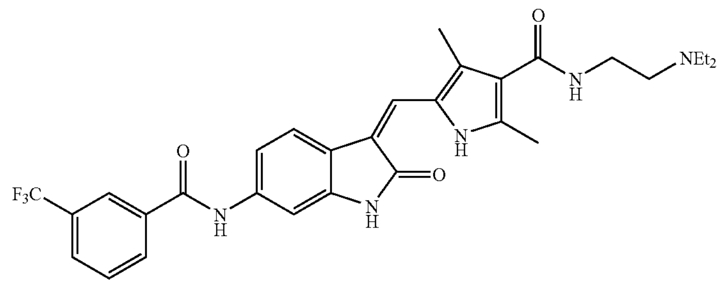 | ¹H NMR (DMSO-$d_6$) δ 1.23 (t, 6H, J = 7.2 Hz), 2.43 (s, 3H), 2.47 (s, 3H), 3.18-3.28 (m, 6H), 3.57 (q, 2H, J = 5.6 Hz), 7.37 (d, 1H, J = 7.2 Hz), 7.58-7.60 (m, 2H), 7.76-7.81 (m, 3H), 7.97 (d, 1H, J = 7.2 Hz), 8.27 (d, 1H, J = 8.0 Hz), 8.29 (s, 1H), 9.32 (s, 1H), 10.52 (s, 1H), 11.02 (s, 1H), 13.61 (s, 1H); m/z [M⁺ + 1] 568.2. |
| 18 | 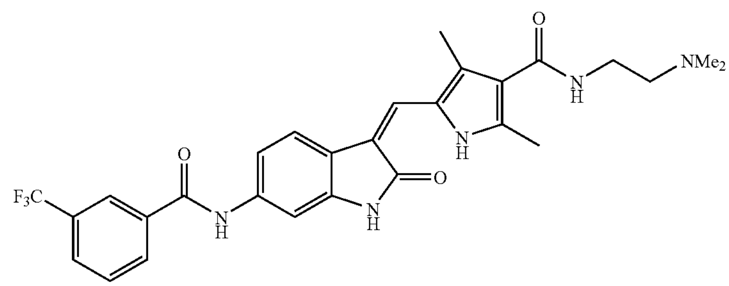 | ¹H NMR (DMSO-$d_6$) δ 2.44 (s, 3H), 2.47 (s, 3H), 2.87 (d, 6H, J = 3.2 Hz), 3.22-3.28 (m, 2H), 3.22 (q, 2H, J = 6.0 Hz), 3.57 (q, 2H, J = 6.0 Hz), 7.37 (dd, 1H, J₁ = 8.0 Hz, J₂ = 2.0 Hz), 7.58-7.61 (m, 2H), 7.73-7.81 (m, 3H), 7.97 (d, 1H, J = 8.0 Hz), 8.27 (d, 1H, J = 8.0 Hz), 8.29 (s, 1H), 9.50 (s, 1H), 10.52 (s, 1H), 11.02 (s, 1H), 13.60 (s, 1H); m/z [M⁺ + 1] 540.1. |
| 19 | 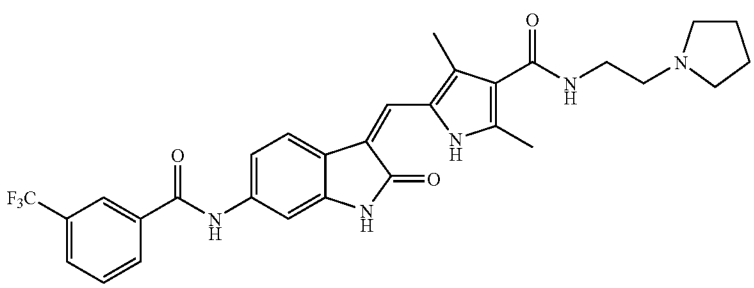 | ¹H NMR (DMSO-$d_6$) δ 1.82-1.92 (m, 2H), 1.98-2.08 (m, 2H), 2.44 (s, 3H), 2.47 (s, 3H), 3.00-3.12 (m, 2H), 3.32 (q, 2H, J = 5.6 Hz), 3.56 (q, 2H, J = 6.0 Hz), 3.60-3.72 (m, 2H), 7.38 (d, 1H, J = 8.0 Hz), 7.58-7.60 (m, 2H), 7.73-7.81 (m, 3H), 7.97 (d, 1H, J = 7.2 Hz), 8.27 (d, 1H, J = 8.0 Hz), 8.29 (s, 1H), 9.66 (s, 1H), 10.52 (s, 1H), 11.01 (s, 1H), 13.60 (s, 1H); m/z [M⁺ + 1] 566.2. |
| 20 | 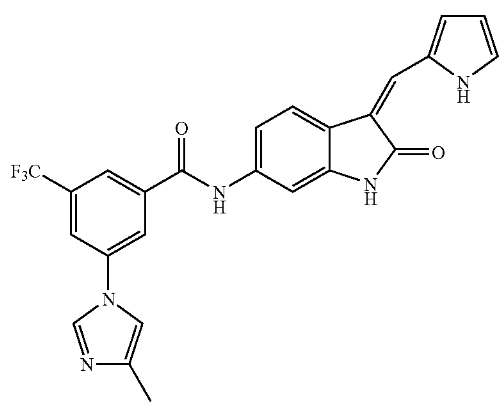 | ¹H NMR (DMSO-$d_6$) δ 2.20 (s, 3H), 6.35 (q, 1H, J = 1.8 Hz), 6.81 (d, 1H, J = 1.8 Hz), 7.34 (d, 1H, J = 1.8 Hz), 7.37 (d, 1H, J = 7.8 Hz), 7.58 (s, 1H), 7.63 (d, 1H, J = 7.8 Hz), 7.67 (s, 1H), 7.72 (s, 1H), 8.17 (s, 1H), 8.24 (s, 1H), 8.40 (s, 1H), 8.45 (s, 1H), 10.54 (s, 1H), 10.98 (s, 1H), 13.25 (s, 1H); m/z [M⁺ + 1] 478.1. |

TABLE 1-continued

| Compound Number | Structure | Physical Data<br>¹H NMR 400 MHz (DMSO-$d_6$) and/or MS(m/z) |
|---|---|---|
| 21 | 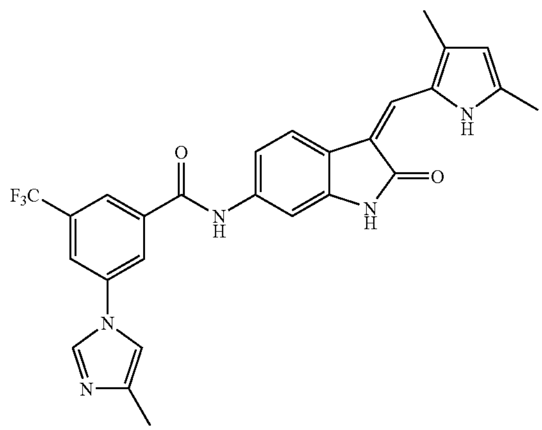 | ¹H NMR (DMSO-$d_6$) δ 2.20 (s, 3H), 2.32 (s, 3H), 2.34 (s, 3H), 6.0 (s, 1H), 7.33 (dd, 1H, $J_1$ = 8.0 Hz, $J_2$ = 1.6 Hz), 7.51 (s, 1H), 7.58 (d, 1H, J = 1.6 Hz), 7.72 (d, 1H, J = 8.0 Hz), 8.11 (s, 1H), 8.40 (s, 2H), 8.58 (s, 1H), 9.45 (s, 1H), 10.60 (s, 1H), 10.91 (s, 1H), 13.25 (s, 1H); m/z [M⁺ + 1] 506.1. |
| 22 | 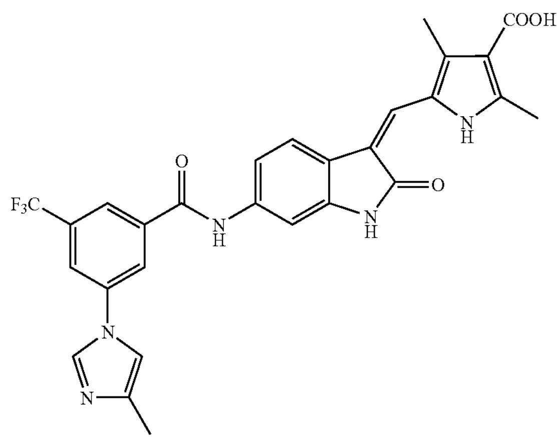 | ¹H NMR (DMSO-$d_6$) δ 2.20 (s, 3H), 2.49 (s, 3H), 2.54 (s, 3H), 7.35 (d, 1H, J = 7.2 Hz), 7.60 (s, 1H), 7.61 (s, 1H), 7.71 (s, 1H), 7.79 (d, 1H, J = 7.2 Hz), 8.17 (s, 1H), 8.23 (s, 1H), 8.40 (s, 1H), 8.45 (s, 1H), 10.51 (s, 1H), 11.03 (s, 1H), 12.0 (bs, 1H), 13.72 (s, 1H); m/z [M⁺ + 1] 550.1. |
| 23 | 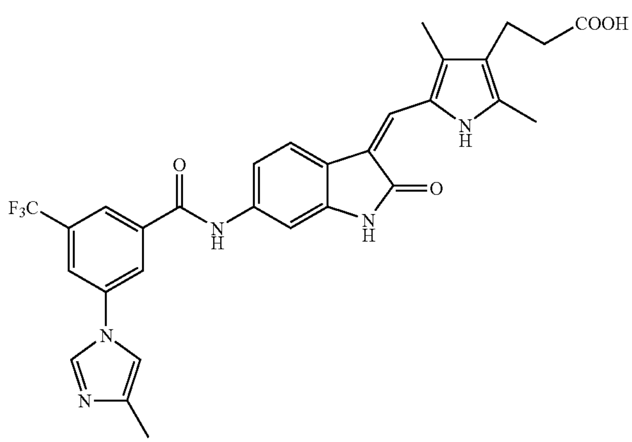 | ¹H NMR (DMSO-$d_6$) δ 2.20 (s, 3H), 2.26 (s, 3H), 2.65 (s, 3H), 7.33 (d, 1H, J = 7.8 Hz), 7.51 (s, 1H), 7.57 (s, 1H), 7.70-7.72 (m, 2H), 8.17 (s, 1H), 8.23 (s, 1H), 8.40 (s, 1H), 8.45 (s, 1H), 10.47 (s, 1H), 10.84 (s, 1H), 12.1 (bs, 1H), 13.29 (s, 1H); m/z [M⁺ + 1] 578.1. |

TABLE 1-continued

| Compound Number | Structure | Physical Data<br>$^1$H NMR 400 MHz<br>(DMSO-$d_6$) and/or<br>MS(m/z) |
|---|---|---|
| 24 | 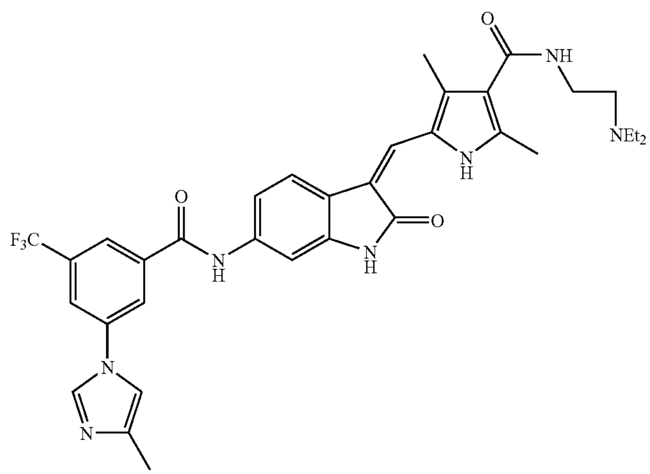 | $^1$H NMR (DMSO-$d_6$) δ 1.23 (t, 6H, J = 7.6 Hz), 2.32 (s, 3H), 2.43 (s, 3H), 2.47 (s, 3H), 3.20-3.28 (m, 6H), 3.54-3.62 (m, 2H), 7.37 (d, 1H, J = 7.2 Hz), 7.61 (s, 1H), 7.78-7.82 (m, 2H), 8.06 (s, 1H), 8.38 (s, 1H), 8.39 (s, 1H), 8.56 (s, 1H), 9.27 (s, 2H), 9.33 (s, 1H), 10.63 (s, 1H), 11.05 (s, 1H), 13.60 (s, 1H); m/z [M$^+$ + 1] 648.2. |
| 25 | 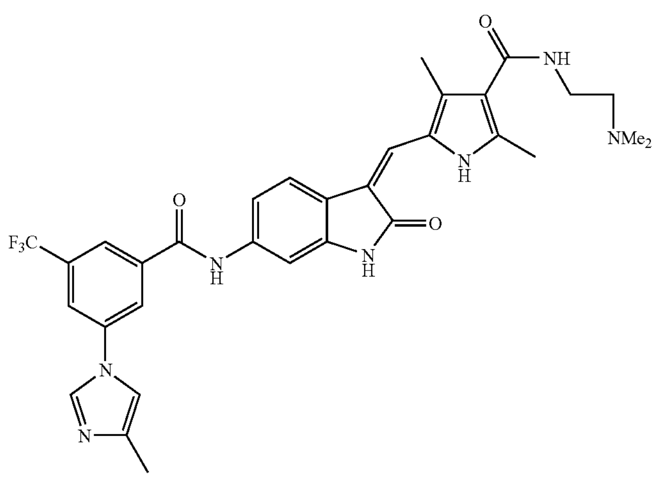 | $^1$H NMR (DMSO-$d_6$) δ 2.34 (s, 3H), 2.44 (s, 3H), 2.47 (s, 3H), 2.87 (s, 6H), 3.26 (t, 2H, J = 6.4 Hz), 3.57 (q, 2H, J = 6.4 Hz), 7.36 (dd, 1H, J$_1$ = 8.0 Hz, J = 1.6 Hz), 7.59-7.61 (m, 2H), 7.77 (t, 1H, J = 5.2 Hz), 7.80 (d, 1H, J = 8.0 Hz), 8.10 (s, 1H), 8.39 (s, 1H), 8.41 (s, 1H), 8.58 (s, 1H), 9.43 (s, 1H), 9.60 (s, 1H), 10.66 (s, 1H), 11.05 (s, 1H), 13.60 (s, 1H); m/z [M$^+$ + 1] 620.2. |
| 26 | 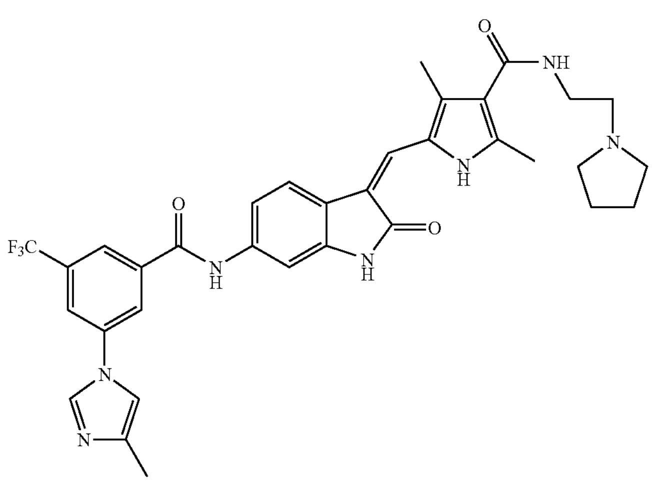 | $^1$H NMR (DMSO-$d_6$) δ 1.82-1.92 (m, 2H), 2.00-2.08 (m, 2H), 2.33 (s, 3H), 2.44 (s, 3H), 2.48 (s, 3H), 3.04-3.12 (m, 4H), 3.32 (t, 2H, J = 6.0 Hz), 3.56 (q, 2H, J = 6.0 Hz), 7.36 (d, 1H, J = 8.0 Hz), 7.59 (s, 1H), 7.60 (s, 1H), 7.76 (t, 1H, J = 6.0 Hz), 7.82 (d, 1H, J = 8.0 Hz), 8.09 (s, 1H), 8.39 (s, 1H), 8.40 (s, 1H), 8.57 (s, 1H), 9.40 (s, 1H), 9.72 (s, 1H), 10.65 (s, 1H), 11.05 (s, 1H), 13.60 (s, 1H); m/z [M$^+$ + 1] 646.2. |

TABLE 1-continued

| Compound Number | Structure | Physical Data<br>¹H NMR 400 MHz<br>(DMSO-d₆) and/or<br>MS(m/z) |
|---|---|---|
| 27 | 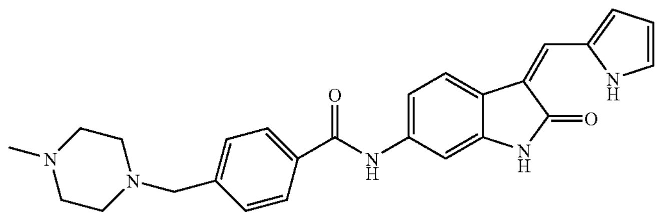 | ¹H NMR (DMSO-d₆) δ 2.79 (s, 3H), 2.48-2.52 (m, 2H), 2.98-3.12 (m, 4H), 3.36-3.44 (m, 2H), 3.78 (s, 2H), 6.35 (s, 1H), 6.80 (s, 1H), 7.33 (s, 1H), 7.36 (d, 1H, J = 8.4 Hz), 7.50 (d, 2H, J = 8.4 Hz), 87.57-7.61 (m, 2H), 7.64 (s, 1H), 7.96 (d, 2H, J = 8.4 Hz), 10.28 (s, 1H), 10.95 (s, 1H), 13.25 (s, 1H); m/z [M⁺ + 1] 442.1. |
| 28 | 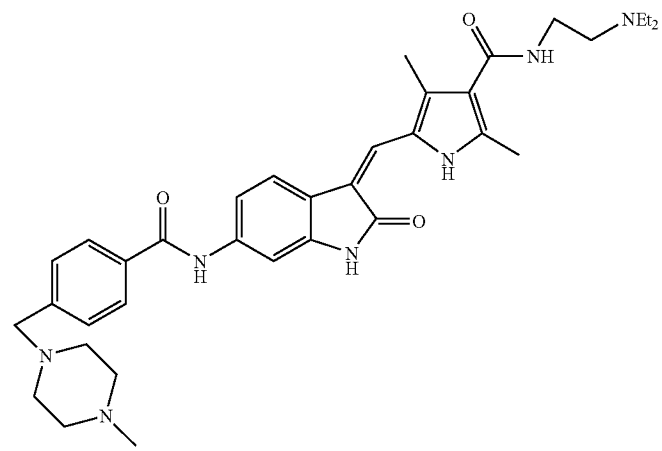 | ¹H NMR (DMSO-d₆) δ 1.23 (t, 6H, J = 6.6 Hz), 2.43 (s, 3H), 2.47 (s, 3H), 2.79 (s, 3H), 2.93-3.12 (m, 4H), 3.20-3.27 (m, 6H), 3.36-3.44 (m, 2H), 3.57 (q, 2H, J = 6.6 Hz), 3.64-3.68 (m, 2H), 3.73 (s, 2H), 7.37 (d, 1H, J = 8.4 Hz), 7.49 (d, 2H, J = 8.4 Hz), 7.57 (s, 1H), 7.60 (s, 1H), 7.73-7.76 (m, 2H), 7.96 (d, 2H, J = 8.4 Hz), 9.36 (s, 1H), 10.27 (s, 1H), 10.99 (s, 1H), 13.60 (s, 1H); m/z [M⁺ + 1] 612.3. |
| 29 | 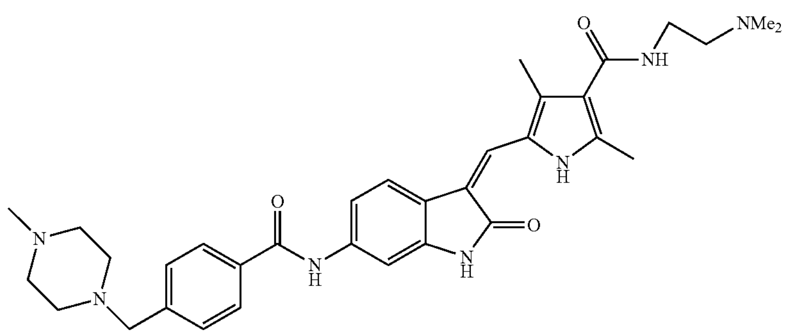 | ¹H NMR (DMSO-d₆) δ 2.43 (s, 3H), 2.47 (s, 3H), 2.79 (s, 3H), 2.87 (d, 6H, J = 3.6 Hz), 2.96-3.10 (m, 4H), 3.24-3.28 (m, 2H), 3.26-3.46 (m, 2H), 3.57 (q, 2H, J = 5.4 Hz), 3.64-3.68 (m, 2H), 3.75 (s, 2H), 7.37 (d, 1H, J = 9.0 Hz), 7.49 (d, 2H, J = 9.0 Hz), 7.57 (s, 1H), 7.60 (s, 1H), 7.73-7.76 (m, 2H), 7.96 (d, 2H, J = 7.8 Hz), 9.56 (s, 1H), 10.27 (s, 1H), 10.98 (s, 1H), 13.60 (s, 1H); m/z [M⁺ + 1] 584.3. |
| 30 | 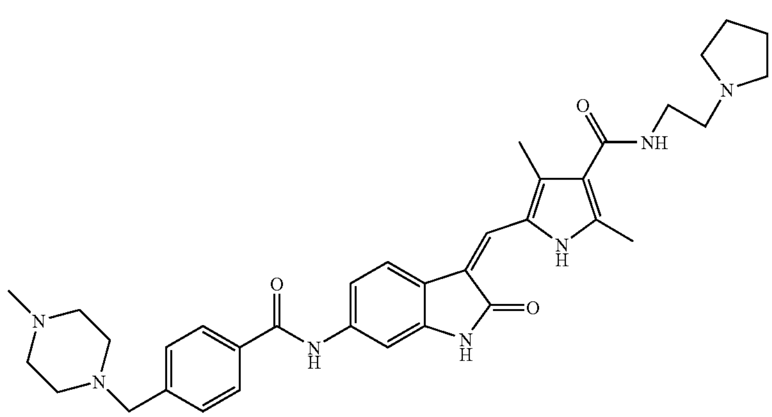 | ¹H NMR (DMSO-d₆) δ 1.84-1.92 (m, 2H), 2.00-2.07 (m, 2H), 2.43 (s, 3H), 2.47 (s, 3H), 2.79 (s, 3H), 2.94-3.04 (m, 2H), 3.04-3.12 (m, 4H), 3.32 (q, 2H, J = 6.6 Hz), 3.36-3.46 (m, 2H), 3.56 (q, 2H, J = 6.6 Hz), 3.64-3.70 (m, 4H), 3.74 (s, 2H), 7.37 (d, 1H, J = 7.8 Hz), 7.49 (d, 2H, J = 9.0 Hz), 7.56 (s, 1H), 7.60 (s, 1H), 7.72-7.76 (m, 2H), 7.96 (d, 2H, J = 9.0 Hz), 9.69 (s, 1H), 10.27 (s, 1H), 10.98 (s, 1H), 13.60 (s, 1H); m/z [M⁺ + 1] 610.3. |

TABLE 1-continued

| Compound Number | Structure | Physical Data ¹H NMR 400 MHz (DMSO-d$_6$) and/or MS(m/z) |
|---|---|---|
| 31 | 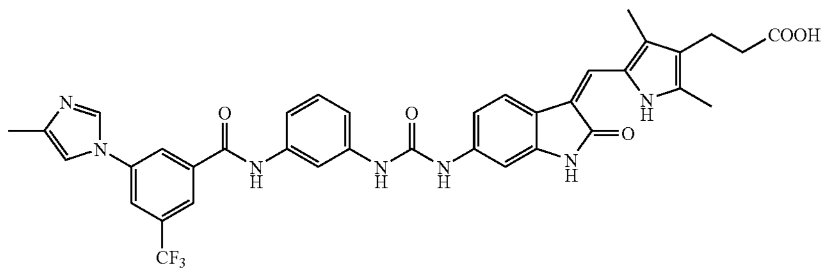 | ¹H NMR (DMSO-d$_6$) 2.24 (s, 3H), 2.28 (s, 3H), 2.34 (s, 3H), 2.64 (t, 2H, J = 7.2 Hz), 2.99 (t, 2H, J = 7.2 Hz), 6.91 (dd, 1H, J$_1$ = 8.0 Hz, J$_2$ = 1.6 Hz), 7.20 (s, 1H), 7.30 (s, 1H), 7.31 (s, 1H), 7.41 (s, 1H), 7.44 (d, 1H, J = 8.0 Hz), 7.60-7.64 (m, 2H), 8.07 (s, 1H), 8.11 (s, 1H), 8.40 (s, 1H), 8.41 (s, 1H), 8.57 (s, 1H), 8.89 (s, 1H), 8.92 (s, 1H), 9.45 (s, 1H), 10.58 (s, 1H), 10.73 (s, 1H), 13.21 (s, 1H); m/z [M$^+$ + 1] 712.2. |
| 32 | 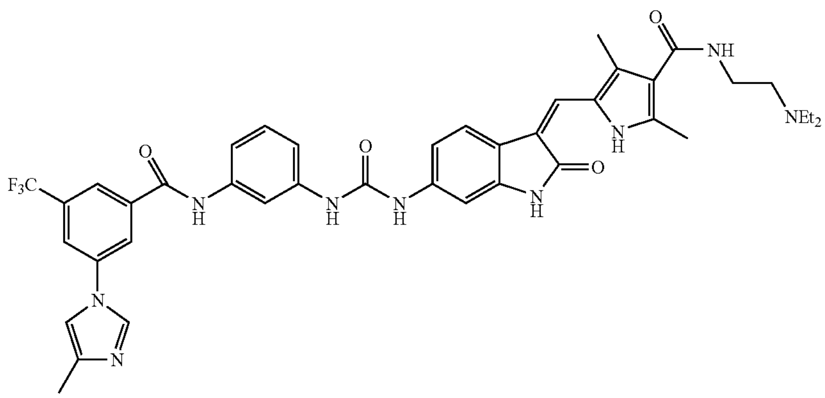 | ¹H NMR (DMSO-d$_6$) δ 1.24 (t, 6H, J = 7.8 Hz), 2.34 (s, 3H), 2.42 (s, 3H), 2.46 (s, 3H), 3.20-3.26 (m, 6H), 3.58 (q, 2H, J = 6.6 Hz), 6.98 (dd, 1H, J$_1$ = 7.8 Hz, J$_2$ = 1.8 Hz), 7.21 (d, 1H, J = 9.0 Hz), 7.29 (t, 1H, J = 7.8 Hz), 7.34 (d, 1H, J = 1.8 Hz), 7.44 (d, 1H, J = 7.8 Hz), 7.49 (s, 1H), 7.66 (d, 1H, J = 7.8 Hz), 7.75 (t, 1H, J = 6.0 Hz), 8.07 (s, 1H), 8.10 (s, 1H), 8.40 (s, 2H), 8.59 (s, 1H), 9.14 (s, 1H), 9.16 (s, 1H), 9.39 (s, 1H), 9.44 (s, 1H), 10.60 (s, 1H), 10.90 (s, 1H), 13.55 (s, 1H); m/z [M$^+$ + 1] 782.3. |
| 33 | 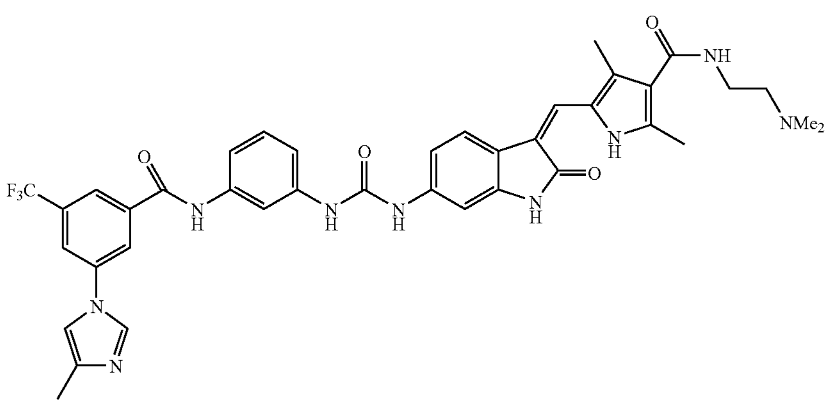 | ¹H NMR (DMSO-d$_6$) δ 2.33 (s, 3H), 2.42 (s, 3H), 2.47 (s, 3H), 2.87 (s, 6H), 3.26 (t, 2H, J = 5.4 Hz), 3.58 (q, 2H, J = 5.4 Hz), 6.98 (d, 1H, J = 9.0 Hz), 7.21 (d, 1H, J = 8.4 Hz), 7.29 (t, 1H, J = 7.2 Hz), 7.34 (s, 1H), 7.43 (d, 1H, J = 8.4 Hz), 7.49 (s, 1H), 7.66 (d, 1H, J = 9.0 Hz), 7.71 (t, 1H, J = 7.2 Hz), 8.06 (s, 1H), 8.08 (s, 1H), 8.39 (s, 2H), 8.58 (s, 1H), 9.12 (s, 1H), 9.14 (s, 1H), 9.38 (s, 1H), 9.56 (s, 1H), 10.59 (s, 1H), 10.90 (s, 1H), 13.55 (s, 1H); m/z [M$^+$ + 1] 754.2. |
| 34 | 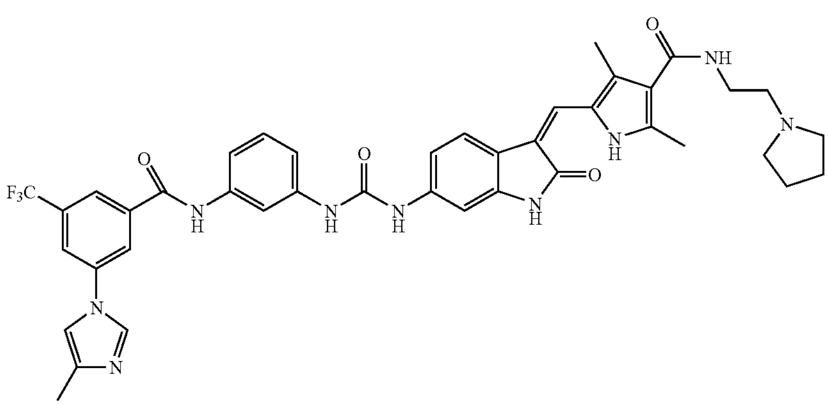 | ¹H NMR (DMSO-d$_6$) δ 1.84-1.90 (m, 2H), 2.00-2.06 (m, 2H), 2.34 (s, 3H), 2.42 (s, 3H), 2.47 (s, 3H), 3.04-3.12 (m, 2H), 3.33-3.35 (m, 2H), 3.57 (q, 2H, J = 5.4 Hz), 3.64-3.68 (m, 2H), 6.99 (d, 1H, J = 6.6 Hz), 7.21 (d, 1H, J = 7.8 Hz), 7.29 (t, 1H, J = 9.0 Hz), 7.34 (s, 1H), 7.44 (d, 1H, J = 7.8 Hz), 7.49 (s, 1H), 7.66 (d, 1H, J = 9.0 Hz), 7.71 (t, 1H, J = 6.6 Hz), 8.06 (s, 1H), 8.09 (s, 1H), 8.40 (s, 2H), 8.58 (s, 1H), 9.13 (s, 1H), 9.15 (s, 1H), 9.41 (s, 1H), 9.71 (s, 1H), 10.59 (s, 1H), 10.90 (s, 1H), 13.55 (s, 1H); m/z [M$^+$ + 1] 780.3. |

TABLE 1-continued

| Compound Number | Structure | Physical Data ¹H NMR 400 MHz (DMSO-$d_6$) and/or MS(m/z) |
|---|---|---|
| 35 | 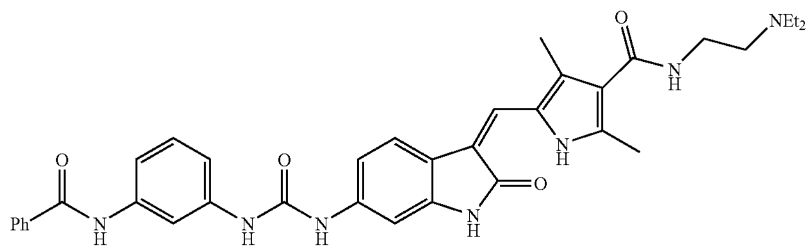 | ¹H NMR (DMSO-$d_6$) δ 1.24 (q, 6H, J = 5.4 Hz), 2.42 (s, 3H), 2.64 (s, 3H), 3.20-3.28 (m, 6H), 3.58 (q, 2H, J = 5.4 Hz), 6.95 (d, 1H, J = 7.8 Hz), 7.24 (d, 2H, J = 4.2 Hz), 7.34 (s, 1H), 7.38 (t, 1H, J = 4.2 Hz), 7.49 (s, 1H), 7.53 (t, 2H, J = 5.4 Hz), 7.59 (t, 1H, J = 5.4 Hz), 7.66 (d, 1H, J = 7.8 Hz), 7.74 (t, 1H, J = 5.4 Hz), 7.96 (d, 2H, J = 7.8 Hz), 8.01 (s, 1H), 8.92 (s, 1H), 8.95 (s, 1H), 9.33 (s, 1H), 10.24 (s, 1H), 10.89 (s, 1H), 13.56 (s, 1H); m/z [M⁺ + 1] 634.2. |
| 36 | 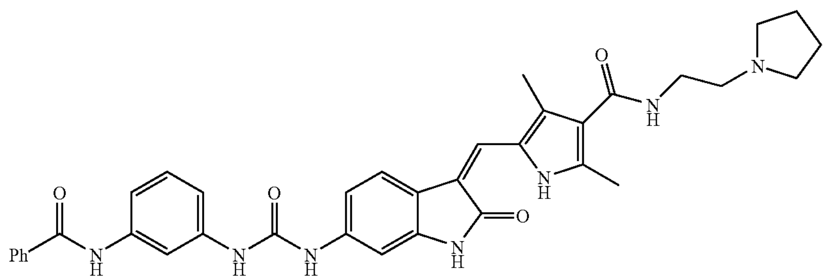 | ¹H NMR (DMSO-$d_6$) δ 1.84-1.90 (m, 2H), 2.00-2.06 (m, 2H), 2.42 (s, 3H), 2.47 (s, 3H), 3.04-3.10 (m, 2H), 3.32-3.36 (m, 2H), 3.56 (q, 2H, J = 5.4 Hz), 3.62-3.68 (m, 2H), 6.96 (d, 1H, J = 7.8 Hz), 7.24 (d, 2H, J = 4.8 Hz), 7.34 (s, 1H), 7.38 (t, 1H, J = 4.8 Hz), 7.49 (s, 1H), 7.53 (t, 2H, J = 6.6 Hz), 7.59 (t, 1H, J = 7.8 Hz), 7.66 (d, 1H, J = 4.8 Hz), 7.70 (t, 1H, J = 5.4 Hz), 7.96 (d, 2H, J = 7.8 Hz), 8.01 (s, 1H), 8.93 (s, 1H), 8.96 (s, 1H), 9.65 (s, 1H), 10.24 (s, 1H), 10.89 (s, 1H), 13.55 (s, 1H); m/z [M⁺ + 1] 632.2. |
| 37 | 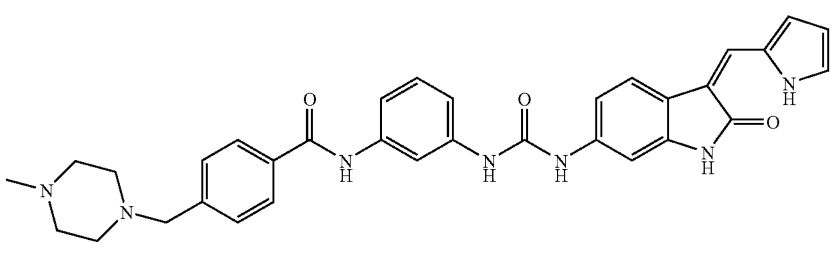 | ¹H NMR (DMSO-$d_6$) δ 2.80 (s, 3H), 2.98-3.04 (m, 4H), 3.02-3.12 (m, 2H), 3.36-3.46 (m, 2H), 3.79 (s, 2H), 6.33 (s, 1H), 6.76 (s, 1H), 6.90 (d, 1H, J = 8.4 Hz), 7.21 (t, 1H, J = 7.2 Hz), 7.24 (t, 1H, J = 6.6 Hz), 7.30 (s, 1H), 7.36-7.41 (m, 2H), 7.49-7.52 (m, 3H), 7.57 (s, 1H), 7.98 (d, 2H, J = 8.4 Hz), 8.02 (s, 1H), 8.35 (bs, 1H), 8.92 (s, 1H), 8.94 (s, 1H), 10.24 (s, 1H), 10.87 (s, 1H), 13.21 (s, 1H); m/z [M⁺ + 1] 576.2. |
| 38 | 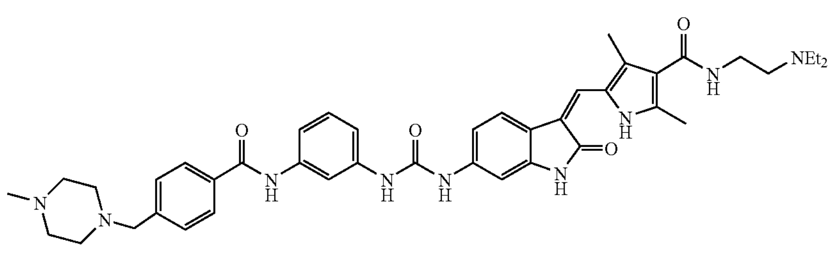 | ¹H NMR (DMSO-$d_6$) δ 1.23 (t, 6H, J = 7.2 Hz), 2.42 (s, 3H), 2.46 (s, 3H), 2.79 (s, 3H), 2.98-3.16 (m, 4H), 3.20-3.26 (m, 6H), 3.37-3.46 (m, 2H), 3.57 (q, 2H, J = 6.0 Hz), 3.62-3.70 (m, 2H), 3.76 (s, 2H), 6.96 (d, 1H, J = 8.4 Hz), 7.21-7.25 (m, 2H), 7.34 (s, 1H), 7.39 (d, 1H, J = 7.2 Hz), 7.49 (d, 2H, J = 8.4 Hz), 7.49 (s, 1H), 7.66 (d, 1H, J = 8.4 Hz), 7.76 (t, 1H, J = 6.0 Hz), 7.97 (d, 2H, J = 8.4 Hz), 8.01 (s, 1H), 9.03 (s, 1H), 9.08 (s, 1H), 9.39 (s, 1H), 10.24 (s, 1H), 10.91 (s, 1H), 13.56 (s, 1H); m/z [M⁺ + 1] 746.3. |

TABLE 1-continued

| Compound Number | Structure | Physical Data $^1$H NMR 400 MHz (DMSO-$d_6$) and/or MS(m/z) |
|---|---|---|
| 39 | 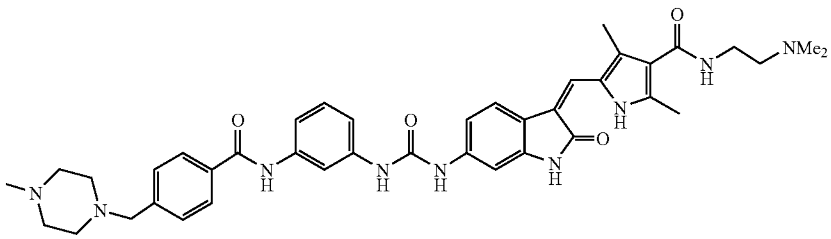 | $^1$H NMR (DMSO-$d_6$) δ 2.42 (s, 3H), 2.46 (s, 3H), 2.79 (s, 3H), 2.86 (d, 6H, J = 3.6 Hz), 2.96-3.02 (m, 2H), 3.00-3.10 (m, 2H), 3.24-3.28 (m, 2H), 3.36-3.46 (m, 2H), 3.57 (q, 2H, J = 6.0 Hz), 3.64-3.68 (m, 2H), 3.74 (s, 2H), 6.97 (d, 1H, J = 8.4 Hz), 7.21-7.25 (m, 2H), 7.34 (s, 1H), 7.39 (d, 1H, J = 7.2 Hz), 7.48 (d, 2H, J = 8.4 Hz), 7.49 (s, 1H), 7.66 (d, 1H, J = 8.4 Hz), 7.72 (t, 1H, J = 6.0 Hz), 7.97 (d, 2H, J = 8.4 Hz), 8.01 (s, 1H), 9.04 (s, 1H), 9.08 (s, 1H), 9.57 (s, 1H), 10.24 (s, 1H), 10.90 (s, 1H), 13.55 (s, 1H); m/z [M$^+$ + 1] 718.3. |
| 40 | 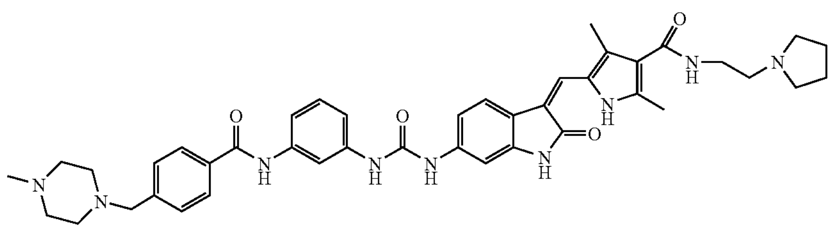 | $^1$H NMR (DMSO-$d_6$) δ 1.86-1.90 (m, 2H), 2.00-2.06 (m, 2H), 2.42 (s, 3H), 2.46 (s, 3H), 2.79 (s, 3H), 2.92-3.02 (m, 2H), 3.04-3.10 (m, 4H), 3.32 (q, 2H, J = 5.4 Hz), 3.36-3.44 (m, 2H), 3.56 (q, 2H, J = 5.4 Hz), 3.62-3.70 (m, 4H), 3.73 (s, 2H), 6.96 (d, 1H, J = 7.8 Hz), 7.21-7.25 (m, 2H), 7.34 (s, 1H), 7.39 (d, 1H, J = 7.2 Hz), 7.49 (d, 2H, J = 7.2 Hz), 7.50 (s, 1H), 7.66 (d, 1H, J = 8.4 Hz), 7.72 (t, 1H, J = 6.0 Hz), 7.97 (d, 2H, J = 8.4 Hz), 8.01 (s, 1H), 9.05 (s, 1H), 9.09 (s, 1N), 9.72 (s, 1H), 10.24 (s, 1H), 10.90 (s, 1H), 13.55 (s, 1H); m/z [M$^+$ + 1] 744.2. |
| 41 | 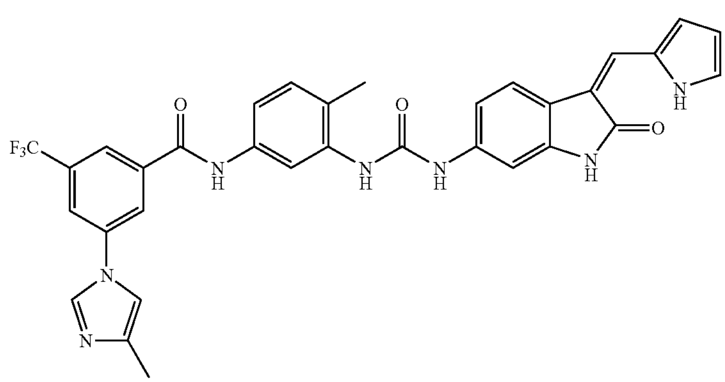 | $^1$H NMR (DMSO-$d_6$) δ 2.25 (s, 3H), 2.34 (s, 3H), 6.33 (s, 1H), 6.76 (s, 1H), 6.92 (d, 1H, J = 8.0 Hz), 7.19 (d, 1H, J = 8.0 Hz), 7.30 (s, 1H), 7.39 (t, 1H, J = 4.8 Hz), 7.48-7.55 (m, 2H), 7.56 (s, 1H), 8.06 (s, 1H), 8.10 (s, 1H), 8.30 (s, 1H), 8.39 (s, 1H), 8.42 (s, 1H), 8.59 (s, 1H), 9.29 (s, 1H), 9.44 (s, 1H), 10.54 (s, 1H), 10.89 (s, 1H), 13.21 (s, 1H); m/z [M$^+$ + 1] 626.2. |
| 42 | 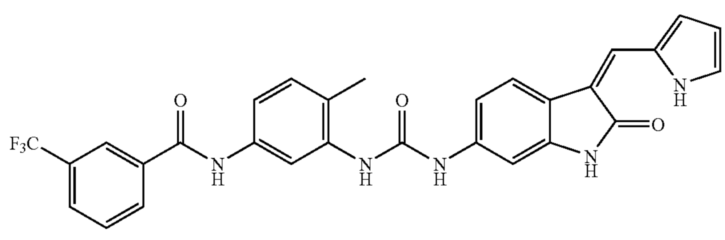 | $^1$H NMR (DMSO-$d_6$) δ 2.24 (s, 3H), 6.33 (s, 1H), 6.76 (s, 1H), 6.90 (d, 1H, J = 8.0 Hz), 7.16 (d, 2H, J = 8.8 Hz), 7.29 (s, 1H), 7.40 (s, 1H), 7.50 (d, 2N, J = 8.8 Hz), 7.52 (d, 1H, J = 8.8 Hz), 7.56 (s, 1H), 7.78 (t, 1H, J = 7.6 Hz), 7.95 (d, 1H, J = 7.6 Hz), 8.01 (s, 1H), 8.32 (s, 1H), 9.23 (s, 1H), 10.43 (s, 1H), 10.88 (s, 1H), 13.21 (s, 1H); m/z [M$^+$+1] 546.1. |

| Compound Number | Structure | Physical Data<br>$^1$H NMR 400 MHz (DMSO-d$_6$) and/or MS(m/z) |
|---|---|---|
| 43 | 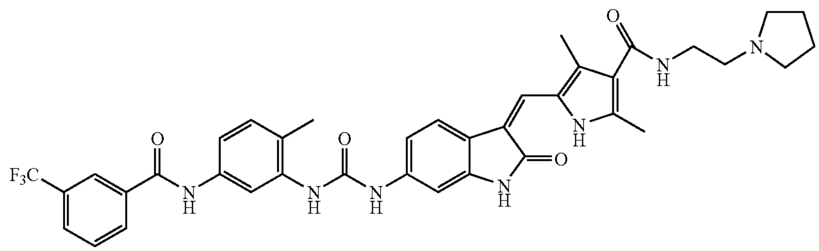 | $^1$H NMR (DMSO-d$_6$) δ 1.84-1.92 (m, 2H), 1.96-2.04 (m, 2H), 2.25(s, 3H), 2.42 (s, 3H), 2.47 (s, 3H), 3.00-3.08 (m, 2H), 3.40-3.44 (m, 2H), 3.57 (q, 2H, J = 6.0 Hz), 3.58-3.64 (m, 2H), 6.96 (d, 1H, J = 8.0 Hz), 7.14 (s, 1H), 7.15 (d, 1H, J = 8.0 Hz), 7.35 (s, 1H), 7.46 (d, 1H, J = 8.0 Hz), 7.49 (s, 1H), 7.67 (t, 1H, J = 7.2 Hz), 7.74-7.80 (m, 2H), 7.95 (d, 1H, J = 8.0 Hz), 8.13 (s, 1H), 8.29 (s, 1H), 8.31 (s, 1H), 9.47 (s, 1H), 10.01 (s, 1H), 10.42 (s, 1H), 10.89 (s, 1H), 13.53 (s, 1H); m/z [M[+] + 1] 714.2. |
| 44 | 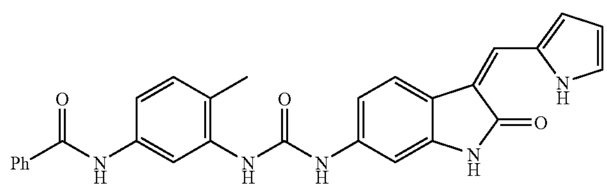 | $^1$H NMR (DMSO-d$_6$) δ 2.22 (s, 3H), 6.32 (s, 1H), 6.76 (s, 1H), 6.88 (d, 1H, J = 7.8 Hz), 7.14 (d, 1H, J = 8.4 Hz), 7.30 (s, 1H), 7.40 (s, 1H), 7.46 (d, 1H, J = 7.8 Hz), 7.51-7.54 (m, 3H), 7.56-7.58 (m, 2H), 7.96 (s, 1H), 7.97 (d, 2H, J = 8.4 Hz), 8.28 (s, 1H), 9.18 (s, 1H), 10.22 (s, 1H), 10.91 (s, 1H), 13.21 (s, 1H); m/z [M[+] + 1] 471.8. |
| 45 | 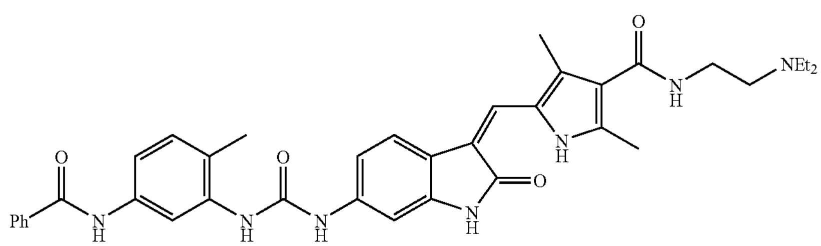 | $^1$H NMR (DMSO-d$_6$) δ 1.23 (t, 6H, J = 6.8 Hz), 2.22(s, 3H), 2.42 (s, 3H), 2.46 (s, 3H), 3.18-3.26 (m, 6H), 3.57 (q, 2H, J = 5.6 Hz), 6.95 (dd, 1H, J$_1$ = 8.4 Hz, J$_2$ = 1.6 Hz), 7.14 (d, 1H, J = 8.4 Hz), 7.36 (d, 1H, J = 1.6 Hz), 7.44 (dd, 1H, J$_1$ = 8.4 Hz, J$_2$ = 1.6 Hz), 7.50 (s, 1H), 7.53 (d, 2H, J = 8.0 Hz), 7.56-7.61 (m, 1H), 7.68 (d, 1H, J = 8.4 Hz), 7.75 (t, 1H, J = 5.6 Hz), 7.97 (d, 2H, 7.2 Hz), 8.01 (s, 1H), 8.28 (d, 1H, J = 1.6 Hz), 9.24 (s, 1H), 9.31 (s, 1H), 10.21 (s, 1H), 10.93 (s, 1H), 13.55 (s, 1H); m/z [M[+] + 1] 648.3. |
| 46 | 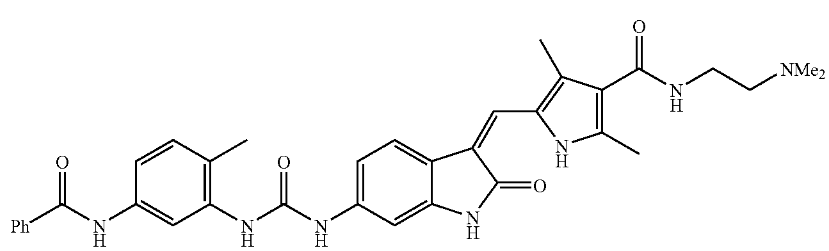 | $^1$H NMR (DMSO-d$_6$) δ 2.22 (s, 3H), 2.42 (s, 3H), 2.46 (s, 3H), 2.86 (s, 6H), 3.20-3.24 (m, 2H), 3.57 (q, 2H, J = 5.6 Hz), 6.95 (dd, 1H, J$_1$ = 8.4 Hz, J$_2$ = 2.0 Hz), 7.14 (d, 1H, J = 8.4 Hz), 7.35 (d, 1H, J = 2.0 Hz), 7.44 (dd, 1H, J$_1$ = 8.0 Hz, J$_2$ = 2.0 Hz), 7.50 (s, 1H), 7.53 (d, 2H, J = 7.2 Hz), 7.56-7.60 (m, 1H), 7.68 (d, 1H, J = 8.4 Hz), 7.71 (t, 1H, J = 5.6 Hz), 7.96 (s, 1H), 7.97 (d, 2H, J = 7.2 Hz), 8.28 (d, 1H, J = 2.0 Hz), 9.19 (s, 1H), 9.37 (s, 1H), 10.21 (s, 1H), 10.92 (s, 1H), 13.55 (s, 1H); m/z [M[+] + 1] 620.3. |

TABLE 1-continued

| Compound Number | Structure | Physical Data ¹H NMR 400 MHz (DMSO-$d_6$) and/or MS(m/z) |
|---|---|---|
| 47 | 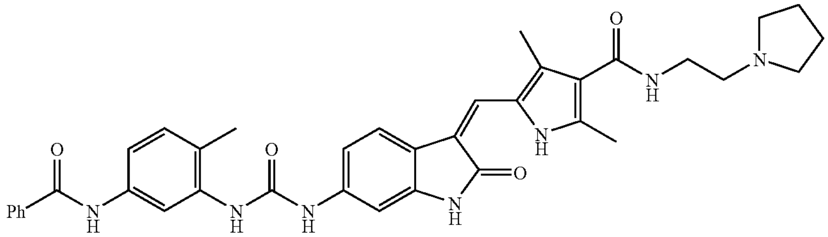 | ¹H NMR (DMSO-$d_6$) δ 1.80-1.86 (m, 2H), 1.96-2.08 (m, 2H), 2.22 (s, 3H), 2.42 (s, 3H), 2.46 (s, 3H), 3.00-3.12 (m, 2H), 3.32 (q, 2H, J = 5.6 Hz), 3.56 (q, 2H, J = 5.6 Hz), 3.60-3.68 (m, 2H), 6.95 (dd, 1H, $J_1$ = 8.8 Hz, $J_2$ = 1.6 Hz), 7.14 (d, 1H, J = 8.8 Hz), 7.35 (d, 1H, J = 1.6 Hz), 7.44 (dd, 1H, $J_1$ = 8.0 Hz, $J_2$ = 1.6 Hz), 7.50 (s, 1H), 7.53 (d, 2H, J = 8.0 Hz), 7.58 (t, 1H, J = 8.0 Hz), 7.68 (d, 1H, J = 7.6 Hz), 7.72 (t, 1H, J = 6.4 Hz), 7.97 (d, 2H, J = 8.0 Hz), 8.01 (s, 1H), 8.28 (d, 1H, J = 1.6 Hz), 9.25 (s, 1H), 9.62 (s, 1H), 10.21 (s, 1H), 10.92 (s, 1H), 13.55 (s, 1H); m/z [M⁺ + 1] 646.3 |
| 48 | 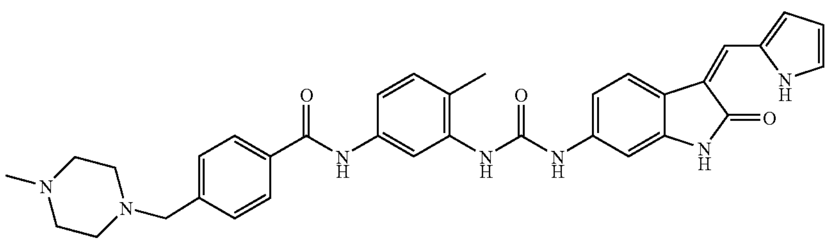 | ¹H NMR (DMSO-$d_6$) δ 2.22 (s, 3H), 2.79 (s, 3H), 2.96-3.16 (m, 4H), 3.36-3.46 (m, 4H), 3.76 (s, 2H), 6.33 (q, 1H, J = 1.6 Hz), 6.76 (d, 1H, J = 1.6 Hz), 6.90 (dd, 1H, $J_1$ = 7.6 Hz, $J_2$ = 1.6 Hz), 7.14 (d, 1H, J = 8.8 Hz), 7.30 (s, 1H), 7.39 (d, 1H, J = 1.6 Hz), 7.45 (dd, 1H, $J_1$ = 8.8 Hz, $J_2$ = 1.6 Hz), 7.48 (d, 2H, J = 8.8 Hz), 7.52 (d, 1H, J = 7.6 Hz), 7.57 (s, 1H), 7.98 (d, 2H, J = 8.8 Hz), 8.01 (s, 1H), 8.26 (d, 1H, J = 1.6 Hz), 9.23 (s, 1H), 10.20 (s, 1H), 10.90 (s, 1H), 13.21 (s, 1H); m/z [M⁺ + 1] 590.3. |
| 49 | 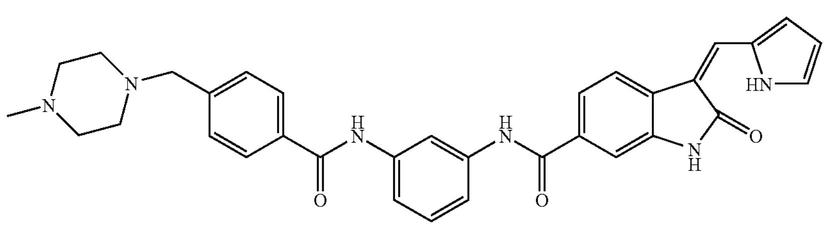 | ¹H NMR (DMSO-$d_6$) δ 2.48-2.52 (m, 2H), 2.80 (s, 3H), 2.96-3.12 (m, 4H), 3.38-3.48 (m, 2H), 3.80 (s, 2H), 6.41 (s, 1H), 6.93 (s, 1H), 7.32 (t, 1H, J = 7.8 Hz), 7.44 (s, 1H), 7.46-7.52 (m, 5H), 7.69 (d, 1H, J = 8.4 Hz), 7.78 (d, 1H, J = 8.4 Hz), 7.92 (s, 1H), 7.99 (d, 2H, J = 7.8 Hz), 8.35 (s, 1H), 10.27 (s, 1H), 10.30 (s, 1H), 11.34 (s, 1H), 13.38 (s, 1H); m/z [M⁺ + 1] 561.2. |
| 50 | 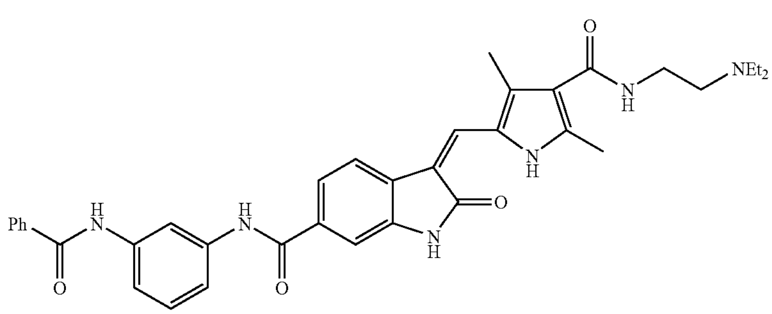 | ¹H NMR (DMSO-$d_6$) δ 1.24 (t, 6H, J = 7.2 Hz), 2.45 (s, 3H), 2.50 (s, 3H), 3.20-3.28 (m, 6H), 3.58 (q, 2H, J = 6.0 Hz), 7.32 (t, 1H, J = 7.8 Hz), 7.47 (d, 1H, J = 8.4 Hz), 7.49 (s, 1H), 7.51 (d, 1H, J = 7.8 Hz), 7.52 (d, 1H, J = 7.8 Hz), 7.54 (t, 2H, J = 7.8 Hz), 7.60 (t, 1H, J = 7.2 Hz), 7.70 (d, 1H, J = 8.4 Hz), 7.82 (s, 1H), 7.95 (d, 1H, J = 7.8 Hz), 7.98 (d, 2H, J = 7.2 Hz), 8.34 (s, 1H), 9.22 (s, 1H), 10.27 (s, 1H), 10.31 (s, 1H), 11.17 (s, 1H), 13.79 (s, 1H); m/z [M⁺ + 1] 619.3. |

TABLE 1-continued

| Compound Number | Structure | Physical Data ¹H NMR 400 MHz (DMSO-$d_6$) and/or MS(m/z) |
|---|---|---|
| 51 | 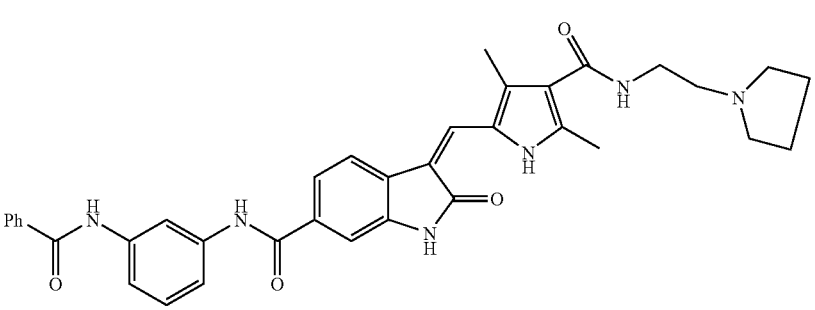 | ¹H NMR (DMSO-$d_6$) δ 1.84-1.92 (m, 2H), 2.00-2.08 (m, 2H), 2.49 (s, 3H), 2.50 (s, 3H), 3.04-3.12 (m, 2H), 3.33 (q, 2H, J = 6.0 Hz), 3.57 (q, 2H, J = 6.0 Hz), 3.63-3.69 (m, 2H), 7.32 (t, 1H, J = 8.4 Hz), 7.47 (d, 1H, J = 8.4 Hz), 7.50 (s, 1H), 7.52 (d, 1H, J = 7.8 Hz), 7.54 (1, 2H, J = 7.2 Hz), 7.60 (t, 1H, J = 6.6 Hz), 7.71 (d, 1H, J = 8.4 Hz), 7.80 (t, 2H, J = 6.0 Hz), 7.81 (s, 1H), 7.95 (d, 1H, J = 7.8 Hz), 7.98 (d, 2H, J = 7.2 Hz), 8.34 (s, 1H), 9.61 (s, 1H), 10.27 (s, 1H), 10.31 (s, 1H), 11.17 (s, 1H), 13.78 (s, 1H); m/z [M⁺ + 617.3. |
| 52 | 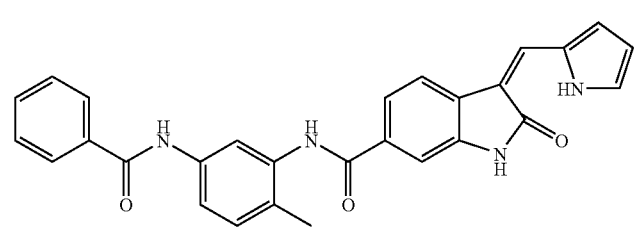 | ¹H NMR (DMSO-$d_6$) δ 2.21 (s, 3H), 6.41 (s, 1H), 6.92 (s, 1H), 7.24 (d, 1H, = 7.8 Hz), 7.43 (s, 1H), 7.50 (s, 1H), 7.51-7.54 (m, 2H), 7.59 (t, 2H, J = 7.8 Hz), 7.70 (d, 1H, J = 7.2 Hz), 7.78 (d, 1H, J = 7.8 Hz), 7.84 (s, 1H), 7.91 (s, 1H), 7.95 (d, 2H, J = 8.4 Hz), 9.90 (s, 1H), 10.25 (s, 1H), 11.12 (s, 1H), 13.38 (s, 1H); m/z [M⁺ + 1] 463.2. |
| 53 | 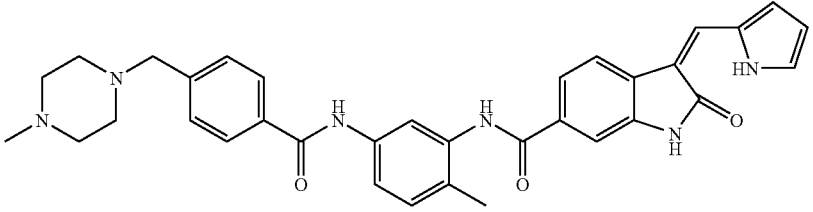 | ¹H NMR (DMSO-$d_6$) δ 2.22 (s, 3H), 2.48-2.52 (m, 2H), 2.80 (s, 3H), 2.92-3.16 (m, 4H), 3.36-3.48 (m, 2H), 3.80 (s, 2H), 6.41 (s, 1H), 6.93 (s, 1H), 7.24 (d, 1H, J = 7.8 Hz), 7.44 (s, 1H), 7.50 (s, 1H), 7.51 (d, 2H, J = 8.4 Hz), 7.59 (d, 1H, J = 7.8 Hz), 7.70 (d, 1H, J = 8.4 Hz), 7.78 (d, 2H, J = 8.4 Hz), 7.84 (s, 1H), 7.91 (s, 1H), 7.98(d, 2H, J = 8.4 Hz), 9.90 (s, 1H), 10.25 (s, 1H), 11.34 (s, 1H), 13.38 (s, 1H); m/z [M⁺ +1] 575.2. |
| 54 | 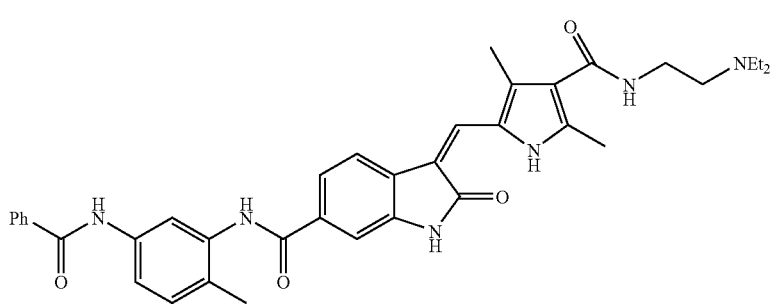 | ¹H NMR (DMSO-$d_6$) δ 1.24 (t, 6H, J = 7.2 Hz), 2.21 (s, 3H), 2.48 (s, 3H), 2.50 (s, 3H), 3.20-3.28 (m, 6H), 3.58 (q, 2H, J = 6.0 Hz), 6.57 (bs, 1H), 7.24 (d, 1H, J = 7.8 Hz), 7.51 (s, 1H), 7.53 (t, 2H, J = 7.2 Hz), 7.56-7.61 (m, 2H), 7.71 (d, 1H, J = 8.4 Hz), 7.81 (s, 1H), 7.83 (t, 1H, J = 6.0 Hz), 7.86 (s, 1H), 7.96 (d, 2H, J = 7.2 Hz), 9.33 (s, 1H), 9.91 (s, 1H), 10.26 (s, 1H), 11.16 (s, 1H), 13.78 (s, 1H); m/z [M⁺ + 1) 633.3 |

TABLE 1-continued

| Compound Number | Structure | Physical Data ¹H NMR 400 MHz (DMSO-d₆) and/or MS(m/z) |
|---|---|---|
| 55 | 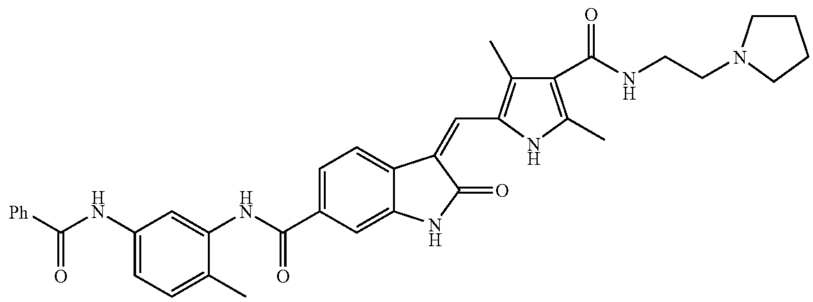 | ¹H NMR (DMSO-d₆) δ 1.84-1.90 (m, 2H), 2.00-2.06 (m, 2H), 2.22 (s, 3H), 2.48 (s, 3H), 2.50 (s, 3H), 3.04-3.12 (m, 2H), 3.33 (q, 2H, J = 6.0 Hz), 3.57 (q, 2H, J = 6.0 Hz), 3.63-3.70 (m, 2H), 6.57 (bs, 1H), 7.23 (d, 1H, J = 7.8 Hz), 7.51 (s, 1H), 7.53 (t, 2H, J = 7.2 Hz), 7.57-7.60 (m, 2H), 7.71 (d, 1H, J = 8.4 Hz), 7.79-7.82 (m, 2H), 7.86 (s, 1H), 7.96 (d, 2H, J = 7.2 Hz), 9.68 (s, 1H), 9.91 (s, 1H), 10.26 (s, 1H), 11.16 (s, 1H), 13.78 (s, 1H); m/z [M⁺ +1] 631.3. |
| 56 | 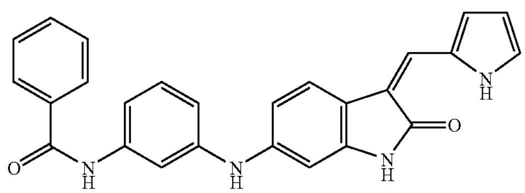 | ¹H NMR (DMSO-d₆) δ 6.82 (q, 1H, J= 3.2 Hz), 7.19 (d, 1H, J = 2.0 Hz), 7.22-7.24 (m, 1H), 7.27 (dd, 1H, J₁ = 8.8 Hz, J₂ = 2.0 Hz), 7.33 (d, 1H, J = 8.8 Hz), 7.73 (t, 1H, J = 8.0 Hz), 7.77-7.81 (m, 2H), 7.98-8.12 (m, 5H), 8.23 (s, 1H), 8.46 (d, 2H, J = 6.8 Hz), 8.90 (s, 1H), 10.70 (s, 1H), 11.27 (s, 1H), 12.22 (s, 1H); m/z [M⁺ + 1] 421.1 |
| 57 | 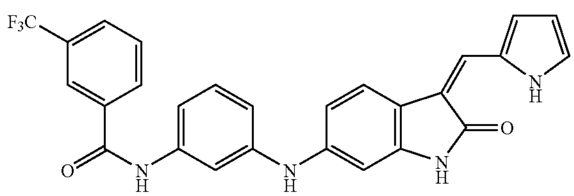 | ¹H NMR (DMSO-d₆) δ 6.82 (s, 1H), 7.21 (s, 1H), 7.24 (s, 1H), 7.28 (d, 1H, J = 8.4 Hz), 7.38 (d, 1H, J = 6.8 Hz), 7.74-7.82 (m, 3H), 8.00-8.02 (m, 2H), 8.22 (s, 1H), 8.30 (t, 1H, J = 7.6 Hz), 8.47 (d, 1H, J = 7.6 Hz), 8.77-8.82 (m, 2H), 8.93 (s, 1H), 11.92 (s, 1H), 11.29 (s, 1H), 12.22 (s, 1H); m/z [M⁺ +1] 489.1 |
| 58 | 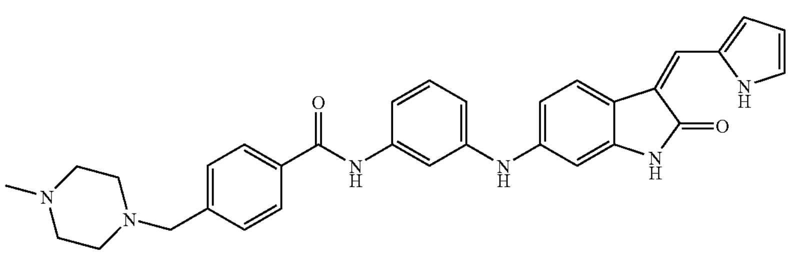 | ¹H NMR (DMSO-d₆) δ 2.79 (s, 3H), 2.96-3.08 (m, 4H), 3.36-3.46 (m, 4H), 3.75 (s, 2H), 6.30 (q, 1H, J = 1.6 Hz), 6.67 (d, 1H, J = 1.6 Hz), 6.71 (s, 1H), 6.74 (dd, 1H, J₁ = 8.0 Hz, J₂ = 1.6 Hz), 6.82 (d, 1H, J = 8.0 Hz), 7.21 (t, 1H, J = 8.8 Hz), 7.24-7.26 (m, 2H), 7.46-7.50 (m, 5H), 7.70 (s, 1H), 7.95 (d, 2H, J = 8.4 Hz), 8.38 (s, 1H), 10.17 (s, 1H), 10.76 (s, 1H), 13.16 (s, 1H); m/z [M⁺ + 1] 533.5. |
| 59 | 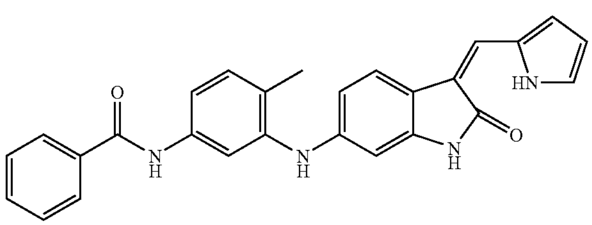 | ¹H NMR (DMSO-d₆) δ 2.19 (s, 3H), 6.29 (s, 1H), 6.50 (s, 1H), 6.59 (d, 1H, J = 8.4 Hz), 6.69 (s, 1H), 7.16 (d, 1H, J = 8.4 Hz), 7.24 (s, 1H), 7.40 (d, 1H, J = 8.4 Hz), 7.43 (d, 1H, J = 7.2 Hz), 7.44 (s, 1H), 7.50 (t, 2H, J = 7.2 Hz), 7.56 (t, 1H, J = 7.2 Hz), 7.75 (s, 1H), 7.92 (d, 2H, J = 7.2 Hz), 10.13 (s, 1H), 10.70 (s, 1H), 13.15 (s, 1H); m/z[M⁺ + 1] 435.1. |

TABLE 1-continued

| Compound Number | Structure | Physical Data $^1$H NMR 400 MHz (DMSO-$d_6$) and/or MS(m/z) |
|---|---|---|
| 60 | 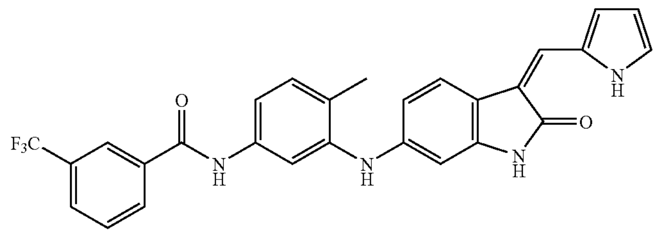 | $^1$H NMR (DMSO-$d_6$) δ 2.20 (s, 3H), 6.29 (dd, 1H, $J_1$ = 1.2 Hz, $J_2$ = 2.8 Hz), 6.50 (d, 1H, J = 2.0 Hz), 6.61 (dd, 1H, $J_1$ = 8.0 Hz, $J_2$ = 2.4 Hz), 6.68-6.72 (m, 1H), 7.19 (d, 1H, J = 8.0 Hz), 7.24 (s, 1H), 7.40 (dd, 1H, $J_1$ = 1.2 Hz, $J_2$ = 8.0 Hz), 7.44 (t, 2H, J = 3.6 Hz), 7.72 (d, 1H, J = 1.6 Hz), 7.76 (t, 1H, J = 8 Hz), 7.94 (d, 1H, J = 8 Hz), 8.24 (d, 1H, J = 8 Hz), 8.26 (s, 1H), 10.32 (s, 1H), 10.69 (s, 1H), 13.15 (s, 1H); m/z [M$^+$ + 1] 503.2. |
| 61 | 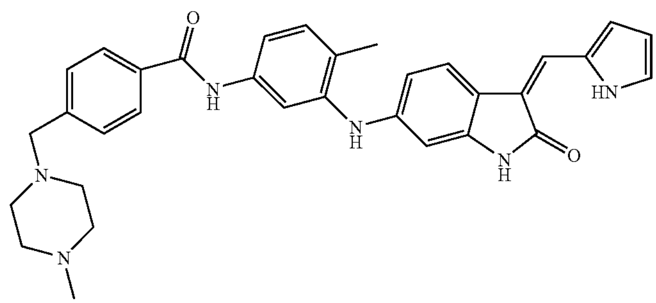 | $^1$H NMR (DMSO-$d_6$) δ 2.19 (s, 3H), 2.44-2.52 (m, 2H), 2.79 (s, 3H), 2.96-3.16 (m, 4H), 3.36-3.44 (m, 2H), 3.76 (s, 2H), 6.30 (s, 1H), 6.49 (s, 1H), 6.59 (d, 1H, J = 8.4 Hz), 6.69 (s, 1H), 7.16 (d, 1H, J = 8.4 Hz), 7.24 (s, 1H), 7.39 (d, 1H, J = 8.4 Hz), 7.43 (d, 1H, J = 7.2 Hz), 7.44 (s, 1H), 7.48 (d, 2H, J = 7.2 Hz), 7.60 (bs, 1H), 7.73 (s, 1H), 7.93 (d, 2H, J = 7.2 Hz), 10.11 (s, 1H), 10.71 (s, 1H), 13.15 (s, 1H); m/z [M$^+$ + 1] 547.2. |
| 62 | 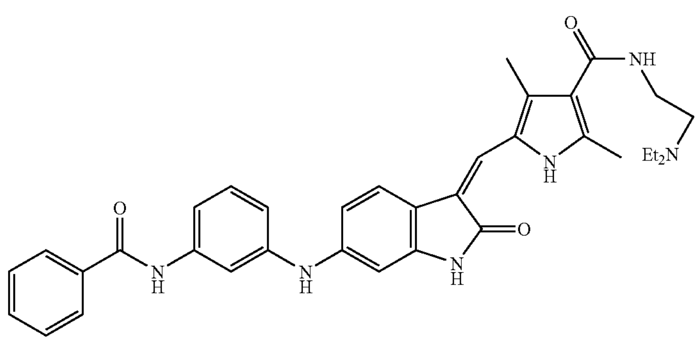 | $^1$H NMR (DMSO-$d_6$) δ 1.23 (t, 6H, J = 6.6 Hz), 2.40 (s, 3H), 2.45 (s, 3H), 3.20-3.24 (m, 6H), 3.57 (q, 2H, J = 6.6 Hz), 6.69 (s, 1H), 6.76 (d, 1H, J = 9.0 Hz), 6.81 (d, 1H, J = 6.6 Hz), 7.20-7.24 (m, 2H), 7.41 (s, 1H), 7.53 (t, 2H, J = 6.6 Hz), 7.59 (t, 1H, J = 6.6 Hz), 7.62 (d, 1H, J = 9.0 Hz), 7.70 (t, 1H, J = 5.4 Hz), 7.75 (s, 1H), 7.94 (d, 2H, J = 7.8 Hz), 8.35 (s, 1H), 10.16 (s, 1H), 10.77 (s, 1H), 13.50 (s, 1H); m/z [M$^+$ + 1] 591.3. |
| 63 | 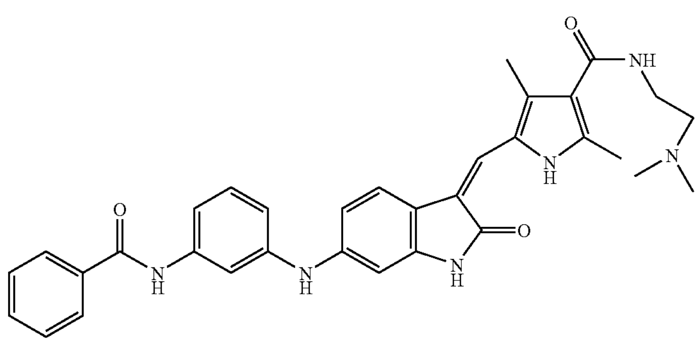 | $^1$H NMR (DMSO-$d_6$) δ 2.39 (s, 3H), 2.44 (s, 3H), 2.57 (s, 6H), 3.06 (q, 2H, J = 6.6 Hz), 3.47 (q, 2H, J = 6.6 Hz), 6.69 (d, 1H, J = 2.4 Hz), 6.75 (dd, 1H, $J_1$ = 7.2 Hz, $J_2$ = 2.4 Hz), 6.81 (d, 1H, J = 7.2 Hz), 7.19-7.25 (m, 2H), 7.40 (s, 1H), 7.52 (t, 2H, J = 4.2 Hz), 7.57-7.62 (m, 3H), 7.73 (s, 1H), 7.95 (d, 2H, J = 5.4 Hz), 8.35 (s, 1H), 10.17 (s, 1H), 10.76 (s, 1H), 13.45 (s, 1H); m/z [M$^+$ + 1] 563.3. |

… TABLE 1-continued

| Compound Number | Structure | Physical Data ¹H NMR 400 MHz (DMSO-$d_6$) and/or MS(m/z) |
|---|---|---|
| 64 | 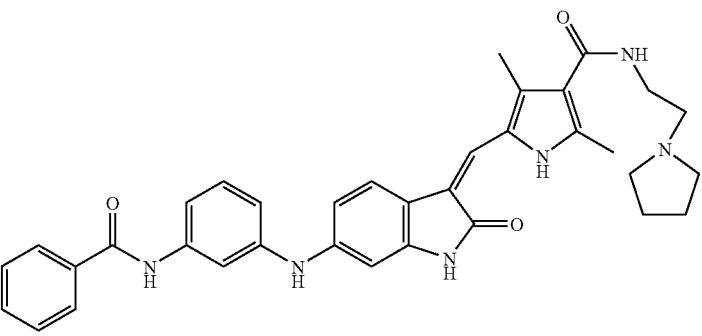 | ¹H NMR (DMSO-$d_6$) δ 1.80-1.84 (m, 4H), 2.39 (s, 3H), 2.44 (s, 3H), 2.88-2.96 (m, 6H), 3.45 (q, 2H, J = 5.4 Hz), 6.69 (d, 1H, J = 1.8 Hz), 6.75 (dd, 1H, $J_1$ = 7.2 Hz, $J_2$ = 1.8 Hz), 6.81 (d, 1H, J = 7.2 Hz), 7.19-7.25 (m, 2H), 7.40 (s, 1H), 7.52 (t, 2H, J = 7.2 Hz), 7.57-7.62 (m, 3H), 7.73 (s, 1H), 7.95 (d, 2H, J = 6.6 Hz), 8.35 (s, 1H), 10.17 (s, 1H), 10.76 (s, 1H), 13.44 (s, 1H); m/z [M$^+$ + 1] 589.3. |
| 65 | 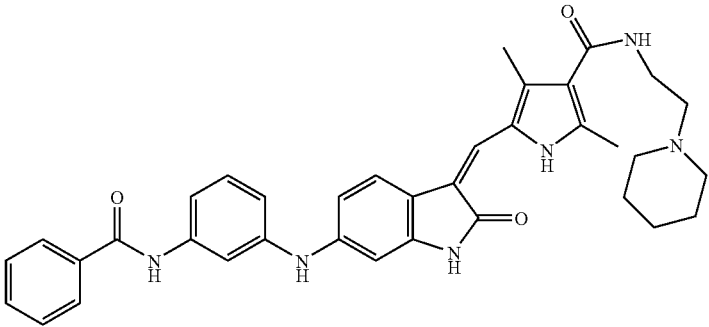 | ¹H NMR (DMSO-$d_6$) δ 1.38-1.50 (m, 2H), 1.54-1.66 (m, 4H), 2.39 (s, 3H), 2.44 (s, 3H), 2.51-2.53 (m, 2H), 3.00-3.08 (m, 2H), 3.38-3.44 (m, 4H), 6.69 (d, 1H, J = 2.4 Hz), 6.75 (dd, 1H, $J_1$ = 8.4 Hz, $J_2$ = 2.4 Hz), 6.82 (d, 1H, J = 7.8 Hz), 7.19-7.25 (m, 2H), 7.40 (s, 1H), 7.52 (t, 2H, J = 7.2 Hz), 7.58 (t, 1H, J = 7.8 Hz), 7.61 (d, 2H, J = 8.4 Hz), 7.73 (s, 1H), 7.94 (d, 2H, J = 7.8 Hz), 8.34 (s, 1H), 10.16 (s, 1H), 10.75 (s, 1H), 13.45 (s, 1H); m/z [M$^+$ + 1] 603.3. |
| 66 | 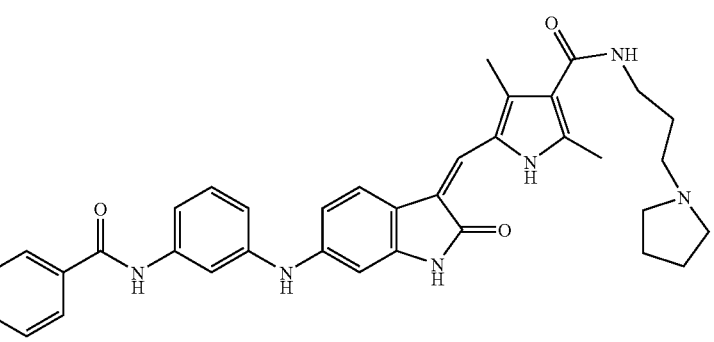 | ¹H NMR (DMSO-$d_6$) δ 1.80-1.88 (m, 6H), 2.38 (s, 3H), 2.43 (s, 3H), 2.92-3.02 (m, 6H), 3.29 (q, 2H, J = 6.6 Hz), 6.69 (d, 1H, J = 1.8 Hz), 6.75 (dd, 1H, $J_1$ = 7.8 Hz, $J_2$ = 1.8 Hz), 6.82 (d, 1H, J = 7.8 Hz), 7.19-7.25 (m, 2H), 7.40 (s, 1H), 7.52 (t, 2H, J = 7.2 Hz), 7.59 (t, 1H, J = 7.8 Hz), 7.61 (d, 1H, J = 8.4 Hz), 7.66 (t, 1H, J = 6.0 Hz), 7.73 (s, 1H), 7.94 (d, 2H, J = 6.6 Hz), 8.35 (s, 1H), 10.16 (s, 1H), 10.75 (s, 1H), 13.45 (s, 1H); m/z [M$^+$ + 1] 603.3. |
| 67 | 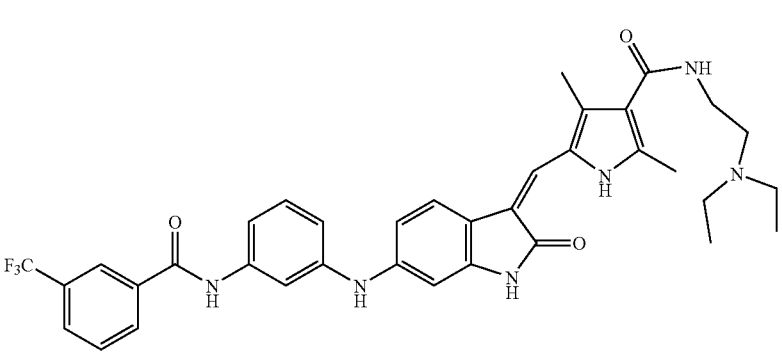 | ¹H NMR (DMSO-$d_6$) δ 1.24 (t, 6H, J = 8.4 Hz), 2.41 (s, 3H), 2.46 (s, 3H), 3.20-3.27 (m, 6H), 3.58 (q, 2H, J = 6.6 Hz), 6.69 (d, 1H, J = 2.4 Hz), 6.77 (dd, 1H, $J_1$ = 8.4 Hz, $J_2$ = 2.4 Hz), 6.88-6.92 (m, 1H), 7.23 (d, 2H, J = 4.8 Hz), 7.42 (s, 1H), 7.63 (d, 1H, J = 8.4 Hz), 7.73 (s, 1H), 7.73 (d, 1H, J = 6.6 Hz), 7.78 (t, 1H, J = 8.4 Hz), 7.96 (d, 1H, J = 7.2 Hz), 8.26 (d, 1H, J = 7.2 Hz), 8.28 (s, 1H), 8.30 (s, 1H), 9.39 (s, 1H), 10.40 (s, 1H), 10.79 (s, 1H), 13.45 (s, 1H); m/z [M$^+$ + 1] 659.3. |

TABLE 1-continued

| Compound Number | Structure | Physical Data<br>$^1$H NMR 400 MHz<br>(DMSO-$d_6$) and/or<br>MS(m/z) |
|---|---|---|
| 68 | 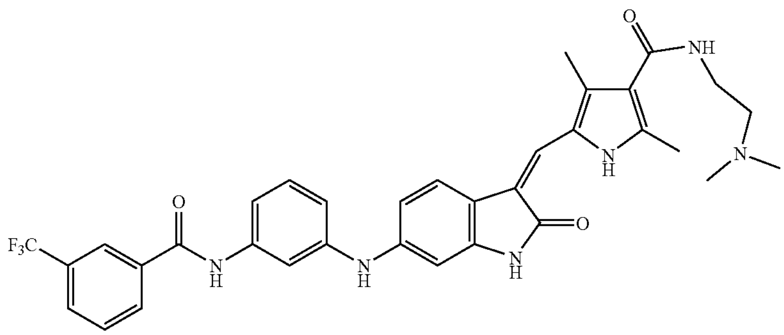 | $^1$H NMR (DMSO-$d_6$) δ 2.41 (s, 3H), 2.46 (s, 3H), 2.87 (d, 6H, J = 3.0 Hz), 3.25 (q, 2H, J = 6.6 Hz), 3.57 (q, 2H, J = 6.6 Hz), 6.69 (d, 1H, J = 2.4 Hz), 6.77 (dd, 1H, J$_1$ = 8.4 Hz, J$_2$ = 2.4 Hz), 6.84-6.86 (m, 1H), 7.22-7.28 (m, 2H), 7.42 (s, 1H), 7.63 (d, 1H, J = 8.4 Hz), 7.69 (t, 1H, J = 4.8 Hz), 7.73 (s, 1H), 7.78 (t, 1H, J = 8.4 Hz), 7.96 (d, 1H, J = 8.4 Hz), 8.26 (d, 1H, J = 7.2 Hz), 8.28 (s, 1H), 8.38 (s, 1H), 9.50 (s, 1H), 10.39 (s, 1H), 10.78 (s, 1H), 13.45 (s, 1H); m/z [M$^+$ + 1] 631.2. |
| 69 | 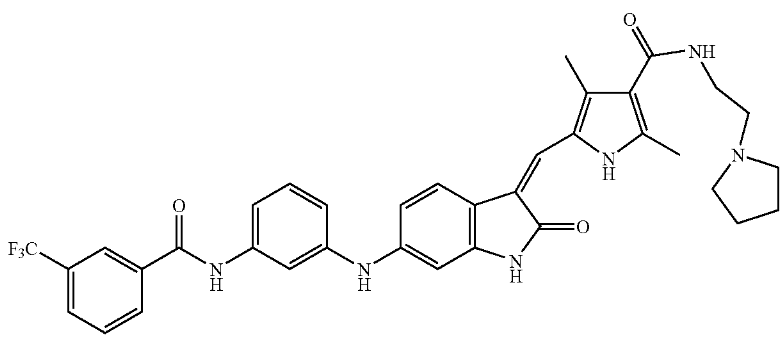 | $^1$H NMR (DMSO-$d_6$) δ 1.84-1.92 (m, 2H), 2.00-2.06 (m, 2H), 2.41 (s, 3H), 2.46 (s, 3H), 3.04-3.12 (m, 2H), 3.33 (q, 2H, J = 6.6 Hz), 3.56 (q, 2H, J = 6.6 Hz), 3.64-3.70 (m, 2H), 6.70 (d, 1H, J = 1.8 Hz), 6.77 (dd, 1H, J$_1$ = 7.8 Hz, J$_2$ = 1.8 Hz), 6.84-6.87 (m, 1H), 7.23-7.27 (m, 2H), 7.42 (s, 1H), 7.63 (d, 1H, J = 7.8 Hz), 7.69 (t, 1H, J = 4.8 Hz), 7.73 (s, 1H), 7.78 (t, 1H, J = 8.4 Hz), 7.96 (d, 1H, J = 7.2 Hz), 8.26 (d, 1H, J = 8.4 Hz), 8.28 (s, 1H), 8.38 (s, 1H), 9.70 (s, 1H), 10.39 (s, 1H), 10.78 (s, 1H), 13.45 (s, 1H); m/z [M$^+$ + 1] 657.3. |
| 70 | 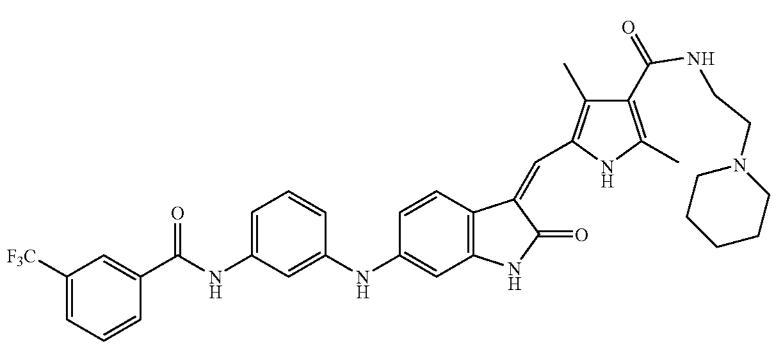 | $^1$H NMR (DMSO-$d_6$) δ 1.36-1.44 (m, 1H), 1.60-1.72 (m, 3H), 1.82-1.86 (m, 2H), 2.40 (s, 3H), 2.45 (s, 3H), 2.94-3.00 (m, 2H), 3.22 (q, 2H, J = 6.0 Hz), 3.54-3.58 (m, 2H), 3.59 (q, 2H, J = 6.0 Hz), 6.70 (d, 1H, J = 2.4 Hz), 6.77 (dd, 1H, J$_1$ = 7.8 Hz, J$_2$ = 2.4 Hz), 6.84-6.86 (m, 1H), 7.22-7.26 (m, 2H), 7.42 (s, 1H), 7.63 (d, 1H, J = 8.4 Hz), 7.72-7.75 (m, 2H), 7.78 (t, 1H, J = 7.2 Hz), 7.96 (d, 1H, J = 8.4 Hz), 8.25 (d, 1H, J = 7.2 Hz), 8.28 (s, 1H), 8.36 (s, 1H), 9.32 (s, 1H), 10.40 (s, 1H), 10.78 (s, 1H), 13.45 (s, 1H); m/z [M$^+$ + 1] 671.3. |

TABLE 1-continued

| Compound Number | Structure | Physical Data $^1$H NMR 400 MHz (DMSO-$d_6$) and/or MS(m/z) |
|---|---|---|
| 71 | 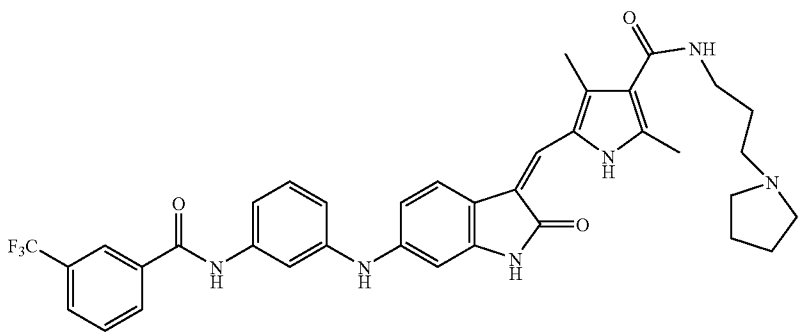 | $^1$H NMR (DMSO-$d_6$) δ 1.84-1.92 (m, 4H), 2.00-2.04 (m, 2H), 2.38 (s, 3H), 2.43 (s, 3H), 2.96-3.04 (m, 2H), 3.16-3.20 (m, 2H), 3.31 (q, 2H, J = 6.0 Hz), 3.56-3.60 (m, 2H), 6.70 (d, 1H, J = 1.8 Hz), 6.77 (dd, 1H, J$_1$ = 8.4 Hz, J$_2$ = 1.8 Hz), 6.83-6.85 (m, 1H), 7.22-7.24 (m, 2H), 7.41 (s, 1H), 7.62 (d, 1H, J = 8.4 Hz), 7.69 (t, 1H, J = 6.0 Hz), 7.72 (s, 1H), 7.78 (t, 1H, J = 8.4 Hz), 7.96 (d, 1H, J = 7.2 Hz), 8.25 (d, 1H, J = 7.2 Hz), 8.28 (s, 1H), 8.38 (s, 1H), 9.70 (s, 1H), 10.39 (s, 1H), 10.77 (s, 1H), 13.45 (s, 1H); m/z [M$^+$ + 1] 671.3. |
| 72 | 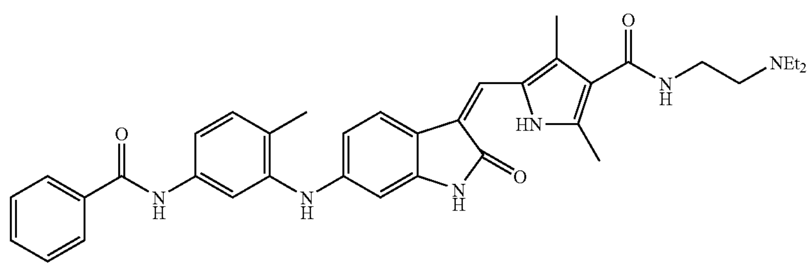 | $^1$H NMR (DMSO-$d_6$) δ 1.22 (t, 6H, J = 7.2 Hz), 2.19 (s, 3H), 2.40 (s, 3H), 2.45 (s, 3H), 3.18-3.28 (m, 6H), 3.52-3.58 (m, 2H), 6.51 (s, 1H), 6.62 (s, 1H), 7.16 (d, 1H, J = 7.8 Hz), 7.35 (d, 1H, J = 7.2 Hz), 7.38 (d, 1H, J = 7.2 Hz), 7.50 (q, 2H, J = 7.2 Hz), 7.55-7.62 (m, 3H), 7.72 (s, 1H), 7.79 (s, 1H), 7.92 (q, 2H, J = 7.2 Hz), 9.37 (s, 1H), 10.13 (s, 1H), 10.75 (s, 1H), 13.49 (s, 1H); m/z [M$^+$ + 1] 605.3. |
| 73 | 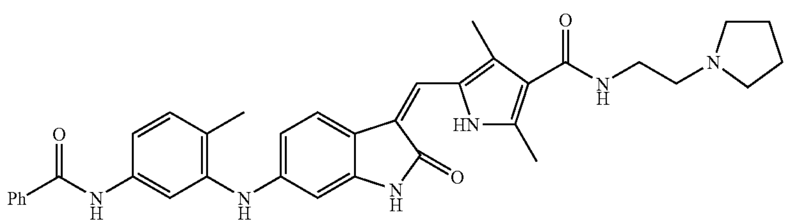 | $^1$H NMR (DMSO-$d_6$) δ 1.84-1.90 (m, 2H), 1.98-2.06 (m, 2H), 2.19 (s, 3H), 2.45 (s, 3H), 2.49 (s, 3H), 3.08-3.20 (m, 2H), 3.30-3.32 (m, 2H), 3.52-3.60 (m, 4H), 6.51 (s, 1H), 6.62 (s, 1H), 7.16 (d, 1H, J = 8.2 Hz), 7.34 (d, 1H, J = 7.2 Hz), 7.37 (s, 1H), 7.50 (t, 2H, J = 7.2 Hz), 7.55-7.62 (m, 3H), 7.69 (s, 1H), 7.79 (s, 1H), 7.92 (d, 2H, J = 7.2 Hz), 9.72 (s, 1H), 10.13 (s, 1H), 10.74 (s, 1H), 13.49 (s, 1H); m/z [M$^+$ + 1] 603.3. |
| 74 | 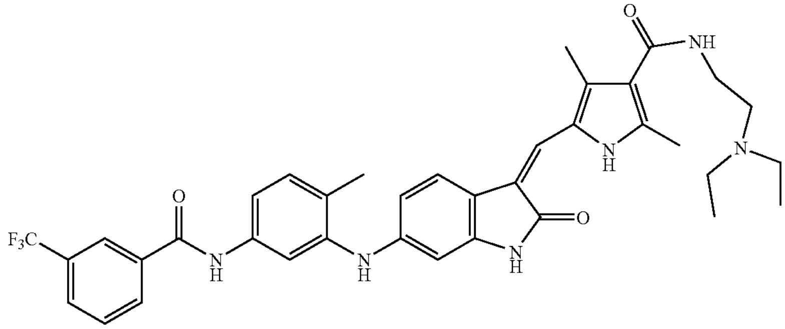 | $^1$H NMR (DMSO-$d_6$) δ 1.23 (t, 6H, J = 7.2 Hz), 2.20 (s, 3H), 2.39 (s, 3H), 2.45 (s, 3H), 3.20-3.28 (m, 6H), 3.57 (q, 2H, J = 6.0 Hz), 6.52 (d, 1H, J = 2.4 Hz), 6.63 (d, 1H, J = 8.4 Hz), 7.18 (d, 1H, J = 8.4 Hz), 7.35 (d, 1H, J = 8.4 Hz), 7.38 (s, 1H), 7.58 (s, 1H), 7.60 (s, 1H), 7.71 (t, 1H, J = 6.6 Hz), 7.75-7.78 (m, 2H), 7.94 (d, 1H, J = 8.4 Hz), 8.23 (d, 1H, J = 7.2 Hz), 8.26 (s, 1H), 9.33 (s, 1H), 10.34 (s, 1H), 10.74 (s, 1H), 13.49 (s, 1H); m/z [M$^+$ + 1] 673.3. |

TABLE 1-continued

| Compound Number | Structure | Physical Data ¹H NMR 400 MHz (DMSO-$d_6$) and/or MS(m/z) |
|---|---|---|
| 75 | 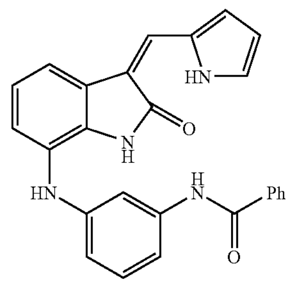 | ¹H NMR (DMSO-$d_6$) 6.36 (s, 1H), 6.71 (d, 1H, J = 7.2 Hz), 6.86 (s, 1H), 6.97 (t, 1H, J = 7.2 Hz), 7.12 (d, 1H, J = 8.0 Hz), 7.19 (t, 1H, J = 8.0 Hz), 7.24-7.30 (m, 2H), 7.36 (s, 1H), 7.44 (s, 1H), 7.49-7.58 (m, 4H), 7.75 (s, 1H), 7.93 (d, 2H, J = 8.0 Hz), 10.13 (s, 1H), 10.58 (s, 1H), 13.37 (s, 1H); m/z [M⁺ + 1] 421.1. |
| 76 | 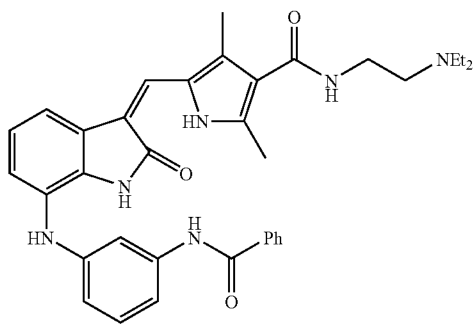 | ¹H NMR (DMSO-$d_6$) 1.24 (q, 6H, J = 7.2 Hz), 2.45 (s, 3H), 2.48 (s, 3H), 3.20-3.28 (m, 6H), 3.58 (q, 2H, J = 5.6 Hz), 6.72 (d, 1H, J = 8.0 Hz), 6.98 (t, 1H, J = 8.4 Hz), 7.12 (d, 1H, J = 7.2 Hz), 7.17-7.24 (m, 2H), 7.45 (d, 1H, J = 7.2 Hz), 7.48-7.50 (m, 1H), 7.52 (d, 2H, J = 7.2 Hz), 7.57 (d, 1H, J = 6.4 Hz), 7.59 (s, 1H), 7.65 (s, 1H), 7.78 (t, 1H, J = 2.8 Hz), 7.93 (d, 2H, J = 8.0 Hz), 9.32 (s, 1H), 10.15 (s, 1H), 10.61 (s, 1H), 13.73 (s, 1H); m/z [M⁺ + 1] 591.2. |
| 77 | 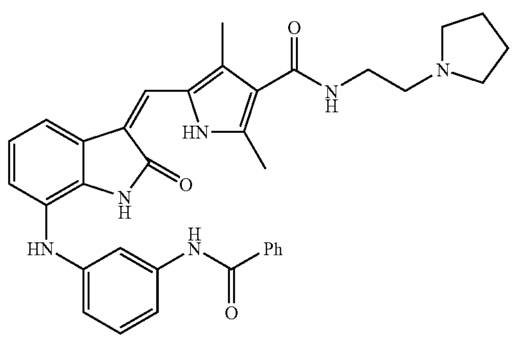 | ¹H NMR (DMSO-$d_6$) δ 1.84-1.92 (m, 2H), 2.00-2.06 (m, 2H), 2.45 (s, 3H), 2.49 (s, 3H), 3.04-3.12 (m, 2H), 3.33 (q, 2H, J = 6.0 Hz), 3.57 (q, 2H, J = 6.0 Hz), 3.60-3.70 (m, 2H), 6.70 (dt, 1H, J₁ = 8.0 Hz, J₂ = 1.6 Hz), 6.97 (t, 1H, J = 7.6 Hz), 7.11 (d, 1H, J = 7.6 Hz), 7.17-7.24 (m, 2H), 7.44 (d, 1H, J = 7.6 Hz), 7.46-7.52 (m, 1H), 7.52 (d, 2H, J = 7.2 Hz), 7.56-7.60 (m, 2H), 7.65 (s, 1H), 7.75 (t, 1H, J = 5.6 Hz), 7.92 (d, 2H, J = 7.2 Hz), 9.32 (s, 1H), 10.14 (s, 1H), 10.61 (s, 1H), 13.73 (s, 1H); m/z [M⁺ + 1] 589.2. |
| 78 | 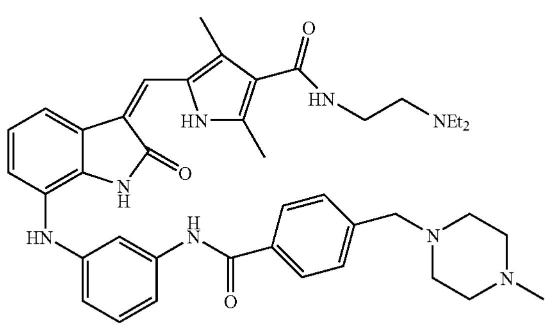 | ¹H NMR (DMSO-$d_6$) δ 1.23 (t, 6H, J = 7.2 Hz), 2.45 (s, 3H), 2.38-2.44 (m, 2H), 2.48 (s, 3H), 2.78 (s, 3H), 2.90-3.02 (m, 2H), 3.00-3.08 (m, 2H), 3.20-3.27 (m, 6H), 3.36-3.44 (m, 2H), 3.58 (q, 2H, J = 6.0 Hz), 3.71 (s, 2H), 6.71 (d, 1H, 7.8 Hz), 6.97 (t, 1H, J = 7.2 Hz), 7.11 (d, 1H, J = 7.8 Hz), 7.17-7.23 (m, 2H), 7.45 (d, 1H, J = 7.2 Hz), 7.47 (d, 2H, J = 7.8 Hz), 7.50 (s, 1H), 7.59 (s, 1H), 7.65 (s, 1H), 7.80 (t, 1H, J = 6.6 Hz), 7.93 (d, 2H, J = 7.8 Hz), 9.37 (s, 1H), 10.14 (s, 1H), 10.63 (s, 1H), 13.73 (s, 1H); m/z [M⁺ + 1] 703.3. |

TABLE 1-continued

| Compound Number | Structure | Physical Data<br>¹H NMR 400 MHz<br>(DMSO-d₆) and/or<br>MS(m/z) |
|---|---|---|
| 79 | 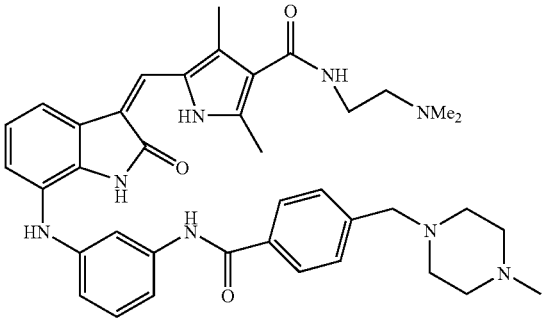 | ¹H NMR (DMSO-d₆) δ 2.45 (s, 3H), 2.48 (s, 3H), 2.79 (s, 3H), 2.86 (d, 6H, J = 4.2 Hz), 2.96-3.08 (m, 4H), 3.26 (q, 2H, J = 5.4 Hz), 3.36-3.44 (m, 2H), 3.58 (q, 2H, J = 5.4 Hz), 3.64-3.68 (m, 2H), 3.73 (s, 2H), 6.71 (d, 1H, 7.8 Hz), 6.97 (t, 1H, J = 7.8 Hz), 7.11 (d, 1H, J = 7.2 Hz), 7.17-7.23 (m, 2H), 7.45 (d, 1H, J = 7.2 Hz), 7.47 (d, 2H, J = 8.4 Hz), 7.50 (s, 1H), 7.59 (s, 1H), 7.65 (s, 1H), 7.77 (t, 1H, J = 5.4 Hz), 7.93 (d, 2H, J = 8.4 Hz), 9.54 (s, 1H), 10.14 (s, 1H), 10.62 (s, 1H), 13.73 (s, 1H); m/z [M⁺ + 1] 675.3. |
| 80 | 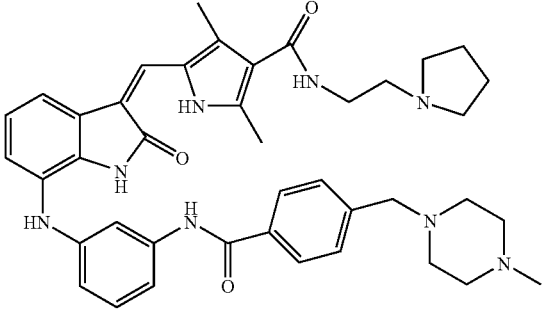 | ¹H NMR (DMSO-d₆) δ 1.84-1.92 (m, 2H), 2.00-2.07 (m, 2H), 2.45 (s, 3H), 2.48 (s, 3H), 2.78 (s, 3H), 2.92-3.00 (m, 2H), 3.04-3.10 (m, 4H), 3.33 (q, 2H, J = 6.0 Hz), 3.36-3.46 (m, 2H), 3.56 (q, 2H, J = 6.0 Hz), 3.64-3.70 (m, 4H), 3.72 (s, 2H); m/z [M⁺ + 1] 701.3. |
| 81 | 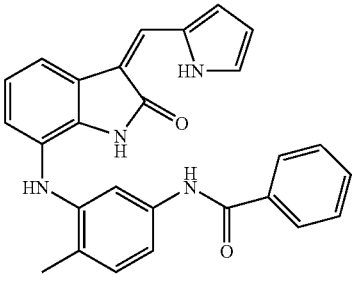 | ¹H NMR (DMSO-d₆) δ 2.24 (s, 3H), 6.37 (s, 1H), 6.61 (s, 1H), 6.85 (s, 1H), 6.89 (d, 1H, J = 8.4 Hz), 6.94 (t, 1H, J = 7.2 Hz), 7.13 (d, 1H, J = 8.4 Hz), 7.27 (d, 1H, J = 7.2 Hz), 7.34 (d, 1H, J = 8.4 Hz), 7.36 (s, 1H), 7.46 (s, 1H), 7.48 (d, 2H, J = 7.2 Hz), 7.54 (t, 1H, J = 7.2 Hz), 7.75 (s, 1H), 7.89 (d, 2H, J = 8.4 Hz), 10.06 (s, 1H), 10.79 (s, 1H), 13.38 (s, 1H); m/z [M⁺ + 1] 435.2. |
| 82 | 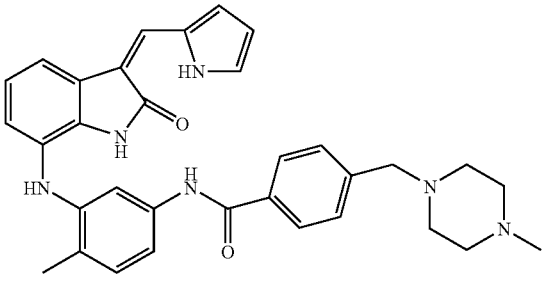 | ¹H NMR (DMSO-d₆) δ 2.24 (s, 3H), 2.78 (s, 3H), 2.96-3.08 (m, 4H), 3.36-3.46 (m, 4H), 3.78 (s, 2H), 6.37 (s, 1H), 6.62 (s, 1H), 6.85 (s, 1H), 6.89 (d, 1H, J = 8.4 Hz), 6.94 (t, 1H, J = 7.8 Hz), 7.13 (d, 1H, J = 8.4 Hz), 7.28 (d, 1H, J = 8.4 Hz), 7.32 (d, 1H, J = 7.8 Hz), 7.36 (s, 1H), 7.43 (s, 1H), 7.45 (d, 2H, J = 8.4 Hz), 7.75 (s, 1H), 7.90 (d, 2H, J = 7.8 Hz), 10.05 (s, 1H), 10.79 (s, 1H), 13.38 (s, 1H); m/z [M⁺ + 1] 547.3. |

TABLE 1-continued

| Compound Number | Structure | Physical Data $^1$H NMR 400 MHz (DMSO-$d_6$) and/or MS(m/z) |
|---|---|---|
| 83 | 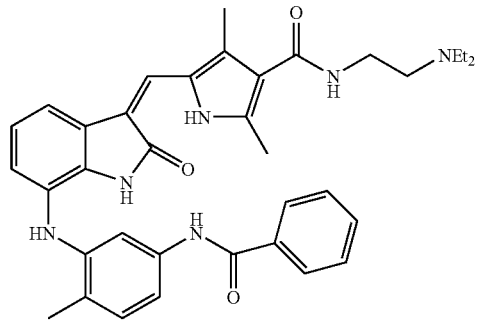 | $^1$H NMR (DMSO-$d_6$) δ 1.24 (t, 6H, J = 7.2 Hz), 2.24 (s, 3H), 2.45 (s, 3H), 2.48 (s, 3H), 3.20-3.28 (m, 6H), 3.58 (q, 2H, J = 6.0 Hz), 6.64 (s, 1H), 6.87 (t, 1H, J = 8.4 Hz), 6.94 (t, 1H, J = 7.8 Hz), 7.14 (d, 1H, J = 8.4 Hz), 7.31 (d, 1H, J = 8.4 Hz), 7.42 (d, 1H, J = 6.6 Hz), 7.48 (t, 2H, J = 8.4 Hz), 7.50 (s, 1H), 7.55 (t, 1H, J = 8.4 Hz), 7.65 (s, 1H), 7.79 (t, 1H, J = 6.6 Hz), 7.89 (d, 2H, J = 8.4 Hz), 9.33 (s, 1H), 10.07 (s, 1H), 10.80 (s, 1H), 13.74 (s, 1H); m/z [M$^+$ + 1] 605.3. |
| 84 | 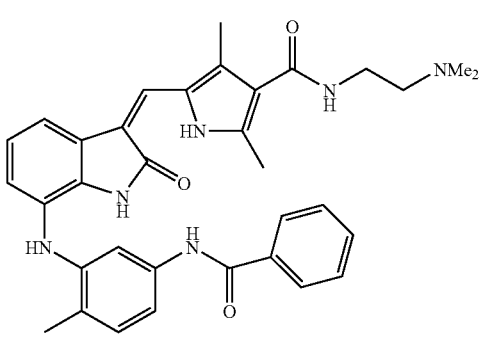 | $^1$H NMR CDMSO-$d_6$) δ2.24 (s, 3H), 2.45 (s, 3H), 2.49 (s, 3H), 2.87 (d, 6H, J = 3.6 Hz), 3.26 (q, 2H, J = 5.4 Hz), 3.58 (q, 2H, J = 5.4 Hz), 6.65 (s, 1H), 6.87 (t, 1H, J = 8.4 Hz), 6.94 (t, 1H, J = 6.6 Hz), 7.14 (d, 1H, J = 8.4 Hz), 7.30 (d, 1H, J = 8.4 Hz), 7.42 (d, 1H, J = 7.8 Hz), 7.48 (t, 2H, J = 7.2 Hz), 7.50 (s, 1H), 7.55 (t, 1H, J = 7.2 Hz), 7.65 (s, 1H), 7.75 (t, 1H, J = 6.0 Hz), 7.88 (d, 2H, J = 8.4 Hz), 9.55 (s, 1H), 10.07 (s, 1H), 10.80 (s, 1H), 13.74 (s, 1H); m/z [M$^+$ + 1] 577.3. |
| 85 | 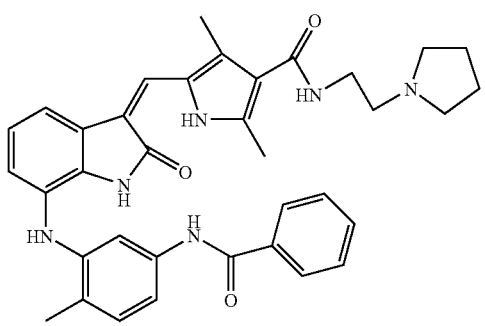 | $^1$H NMR (DMSO-$d_6$) δ 1.84-1.92 (m, 2H), 2.00-2.06 (m, 2H), 2.24 (s, 3H), 2.45 (s, 3H), 2.49 (s, 3H), 3.04-3.12 (m, 2H), 3.32 (q, 2H, J = 6.0 Hz), 3.57 (q, 2H, J = 6.0 Hz), 3.64-3.68 (m, 2H), 6.64 (s, 1H), 6.88 (t, 1H, J = 8.4 Hz), 6.93 (t, 1H, J = 6.6 Hz), 7.14 (d, 1H, J = 8.4 Hz), 7.31 (d, 1H, J = 8.4 Hz), 7.42 (d, 1H, J = 6.6 Hz), 7.48 (t, 2H, J = 7.2 Hz), 7.50 (s, 1H), 7.55 (t, 1H, J = 7.2 Hz), 7.65 (s, 1H), 7.75 (t, 1H, J = 6.0 Hz), 7.88 (d, 2H, J = 7.2 Hz), 9.63 (s, 1H), 10.07 (s, 1H), 10.79 (s, 1H), 13.74 (s, 1H); m/z [M$^+$ + 1] 603.3. |
| 86 | 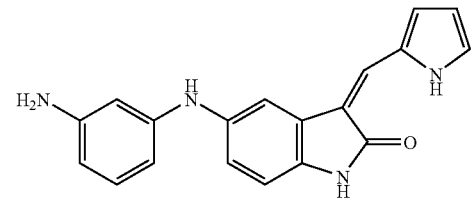 | $^1$H NMR (DMSO-$d_6$) δ 6.35 (s, 1H), 6.45 (d, 1H, J = 7.2 Hz), 6.66 (s, 1H), 6.70 (d, 1H, J = 7.2 Hz), 6.83 (s, 1H), 6.84 (d, 1H, J = 8.4 Hz), 6.91 (d, 1H, J = 8.4 Hz), 7.14 (t, 1H, J = 8.4 Hz), 7.35 (s, 1H), 7.42 (s, 1H), 7.68 (s, 1H), 8.03 (bs, 1H), 8.80 (bs, 2H), 10.79 (s, 1H), 13.38 (s, 1H); m/z [M$^+$ + 1] 317.1. |

TABLE 1-continued

| Compound Number | Structure | Physical Data $^1$H NMR 400 MHz (DMSO-$d_6$) and/or MS(m/z) |
|---|---|---|
| 87 | 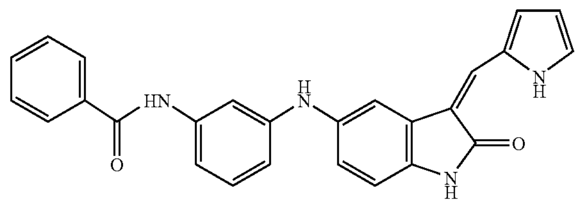 | $^1$H NMR (DMSO-$d_6$) δ 6.33-6.35 (m, 1H), 6.68 (d, 1H, J = 7.2 Hz), 6.81-6.84 (m, 2H), 6.93 (dd, 1H, J$_1$ = 7.8 Hz, J$_2$ = 2.4 Hz), 7.12-7.17 (m, 2H), 7.32-7.34 (m, 1H), 7.44 (d, 1H, J = 2.4 Hz), 7.49 (s, 1H), 7.50 (t, 2H, J = 8.4 Hz), 7.57 (t, 1H, J = 7.2 Hz), 7.68 (s, 1H), 7.92 (d, 2H, J = 8.4 Hz), 10.08 (s, 1H), 10.74 (s, 1H), 13.39 (s, 1H); m/z [M$^+$ + 1] 421.1. |
| 88 | 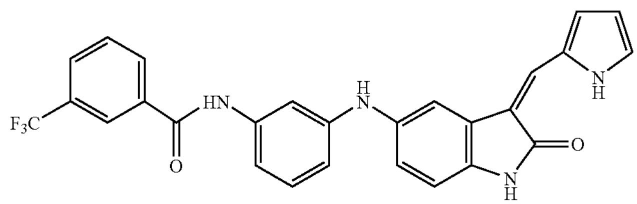 | $^1$H NMR (DMSO-$d_6$) δ 6.32-6.35 (m, 1H), 6.70 (d, 1H, J = 6.6 Hz), 6.82-6.85 (m, 2H), 6.93 (d, 1H, J = 7.8 Hz), 7.14-7.18 (m, 2H), 7.34 (s, 1H), 7.47 (d, 2H, J = 6.6 Hz), 7.70 (s, 1H), 7.76 (t, 1H, J = 7.8 Hz), 7.94 (d, 1H, J = 7.2 Hz), 7.95 (bs, 1H), 8.24 (d, 1H, J = 7.2 Hz), 8.26 (s, 1H), 10.31 (s, 1H), 10.75 (s, 1H), 13.38 (s, 1H); m/z [M$^+$ + 1] 489.1. |
| 89 | 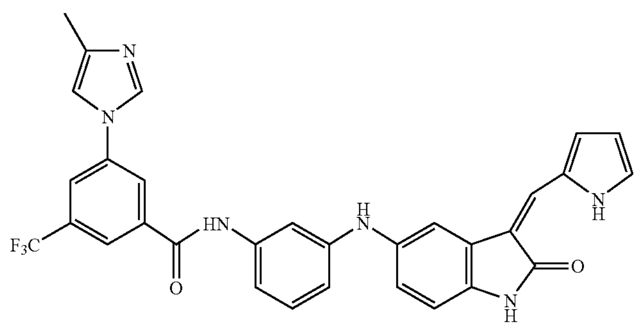 | $^1$H NMR (DMSO-$d_6$) δ 2.32 (s, 3H), 6.32-6.34 (m, 1H), 6.73 (d, 1H, J = 7.8 Hz), 6.82 (s, 1H), 6.83 (d, 1H, J = 7.8 Hz), 6.93 (dd, 1H, J$_1$ = 6.6 Hz, J$_2$ = 2.4 Hz), 7.13 (d, 1H, J = 7.8 Hz), 7.19 (t, 1H, J = 7.8 Hz), 7.34 (s, 1H), 7.47 (s, 1H), 7.48 (d, 1H, J = 2.4 Hz), 7.70 (s, 1H), 7.98 (bs, 1H), 8.08 (s, 1H), 8.38 (s, 2H), 8.54 (s, 1H), 9.44 (s, 1H), 10.43 (s, 1H), 10.76 (s, 1H), 13.38 (s, 1H); m/z [M$^+$ + 1] 569.2. |
| 90 | 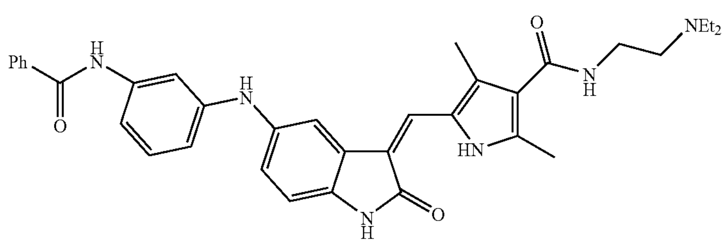 | $^1$H NMR CDMSO-$d_6$) δ 1.22 (t, 6H, J = 8.0 Hz), 2.41 (s, 3H), 2.47 (s, 3H), 3.19-3.26 (m, 6H), 3.50-3.58 (m, 2H), 6.64 (d, 1H, J = 8.0 Hz), 6.83 (d, 1H, J = 8.0 Hz), 6.92 (dd, 1H, J$_1$ = 2.4 Hz, J$_2$ = 8.0 Hz), 7.10-7.15 (m, 2H), 7.50 (t, 2H, J = 7.6 Hz), 7.55-7.64 (m, 4H), 7.76-7.78 (m, 1H), 7.91 (d, 2H, J = 6.8 Hz), 9.27 (bs, 1H), 10.11 (s, 1H), 10.82 (s, 1H), 13.80 (s, 1H); m/z [M$^+$ + 1] 591.2. |
| 91 | 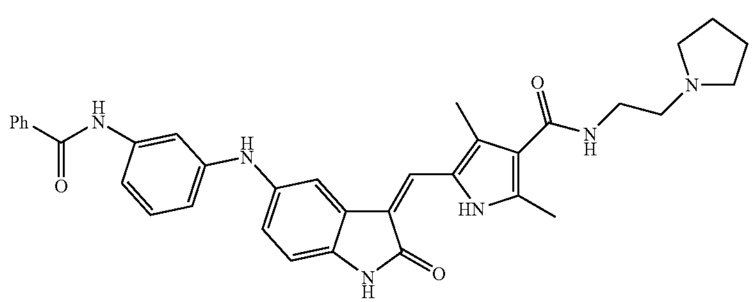 | $^1$H NMR (DMSO-$d_6$) δ 1.80-1.92 (m, 2H), 1.96-2.08 (m, 2H), 2.42 (s, 3H), 2.47 (s, 3H), 3.00-3.12 (m, 2H), 3.31 (q, 2H, J = 6.4 Hz), 3.50-3.58 (m, 4H), 6.65 (d, 1H, J = 8.0 Hz), 6.83 (d, 1H, J = 8.0 Hz), 6.92 (dd, 1H, J$_1$ = 2.4 Hz, J$_2$ = 6.4 Hz), 7.09-7.15 (m, 2H), 7.50 (t, 2H, J = 7.7 Hz), 7.55-7.64 (m, 4H), 7.74 (t, 1H, J = 6.4 Hz), 7.91 (d, 2H, J = 6.8 Hz), 9.63 (bs, 1H), 10.11 (s, 1H), 10.81 (s, 1H), 13.79 (s, 1H); m/z [M$^+$ + 1] 589.2. |

TABLE 1-continued

| Compound Number | Structure | Physical Data<br>$^1$H NMR 400 MHz<br>(DMSO-$d_6$) and/or<br>MS(m/z) |
|---|---|---|
| 92 | 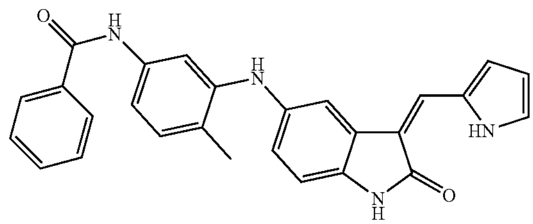 | $^1$H NMR (DMSO-$d_6$) δ 2.20 (s, 3H), 6.32 (q, 1H, J = 2.4 Hz), 6.80-6.83 (m, 2H), 6.89 (dd, 1H, $J_1$ = 7.2 Hz, $J_2$ = 2.4 Hz), 7.07 (d, 1H, J = 8.4 Hz), 7.25 (dd, 1H, $J_1$ = 7.2 Hz, $J_2$ = 2.4 Hz), 7.33 (s, 1H), 7.37 (s, 1H), 7.44 (s, 1H), 7.46 (t, 2H, J = 7.2 Hz), 7.53 (t, 1H, J = 7.2 Hz), 7.64 (s, 1H), 7.88 (d, 2H, J = 7.2 Hz), 10.02 (s, 1H), 10.76 (s, 1H), 13.39 (s, 1H); m/z [M$^+$ + 1] 435.1. |
| 93 | 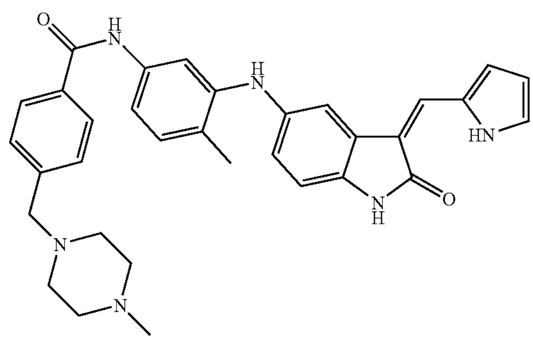 | $^1$H NMR (DMSO-$d_6$) δ $^1$H NMR (DMSO-$d_6$) δ 2.20 (s, 3H), 2.44-2.52 (m, 2H), 2.54 (s, 3H), 2.90-3.12 (m, 2H), 3.28-3.44 (m, 2H), 3.60-3.80 (m, 2H), 3.79 (s, 2H), 6.32 (q, 1H, J = 2.0 Hz), 6.80 (s, 1H), 6.81 (d, 1H, J = 8.0 Hz), 6.90 (dd, 1H, $J_1$ = 8.8 Hz, $J_2$ = 2.0 Hz), 7.07 (d, 1H, J = 8.4 Hz), 7.23 (dd, 1H, $J_1$ = 8.8 Hz, $J_2$ = 2.0 Hz), 7.33 (s, 1H), 7.38 (s, 1H), 7.43 (s, 1H), 7.44 (d, 2H, J = 8.0 Hz), 7.64 (s, 1H), 7.89 (d, 2H, J = 8.0 Hz), 10.02 (s, 1H), 10.77 (s, 1H), 13.37 (s, 1H); m/z [M$^+$ + 1] 547.2. |
| 94 | 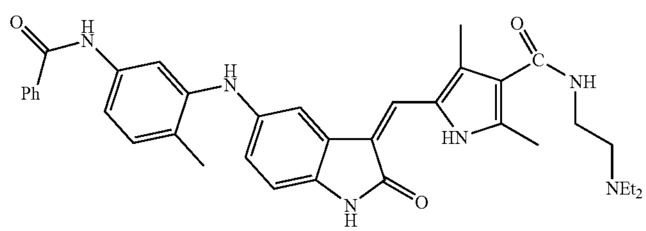 | $^1$H NMR (DMSO-$d_6$) δ 1.22 (t, 6H, J = 6.8 Hz), 2.01 (s, 3H), 2.39 (s, 3H), 2.46 (s, 3H), 3.18-3.25 (m, 6H), 3.56 (q, 2H, J = 5.6 Hz), 6.60 (bs, 1H), 6.83 (d, 1H, J = 8.0 Hz), 6.91 (dd, 1H, $J_1$ = 1.6 Hz, $J_2$ = 8.0 Hz), 7.02 (bs, 1H), 7.16 (dd, 1H, $J_1$ = 1.6 Hz, $J_2$ = 8.0 Hz), 7.46 (s, 1H), 7.46 (t, 2H, J = 6.8 Hz), 7.54 (t, 1H, J = 7.2 Hz), 7.56-7.59 (m, 2H), 7.70 (t, 1H, J = 5.2 Hz), 7.87 (d, 2H, J = 6.8 Hz), 9.33 (bs, 1H), 10.03 (s, 1H), 10.81 (s, 1H); m/z [M$^+$ + 1] 605.3. |
| 95 | 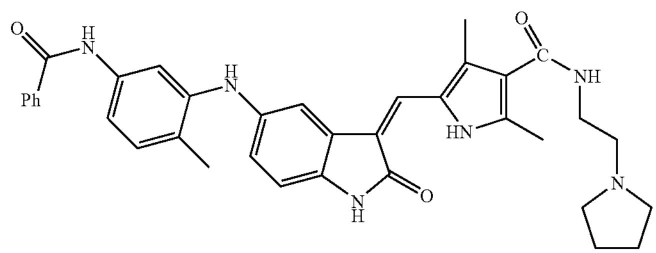 | $^1$H NMR (DMSO-$d_6$) δ 1.80-1.92 (m, 2H), 1.97-2.05 (m, 2H), 2.21 (s, 3H), 2.39 (s, 3H), 2.47 (s, 3H), 3.02-3.10 (m, 2H), 3.31 (q, 2H, J = 6.0 Hz), 3.55 (q, 2H, J = 6.0 Hz), 3.60-3.68 (m, 2H), 6.83 (d, 1H, J = 8.0 Hz), 6.91 (dd, 1H, $J_1$ = 2.0 Hz, $J_2$ = 8.0 Hz), 7.01 (bs, 1H), 7.06 (d, 1H, J = 8.0 Hz), 7.16 (dd, 1H, $J_1$ = 2.0 Hz, $J_2$ = 7.6 Hz), 7.46 (t, 2H, J = 6.4 Hz), 7.46 (s, 1H), 7.54 (t, 1H, J = 7.2 Hz), 7.56-7.58 (m, 2H), 7.41 (t, 1H, J = 4.8 Hz), 7.87 (d, 2H, J = 6.4 Hz), 9.64 (bs, 1H), 10.03 (s, 1H), 10.81 (s, 1H); m/z [M$^+$ + 1] 603.3. |

TABLE 1-continued

| Compound Number | Structure | Physical Data $^1$H NMR 400 MHz (DMSO-$d_6$) and/or MS(m/z) |
|---|---|---|
| 96 | 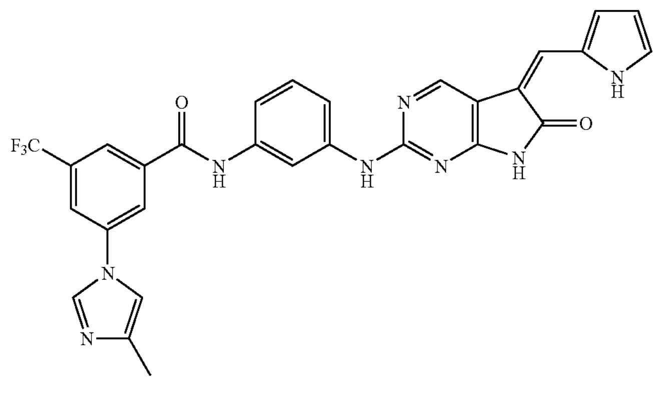 | LC/MS (m/z) 571.1 (MH+) |
| 97 | 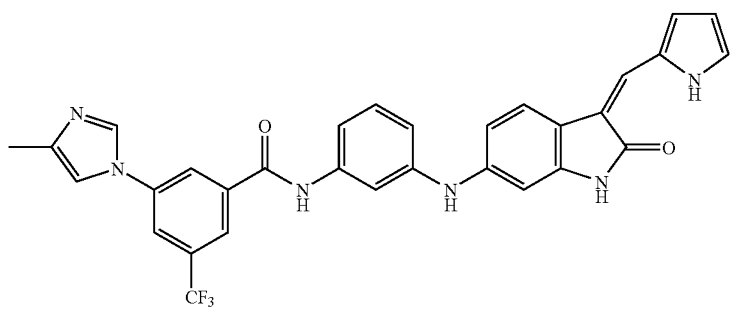 | $^1$H NMR (DMSO-$d_6$) δ 10.78 (s, 1H), 10.52 (s, 1H), 9.58 (s, 1H), 8.57 (s, 1H), 8.43 (s, 1H), 8.16 (s, 1H), 7.68 (s, 1H), 7.50-7.48 (m, 2H), 7.27-7.54 (m, 3H), 6.88-6.86 (m, 1H), 6.79-6.76 (m, 1H), 6.72 (m, 1H), 6.67 (s, 1H), 6.31 (m, 1H), 2.35 (s, 3H); LC/MS (m/z) 569.1 (MH+) |
| 98 | 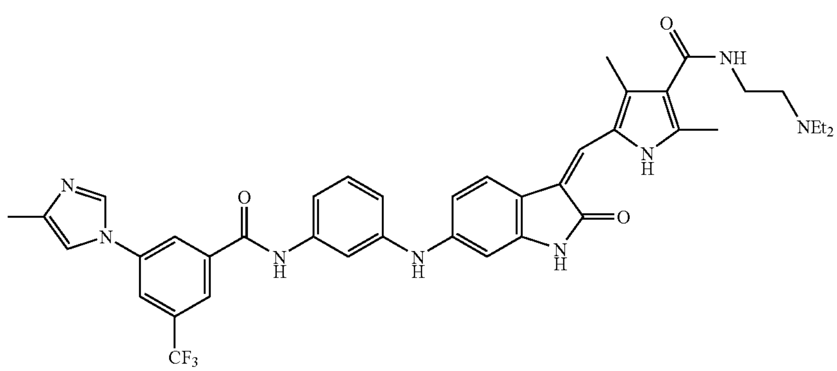 | $^1$H NMR (DMSO-$d_6$) δ 10.79 (s, 1H), 10.50 (s, 1H), 9.44-9.34 (b, 1H), 9.20-9.12 (b, 1H), 8.53 (s, 1H), 8.44-8.39 (b, 1H), 8.36 (s, 1H), 8.32 (s, 1H), 8.00 (s, 1H), 7.76-7.70 (m, 2H), 7.64 (d, 1H), 7.42 (s, 1H), 7.30-7.20 (m, 3H), 7.14 (s, 1H), 7.02 (s, 1H), 6.87 (d, 1H), 6.80-6.76 (dd, 1H), 6.69 (dd, 1H), 3.60-3.54 (q, 2H), 3.28-3.18 (m, 6H), 2.46 (3, 3H), 2.40 (s, 3H), 2.30 (s, 3H), 1.24 (t, 6H); LC/MS (m/z) 738.2 (MH+) |
| 99 | 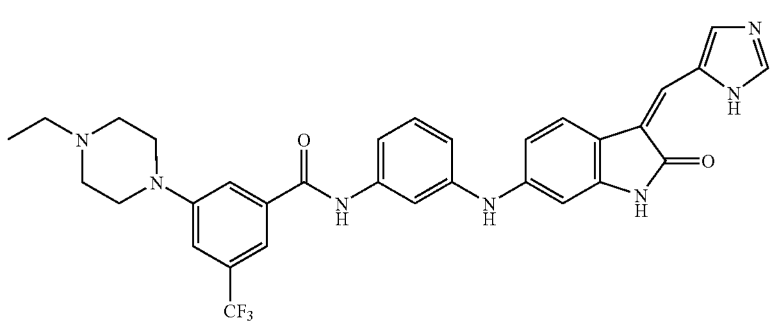 | LC/MS (m/z) 602.3 (MH+) |

TABLE 1-continued

| Compound Number | Structure | Physical Data $^1$H NMR 400 MHz (DMSO-$d_6$) and/or MS(m/z) |
|---|---|---|
| 100 | 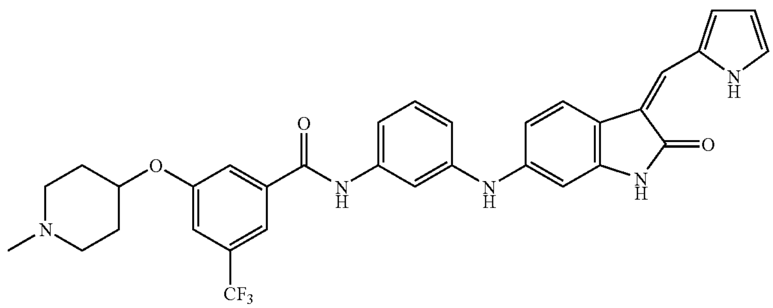 | LC/MS (m/z) 602.2 (MH+) |
| 101 | 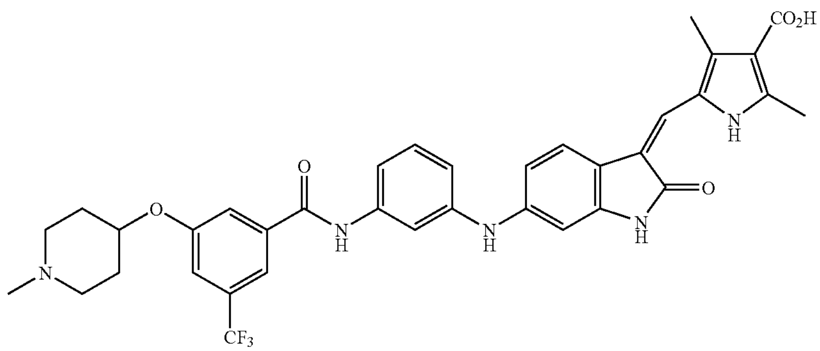 | LC/MS (m/z) 674.2 (MH+) |
| 102 | 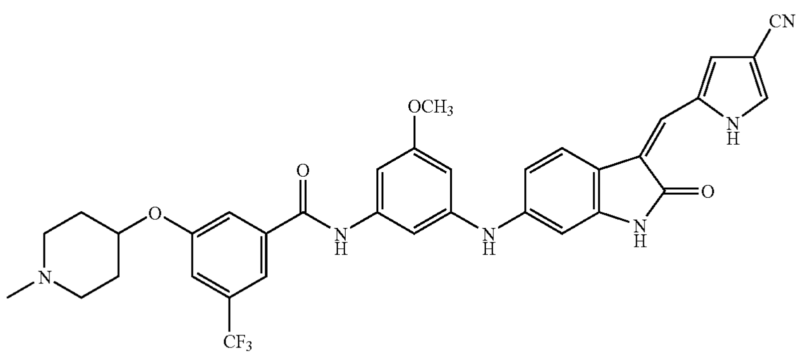 | 1H NMR (DMSO) δ 10.90 (s, 1H), 10.28 (s, 1H), 9.90 (m, 1H), 8.48 (s, 1H), 7.80 (m, 3H), 7.45 (m, 3H), 7.27 (s, 1H), 7.01 (m, 1H), 6.92 (m, 1H), 6.70 (m, 1H), 6.62 (m, 1H), 6.36 (m, 1H), 4.90 (m, 1H), 3.68 (s, 3H), 3.20 (m, 4H), 2.72 (3H), 2.22 (m, 1H), 2.02 (m, 2H), 1.80 (m, 1H); LC/MS (m/z) 657.3 (MH+). |
| 103 | 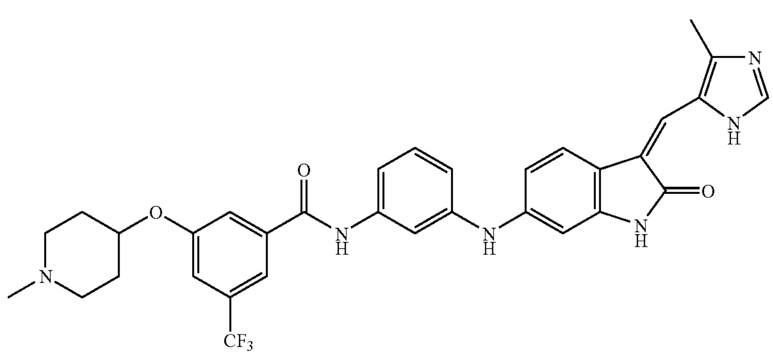 | $^1$H NMR (DMSO-$d_6$) δ 11.26 (s, 1H), 10.53 (d, 1H), 9.01 (d, 1H), 7.98-7.87 (m, 2H), 7.80-7.76 (m, 2H), 7.61-7.58 (m, 2H), 7.34-7.28 (m, 2H), 6.90 (d, 1H), 6.81 (d, 1H), 6.70 (d, 1H), 3.49-3.46 (m, 1H), 3.40-3.00 (m, 4H), 2.77-2.73 (m, 3H), 2.40-1.90 (m, 4H); LC/MS (m/z) 617.2 (MH+) |

TABLE 1-continued

| Compound Number | Structure | Physical Data $^1$H NMR 400 MHz (DMSO-$d_6$) and/or MS(m/z) |
|---|---|---|
| 104 | 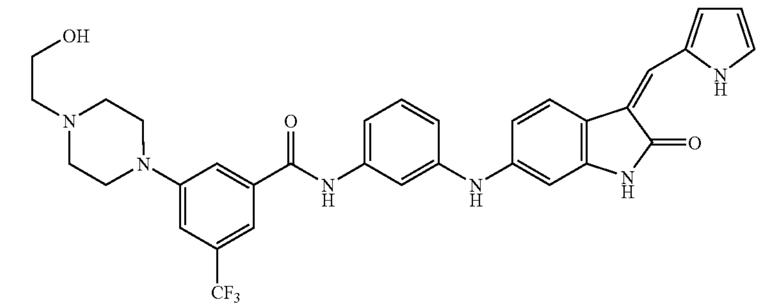 | LC/MS (m/z) 617.2 (MH$^+$) |
| 105 | 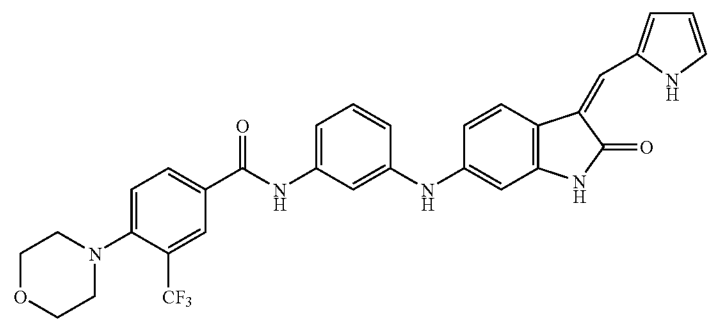 | LC/MS (m/z) 574.2 (MH$^+$) |
| 106 | 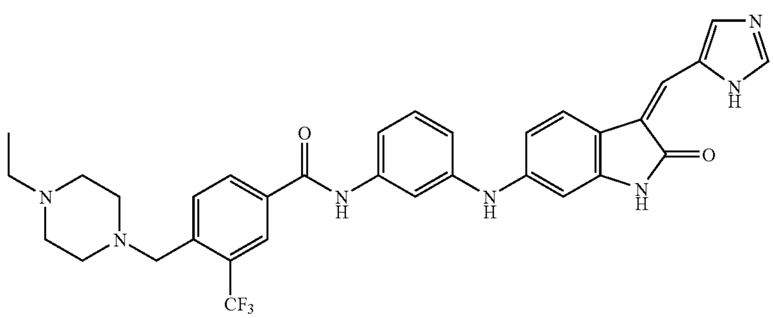 | LC/MS (m/z) 616.2 (MH$^+$) |
| 107 | 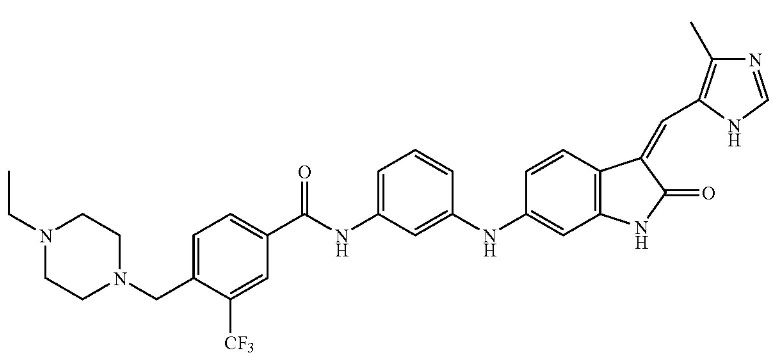 | LC/MS (m/z) 630.5 (MH$^+$). |

TABLE 1-continued

| Compound Number | Structure | Physical Data ¹H NMR 400 MHz (DMSO-$d_6$) and/or MS(m/z) |
|---|---|---|
| 108 | 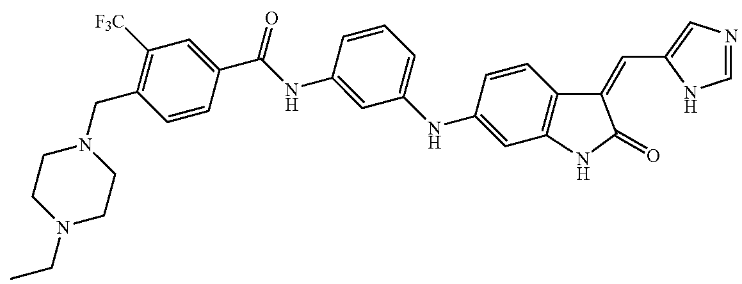 | ¹H NMR (DMSO-$d_6$) δ 11.09 (s, 1H), 10.49 (s, 1H), 8.95 (s, 1H), 8.73 (s, 1H), 8.29-8.28 (m, 2H), 8.14 (s, 1H), 7.93 (d, 1H), 7.53-7.50 (m, 2H), 7.34-7.26 (m, 2H), 6.91 (d, 1H), 6.79 (d, 1H), 6.69 (d, 1H), 3.43 (m, 2H), 3.11-3.09 (m, 2H), 2.98-2.88 (m, 4H), 2.61-2.58 (m, 2H), 1.25 (t, 3H); LC/MS (m/z) 616.3 (MH⁺) |
| 109 | 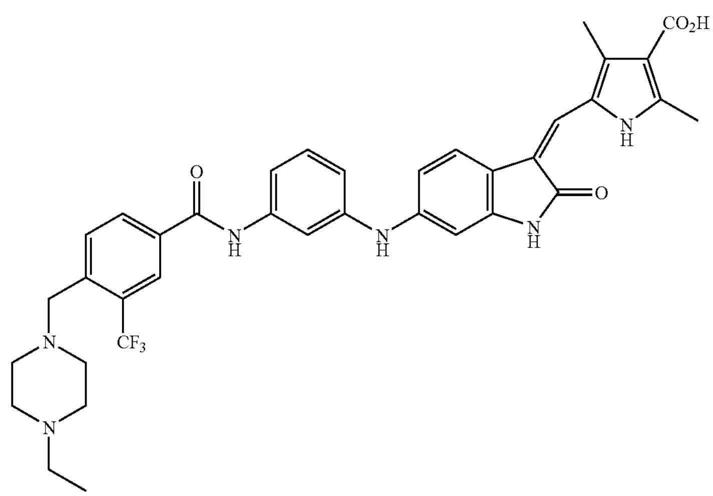 | LC/MS (m/z) 687.3 (MH⁺) |
| 110 | 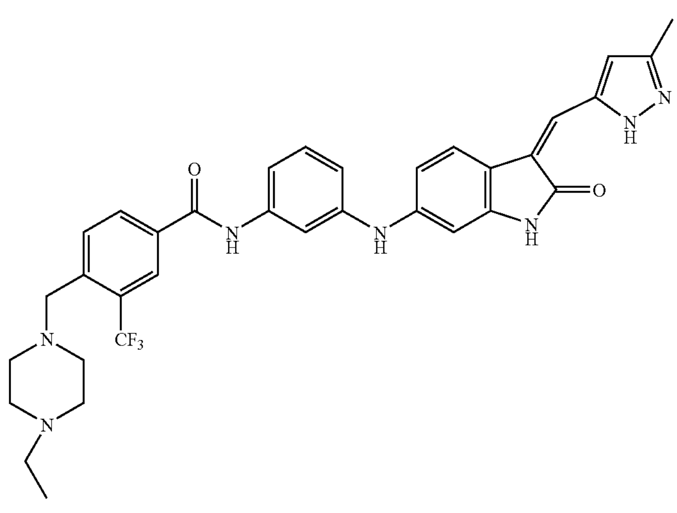 | LC/MS (m/z) 630.2 (MH⁺) |

TABLE 1-continued
| Compound Number | Structure | Physical Data ¹H NMR 400 MHz (DMSO-$d_6$) and/or MS(m/z) |
|---|---|---|
| 111 | 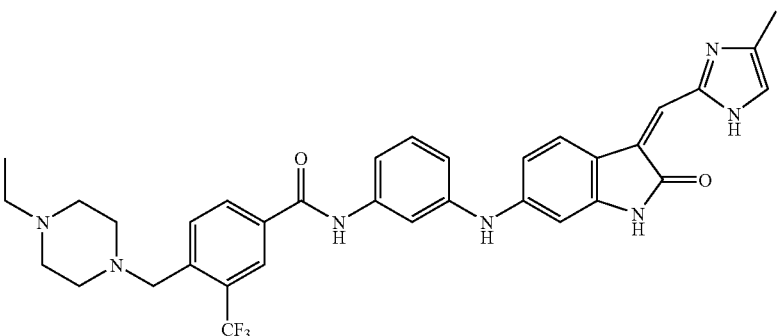 | LC/MS (m/z) 630.2 (MH+) |
| 112 | 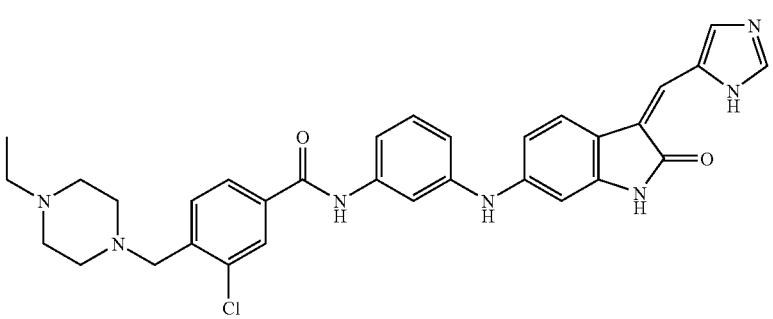 | LC/MS (m/z) 582.3 (MH+) |
| 113 | 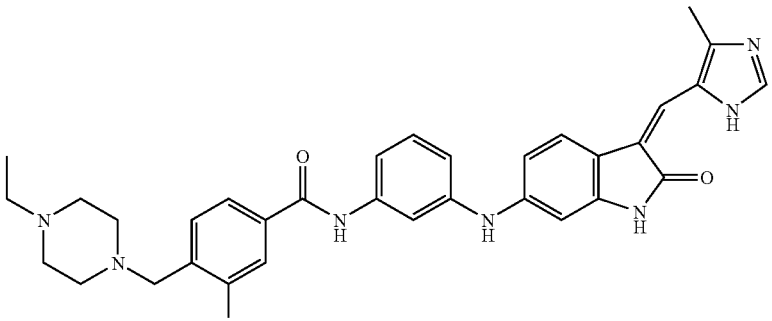 | ¹H NMR (DMSO-$d_6$) δ 11.26 (s, 1H), 10.44 (s, 1H), 9.02 (d, 1H), 8.13 (s, 1H), 8.03-7.98 (m, 1H), 7.98-7.88 (b, 1H), 7.80 (s, 1H), 7.77 (d, 1H), 7.58 (s, 1H), 7.34-7.24 (m, 2H), 6.90 (d, 1H), 6.80 (d, 1H), 6.70 (d, 1H), 3.54-3.50 (m, 2H), 3.40-3.00 (m, 8H), 2.57 (s, 3H), 1.25 (t, 3H); LC/MS (m/z) 596.2 (MH+) |
| 114 | 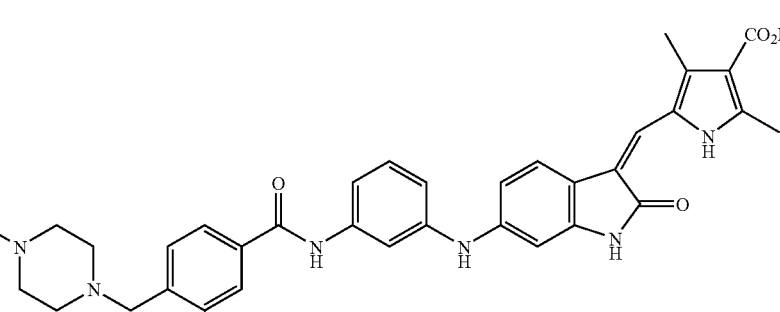 | ¹H NMR (DMSO-$d_6$) δ 10.84 (s, 1H), 10.35 (s, 1H), 8.12 (s, 1H), 7.99 (d, 1H), 7.94-7.86 (b, 1H), 7.71 (s, 1H), 7.64 (d, 1H), 7.44 (s, 1H), 7.28-7.20 (m, 2H), 6.84 (d, 1H), 6.75 (d, 1H), 6.69 (s, 1H), 3.64-3.56 (m, 2H), 4.30-4.20 (m, 2H), 3.50-3.20 (m, 8H), 3.16 (s, 2H), 2.52 (s, 3H), 2.46 (s, 3H), 1.25 (t, 3H); LC/MS (m/z) 653.2 (MH+) |

TABLE 1-continued

| Compound Number | Structure | Physical Data $^1$H NMR 400 MHz (DMSO-$d_6$) and/or MS(m/z) |
|---|---|---|
| 115 | 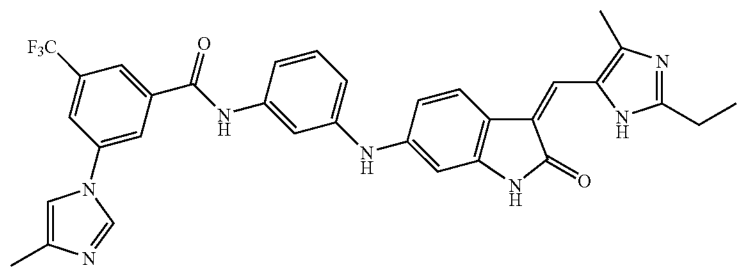 | $^1$H NMR (DMSO-$d_6$) δ 11.27 (s, 1H), 10.93 (s, 1H), 9.90 (s, 1H), 8.85 (s, 1H), 8.45 (s, 1H), 8.42 (s, 1H), 8.32 (s, 1H), 7.86 (s, 1H), 7.75 (d, 1H), 7.58 (s, 1H), 7.41 (d, 1H), 7.30 (t, 1H), 6.95-6.91 (dd, 1H), 6.85-6.81 (dd, 1H), 6.73 (d, 1H), 3.03 (q, 2H), 2.55 (s, 3H), 2.37 (s, 3H), 1.36 (t, 3H); LC/MS (m/z) 612.2 (MH+) |
| 116 | 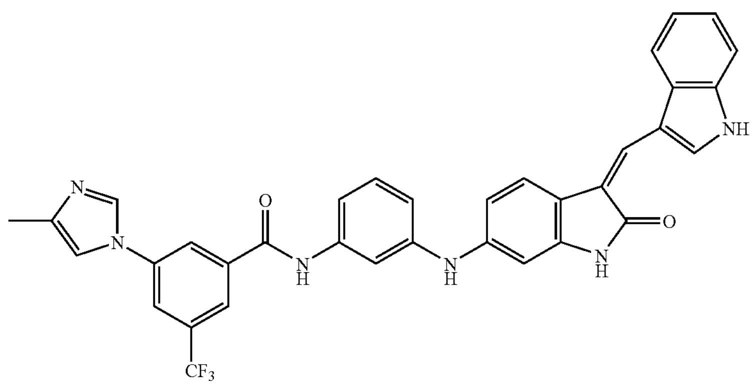 | LC/MS (m/z) 619.2 (MH+) |
| 117 | 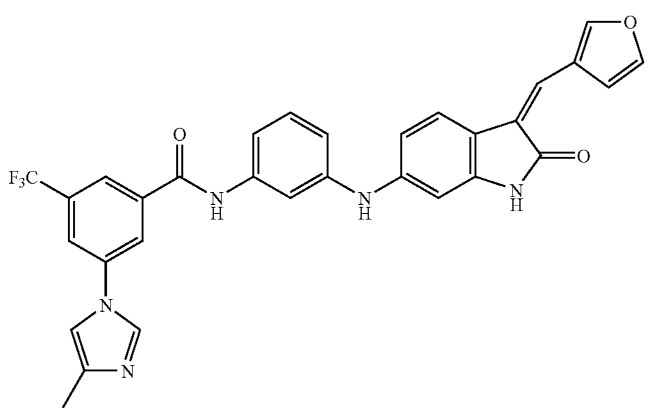 | LC/MS (m/z) 570.2 (MH+) |
| 118 | 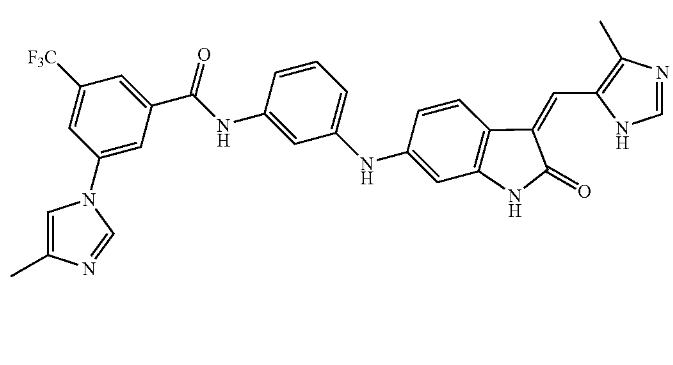 | $^1$H NMR (DMSO-$d_6$) δ 11.23 (s, 1H), 10.94 (s, 1H), 9.89 (s, 1H), 9.00 (s, 1H), 8.85 (s, 1H), 8.45 (s, 1H), 8.42 (s, 1H), 8.32 (s, 1H), 7.87 (s, 1H), 7.76 (d, 1H), 7.57 (s, 1H), 7.42 (d, 1H), 7.30 (t, 1H), 6.93-6.90 (m, 1H), 6.83-6.80 (m, 1H), 6.71 (d, 1H), 2.57 (s, 3H), 2.37 (d, 3H); LC/MS (m/z) 584.2 (MH+) |

TABLE 1-continued

| Compound Number | Structure | Physical Data $^1$H NMR 400 MHz (DMSO-$d_6$) and/or MS(m/z) |
|---|---|---|
| 119 | 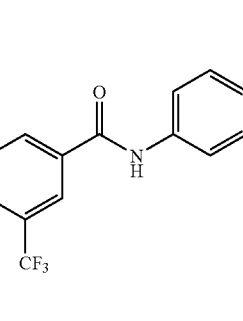 | $^1$H NMR (DMSO-$d_6$) δ 11.34 (s, 1H), 10.96 (s, 1H), 9.84 (s, 1H), 9.07 (s, 1H), 8.84 (s, 1H), 8.44 (s, 1H), 8.42 (s, 1H), 8.30 (s, 1H), 7.89 (s, 1H), 7.57-7.53 (m, 2H), 7.50-7.46 (m, 1H), 7.34 (t, 1H), 7.27 (s, 1H), 2.38 (s, 3H), 2.37 (d, 3H); LC/MS (m/z) 584.2 (MH+) |
| 120 | 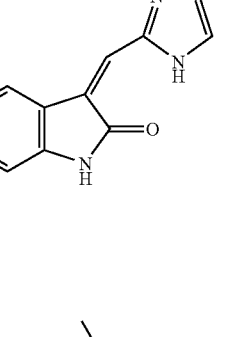 | $^1$H NMR (DMSO-$d_6$) δ 10.81 (s, 1H), 10.75 (s, 1H), 9.89 (d, 1H), 8.76 (s, 1H), 8.44 (m, 2H), 8.29 (s, 1H), 7.76 (s, 1H), 7.64 (d, 1H), 7.44 (s, 1H), 7.32 (d, 1H), 7.26 (t, 1H), 6.89-6.85 (m, 1H), 6.80-6.76 (m, 1H), 6.70 (d, 1H), 2.51 (s, 3H), 2.46 (s, 3H), 2.38 (s, 3H); LC/MS (m/z) 641.2 (MH+) |
| 121 | 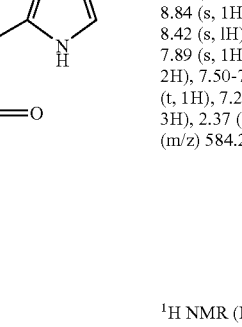 | $^1$H NMR (DMSO-$d_6$) δ 11.12 (s, 1H), 10.90 (s, 1H), 9.82 (s, 1H), 9.05 (s, 1H), 8.82 (s, 1H), 8.44 (s, 1H), 8.41 (s, 1H), 8.29 (s, 1H), 8.18 (s, 1H), 7.84 (s, 1H), 7.54-7.49 (m, 2H), 7.44-7.40 (m, 1H), 7.31 (t, 1H), 6.96-6.92 (m, 1H), 6.83-6.79 (m, 1H), 6.70 (d, 1H), 2.37 (s, 3H); LC/MS (m/z) 570.2 (MH+) |
| 122 | 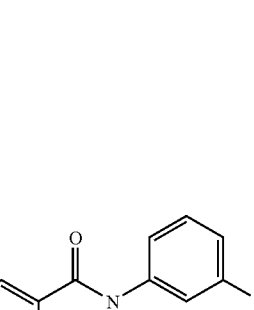 | $^1$H NMR (DMSO-$d_6$) δ 10.98 (s, 1H), 10.81 (s, 1H), 9.93 (s, 1H), 8.79 (s, 1H), 8.46 (s, 1H), 8.44 (s, 1H), 8.32 (s, 1H), 7.95-7.92 (m, 1H), 7.78 (s, 1H), 7.50 (d, 1H), 7.47 (s, 1H), 7.36 (d, 1H), 7.30-7.25 (t, 1H), 7.08 (s, 1H), 6.92-6.88 (m, 1H), 6.81-6.77 (m, 1H), 6.68 (d, 1H), 2.38 (s, 3H); LC/MS m/z 594.2 (MH+) |
| 123 | 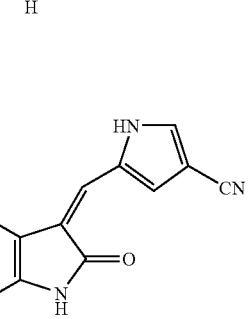 | $^1$H NMR (DMSO-$d_6$) δ 12.86 (s, 1H), 10.91 (s, 1H), 10.80 (s, 1H), 9.92 (d, 1H), 8.79 (s, 1H), 8.45 (s, 2H), 8.31 (s, 1H), 7.80 (s, 1H), 7.65-7.61 (m, 2H), 7.59-7.52 (m, 2H), 7.37 (d, 1H), 7.31-7.20 (m, 2H), 7.06 (t, 1H), 7.01 (s, 1H), 6.92-6.89 (dd, 1H), 6.82-6.78 (dd, 1H), 6.70 (d, 1H), 2.38 (s, 3H); LC/MS (m/z) 619.2 (MH+) |

TABLE 1-continued

| Compound Number | Structure | Physical Data<br>$^1$H NMR 400 MHz<br>(DMSO-$d_6$) and/or<br>MS(m/z) |
|---|---|---|
| 124 | 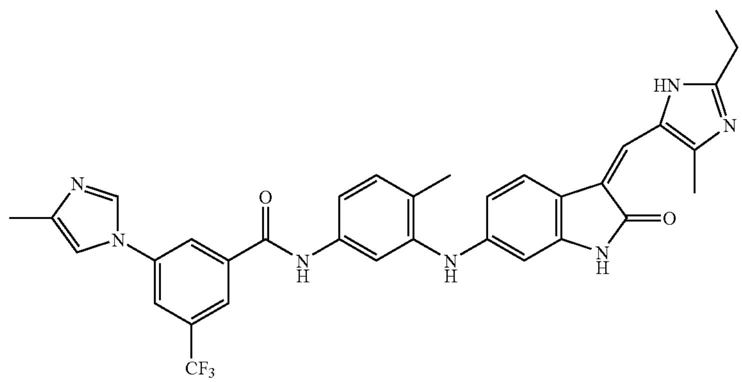 | 1H NMR (DMSO) δ 11.17 (s, 1H), 10.50 (s, 1H), 9.00 (s, 1H), 8.50 (s, 1H), 8.32 (s, 1H), 8.28 (s, 1H), 7.98 (s, 1H), 7.92 (s, 1H), 7.81 (s, 1H), 7.69 (d, 1H), 7.52 (s, 1H), 7.40 (d, 1H), 7.26 (d, 1H), 3.01 (q, 2H), 2.52 (s, 3H), 2.27 (s, 3H), 2.21 (s, 3H), 1.34 (t, 3H); LC/MS (m/z) 626.3 (MH$^+$). |
| 125 | 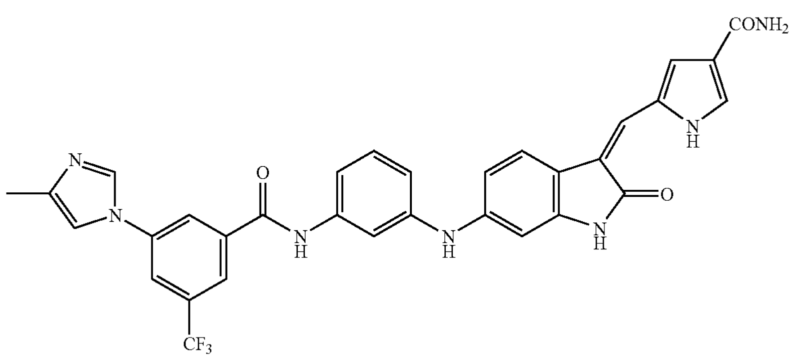 | $^1$H NMR (DMSO-$d_6$) δ 10.86 (s, 1H), 10.80 (s, 1H), 9.94 (d, 1H), 8.79 (s, 1H), 8.46 (s, 1H), 8.44 (s, 1H), 8.32 (s, 1H), 7.77 (s, 1H), 7.71-7.70 (m, 1H), 7.53 (d, 1H), 7.45 (s, 1H), 7.34 (d, 1H), 7.26 (t, 1H), 7.05 (s, 1H), 6.90-6.86 (m, 1H), 6.80-6.76 (m, 1H), 6.68 (d, 1H), 2.38 (s, 3H); LC/MS (m/z) 612.2 (MH+) |
| 126 | 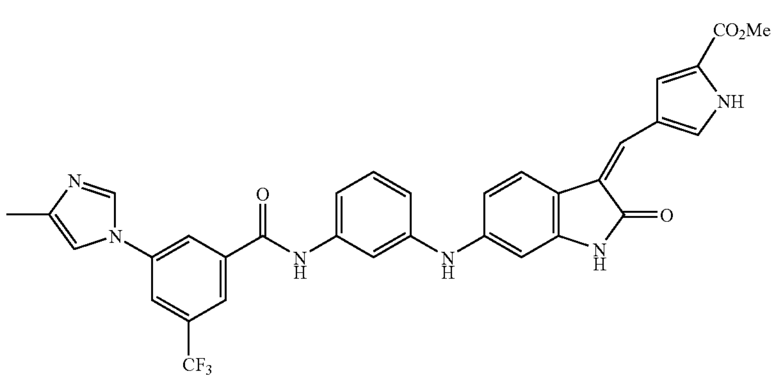 | LC/MS (m/z) 627.2 (MH+) |

TABLE 1-continued

| Compound Number | Structure | Physical Data $^1$H NMR 400 MHz (DMSO-$d_6$) and/or MS(m/z) |
|---|---|---|
| 127 | 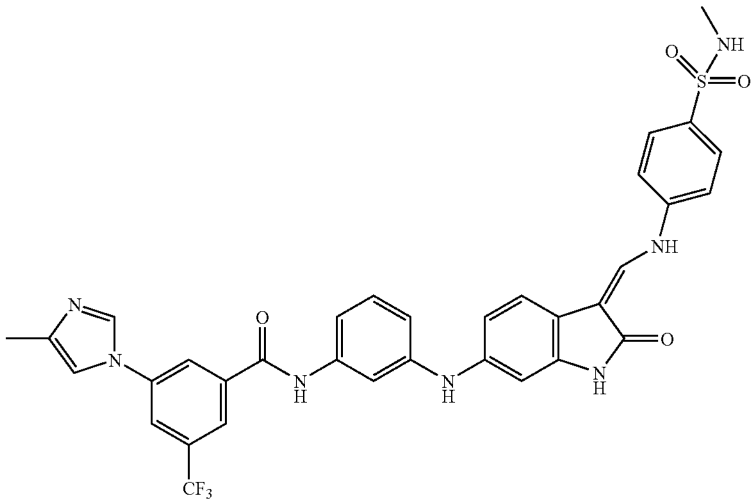 | LC/MS (m/z) 687.2 (MH+) |
| 128 | 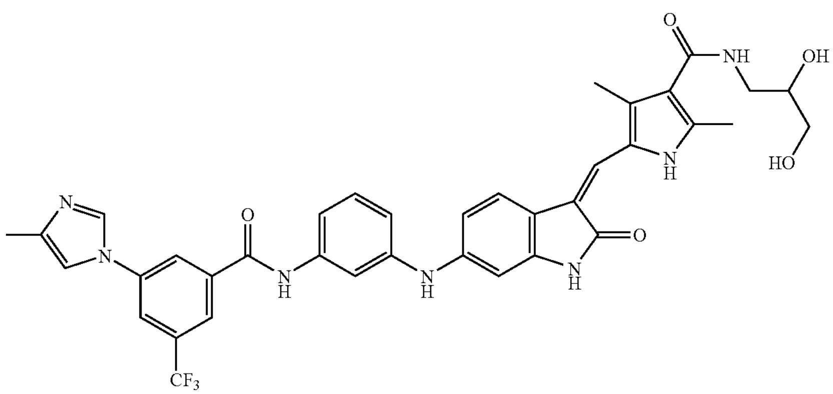 | $^1$H NMR (DMSO-$d_6$) δ 10.78 (s, 1H), 10.42 (s, 1H), 8.43 (d, 1H), 8.40 (s, 2H), 8.24 (s, 1H), 8.15 (s, 1H), 7.72 (s, 1H), 7.70 (s, 1H), 7.64 (d, 1H), 7.45 (t, 1H), 7.41 (s, 1H), 7.28-7.20 (m, 2H), 6.86 (d, 1H), 6.77 (d, 1H), 6.69 (d, 1H), 4.83 (d, 1H), 4.62 (t, 1H), 3.64-3.56 (m, 1H), 3.23-3.14 (m, 1H), 3.40-3.30 (m, 4H), 2.43 (3, 3H), 2.38 (s, 3H), 2.19 (s, 3H); LC/MS (m/z) 714.3 (MH+) |
| 129 | 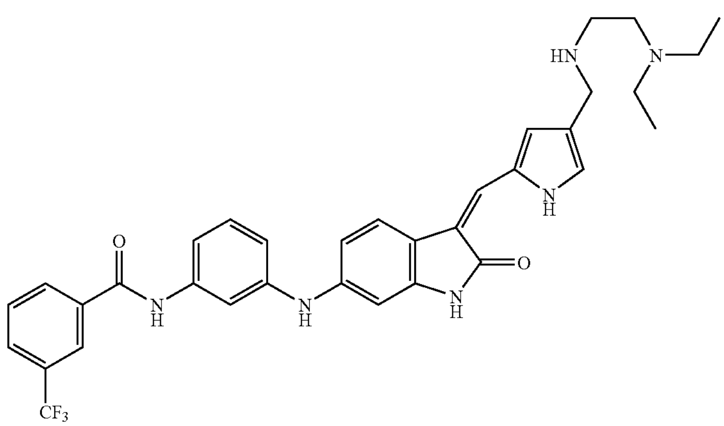 | LC/MS (m/z) 617.2 (MH+). |

TABLE 1-continued

| Compound Number | Structure | Physical Data<br>¹H NMR 400 MHz (DMSO-d₆) and/or MS(m/z) |
|---|---|---|
| 130 | 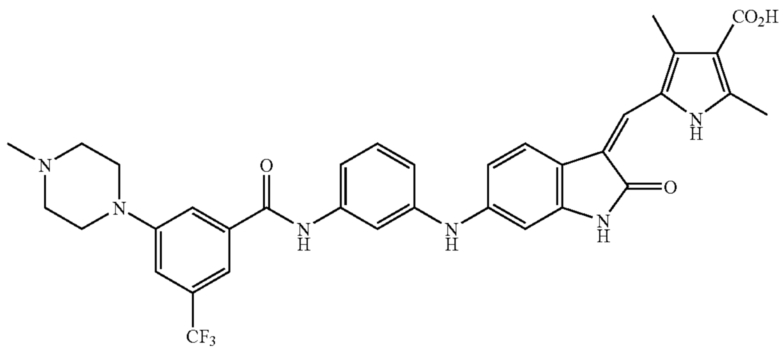 | ¹H NMR (DMSO-d₆) δ 10.83 (s, 1H), 10.72-10.62 (b, 1H), 10.35 (s, 1H), 7.78 (s, 1H), 7.70 (s, 1H), 7.65 (d, 1H), 7.50 (s, 1H), 7.44 (s, 1H), 7.23 (d, 1H), 6.86-6.81 (b, 1H), 6.78-6.74 (dd, 1H), 6.69 (d, 1H), 4.10 (d, 2H), 3.52 (d, 2H), 3.38-3.10 (m, 4H), 2.83 (d, 3H), 2.52 (s, 3H), 2.46 (s, 3H); LC/MS (m/z) 659.2 (MH+) |
| 131 | 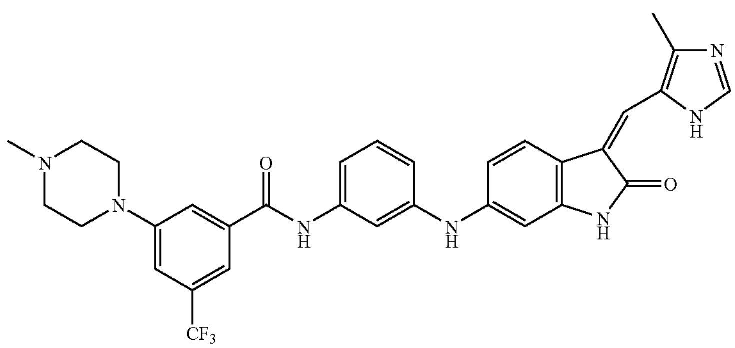 | ¹H NMR (DMSO-d₆) δ 11.24 (s, 1H), 11.12-11.00 (b, 1H), 10.48 (s, 1H), 9.00 (s, 1H), 8.74 (s, 1H), 7.81 (d, 2H), 7.76 (d, 3H), 7.70 (s, 1H), 7.58 (s, 1H), 7.50 (s, 1H), 7.32-7.24 (m, 2H), 6.92-6.88 (dd, 1H), 6.84-6.78 (dd, 1H), 6.69 (d, 1H), 4.11 (d, 2H), 3.51 (d, 2H), 3.32-3.22 (m, 2H), 3.20-3.10 (m, 2H), 2.82 (s, 3H), 2.57 (s, 3H); LC/MS (m/z) 602.3 (MH+) |
| 132 | 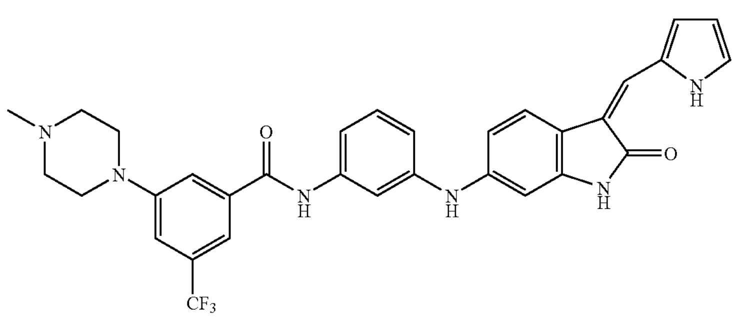 | ¹H NMR (DMSO-d₆) δ 10.77 (s, 1H), 10.37 (s, 1H), 7.79 (s, 1H), 7.72-7.66 (m, 2H), 7.52-7.46 (m, 3H), 7.28-7.20 (m, 3H), 6.86-6.82 (m, 1H), 6.78-6.74 (dd, 1H), 6.76-6.70 (m, 1H), 6.67 (d, 1H), 6.32-6.27 (m, 1H), 4.10 (d, 2H), 3.51 (d, 2H), 3.26 (t, 2H), 3.20-3.10 (m, 2H), 2.82 (d, 3H); LC/MS (m/z) 587.2 (MH⁺) |
| 133 | 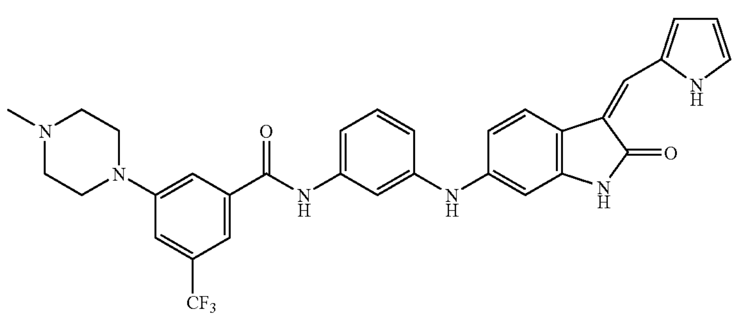 | ¹H NMR (DMSO) δ 10.90 (s, 1H), 10.40 (s, 1H), 7.71 (s, 1H), 7.64 (m, 2H), 7.56 (m, 2H), 7.52 (m, 1H), 7.39 (m, 1H), 6.80 (m, 1H), 6.71 (t, 1H), 7.34 (m, 2H), 6.85 (dd, 1H), 6.51 (d, 1H), 6.45 (m, 1H), 3.30 (m, 4H), 2.46 (m, 4H), 2.23 (s, 3H). |

TABLE 1-continued

| Compound Number | Structure | Physical Data ¹H NMR 400 MHz (DMSO-$d_6$) and/or MS(m/z) |
|---|---|---|
| 134 | 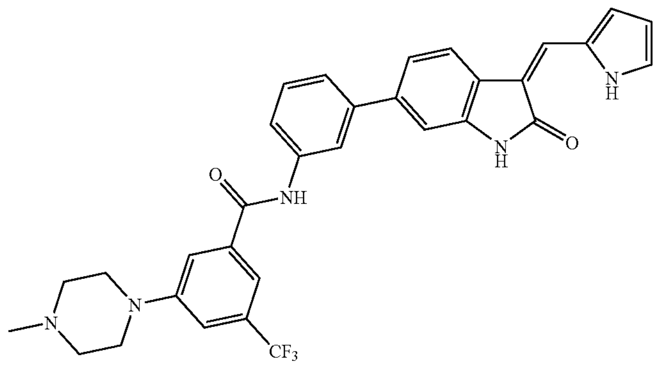 | ¹H NMR (DMSO) δ 11.01 (s, 1H), 10.49 (s, 1H), 8.04 (s, 1H), 7.70 (m, 5H), 7.45 (m, 5H), 7.08 (m, 1H), 6.80 (m, 2H), 3.50 (m, 2H), 3.15 (m, 1H), 6.31 (m, 1H), 4.05 (m, 4H), 2.78 (s, 3H); LC/MS (m/z) 572.2 (MH⁺). |
| 135 | 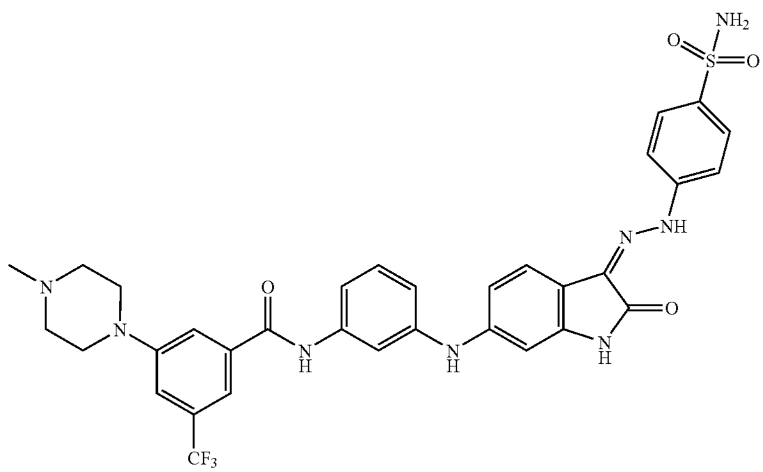 | LC/MS (m/z) 693.2 (MH⁺). |
| 136 | 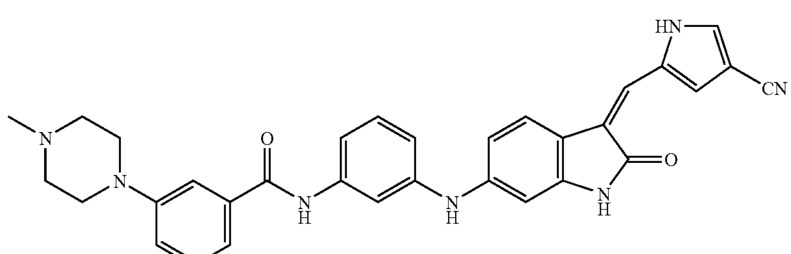 | ¹H NMR (DMSO-$d_6$) δ 10.94 (s, 1H), 10.78-10.66 (b, 1H), 10.36 (s, 1H), 7.94-7.91 (m, 1H), 7.79 (s, 1H), 7.72-7.69 (m, 2H), 7.46 (s, 1H), 7.30-7.23 (m, 2H), 7.07 (s, 1H), 6.89-6.85 (m, 1H), 6.79-6.75 (m, 1H), 6.67 (d, 1H), 4.10 (d, 2H), 3.52 (d, 2H), 3.30-3.10 (m, 4H), 2.83 (d, 3H); LC/MS (m/z) 612.3 (MH⁺) |
| 137 | 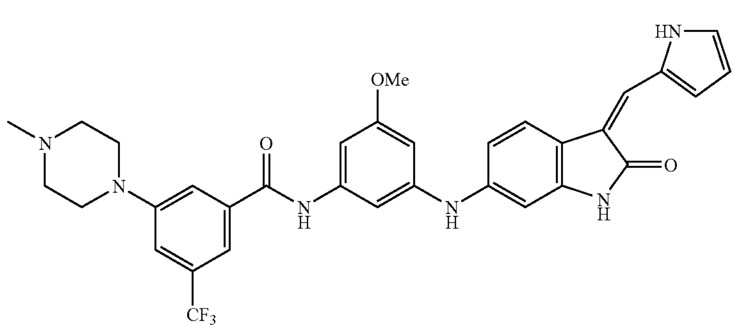 | LC/MS (m/z) 617.3 (MH⁺). |

| Compound Number | Structure | Physical Data<br>¹H NMR 400 MHz<br>(DMSO-d₆) and/or<br>MS(m/z) |
|---|---|---|
| 138 | (structure) | ¹H NMR (DMSO-d₆) δ 11.15-11.05 (b, 1H), 10.86 (d, 1H), 10.41 (d, 1H), 7.81 (s, 1H), 7.72-7.67 (m, 3H), 7.55-7.46 (m, 2H), 7.30-7.20 (m, 2H), 7.05 (s, 1H), 6.88-6.82 (m, 1H), 6.78-6.73 (m, 1H), 6.69-6.64 (m, 1H), 4.12-4.08 (d, 2H), 3.52-3.49 (d, 2H), 3.35-3.23 (m, 2H), 3.20-3.09 (m, 2H), 2.81 (s, 3H); LC/MS (m/z) 630.2 (MH⁺) |
| 139 | (structure) | LC/MS (m/z) 642.2 (MH⁺). |
| 140 | (structure) | LC/MS (m/z) 633.3 (MH⁺). |
| 141 | (structure) | ¹H NMR (DMSO-d₆) δ 10.96 (s, 1H), 10.31 (s, 1H), 7.94-7.93 (m, 1H), 7.74- (s, 1H), 7.70 (s, 1H), 7.50 (d, 1H), 7.46 (s, 1H), 7.40 (s, 1H), 7.27-7.25 (m, 2H), 7.07 (s, 1H), 6.87 (d, 1H), 6.76 (d, 1H), 6.67 (d, 1H), 3.73-3.67 (m, 3H), 3.09-3.03 (m, 2H); 1.88-1.84 (m, 2H), 1.54-1.46 (m, 2H); LC/MS (m/z) 613.2 (MH⁺) |

TABLE 1-continued

| Compound Number | Structure | Physical Data $^1$H NMR 400 MHz (DMSO-$d_6$) and/or MS(m/z) |
|---|---|---|
| 142 | 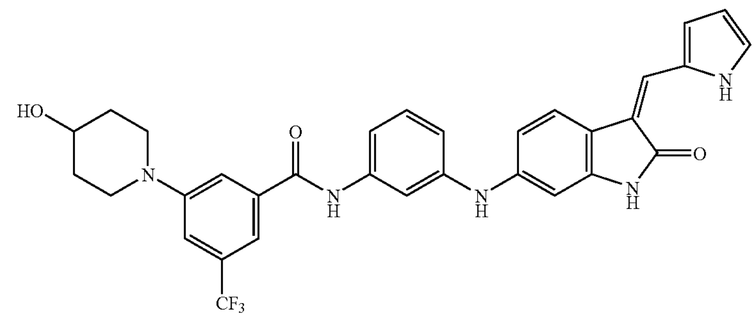 | LC/MS (m/z) 588.2 (MH$^+$) |
| 143 | 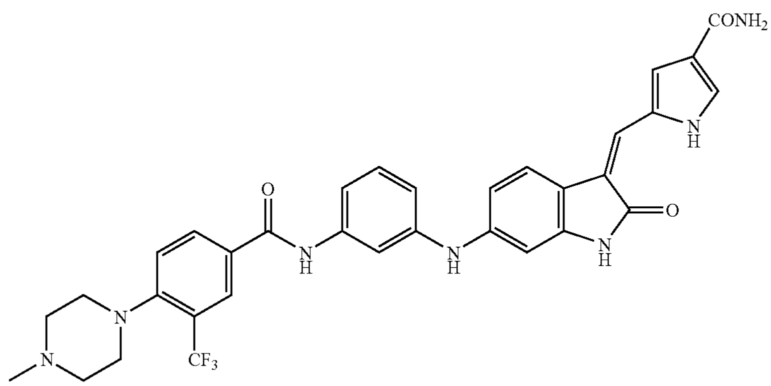 | $^1$H NMR (DMSO-$d_6$) δ 11.05-10.95 (b, 1H), 10.85 (s, 1H), 10.38 (s, 1H), 8.30-8.25 (m, 2H), 7.71-7.69 (m, 2H), 7.65 (d, 1H), 7.53 (d, 1H), 7.46 (s, 1H), 7.39-7.20 (m, 2H), 7.04 (s, 1H), 6.85 (d, 1H), 6.76 (d, 1H), 6.67 (d, 1H), 3.50 (d, 2H), 3.33-3.24 (m, 2H), 3.23-3.10 (m, 4H), 2.84 (d, 3H); LC/MS (m/z) 630.3 (MH$^+$) |
| 144 | 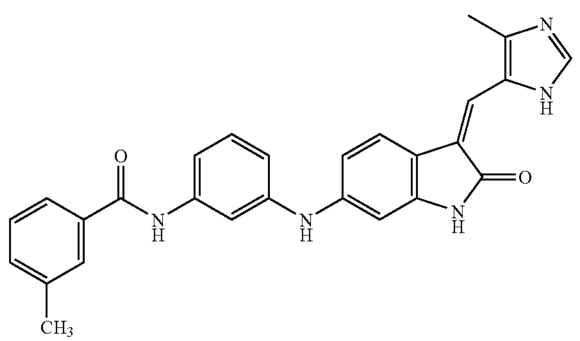 | LC/MS (m/z) 450.2 (MH$^+$). |
| 145 | 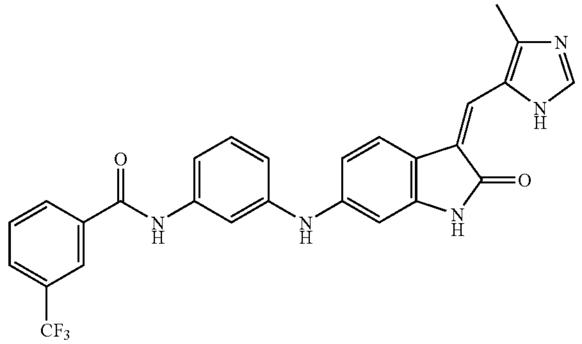 | $^1$H NMR (DMSO) δ 11.22 (s, 1H), 11.49 (s, 1H), 8.97 (s, 1H), 8.73 (s, 1H), 8.28 (m, 1H), 8.26 (m, 1H), 7.97 (m, 1H), 7.78 (m, 3H), 7.57 (s, 1H), 7.28 (m, 2H), 6.90 (m, 1H), 6.80 (dd, 1H), 6.69 (d, 1H), 2.56 (s, 3H); LC/MS (m/z) 504.2 (MH$^+$). |

TABLE 1-continued

| Compound Number | Structure | Physical Data <br> ¹H NMR 400 MHz (DMSO-d₆) and/or MS(m/z) |
|---|---|---|
| 146 | 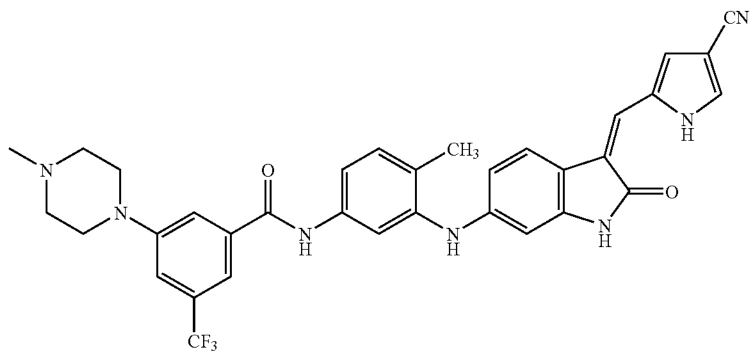 | LC/MS (m/z) 626.2 (MH⁺). |
| 147 | 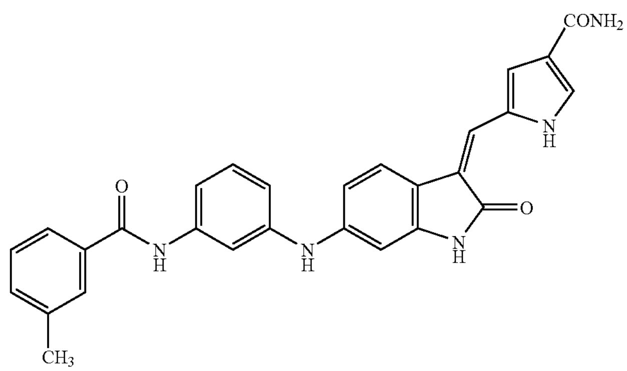 | LC/MS (m/z) 478.2 (MH⁺). |
| 148 | 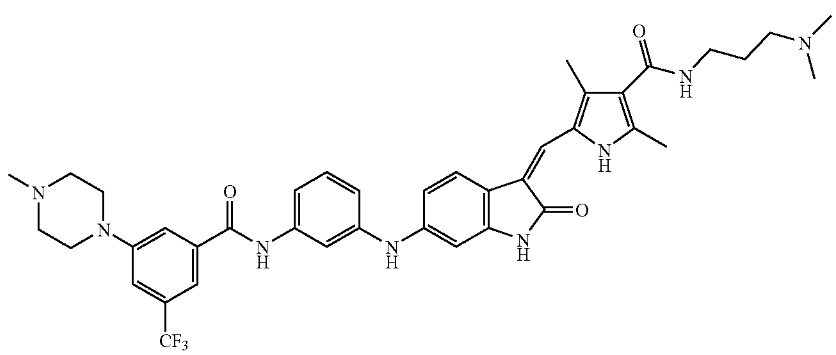 | ¹H NMR (DMSO-d₆) δ 11.20-11.08 (b, 1H), 10.80 (s, 1H), 10.42 (s, 1H), 10.36-10.29 (b, 1H), 7.81 (s, 1H), 7.76-7.68 (m, 3H), 7.63 (d, 1H), 7.49 (s, 1H), 7.41 (s, 1H), 7.23 (d, 1H), 6.86-6.81 (m, 1H), 6.76-6.75 (dd, 1H), 6.70 (d, 1H), 4.10 (d, 2H), 3.50 (d, 1H), 3.34-3.24 (m, 4H), 3.20-3.04 (m, 4H), 2.81 (s, 3H), 2.75 (d, 6H), 2.44 (s, 3H), 2.39 (s, 3H), 1.94-1.86 (m, 2H); LC/MS (m/z) 743.2 (MH⁺). |
| 149 | 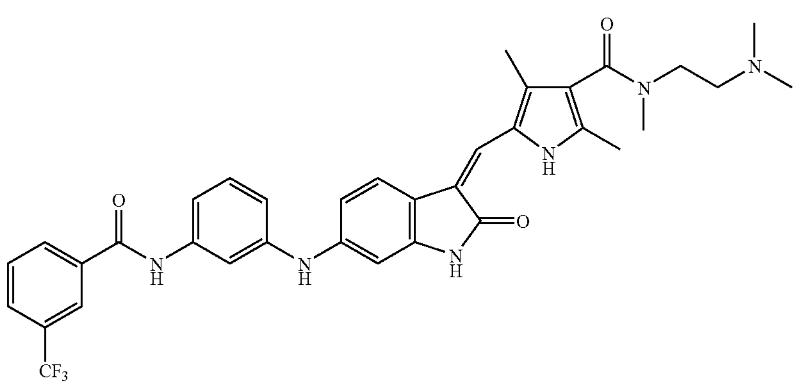 | ¹H NMR (DMSO) δ 10.94 (s, 1H), 10.56 (s, 1H), 8.26-8.23 (m, 2H), 7.97-7.95 (m, 1H), 7.82-7.74 (m, 2H); 7.71-7.64 (m, 2H), 7.45-7.33 (m, 1H), 6.90-6.80 (m, 1H), 7.74-7.71 (m, 1H), 6.53-6.51 (m, 1H), 2.96-2.84 (m, 13H) 2.30 (s, 6 H); LC/MS (m/z) 646.4 (MH⁺). |

TABLE 1-continued
| Compound Number | Structure | Physical Data ¹H NMR 400 MHz (DMSO-d₆) and/or MS(m/z) |
|---|---|---|
| 150 | 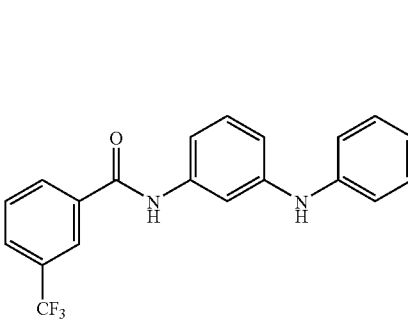 | ¹H NMR (400 MHz, DMSO) δ 11.02 (s, 1H), 10.57 (s, 1H), 8.26-8.23 (m, 2H), 7.97-7.95 (m, 1H), 7.79-7.54 (m, 5H); 7.43-7.39 (m, 1H), 7.02 (s, 1H), 6.88-6.85 (m, 1H), 6.75-6.72 (m, 1H), 6.54-6.53 (m, 1H) 2.79 (s, 3H), 2.52-2.55 (m, 8H), 2.30 (s, 6H); LC/MS (m/z) 644.4 (MH⁺). |
| 151 | 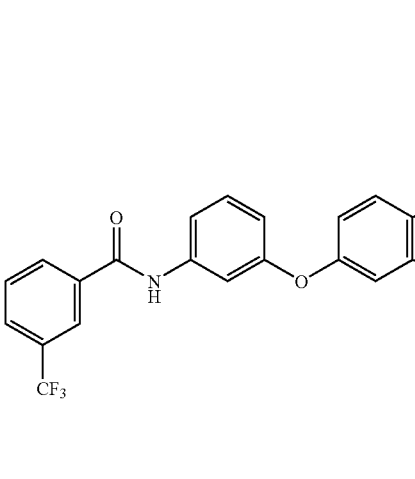 | ¹H NMR (400 MHz, DMSO) δ 10.94 (s, 1H), 10.55 (s, 1H), 8.25-8.23 (m, 2H), 7.84-7.66 (m, 3H), 7.61-7.55 (m, 3H), 7.41-7.37 (m, 1H), 6.86-6.83 (m, 1H), 6.74-6.71 (m, 1H), 6.54 (s, 1H), 3.32-3.37 (m, 2H), 3.10-3.35 (m, 2H), 2.45 (s, 3H), 2.41 (s, 3H), 1.92-1.85 (m, 2H); LC/MS (m/z) 646.4 (MH⁺). |
| 152 | 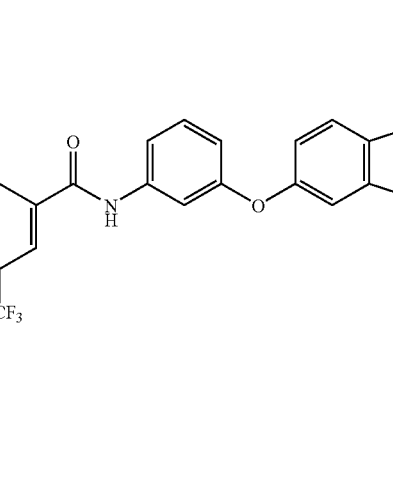 | ¹H NMR (400 MHz, DMSO) δ 10.94 (s, 1H), 10.55 (s, 1H), 8.26-8.25 (m, 2H), 7.97-7.96 (m, 1H), 7.84-7.58 (m, 6H); 7.49-7.31 (m, 1H), 6.87-6.83 (m, 1H), 6.74-6.72 (m, 1H), 6.55 (s, 1H), 3.41-3.31 (m, 2H), 3.20-3.15 (m, 4H), 2.45 (s, 3H), 3.01-3.98 (m, 2H), 2.41 (s, 6H), 1.92-1.84 (m, 6H); LC/MS (m/z) 672.4 (MH⁺). |
| 153 | 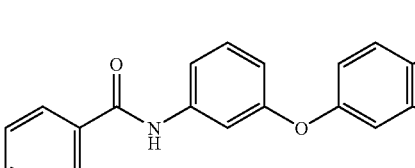 | ¹H NMR (400 MHz, DMSO) δ 10.92 (s, 1H), 10.55 (s, 1H), 8.63-8.58 (m, 1H), 8.25-8.23 (m, 2H), 7.97-7.95 (m, 1H), 7.82-7.65 (m, 3H), 7.59-7.56 (m, 3H), 7.41-7.37 (m, 1H), 6.85-6.83 (m, 1H), 6.74-6.71 (m, 1H), 6.54 (s, 1H), 2.93 (s, 6H), 2.52-2.54 (m, 4H), 2.29-2.25 (m, 6H); LC/MS (m/z) 646.3 (MH⁺). |

TABLE 1-continued

| Compound Number | Structure | Physical Data $^1$H NMR 400 MHz (DMSO-$d_6$) and/or MS(m/z) |
|---|---|---|
| 154 | 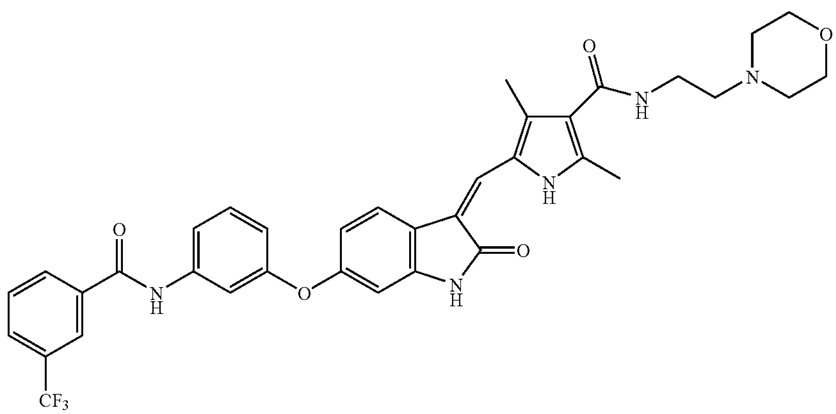 | LC/MS (m/z) 674.3 (MH$^+$). |
| 155 | 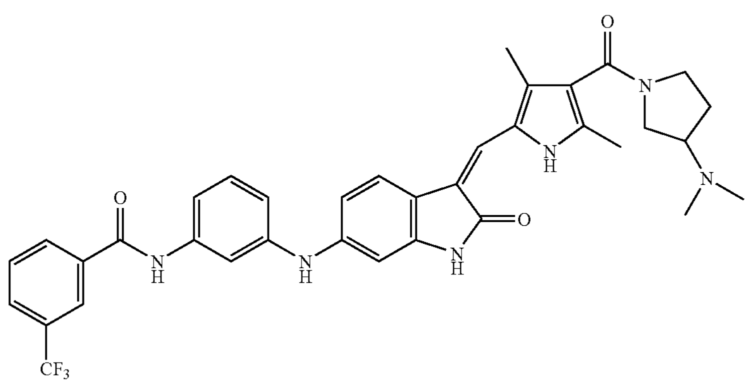 | LC/MS (m/z) 657.3 (MH$^+$). |
| 156 | 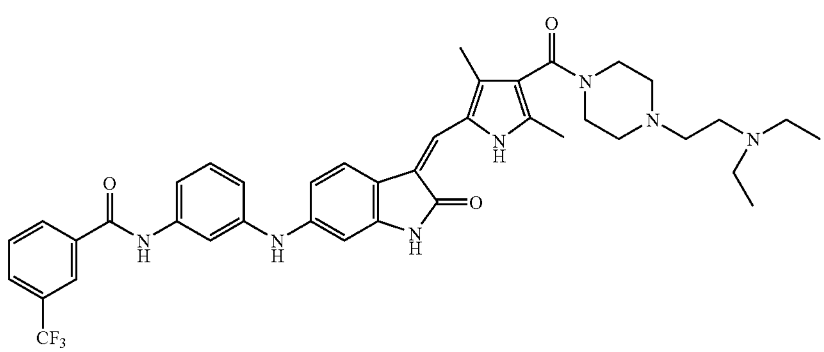 | LC/MS (m/z) 729.3 (MH$^+$). |
| 157 | 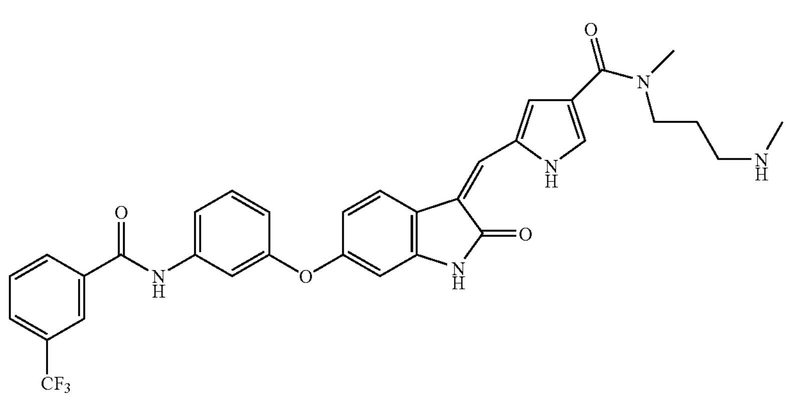 | LC/MS (m/z) 618.2 (MH$^+$). |

TABLE 1-continued

| Compound Number | Structure | Physical Data ¹H NMR 400 MHz (DMSO-$d_6$) and/or MS(m/z) |
|---|---|---|
| 158 | 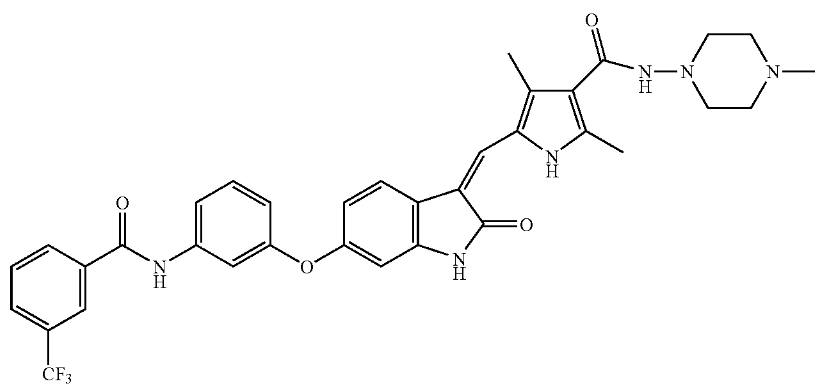 | LC/MS (m/z) 659.3 (MH⁺). |
| 159 | 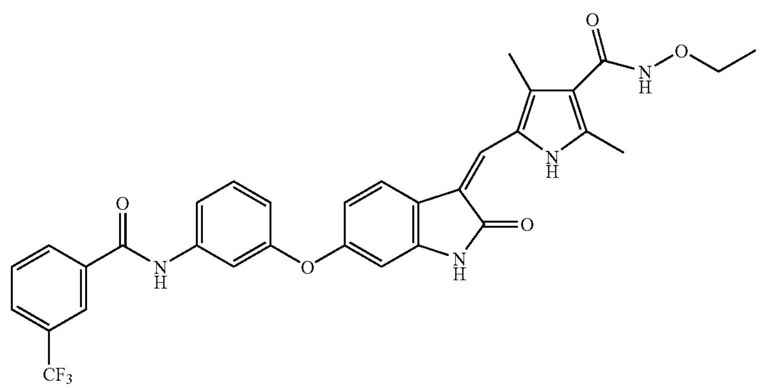 | LC/MS (m/z) 605.2 (MH⁺). |
| 160 | 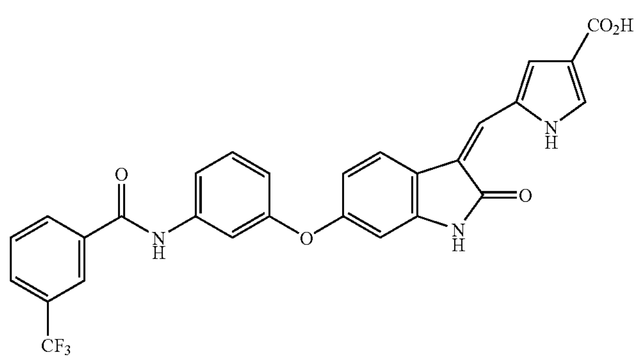 | ¹H NMR (DMSO) δ 11.02 (s, 1H), 10.53 (s, 1H), 8.26-8.22 (m, 2H), 7.79-7.73 (m, 2H), 7.68-7.55 (m, 3H); 7.44-7.39 (m, 3H), 7.10 (s, 1H), 6.88-6.85 (m, 1H), 6.75-6.73 (m, 1H), 6.53-6.52 (m, 1H); LC/MS (m/z) 534.1 (MH⁺). |
| 161 | 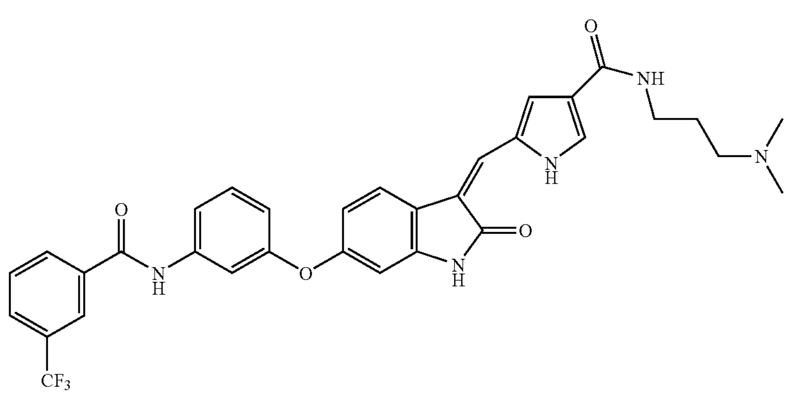 | ¹H NMR (DMSO) δ 11.01 (s, 1H), 10.56 (s, 1H), 8.35-8.32 (m, 1H), 8.26-8.23 (m, 2H), 8.00-7.95 (m, 1H); 7.79-7.66 (m, 3H), 7.62-7.57 (m, 2H), 7.42-7.38 (m, 1H), 7.17 (s, 1H), 6.87-6.84 (m, 1H), 6.75-6.72 (m, 1H) 6.53-6.51 (m, 1H), 3.34-3.27 (m, 2H), 3.09-3.04 (m, 2H), 2.76-2.75 (m, 6H); LC/MS (m/z) 618.2 (MH⁺). |

TABLE 1-continued

| Compound Number | Structure | Physical Data <br> $^1$H NMR 400 MHz (DMSO-$d_6$) and/or MS(m/z) |
|---|---|---|
| 162 | 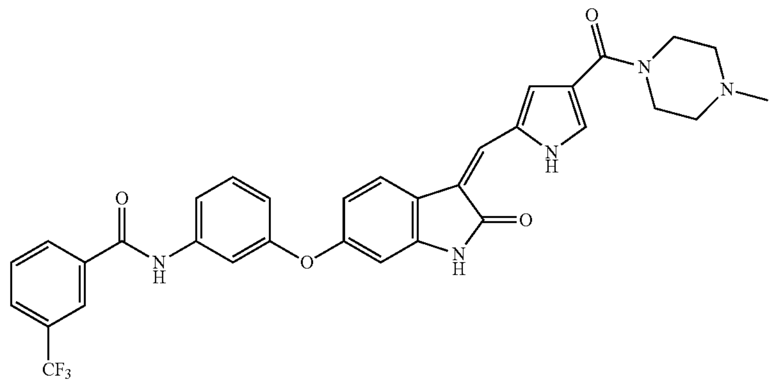 | LC/MS (m/z) 616.2 (MH$^+$). |
| 163 | 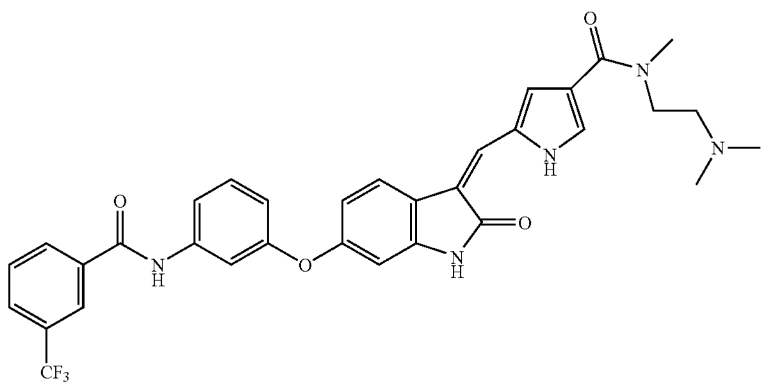 | LC/MS (m/z) 618.2 (MH$^+$). |
| 164 | 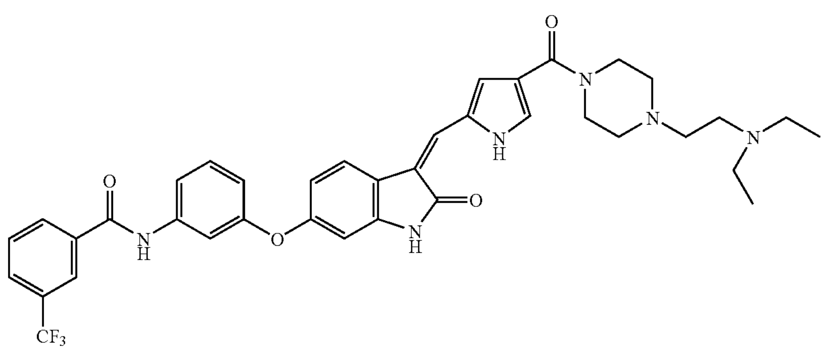 | LC/MS (m/z) 701.3 (MH$^+$). |
| 165 | 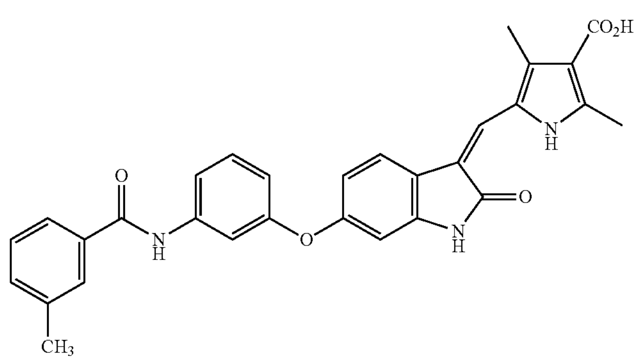 | $^1$H NMR (DMSO) δ 10.95 (s, 1H), 10.28 (s, 1H), 8.85-8.83 (m, 1H), 7.73-7.55 (m, 5H), 7.40-7.34 (m, 3H), 6.82-6.80 (m, 1H), 6.73-6.71 (m, 1H), 6.53-6.52 (m, 1H), 2.51 (s, 6H) 2.30 (s, 3H); LC/MS (m/z) 508.2 (MH$^+$). |

TABLE 1-continued

| Compound Number | Structure | Physical Data ¹H NMR 400 MHz (DMSO-$d_6$) and/or MS(m/z) |
|---|---|---|
| 166 | 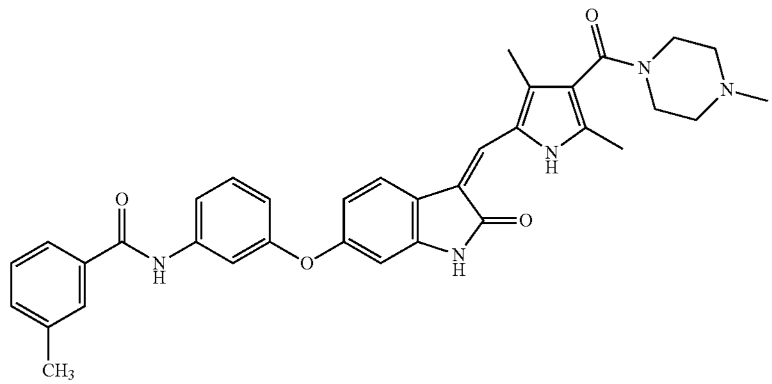 | ¹H NMR (DMSO) δ 10.93 (s, 1H), 10.29 (s, 1H), 8.82-8.80 (m, 1H), 7.73-7.70 (m, 2H), 7.60-7.57 (m, 3H), 7.42-7.34 (m, 3H), 6.82-6.79 (m, 1H), 6.73-6.71 (m, 1H), 6.53-6.52 (m, 1H) 2.81 (s, 3H) 2.51-2.53 (m, 8H) 2.38 (s, 3H), 2.33 (s, 6H); LC/MS (m/z) 590.3 (MH⁺). |
| 167 | 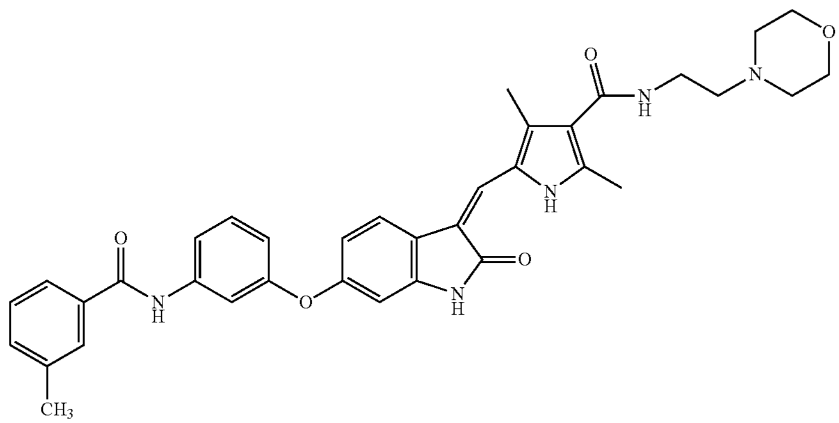 | LC/MS (m/z) 620.3 (MH⁺). |
| 168 | 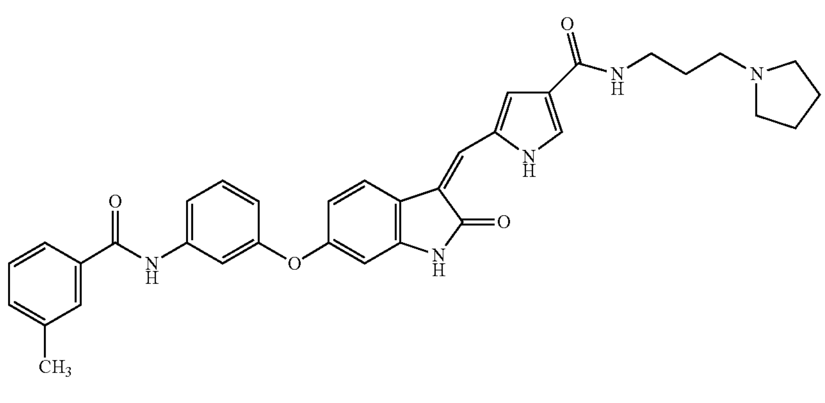 | LC/MS (m/z) 590.2 (MH⁺). |

TABLE 1-continued

| Compound Number | Structure | Physical Data ¹H NMR 400 MHz (DMSO-$d_6$) and/or MS(m/z) |
|---|---|---|
| 169 | 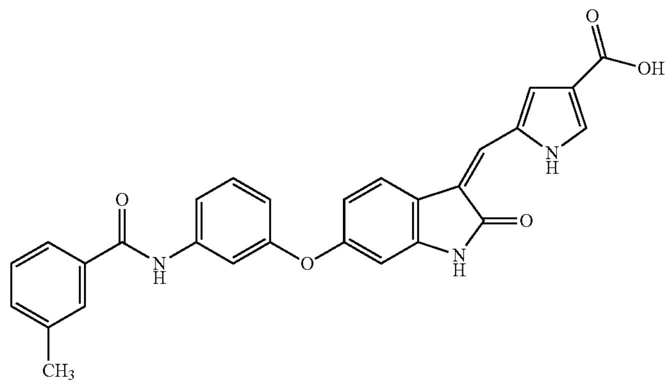 | ¹H NMR (DMSO) δ 10.99 (s, 1H), 10.31 (s, 1H), 7.73-7.71 (m, 3H), 7.66-7.56 (m, 3H), 7.40-7.35 (m, 3H), 7.08 (s, 1H), 6.73-6.71 (m, 1H), 6.52-6.48 (m, 1H) 2.38 (s, 3H); LC/MS (m/z) 480.2 (MH⁺) |
| 170 | 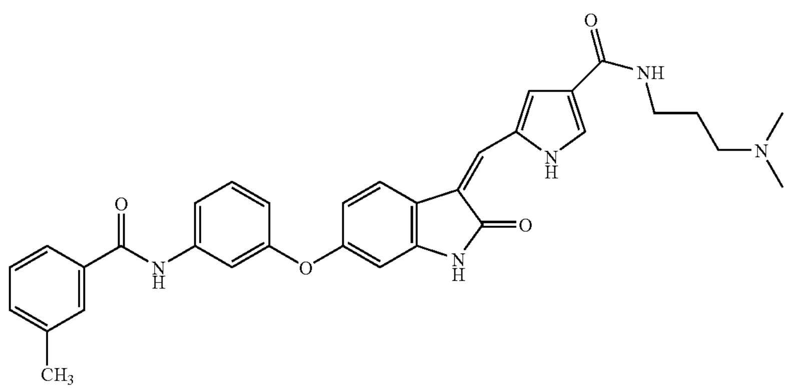 | ¹H NMR (DMSO) δ 11.00 (s, 1H), 10.30 (s, 1H), 10.00-9.92 (m, 1H), 8.34-8.33 (m, 1H), 7.79-7.59 (m, 6H), 7.39-7.35 (m, 3H), 7.17 (s, 1H), 6.83-6.81 (m, 1H), 6.74-6.72 (m, 1H), 6.51-6.52 (m, 1H), 3.31-3.27 (m, 2H), 3.07-3.06 (m, 2H), 2.75 (s, 6H), 2.38 (s, 3H), 1.92-1.98 (m, 2H); LC/MS (m/z) 564.3 (MH⁺). |
| 171 | 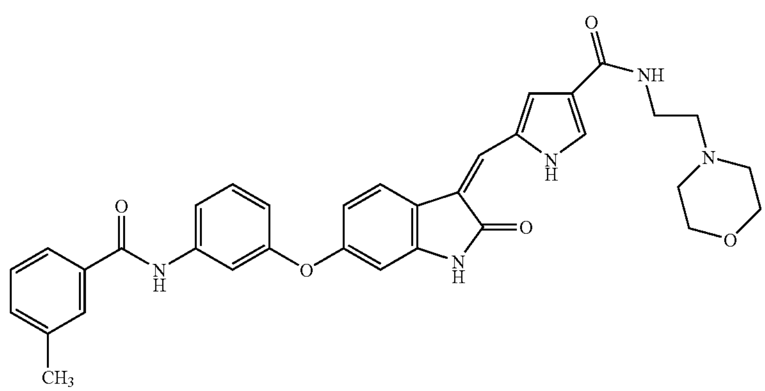 | LC/MS (m/z) 592.3 (MH⁺). |
| 172 | 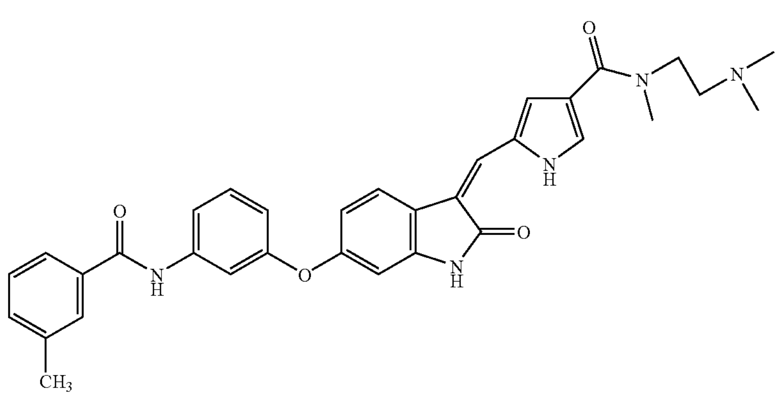 | LC/MS (m/z) 564.3 (MH⁺). |

TABLE 1-continued

| Compound Number | Structure | Physical Data $^1$H NMR 400 MHz (DMSO-$d_6$) and/or MS(m/z) |
|---|---|---|
| 173 | 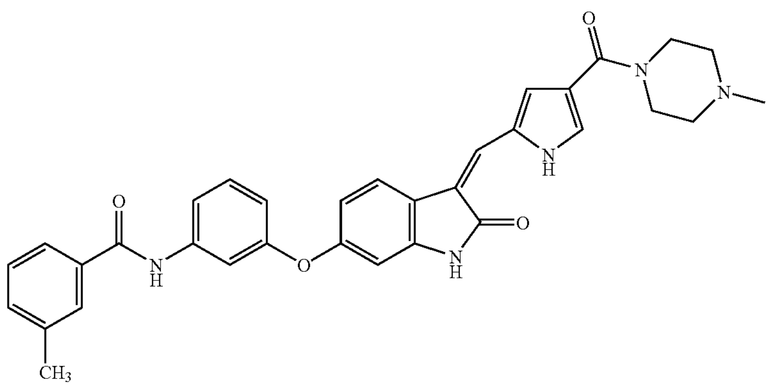 | LC/MS (m/z) 562.2 (MH$^+$). |
| 174 | 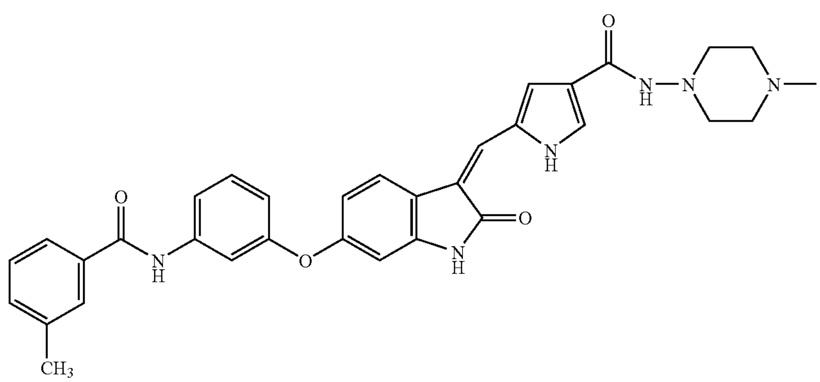 | LC/MS (m/z) 577.3 (MH$^+$). |
| 175 | 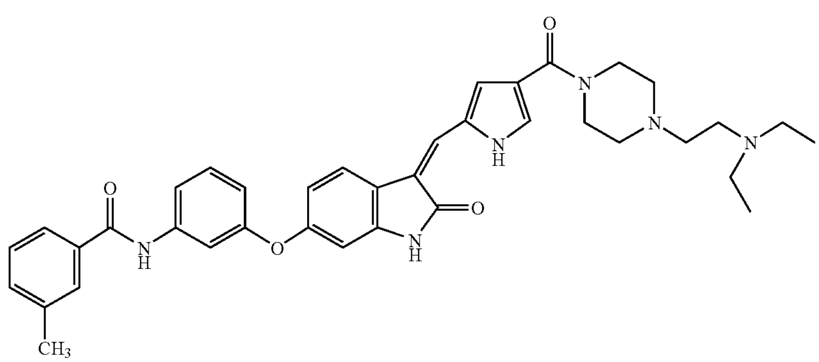 | LC/MS (m/z) 647.3 (MH$^+$). |
| 176 | 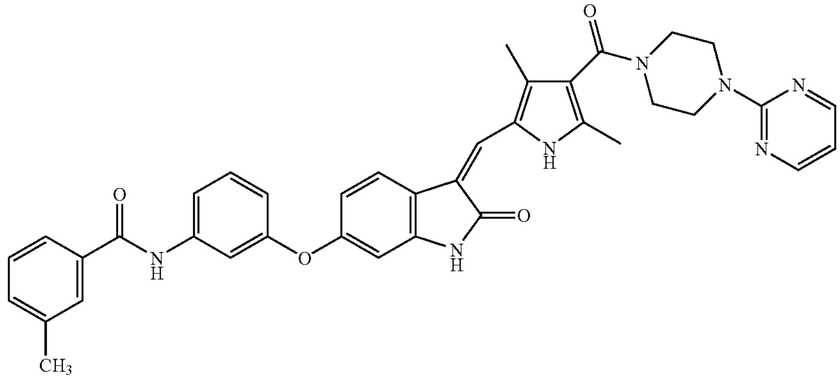 | LC/MS (m/z) 708.3 (MH$^+$). |

TABLE 1-continued

| Compound Number | Structure | Physical Data ¹H NMR 400 MHz (DMSO-$d_6$) and/or MS(m/z) |
|---|---|---|
| 177 | 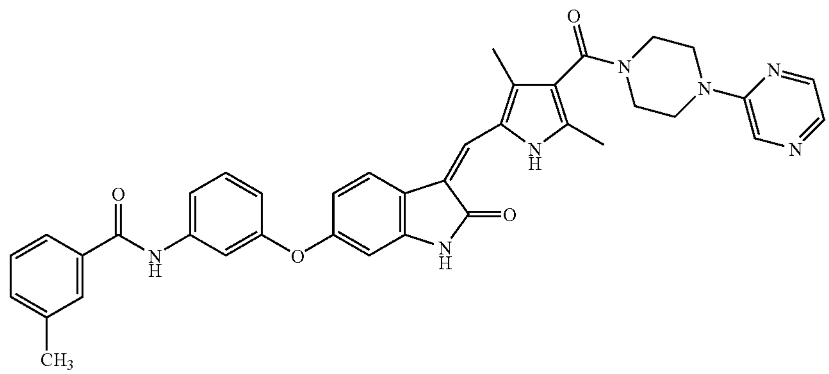 | LC/MS (m/z) 708.3 (MH$^+$). |
| 178 | 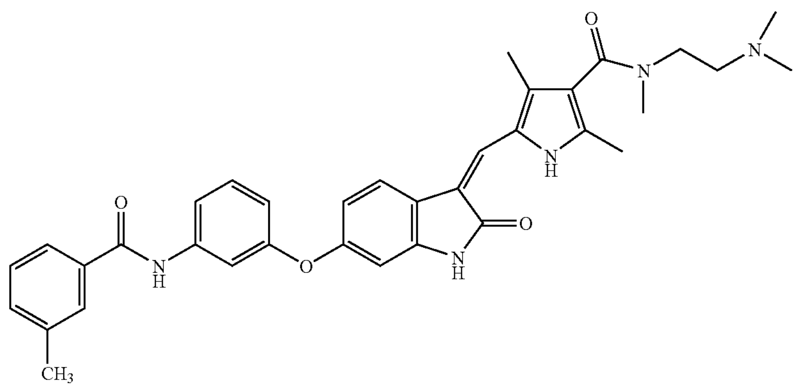 | LC/MS (m/z) 592.2 (MH$^+$). |
| 179 | 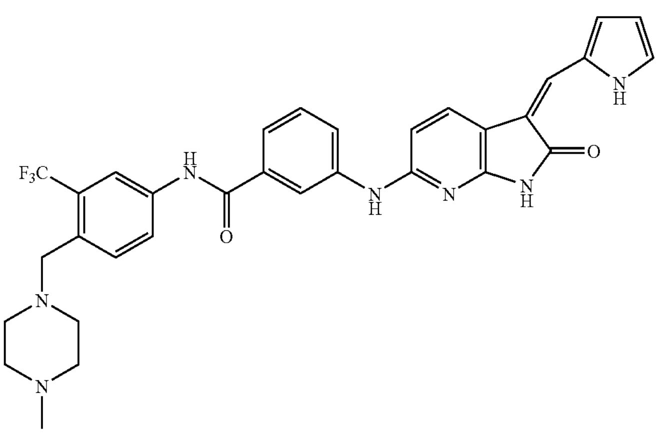 | |
| 180 | 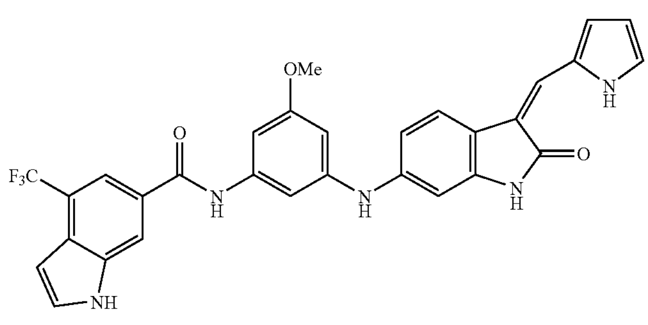 | |

TABLE 1-continued

| Compound Number | Structure | Physical Data $^1$H NMR 400 MHz (DMSO-$d_6$) and/or MS(m/z) |
|---|---|---|
| 181 | 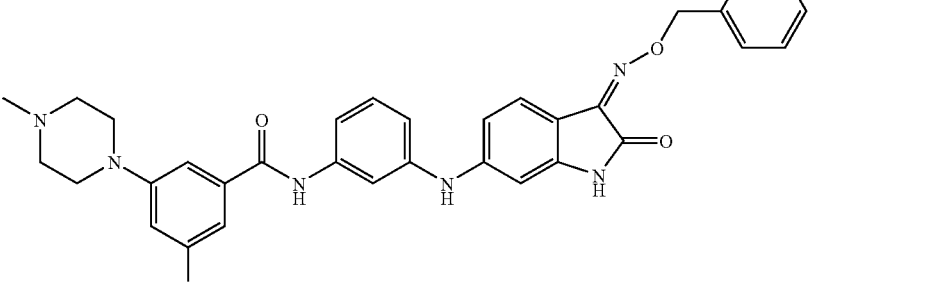 | |
| 182 | 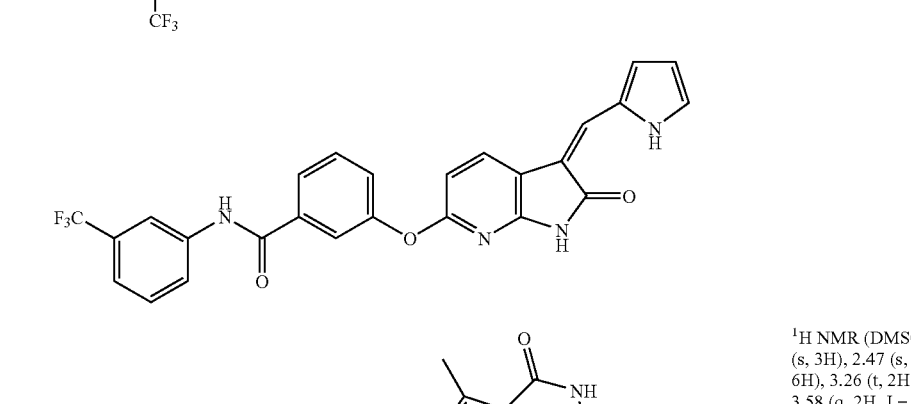 | |
| 183 | 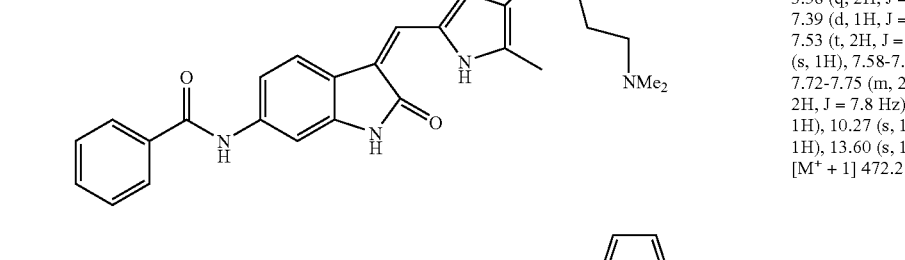 | $^1$H NMR (DMSO-$d_6$) δ 2.44 (s, 3H), 2.47 (s, 3H), 2.87 (s, 6H), 3.26 (t, 2H, J = 6.6 Hz), 3.58 (q, 2H, J = 6.6 Hz), 7.39 (d, 1H, J = 7.8 Hz), 7.53 (t, 2H, J = 7.8 Hz), 7.56 (s, 1H), 7.58-7.61 (m, 2H), 7.72-7.75 (m, 2H), 7.96 (d, 2H, J = 7.8 Hz), 9.50 (s, 1H), 10.27 (s, 1H), 10.96 (s, 1H), 13.60 (s, 1H); m/z [M$^+$ + 1] 472.2. |
| 184 | 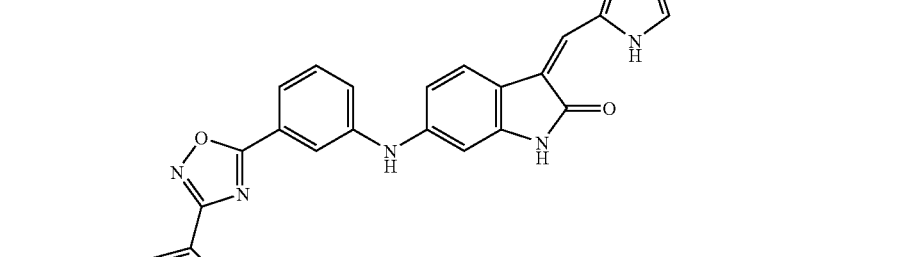 | |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl.

Compounds of the present invention are also assayed to measure their capacity to selectively inhibit cell proliferation of Ba/F3 cells expressing ETV6-NTRK3 (Ba/F3 EN) compared with parental Ba/F3 cells. Compounds selectively inhibiting the proliferation of these ETV6-NTRK3 transformed cells are tested for anti-proliferative activity on Ba/F3 cells expressing either Tel fusions of Trk family members, specifically NTRK1 and NTRK2.

In addition, compounds are assayed to measure their capacity to inhibit Abl, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and TrkC kinases.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (ST1571 is included as a positive control). The cells are incubated for 72 hours at 37° C., 5% $CO_2$. 10 μl of a 60% Alamar Blue solution (Tek diagnostics) is added to each well and the cells are incubated for an additional 24 hours. The fluorescence intensity (Excitation at 530 nm, Emission at 580 m-n) is quantified using the Acquest™ system (Molecular Devices).

Inhibition of Cellular BCR-Abl Dependent Proliferation 2D-p210 cells are plated into 96 well TC plates at a density of 15,000 cells per well. 50 μL of two fold serial dilutions of the test compound ($C_{max}$ is 40 μM) are added to each well (STI571 is included as a positive control). After incubating the cells for 48 hours at 37° C., 5% $CO_2$, 15 μL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

Effect on Cell Cycle Distribution 32D and 32D-p210 cells are plated into 6 well TC plates at $2.5 \times 10^6$ cells per well in 5 ml of medium and test compound at 1 or 10 μM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2 \times 10^5$ cells per well in 50 μL of medium. 50 μL of two fold serial dilutions of test compounds ($C_{max}$ is 10 μM) are added to each well (STJ571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to ST1571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

FLT3 and PDGFRβ

The effects of compounds of the invention on the cellular activity of ELT3 and PDGFRβ are conducted using the following method. For FLT3 and PDGFRβ, Ba/F3-FLT3-ITD and Ba/F3-Tel-PDGFRβ are used, respectively.

Compounds of the invention are tested for their ability to inhibit transformed Ba/F3-FLT3-ITD or Ba/F3-Tel-PDGFRβ cells proliferation, which is depended on FLT3 or PDGFRβ cellular kinase activity. Ba/F3-FLT3-ITD or Ba/F3-Tel-PDGFRβ are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsulfoxide (DMSO). Twelve points 1:3 serial dilutions are made into DMSO to create concentrations gradient ranging typically from 10 mM to 0.05 μM. Cells are added with 50 mL of diluted compounds and incubated for 48 hours in cell culture incubator. AlamarBlue® (TREK Diagnostic Systems), which can be used to monitor the reducing environment created by proliferating cells, are added to cells at final concentration of 10%. After additional four hours of incubation in a 37° C. cell culture incubator, fluorescence signals from reduced AlamarBlue® (Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

Inhibition of Cellular ETV6-NTRK3 Dependent Proliferation (High Throughput Method)

The murine cell line used is the Ba/F3 hematopoietic progenitor cell line transformed with ETV6-NTRK3 cDNA (Ba/13 EN). These cells are maintained in RPMI/10% fetal calf serum (RPMI/FCS) supplemented with penicillin 50 μg/mL, streptomycin 50 μg/mL and L-glutamine 200 mM. Untransformed Ba/F3 cells are similarly maintained with the addition of 10% of WEHI conditioned medium as a source of IL3.

50 μl of a Ba/F3 or Ba/F3 EN cells suspension are plated in Greiner 384 well microplates (black) at a density of 2000 cells per well. 50 nl of test compound (1 mM in DMSO stock solution) is added to each well. The cells are incubated for 72 hours at 37° C., 5% $CO_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular ETV6-NTRK3 Dependent Proliferation 10,000 cells per well contained in 90 μL of media Ba/F3 EN cells are plated into 96 well TC plates. 10 μL of three fold serial dilutions of the test compound ($C_{max}$ is 10 μM) are added to each well (STI571 is included as a positive control). After incubating the cells for 72 hours at 37° C., 5% $CO_2$, 15

µL of MTT (Promega) is added to each well and the cells are incubated for an additional 5 hours. The optical density at 570 nm is quantified spectrophotometrically and $IC_{50}$ values, the concentration of compound required for 50% inhibition, determined from a dose response curve.

For example, 3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide (Example 1) has an $IC_{50}$ of 8.2 nm and 16.7 nM for TrkB and trkC, respectively. Further, N-{3-[2-oxo-3-(1H-pyrrol-2-ylmethylene)-2,3-dihydro-1H-indol-6-ylamino]-phenyl}-3-trifluoromethyl-benzamide (compound 56), has an $IC_{50}$ of 29.8 nM and 33.8 nM for TrkB and TrkC, respectively.

Effect on Proliferation of Cells

Compounds of the invention are tested for their antiproliferative effect on Ba/F3 cells expressing either ETV6-NTRK3 or ETV6-NTRK1, ETV6-NTRK2, Bcr-Abl, FLT3, FGFR3, NPM-Alk, FIG-Ros and Ror1. The antiproliferative effect of these compounds on the different cell lines and on the non transformed cells were tested at 3-fold serial dilutions in 384 well plates as described above (in media lacking IL3). The $IC_{50}$ values of the compounds the different cell lines were determined from the dose response curves obtained as describe above.

Upstate KinaseProfiler™—Radio-Enzymatic Filter Binding Assay

Compounds of the invention are assessed for their ability to inhibit individual members of a panel of kinases (a partial, non-limiting list of kinases includes: Abl, Aurora, cSrc, TPR-Met, Tie2, MET, FGFR3, Axl, Bmx, BTK, c-kit, CH, Flt3, MST2, p70S6K, PDGFR, PKB, PKCα, Raf, ROCK-II, Rsk1, SGK, TrkA, TrkB and TrkC). The compounds are tested in duplicates at a final concentration of 10 µM following this generic protocol. Note that the kinase buffer composition and the substrates vary for the different kinases included in the "Upstate KinaseProfiler™" panel. The compounds are tested in duplicates at a final concentration of 10 µM following this generic protocol. Note that the kinase buffer composition and the substrates vary for the different kinases included in the "Upstate KinaseProfiler™" panel. Kinase buffer (2.5 µL, 10×—containing MnCl$_2$ when required), active kinase (0.001-0.01 Units; 2.5 µL), specific or Poly(Glu-4-Tyr) peptide (5-500 µM or 0.01 mg/ml) in kinase buffer and kinase buffer (50 µM; 5 µL) are mixed in an eppendorf on ice. A Mg/ATP mix (10 µL; 67.5 (or 33.75) mM MgCl$_2$, 450 (or 225) µM ATP and 1 µCi/µl [γ-$^{32}$P]-ATP (3000 Ci/mmol)) is added and the reaction is incubated at about 30° C. for about 10 minutes. The reaction mixture is spotted (20 µL) onto a 2 cm×2 cm P81 (phosphocellulose, for positively charged peptide substrates) or Whatman No. 1 (for Poly (Glu-4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an $IC_{50}$ in the range of $1×10^{-10}$ to $1×10^{-5}$ M, preferably less than 150 nM for at least one of the following kinases: Abl, Bcr-Abl, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and TrkC. For example, 3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide (Example 1) has an $IC_{50}$ of 14 nM, 15 nM, 116 nM and 53 nM for TrkB, Aurora-A, c-RAF and cSRC, respectively.

Compounds of Formula I, at a concentration of 10 µM, preferably show a percentage inhibition of greater than 50%, preferably greater than about 70%, against one or more of the following kinases: Abl, Bcr-Abl, cSrc, TPR-Met, Tie2, MET, FGFR3, Aurora, Axl, Bmx, BTK, c-kit, CHK2, Flt3, MST2, p70S6K, PDGFR, PKB, PKCα, Raf, ROCK-II, Rsk1, SGK, TrkA, TrkB and TrkC.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

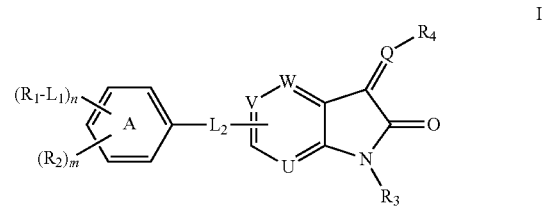

in which:
U, V and W are independently selected from $CR_5$ and N;
Q is selected from N, $NNR_5$, NO and $CR_5$;
$L_1$ is selected from —$NR_5C(O)$—, —$NR_5C(O)NR_5$—, —$C(O)NR_5$—, —$NR_5$— and $C_{5-10}$heteroaryl;
$L_2$ is selected from —O—, —$NR_5C(O)$—, —$NR_5C(O)NR_5$—, —$C(O)NR_5$— and —$NR_5$—;
n is selected from 0 and 1;
m is selected from 0, 1, 2, 3 and 4;
$R_1$ is selected from $C_{6-10}$aryl, $C_{5-10}$heteroaryl, $C_{3-12}$cycloalkyl and $C_{3-8}$heterocycloalkyl;
  wherein any aryl, heteroaryl, cycloalkyl or heterocycloalkyl of $R_1$ is optionally substituted by one to three radicals independently selected from halo, amino, nitro, cyano, $C_{1-6}$alkyl, $C_{1-6}$alkoxy, halo-substituted-$C_{1-6}$alkyl, halo-substituted $C_{1-6}$alkoxy, $C_{6-10}$aryl-$C_{0-4}$ alkyl, $C_{5-10}$heteroaryl-$C_{0-4}$alkyl, $C_{3-12}$cycloalkyl-$C_{0-4}$alkyl and $C_{3-8}$heterocycloalkyl-$C_{0-4}$ alkyl; wherein a methylene of any alkyl group can be optionally replaced by oxygen;
  wherein any aryl, heteroaryl, cycloalkyl or heterocycloalkyl substituent of $R_1$ can be optionally substituted by 1 to 3 radicals independently selected from $C_{1-6}$alkyl, $C_{1-6}$alkoxy, halo-substituted-$C_{1-6}$alkyl, halo-substituted $C_{1-6}$alkoxy and hydroxy-substituted-$C_{1-6}$alkyl;
$R_2$ is selected from halo, amino, nitro, cyano, $C_{1-6}$alkyl, $C_{1-6}$alkoxy, halo-substituted-$C_{1-6}$alkyl, halo-substituted $C_{1-6}$alkoxy, $C_{6-10}$aryl-$C_{0-4}$alkyl, $C_{5-10}$heteroaryl-$C_{0-4}$ alkyl, $C_{3-12}$cycloalkyl-$C_{0-4}$alkyl and $C_{3-8}$heterocycloalkyl-$C_{0-4}$alkyl; wherein any aryl, heteroaryl, cycloalkyl or heterocycloalkyl of $R_2$ is optionally substituted by one to three radicals independently selected from halo, amino, nitro, cyano, $C_{1-6}$alkyl, $C_{1-6}$alkoxy, halo-substituted-$C_{1-6}$alkyl and halo-substituted $C_{1-6}$alkoxy;

$R_3$ is selected from hydrogen and $C_{1-6}$alkyl; and $R_4$ is selected from hydrogen, —$R_6$, —$NR_5R_6$, and —$OR_6$;

$R_5$ is selected from hydrogen and $C_{1-6}$alkyl; and $R_6$ is selected from pyrrolyl, imidazolyl, indolyl, furanyl, thiazolyl, and cyclopentyl, each of which is optionally substituted with 1 to 3 radicals independently selected from $C_{1-6}$alkyl, hydroxy, cyano, —$NR_5S(O)_{0-2}R_5$, —$S(O)_{0-2}NR_5R_5$, —$NR_5S(O)_{0-2}NR_5R_5$, —$C(O)NR_5XNR_5R_5$, —$XNR_5XNR_5R_5$, —$C(O)R_7$, —$C(O)NR_5XOR_5$, —$C(O)NR_5R_5$, —$C(O)NR_5R_7$, —$C(O)NR_5XR_7$ and —$XC(O)OR_5$; wherein each X is independently selected from a bond and $C_{1-4}$alkylene; wherein any alkylene of X can be optionally substituted with hydroxy; and $R_7$ is $C_{3-10}$heterocycloalkyl-$C_{0-4}$alkyl optionally substituted with a radical selected from dimethylamino, pyrimidinyl, pyrazinyl, diethylamino-ethyl, amino and methyl;

or the pharmaceutically acceptable salts, thereof.

2. The compound of claim 1 in which:

W is CH;

$L_1$ is selected from —$NR_5C(O)$—, —$C(O)NR_5$—, —$NR_5C(O)NR_5$—, and $C_{5-10}$heteroaryl;

m is selected from 0, 1, 2 and 3;

$R_1$ is selected from $C_{6-10}$aryl and $C_{5-10}$heteroaryl;
  wherein any aryl or heteroaryl is optionally substituted by one to three radicals independently selected from halo, $C_{1-6}$alkyl, halo-substituted-$C_{1-6}$alkyl, $C_{5-10}$heteroaryl-$C_{0-4}$alkyl and $C_{3-8}$heterocycloalkyl-$C_{0-4}$alkyl; wherein a methylene of any alkyl group can be optionally replaced by oxygen;
    wherein any heteroaryl or heterocycloalkyl substituent of $R_1$ can be optionally substituted by 1 to 3 radicals independently selected from $C_{1-6}$alkyl and hydroxy-substituted-$C_{1-6}$alkyl;

$R_2$ is selected from $C_{1-6}$alkyl, $C_{1-6}$alkoxy, halo-substituted-$C_{1-6}$alkyl and $C_{3-8}$heterocycloalkyl-$C_{0-4}$alkyl optionally substituted by 1 to 3 $C_{1-6}$alkyl radicals; and $R_6$ is selected from pyrrolyl, imidazolyl, indolyl, furanyl, thiazolyl, and cyclopentyl.

3. The compound of claim 2 in which:

$L_1$ is selected from —NHC(O)—, —C(O)NH—, —NHC(O)NH—, and [1,2,4]oxadiazole;

$L_2$ is selected from —O—, —NHC(O)—, —NHC(O)NH—, —C(O)NH— and —NH—; and n is 1; and m is selected from 0 and 1.

4. The compound of claim 3 in which $R_1$ is selected from phenyl, indolyl and pyrazolyl; wherein any phenyl, indolyl or pyrazolyl is optionally substituted by one to three radicals independently selected from halo, methyl, trifluoromethyl, tert-butyl, morpholino, piperazinyl, piperazinyl-oxy, piperazinyl-methyl, piperidinyl, piperidinyl-oxy and imidazolyl; wherein any heteroaryl or heterocycloalkyl substituent of $R_1$ can be optionally substituted by 1 to 3 radicals independently selected from methyl, ethyl, hydroxy and hydroxy-ethyl.

5. The compound of claim 4 in which $R_2$ is selected from methyl, methoxy, trifluoromethyl and imidazolyl optionally substituted by methyl.

6. The compound of claim 5 in which
$R_6$ is pyrrolyl.

7. A compound selected from:

3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide;

N-[2-Oxo-3-(1H-pyrrol-2-ylmethylene)-2,3-dihydro-1H-indol-6-yl]-benzamide;

5-(6-Benzoylamino-2-oxo-1,2-dihydro-indol-3-ylidenemethyl)-2,4-dimethyl-1H-pyrrole-3-carboxylic acid (2-diethylamino-ethyl)-amide;

3-(4-Methyl-imidazol-1-yl)-N-(3-{3-[2-oxo-3-(1H-pyrrol-2-ylmethylene)-2,3-dihydro-1H-indol-6-yl]-ureido}-phenyl)-5-trifluoromethyl-benzamide;

2-Oxo-3-(1H-pyrrol-2-ylmethylene)-2,3-dihydro-1H-indole-6-carboxylic acid (3-benzoylamino-phenyl)-amide;

6-(3-Amino-phenylamino)-3-(1H-pyrrol-2-ylmethylene)-1,3-dihydro-indol-2-one;

4-(4-Methyl-piperazin-1-ylmethyl)-N-{3-[2-oxo-3-(1H-pyrrol-2-ylmethylene)-2,3-dihydro-1H-indol-7-ylamino]-phenyl}-benzamide;

4-(4-Methyl-piperazin-1-ylmethyl)-N-{3-[2-oxo-3-(1H-pyrrol-2-ylmethylene)-2,3-dihydro-1H-indol-5-ylamino]-phenyl}-benzamide;

4-(4-Ethyl-piperazin-1-ylmethyl)-N-{3-[2-oxo-3-(1H-pyrrol-2-ylmethylene)-2,3-dihydro-1H-indol-6-ylamino]-phenyl}-3-trifluoromethyl-benzamide;

3-(4-Methyl-piperazin-1-yl)-N-{3-[2-oxo-3-(1H-pyrrol-2-ylmethylene)-2,3-dihydro-1H-indol-6-yloxy]-phenyl}-5-trifluoromethyl-benzamide;

5-(6-Benzoylamino-2-oxo-1,2-dihydro-indol-3-ylidenemethyl)-2,4-dimethyl-1H-pyrrole-3-carboxylic acid (2-pyrrolidin-1-yl-ethyl)-amide;

5-(6-Benzoylamino-2-oxo-1,2-dihydro-indol-3-ylidenemethyl)-2,4-dimethyl-1H-pyrrole-3-carboxylic acid (2-piperidin-1-yl-ethyl)-amide;

5-(6-Benzoylamino-2-oxo-1,2-dihydro-indol-3-ylidenemethyl)-2,4-dimethyl-1H-pyrrole-3-carboxylic acid (3-pyrrolidin-1-yl-propyl)-amide;

N-[2-Oxo-3-(1H-pyrrol-2-ylmethylene)-2,3-dihydro-1H-indol-6-yl]-3-trifluoromethyl-benzamide;

3-{2,4-Dimethyl-5-[2-oxo-6-(3-trifluoromethyl-benzoylamino)-1,2-dihydro-indol-3-ylidenemethyl]-1H-pyrrol-3-yl}-propionic acid;

2,4-Dimethyl-5-[2-oxo-6-(3-trifluoromethyl-benzoylamino)-1,2-dihydro-indol-3-ylidenemethyl]-1H-pyrrole-3-carboxylic acid;

2,4-Dimethyl-5-[2-oxo-6-(3-trifluoromethyl-benzoylamino)-1,2-dihydro-indol-3-ylidenemethyl]-1H-pyrrole-3-carboxylic acid (2-dimethylamino-ethyl)-amide;

2,4-Dimethyl-5-[2-oxo-6-(3-trifluoromethyl-benzoylamino)-1,2-dihydro-indol-3-ylidenemethyl]-1H-pyrrole-3-carboxylic acid (2-pyrrolidin-1-yl-ethyl)-amide;

2,4-Dimethyl-5-[2-oxo-6-(3-trifluoromethyl-benzoylamino)-1,2-dihydro-indol-3-ylidenemethyl]-1H-pyrrole-3-carboxylic acid (2-diethylamino-ethyl)-amide;

N-[3-(3,5-Dimethyl-1H-pyrrol-2-ylmethylene)-2-oxo-2,3-dihydro-1H-indol-6-yl]-3-(4-methyl-imidazol-1-yl)-5-trifluoromethyl-benzamide;

3-(4-Methyl-imidazol-1-yl)-N-[2-oxo-3-(1H-pyrrol-2-ylmethylene)-2,3-dihydro-1H-indol-6-yl]-5-trifluoromethyl-benzamide;

2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid;

3-(2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrol-3-yl)-propionic acid;

4-(4-Methyl-piperazin-1-ylmethyl)-N-[2-oxo-3-(1H-pyrrol-2-ylmethylene)-2,3-dihydro-1H-indol-6-yl]-benzamide;

2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-diethylamino-ethyl)-amide;

2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-diethylamino-ethyl)-amide;

2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-dimethylamino-ethyl)-amide;

2,4-Dimethyl-5-{6-[3-(4-methyl-imidazol-1-yl)-5-trifluoromethyl-benzoylamino]-2-oxo-1,2-dihydro-indol-3-ylidenemethyl}-1H-pyrrole-3-carboxylic acid (2-pyrrolidin-1-yl-ethyl)-amide;

2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-dimethylamino-ethyl)-amide;

2,4-Dimethyl-5-{6-[4-(4-methyl-piperazin-1-ylmethyl)-benzoylamino]-2-oxo-1,2-dihydro-indol-3-ylidenemethyl}-1H-pyrrole-3-carboxylic acid (2-pyrrolidin-1-yl-ethyl)-amide;

3-{2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrol-3-yl}-propionic acid;

5-{6-[3-(3-Benzoylamino-phenyl)-ureido]-2-oxo-1,2-dihydro-indol-3-ylidenemethyl}-2,4-dimethyl-1H-pyrrole-3-carboxylic acid (2-pyrrolidin-1-yl-ethyl)-amide;

4-(4-Methyl-piperazin-1-ylmethyl)-N-(3-{3-[2-oxo-3-(1H-pyrrol-2-ylmethylene)-2,3-dihydro-1H-indol-6-yl]-ureido}-phenyl)-benzamide;

2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-diethylamino-ethyl)-amide;

2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-dimethylamino-ethyl)-amide;

2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-diethylamino-ethyl)-amide;

2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-dimethylamino-ethyl)-amide;

5-{6-[3-(3-Benzoylamino-phenyl)-ureido]-2-oxo-1,2-dihydro-indol-3-ylidenemethyl}-2,4-dimethyl-1H-pyrrole-3-carboxylic acid (2-diethylamino-ethyl)-amide;

2,4-Dimethyl-5-[6-(3-{3-[3-(4-methyl-imidazol-1-yl)-5-trifluoromethyl-benzoylamino]-phenyl}-ureido)-2-oxo-1,2-dihydro-indol-3-ylidenemethyl]-1H-pyrrole-3-carboxylic acid (2-pyrrolidin-1-yl-ethyl)-amide;

2,4-Dimethyl-5-[6-(3-{3-[4-(4-methyl-piperazin-1-ylmethyl)-benzoylamino]-phenyl}-ureido)-2-oxo-1,2-dihydro-indol-3-ylidenemethyl]-1H-pyrrole-3-carboxylic acid (2-pyrrolidin-1-yl-ethyl)-amide;

3-(4-Methyl-imidazol-1-yl)-N-(4-methyl-3-{3-[2-oxo-3-(1H-pyrrol-2-ylmethylene)-2,3-dihydro-1H-indol-6-yl]-ureido}-phenyl)-5-trifluoromethyl-benzamide;

N-(4-Methyl-3-{3-[2-oxo-3-(1H-pyrrol-2-ylmethylene)-2,3-dihydro-1H-indol-6-yl]-ureido}-phenyl)-3-trifluoromethyl-benzamide;

2,4-Dimethyl-5-(6-{3-[2-methyl-5-(3-trifluoromethyl-benzoylamino)-phenyl]-ureido}-2-oxo-1,2-dihydro-indol-3-ylidenemethyl)-1H-pyrrole-3-carboxylic acid (2-pyrrolidin-1-yl-ethyl)-amide;

N-(4-Methyl-3-{3-[2-oxo-3-(1H-pyrrol-2-ylmethylene)-2,3-dihydro-1H-indol-6-yl]-ureido}-phenyl)-benzamide;

5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-diethylamino-ethyl)-amide;

5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-dimethylamino-ethyl)-amide;

5-{6-[3-(5-Benzoylamino-2-methyl-phenyl)-ureido]-2-oxo-1,2-dihydro-indol-3-ylidenemethyl}-2,4-dimethyl-1H-pyrrole-3-carboxylic acid (2-pyrrolidin-1-yl-ethyl)-amide;

N-(4-Methyl-3-{3-[2-oxo-3-(1H-pyrrol-2-ylmethylene)-2,3-dihydro-1H-indol-6-yl]-ureido}-phenyl)-4-(4-methyl-piperazin-1-yl-methyl)-benzamide;

2-Oxo-3-(1H-pyrrol-2-ylmethylene)-2,3-dihydro-1H-indole-6-carboxylic acid {3-[4-(4-methyl-piperazin-1-ylmethyl)-benzoylamino]-phenyl}-amide;

3-[4-(2-Diethylamino-ethylcarbamoyl)-3,5-dimethyl-1H-pyrrol-2-ylmethylene]-2-oxo-2,3-dihydro-1H-indole-6-carboxylic acid (3-benzoylamino-phenyl)-amide;

3-[3,5-Dimethyl-4-(2-pyrrolidin-1-yl-ethylcarbamoyl)-1H-pyrrol-2-ylmethylene]-2-oxo-2,3-dihydro-1H-indole-6-carboxylic acid (3-benzoylamino-phenyl)-amide;

2-Oxo-3-(1H-pyrrol-2-ylmethylene)-2,3-dihydro-1H-indole-6-carboxylic acid (5-benzoylamino-2-methyl-phenyl)-amide;

2-Oxo-3-(1H-pyrrol-2-ylmethylene)-2,3-dihydro-1H-indole-6-carboxylic acid {2-methyl -5-[4-(4-methyl-piperazin-1-ylmethyl)-benzoylamino]-phenyl}-amide;

3-[4-(2-Diethylamino-ethylcarbamoyl)-3,5-dimethyl-1H-pyrrol-2-ylmethylene]-2-oxo-2,3-dihydro-1H-indole-6-carboxylic acid (5-benzoylamino-2-methyl-phenyl)-amide;

3-[3,5-Dimethyl-4-(2-pyrrolidin-1-yl-ethylcarbamoyl)-1H-pyrrol-2-ylmethylene]-2-oxo-2,3-dihydro-1H-indole-6-carboxylic acid (5-benzoylamino-2-methyl-phenyl)-amide;

N-{3-[2-Oxo-3-(1H-pyrrol-2-ylmethylene)-2,3-dihydro-1H-indol-6-ylamino]-phenyl}-benzamide;

N-{3-[2-Oxo-3-(1H-pyrrol-2-ylmethylene)-2,3-dihydro-1H-indol-6-ylamino]-phenyl}-3-trifluoromethyl-benzamide;

4-(4-Methyl-piperazin-1-ylmethyl)-N-{3-[2-oxo-3-(1H-pyrrol-2-ylmethylene)-2,3-dihydro-1H-indol-6-ylamino]-phenyl}-benzamide;

N-{4-Methyl-3-[2-oxo-3-(1H-pyrrol-2-ylmethylene)-2,3-dihydro-1H-indol-6-ylamino]-phenyl}-benzamide;

N-{4-Methyl-3-[2-oxo-3-(1H-pyrrol-2-ylmethylene)-2,3-dihydro-1H-indol-6-ylamino]-phenyl}-3-trifluoromethyl-benzamide;

N-{4-Methyl-3-[2-oxo-3-(1H-pyrrol-2-ylmethylene)-2,3-dihydro-1H-indol-6-ylamino]-phenyl}-4-(4-methyl-piperazin-1-ylmethyl)-benzamide;

5-[6-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide;

5-[6-(3-Benzoylamino-phenylamino)-2-oxo-1,2-dihydro-indol-3-ylidenemethyl]-2,4-dimethyl-1H-pyrrole-3-carboxylic acid (2-dimethylamino-ethyl)-amide;

5-[6-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

5-[6-(3-Benzoylamino-phenylamino)-2-oxo-1,2-dihydro-indol-3-ylidenemethyl]-2,4-dimethyl-1H-pyrrole-3-carboxylic acid (2-piperidin-1-yl-ethyl)-amide;

5-[6-(3-Benzoylamino-phenylamino)-2-oxo-1,2-dihydro-indol-3-ylidenemethyl]-2,4-dimethyl-1H-pyrrole-3-carboxylic acid (3-pyrrolidin-1-yl-propyl)-amide;

2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid(2-dimethylamino-ethyl)-amide;

2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid(2-diethylamino-ethyl)-amide;

2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid(2-pyrrolidin-1-yl-ethyl)-amide;

2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid(2-piperidin-1-yl-ethyl)-amide;

2,4-Dimethyl-5-{2-oxo-6-[3-(3-trifluoromethyl-benzoylamino)-phenylamino]-1,2-dihydro-indol-3-ylidenemethyl}-1H-pyrrole-3-carboxylic acid(3-pyrrolidin-1-yl-propyl)-amide;

5-[6-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide;

5-[6-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

2,4-Dimethyl-5-{6-[2-methyl-5-(3-trifluoromethyl-benzoylamino)-phenylamino]-2-oxo-1,2-dihydro-indol-3-ylidenemethyl}-1H-pyrrole-3-carboxylic acid (2-diethylamino-ethyl)-amide;

N-{3-[2-Oxo-3-(1H-pyrrol-2-ylmethylene)-2,3-dihydro-1H-indol-7-ylamino]-phenyl}-benzamide;

5-[7-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide;

5-[7-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-diethylamino-ethyl)-amide;

2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-dimethylamino-ethyl)-amide;

2,4-Dimethyl-5-(7-{3-[4-(4-methyl-piperazin-1-ylmethyl)-benzoylamino]-phenylamino}-2-oxo-1,2-dihydro-indol-3-ylidenemethyl)-1H-pyrrole-3-carboxylic acid (2-pyrrolidin-1-yl-ethyl)-amide;

N-{4-Methyl-3-[2-oxo-3-(1H-pyrrol-2-ylmethylene)-2,3-dihydro-1H-indol-7-ylamino]-phenyl}-benzamide;

N-{4-Methyl-3-[2-oxo-3-(1H-pyrrol-2-ylmethylene)-2,3-dihydro-1H-indol-7-ylamino]-phenyl}-4-(4-methyl-piperazin-1-ylmethyl)-benzamide;

5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide;

5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-dimethylamino-ethyl)-amide;

5-[7-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

5-(3-Amino-phenylamino)-3-(1H-pyrrol-2-ylmethylene)-1,3-dihydro-indol-2-one;

N-{3-[2-Oxo-3-(1H-pyrrol-2-ylmethylene)-2,3-dihydro-1H-indol-5-ylamino]-phenyl}-benzamide;

N-{3-[2-Oxo-3-(1H-pyrrol-2-ylmethylene)-2,3-dihydro-1H-indol-5-ylamino]-phenyl}-3-trifluoromethyl-benzamide;

3-(4-Methyl-imidazol-1-yl)-N-{3-[2-oxo-3-(1H-pyrrol-2-ylmethylene)-2,3-dihydro-1H-indol-5-ylamino]-phenyl}-5-trifluoromethyl-benzamide;

5-[5-(3-Benzoylamino-phenylamino)-2-oxo-1,2-dihydro-indol-3-ylidenemethyl]-2,4-dimethyl-1H-pyrrole-3-carboxylic acid (2-diethylamino-ethyl)-amide;

5-[5-(3-Benzoylamino-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

N-{4-Methyl-3-[2-oxo-3-(1H-pyrrol-2-ylmethylene)-2,3-dihydro-1H-indol-5-ylamino]-phenyl}-benzamide;

N-{4-Methyl-3-[2-oxo-3-(1H-pyrrol-2-ylmethylene)-2,3-dihydro-1H-indol-5-ylamino]-phenyl}-4(4-methyl-piperazin-1-ylmethyl)-benzamide;

5-[5-(5-Benzoylamino-2-methyl-phenylamino)-2-oxo-1,2-dihydro-indol-3-ylidenemethyl]-2,4-dimethyl-1H-pyrrole-3-carboxylic acid (2-diethylamino-ethyl)-amide;

5-[5-(5-Benzoylamino-2-methyl-phenylamino)-2-oxo-1,2-dihydro-indol-3-ylidenemethyl]-2,4-dimethyl-1H-pyrrole-3-carboxylic acid (2-pyrrolidin-1-yl-ethyl)-amide;

3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide;

3-(4-Methyl-imidazol-1-yl)-N-{3-[6-oxo-5-(1H-pyrrol-2-ylmethylene)-6,7-dihydro-5H-pyrrolo[2,3-d]pyrimidin-2-ylamino]-phenyl}-5-trifluoromethyl-benzamide;

3-(4-Ethyl-piperazin-1-yl)-N-{3-[3-(3H-imidazol-4-ylmethylene)-2-oxo-2,3-dihydro-1H-indol-6-ylamino]-phenyl}-5-trifluoromethyl-benzamide;

2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid (2-diethylamino-ethyl)-amide;

2,4-Dimethyl-5-(6-{3-[3-(1-methyl-piperidin-4-yloxy)-5-trifluoromethyl-benzoylamino]-phenylamino}-2-oxo-1,2-dihydro-indol-3-ylidenemethyl)-1H-pyrrole-3-carboxylic acid;

3-(1-Methyl-piperidin-4-yloxy)-N-{3-[2-oxo-3-(1H-pyrrol-2-ylmethylene)-2,3-dihydro-1H-indol-6-ylamino]-phenyl}-5-trifluoromethyl-benzamide;

N-{3-[3-(4-Cyano-1H-pyrrol-2-ylmethylene)-2-oxo-2,3-dihydro-1H-indol-6-ylamino]-5-methoxy-phenyl}-3-(1-methyl-piperidin-4-yloxy)-5-trifluoromethyl-benzamide;

N-{3-[3-(5-Methyl-3H-imidazol-4-ylmethylene)-2-oxo-2,3-dihydro-1H-indol-6-ylamino]-phenyl}-3-(1-methyl-piperidin-4-yloxy)-5-trifluoromethyl-benzamide;

3-[4-(2-Hydroxy-ethyl)-piperazin-1-yl]-N-{3-[2-oxo-3-(1H-pyrrol-2-ylmethylene)-2,3-dihydro-1H-indol-6-ylamino]-phenyl}-5-trifluoromethyl-benzamide;

4-Morpholin-4-yl-N-{3-[2-oxo-3-(1H-pyrrol-2-ylmethylene)-2,3-dihydro-1H-indol-6-ylamino]-phenyl}-3-trifluoromethyl-benzamide;

4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide;

4-(4-Ethyl-piperazin-1-ylmethyl)-N-{3-[3-(5-methyl-3H-imidazol-4-ylmethylene)-2-oxo-2,3-dihydro-1H-indol-6-ylamino]-phenyl}-3-trifluoromethyl-benzamide;

4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide;

5-(6-{3-[4-(4-Ethyl-piperazin-1-ylmethyl)-3-trifluoromethyl-benzoylamino]-phenylamino}-2-oxo-1,2-dihydro-indol-3-ylidenemethyl)-2,4-dimethyl-1H-pyrrole-3-carboxylic acid;

4-(4-Ethyl-piperazin-1-ylmethyl)-N-{3-[3-(5-methyl-2H-pyrazol-3-ylmethylene)-2-oxo-2,3-dihydro-1H-indol-6-ylamino]-phenyl}-3-trifluoromethyl-benzamide;

4-(4-Ethyl-piperazin-t-ylmethyl)-N-{3-[3-(4-methyl-1H-imidazol-2-ylmethylene)-2-oxo-2,3-dihydro-1H-indol-6-ylamino]-phenyl}-3-trifluoromethyl-benzamide;

3-Chloro-4-(4-ethyl-piperazin-1-ylmethyl)-N-{3-[3-(3H-imidazol-4-ylmethylene)-2-oxo-2,3-dihydro-1H-indol-6-ylamino]-phenyl}-benzamide;

3-Chloro-4-(4-ethyl-piperazin-1-ylmethyl)-N-{3-[3-(5-methyl-3H-imidazol-4-ylmethylene)-2-oxo-2,3-dihydro-1H-indol-6-ylamino]-phenyl}-benzamide;

5-(6-{3-[3-Chloro-4-(4-ethyl-piperazin-1-ylmethyl)-benzoylamino]-phenylamino}-2-oxo-1,2-dihydro-indol-3-ylidenemethyl)-2,4-dimethyl-1H-pyrrole-3-carboxylic acid;

N-{3-[3-(2-Ethyl-5-methyl-3H-imidazol-4-ylmethylene)-2-oxo-2,3-dihydro-1H-indol-6-ylamino]-phenyl}-3-(4-methyl-imidazol-1-yl)-5-trifluoromethyl-benzamide;

N-{3-[3-(1H-Indol-3-ylmethylene)-2-oxo-2,3-dihydro-1H-indol-6-ylamino]-phenyl}-3-(4-methyl-imidazol-1-yl)-5-trifluoromethyl-benzamide;

N-[3-(3-Furan-3-ylmethylene-2-oxo-2,3-dihydro-1H-indol-6-ylamino)-phenyl]-3-(4-methyl-imidazol-1-yl)-5-trifluoromethyl-benzamide;

3-(4-Methyl-imidazol-1-yl)-N-{3-[3-(5-methyl-3H-imidazol-4-ylmethylene)-2-oxo-2,3-dihydro-1H-indol-6-ylamino]-phenyl}-5-trifluoromethyl-benzamide;

3-(4-Methyl-imidazol-1-yl)-N-{3-[3-(4-methyl-1H-imidazol-2-ylmethylene)-2-oxo-2,3-dihydro-1H-indol-6-ylamino]-phenyl}-5-trifluoromethyl-benzamide;

N-{3-[3-(3H-imidazol-4-ylmethylene)-2-oxo-2,3-dihydro-1H-indol-6-ylamino]-phenyl}-3-(4-methyl-imidazol-1-yl)-5-trifluoromethyl-benzamide;

2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid;

N-{3-[3-(4-Cyano-1H-pyrrol-2-ylmethylene)-2-oxo-2,3-dihydro-1H-indol-6-ylamino]-phenyl}-3-(4-methyl-imidazol-1-yl)-5-trifluoromethyl-benzamide;

N-{3-[3-(1H-indol-2-ylmethylene)-2-oxo-2,3-dihydro-1H-indol-6-ylamino]-phenyl}-3-(4-methyl-imidazol-1-yl)-5-trifluoromethyl-benzamide;

N-{3-[3-(2-Ethyl-5-methyl-3H-imidazol-4-ylmethylene)-2-oxo-2,3-dihydro-1H-indol-6-ylamino]-4-methyl-phenyl}-3-(4-methyl-imidazol-1-yl)-5-trifluoromethyl-benzamide;

5-(6-{3-[3-(4-Methyl-imidazol-1-yl)-5-trifluoromethyl-benzoylamino]-phenylamino}-2-oxo-1,2-dihydro-indol-3-ylidenemethyl)-1H-pyrrole-3-carboxylic acid amide;

4-(6-{3-[3-(4-Methyl-imidazol-1-yl)-5-trifluoromethyl-benzoylamino]-phenylamino}-2-oxo-1,2-dihydro-indol-3-ylidenemethyl)-1H-pyrrole-2-carboxylic acid methyl ester;

2,4-Dimethyl-5-(6-{3-[3-(4-methyl-imidazol-1-yl)-5-trifluoromethyl-benzoylamino]-phenylamino}-2-oxo-1,2-dihydro-indol-3-ylidenemethyl)-1H-pyrrole-3-carboxylic acid (2,3-dihydroxy-propyl)-amide;

N-[3-(3-{4-[(2-Diethylamino-ethylamino)-methyl]-1H-pyrrol-2-ylmethylene}-2-oxo-2,3-dihydro-1H-indol-6-ylamino)-phenyl]-3-trifluoromethyl-benzamide;

2,4-Dimethyl-5-(6-{3-[3-(4-methyl-piperazin-1-yl)-5-trifluoromethyl-benzoylamino]-phenylamino}-2-oxo-1,2-dihydro-indol-3-ylidenemethyl)-1H-pyrrole-3-carboxylic acid;

N-{3-[3-(5-Methyl-3H-imidazol-4-ylmethylene)-2-oxo-2,3-dihydro-1H-indol-6-ylamino]-phenyl}-3-(4-methyl-piperazin-1-yl)-5-trifluoromethyl-benzamide;

3-(4-Methyl-piperazin-1-yl)-N-{3-[2-oxo-3-(1H-pyrrol-2-ylmethylene)-2,3-dihydro-1H -indol-6-ylamino]-phenyl}-5-trifluoromethyl-benzamide;

3-(4-Methyl-piperazin-1-yl)-N-(3-{2-oxo-3-[(4-sulfamoyl-phenyl)hydrazono]-2,3-dihydro-1H-indol-6-ylamino}-phenyl)-5-trifluoromethyl-benzamide;

N-{3-[3-(4-Cyano-1H-pyrrol-2-ylmethylene)-2-oxo-2,3-dihydro-1H-indol-6-ylamino]-phenyl}-3-(4-methyl-piperidin-1-yl)-5-trifluoromethyl-benzamide;

N-{3-Methoxy-5-[2-oxo-3-(1H-pyrrol-2-ylmethylene)-2,3-dihydro-1H-indol-6-ylamino]-phenyl}-3-(4-methyl-piperazin-1-yl)-5-trifluoromethyl-benzamide;

5-(6-{3-[3-(4-Methyl-piperazin-1-yl)-5-trifluoromethyl-benzoylamino]-phenylamino}-2-oxo-1,2-dihydro-indol-3-ylidenemethyl)-1H-pyrrole-3-carboxylic acid amide;

N-{3-[3-(4-Cyano-1H-pyrrol-2-ylmethylene)-2-oxo-2,3-dihydro-1H-indol-6-ylamino]-5-methoxy-phenyl}-3-(4-methyl-piperazin-1-yl)-5-trifluoromethyl-benzamide;

N-{4-Methyl-3-[2-oxo-3-(1H-pyrrol-2-ylmethylene)-2,3-dihydro-1H-indol-6-ylamino]-phenyl}-3-(4-Methyl-piperazin-1-yl)-5-trifluoromethyl-benzamide;

N-{3-[3-(4-Cyano-1H-pyrrol-2-ylmethylene)-2-oxo-2,3-dihydro-1H-indol-6-ylamino]-phenyl}-3-(4-hydroxy-piperidin-1-yl)-5-trifluoromethyl-benzamide;

3-(4-Hydroxy-piperidin-1-yl)-N-{3-[2-oxo-3-(1H-pyrrol-2-ylmethylene)-2,3-dihydro-1H -indol-6-ylamino]-phenyl}-5-trifluoromethyl-benzamide;

5-(6-{3-[4-(4-Methyl-piperazin-1-yl)-3-trifluoromethyl-benzoylamino]-phenylamino}-2-oxo-1,2-dihydro-indol-3-ylidenemethyl)-1H-pyrrole-3-carboxylic acid amide;

3-Methyl-N-{3-[3-(5-methyl-3H-imidazol-4-ylmethylene)-2-oxo-2,3-dihydro-1H-indol-6-ylamino]-phenyl}-benzamide;

N-{3-[3-(5-Methyl-3H-imidazol-4-ylmethylene)-2-oxo-2,3-dihydro-1H-indol-6-ylamino]-phenyl}-3-trifluoromethyl-benzamide;

N-{3-[3-(4-Cyano-1H-pyrrol-2-ylmethylene)-2-oxo-2,3-dihydro-1H-indol-6-ylamino]-4-methyl-phenyl}-3-(4-methyl-piperazin-1-yl)-5-trifluoromethyl-benzamide;

5-{6-[3-(3-Methyl-benzoylamino)-phenylamino]-2-oxo-1,2-dihydro-indol-3-ylidenemethyl}-1H-pyrrole-3-carboxylic acid amide;

2,4-Dimethyl-5-(6-{3-[3-(4-methyl-piperazin-1-yl)-5-trifluoromethyl-benzoylamino]-phenylamino}-2-oxo-1,2-dihydro-indol-3-ylidenemethyl)-1H-pyrrole-3-carboxylic acid (3-dimethylamino-propyl)-amide;

2,4-Dimethyl-5-{2-oxo-6-[3-(3-trifluoromethyl-benzoylamino)-phenoxy]-1,2-dihydro -indol-3-ylidenemethyl}-1H-pyrrole-3-carboxylic acid (2-dimethylamino-ethyl)-methyl-amide;

N-(3-{3-[3,5-Dimethyl-4-(4-methyl-piperazine-1-carbonyl)-1H-pyrrol-2-ylmethylene]-2-oxo-2,3-dihydro-1H-indol-6-yloxy}-phenyl)-3-trifluoromethyl-benzamide;

2,4-Dimethyl-5-{2-oxo-6-[3-(3-trifluoromethyl-benzoylamino)-phenoxy]-1,2-dihydro -indol-3-ylidenemethyl}-1H-pyrrole-3-carboxylic acid (3-dimethylamino-propyl)-amide;

2,4-Dimethyl-5-{2-oxo-6-[3-(3-trifluoromethyl-benzoylamino)-phenoxy]-1,2-dihydro -indol-3-ylidenemethyl}-1H-pyrrole-3-carboxylic acid (3-pyrrolidin-1-yl-propyl)-amide;

2,4-Dimethyl-5-{2-oxo-6-[3-(3-trifluoromethyl-benzoylamino)-phenoxy]-1,2-dihydro -indol-3-ylidenemethyl}1H-pyrrole-3-carboxylic acid methyl-(3-methylamino-propyl)-amide;

2,4-Dimethyl-5-{2-oxo-6-[3-(3-trifluoromethyl-benzoylamino)-phenoxy]-1,2-dihydro -indol-3-ylidenemethyl}-1H-pyrrole-3-carboxylic acid (2-morpholin-4-yl-ethyl)-amide;

N-(3-{3-[4-(3-Dimethylamino-pyrrolidine-1-carbonyl)-3,5-dimethyl-1H-pyrrol-2-ylmethylene]-2-oxo-2,3-dihydro-1H-indol-6-yloxy}-phenyl)-3-trifluoromethyl-benzamide;

N-[3-(3-{4-[4-(2-Diethylamino-ethyl)-piperazine-1-carbonyl]-3,5-dimethyl-1H-pyrrol-2-ylmethylene}-2-oxo-2,3-dihydro-1H-indol-6-yloxy)-phenyl]-3-trifluoromethyl-benzamide;

5-{2-Oxo-6-[3-(3-trifluoromethyl-benzoylamino)-phenoxy]-1,2-dihydro-indol-3-ylidenemethyl}-1H-pyrrole-3-carboxylic acid methyl-(3-methylamino-propyl)-amide;

2,4-Dimethyl-5-{2-oxo-6-[3-(3-trifluoromethyl-benzoylamino)-phenoxy]-1,2-dihydro -indol-3-ylidenemethyl}-1H-pyrrole-3-carboxylic acid ethoxy-amide;

2,4-Dimethyl-5-{2-Oxo-6-[3-(3-trifluoromethyl-benzoylamino)-phenoxy]-1,2-dihydro -indol-3-ylidenemethyl}-1H-pyrrole-3-carboxylic acid (4-methyl-piperazin 1-yl)-amide;

5-{2-Oxo-6-[3-trifluoromethyl-benzoylamino)-phenoxy]-1,2-dihydro-indol-3-ylidenemethyl}-1H-pyrrole-3-carboxylic acid;

5-{2-Oxo-6-[3-(3-trifluoromethyl-benzoylamino)-phenoxy]-1,2-dihydro-indol-3-ylidenemethyl}-1H-pyrrole-3-carboxylic acid (3-dimethylamino-propyl)-amide;

N-(3-{3-[4-(4-Methyl-piperazine-1-carbonyl)-1H-pyrrol-2-ylmethylene]-2-oxo-2,3-dihydro-1H-indol-6-yloxy}-phenyl)-3-trifluoromethyl-benzamide;

5-{2-Oxo-6-[3-(3-trifluoromethyl-benzoylamino)-phenoxy]-1,2-dihydro-indol-3-ylidenemethyl}-1H-pyrrole-3-carboxylic acid (2-dimethylamino-ethyl)-methyl-amide;

N-[3-(3-{4-[4-(2-Diethylamino-ethyl)-piperazine-1-carbonyl]-1H-pyrrol-2-ylmethylene}-2-oxo-2,3-dihydro-1H-indol-6-yloxy)-phenyl]-3-trifluoromethyl-benzamide;

2,4-Dimethyl-5-{6-[3-(3-methyl-benzoylamino)-phenoxy]-2-oxo-1,2-dihydro-indol-3-ylidenemethyl}-1H-pyrrole-3-carboxylic acid;

N-(3-{3-[3,5-Dimethyl-4-(4-methyl-piperazine-1-carbonyl)-1H-pyrrol-2-ylmethylene]-2-oxo-2,3-dihydro-1H-indol-6-yloxy}-phenyl)-3-methyl-benzamide;

2,4-Dimethyl-5-{6-[3-(3-methyl-benzoylamino)-phenoxy]-2-oxo-1,2-dihydro-indol-3-ylidenemethyl}-1H-pyrrole-3-carboxylic acid (2-morpholin-4-yl-ethyl)-amide;

5-{6-[3-(3-Methyl-benzoylamino)-phenoxy]-2-oxo-1,2-dihydro-indol-3-ylidenemethyl}-1H-pyrrole-3-carboxylic acid (3-pyrrolidin-1-yl-propyl)-amide;

5-{6-[3-(3-Methyl-benzoylamino)-phenoxy]-2-oxo-1,2-dihydro-indol-3-ylidenemethyl}-1H-pyrrole-3-carboxylic acid;

5-{6-[3-(3-Methyl-benzoylamino)-phenoxy]-2-oxo-1,2-dihydro-indol-3-ylidenemethyl}-1H-pyrrole-3-carboxylic acid (3-dimethylamino-propyl)-amide;

5-{6-[3-(3-Methyl-benzoylamino)-phenoxy]-2-oxo-1,2-dihydro-indol-3-ylidenemethyl}-1H-pyrrole-3-carboxylic acid (2-morpholin-4-yl-ethyl)-amide;

5-{6-[3-(3-Methyl-benzoylamino)-phenoxy]-2-oxo-1,2-dihydro-indol-3-ylidenemethyl}-1H-pyrrole-3-carboxylic acid (2-dimethylamino-ethyl)-methyl-amide;

3-Methyl-N-(3-{3-[4-(4-methyl-piperazine-1-carbonyl)-1H-pyrrol-2-ylmethylene]-2-oxo-2,3-dihydro-1H-indol-6-yloxy}-phenyl)-benzamide;

5-{6-[3-(3-Methyl-benzoylamino)-phenoxy]-2-oxo-1,2-dihydro-indol-3-ylidenemethyl}-1H-pyrrole-3-carboxylic acid (4-methyl-piperazin-1-yl)-amide;

N-[3-(3-{4-[4-(2-Diethylamino-ethyl)-piperazine-1-carbonyl]-1H-pyrrol-2-ylmethylene}-2-oxo-2,3-dihydro-1H-indol-6-yloxy)-phenyl]-3-methyl-benzamide;

N-(3-{3-[3,5-Dimethyl-4-(4-pyrimidin-2-yl-piperazine-1-carbonyl)-1H-pyrrol-2-ylmethylene]-2-oxo-2,3-dihydro-1H-indol-6-yloxy}-phenyl)-3-trifluoromethyl-benzamide;

N-(3-{3-[3,5-Dimethyl-4-(2,3,5,6-tetrahydro-[1,2']bipyrazinyl-4-carbonyl)-1H-pyrrol-2-ylmethylene]-2-oxo-2,3-dihydro-1H-indol-6-yloxy}-phenyl)-3-trifluoromethyl-benzamide;

2,4-Dimethyl-5-{6-[3-(3-methyl-benzoylamino)-phenoxy]-2-oxo-1,2-dihydro-indol-3-ylidenemethyl}-1H-pyrrole-3-carboxylic acid (2-dimethylamino-ethyl)-methyl-amide;

N-[4-(4-Methyl-piperazin-1-ylmethyl)-3-trifluoromethyl-phenyl]-3-[2-oxo-3-(1H-pyrrol-2-ylmethylene)-2,3-dihydro-1H-pyrrolo[2,3-b]pyridin-6-ylamino]benzamide;

4-Trifluoromethyl-1H-indole-6-carboxylic acid {3-methoxy-5-[2-oxo-3-(1H-pyrrol-2-ylmethylene)-2,3-dihydro-1H-indol-6-ylamino]-phenyl}-amide;

N-[3-(3-Benzyloxyimino-2-oxo-2,3-dihydro-1H-indol-6-ylamino)-phenyl]-3-(4-methyl -piperazin-1-yl)-5-trifluoromethyl-benzamide;

3-[2-Oxo-3-(1H-pyrrol-2-ylmethylene)-2,3-dihydro-1H-pyrrolo[2,3-b]pyridin-6-yloxy]-N-(3-trifluoromethyl-phenyl)-benzamide;

5-(6-Benzoylamino-2-oxo-1,2-dihydro-indol-3-ylidenemethyl)-2,4-dimethyl-1H-pyrrole-3-carboxylic acid (2-dimethylamino-ethyl)-amide; and
3-(1H-Pyrrol-2-ylmethylene)-6-{3-[3-(3-trifluoromethylphenyl)-[1,2,4]oxadiazol-5-yl]-phenylamino}-1,3-dihydro-indol-2-one;

or the pharmaceutical acceptable salts thereof.

8. A pharmaceutical composition comprising a therapeutically effective amount of a compound of claim 1 in combination with a pharmaceutically acceptable excipient.

9. A compound selected from the group consisting of:
3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide;
3-(4-Methyl-imidazol-1-yl)-N-(3-{3-[2-oxo-3-(1H-pyrrol-2-ylmethylene)-2,3-dihydro-1H-indol-6-yl]-ureido}-phenyl)-5-trifluoromethyl-benzamide;
2-Oxo-3-(1H-pyrrol-2-ylmethylene)-2,3-dihydro-1H-indole-6-carboxylic acid (3-benzoylamino-phenyl)-amide;
4-(4-Methyl-piperazin-1-ylmethyl)-N-{3-[2-oxo-3-(1H-pyrrol-2-ylmethylene)-2,3-dihydro-1H-indol-7-ylamino]-phenyl}-benzamide;
4-(4-Methyl-piperazin-1-ylmethyl)-N-{3-[2-oxo-3-(1H-pyrrol-2-ylmethylene)-2,3-dihydro-1H-indol-5-ylamino]-phenyl}-benzamide;
4-(4-Ethyl-piperazin-1-ylmethyl)-N-{3-[2-oxo-3-(1H-pyrrol-2-ylmethylene)-2,3-dihydro-1H-indol-6-ylamino]-phenyl}-3-trifluoromethyl-benzamide;
3-(4-Methyl-piperazin-1-yl)-N-{3-[2-oxo-3-(1H-pyrrol-2-ylmethylene)-2,3-dihydro-1H-indol-6-yloxy]-phenyl}-5-trifluoromethyl-benzamide;
4-(4-Methyl-piperazin-1-ylmethyl)-N-(3-{3-[2-oxo-3-(1H-pyrrol-2-ylmethylene)-2,3-dihydro-1H-indol-6-yl]-ureido}-phenyl)-benzamide;
3-(4-Methyl-imidazol-1-yl)-N-(4-methyl-3-{3-[2-oxo-3-(1H-pyrrol-2-ylmethylene)-2,3-dihydro-1H-indol-6-yl]-ureido}-phenyl)-5-trifluoromethyl-benzamide;
N-(4-Methyl-3-{3-[2-oxo-3-(1H-pyrrol-2-ylmethylene)-2,3-dihydro-1H-indol-6-yl]-ureido}-phenyl)-3-trifluoromethyl-benzamide;
N-(4-Methyl-3-{3-[2-oxo-3-(1H-pyrrol-2-ylmethylene)-2,3-dihydro-1H-indol-6-yl]-ureido}-phenyl)-benzamide;
N-(4-Methyl-3-{3-[2-oxo-3-(1H-pyrrol-2-ylmethylene)-2,3-dihydro-1H-indol-6-yl]-ureido}-phenyl)-4-(4-methyl-piperazin-1-ylmethyl)-benzamide;
2-Oxo-3-(1H-pyrrol-2-ylmethylene)-2,3-dihydro-1H-indole-6-carboxylic acid {3-[4-(4-methyl-piperazin-1-ylmethyl)-benzoylamino]-phenyl}-amide;
2-Oxo-b 3-(1H-pyrrol-2-ylmethylene)-2,3-dihydro-1H-indole-6-carboxylic acid (5-benzoylamino-2-methylphenyl)-amide;
2-Oxo-3-(1H-pyrrol-2-ylmethylene)-2,3-dihydro-1H-indole-6-carboxylic acid {2-methyl-5-[4-(4-methyl-piperazin-1-ylmethyl)-benzoylamino]-phenyl}-amide;
N-{3-[2-Oxo-3-(1H-pyrrol-2-ylmethylene)-2,3-dihydro-1H-indol-6-ylamino]-phenyl}-benzamide;
N-{3-[2-Oxo-3-(1H-pyrrol-2-ylmethylene)-2,3-dihydro-1H-indol-6-ylamino]-phenyl}-3-trifluoromethyl-benzamide;
4-(4-Methyl-piperazin-1-ylmethyl)-N-{3-[2-oxo-3-(1H-pyrrol-2-ylmethylene)-2,3-dihydro-1H-indol-6-ylamino]-phenyl}-benzamide;
N-{4-Methyl-3-[2-oxo-3-(1H-pyrrol-2-ylmethylene)-2,3-dihydro-1H-indol-6-ylamino]-phenyl}-benzamide;
N-{4-Methyl-3-[2-oxo-3-(1H-pyrrol-2-ylmethylene)-2,3-dihydro-1H-indol-6-ylamino]-phenyl}-3-trifluoromethyl-benzamide;
N-{4-Methyl-3-[2-oxo-3-(1H-pyrrol-2-ylmethylene)-2,3-dihydro-1H-indol-6-ylamino]-phenyl}-4-(4-methyl-piperazin-1-ylmethyl)-benzamide;
N-{3-[2-Oxo-3-(1H-pyrrol-2-ylmethylene)-2,3-dihydro-1H-indol-7-ylamino]-phenyl}-benzamide;
N-{4-Methyl-3-[2-oxo-3-(1H-pyrrol-2-ylmethylene)-2,3-dihydro-1H-indol-7-ylamino]-phenyl}-benzamide;
N-{4-Methyl-3-[2-oxo-3-(1H-pyrrol-2-ylmethylene)-2,3-dihydro-1H-indol-7-ylamino]-phenyl}-4-(4-methyl-piperazin-1-ylmethyl)-benzamide;
N-{3-[2-Oxo-3-(1H-pyrrol-2-ylmethylene)-2,3-dihydro-1H-indol-5-ylamino]-phenyl}-benzamide;
N-{3-[2-Oxo-3-(1H-pyrrol-2-ylmethylene)-2,3-dihydro-1H-indol-5-ylamino]-phenyl}-3-trifluoromethyl-benzamide;
3-(4-Methyl-imidazol-1-yl)-N-{3-[2-oxo-3-(1H-pyrrol-2-ylmethylene)-2,3-dihydro-1H-indol-5-ylamino]-phenyl}-5-trifluoromethyl-benzamide;
N-{4-Methyl-3-[2-oxo-3-(1H-pyrrol-2-ylmethylene)-2,3-dihydro-1H-indol-5-ylamino]-phenyl}-benzamide;
N-{4-Methyl-3-[2-oxo-3-(1H-pyrrol-2-ylmethylene)-2,3-dihydro-1H-indol-5-ylamino]-phenyl}-4-(4-methyl-piperazin-1-ylmethyl)-benzamide;
3-(4-Methyl-imidazol-1-yl)-N-{3-[2-oxo-3-(1H-pyrrol-2-ylmethylene)-2,3-dihydro-1H-indol-6-ylamino]-phenyl}-5-trifluoromethyl-benzamide;
3-(4-Methyl-imidazol-1-yl)-N-{3-[6-oxo-5-(1H-pyrrol-2-ylmethylene)-6,7-dihydro-5H-pyrrolo[2,3-d]pyrimidin-2-ylamino]-phenyl}-5-trifluoromethyl-benzamide;
3-(4-Ethyl-piperazin-1-yl)-N-{3-[3-(3H-imidazol-4-ylmethylene)-2-oxo-2,3-dihydro-1H-indol-6-ylamino]-phenyl}-5-trifluoromethyl-benzamide;
3-(1-Methyl-piperidin-4-yloxy)-N-{3-[2-oxo-3-(1H-pyrrol-2-ylmethylene)-2,3-dihydro-1H-indol-6-ylamino]-phenyl}-5-trifluoromethyl-benzamide;
3-[4-(2-Hydroxy-ethyl)-piperazin-1-yl]-N-{3-[2-oxo-3-(1H-pyrrol-2-ylmethylene)-2,3-dihydro-1H-indol-6-ylamino]-phenyl}-5-trifluoromethyl-benzamide;
4-Morpholin-4-yl-N-{3-[2-oxo-3-(1H-pyrrol-2-ylmethylene)-2,3-dihydro-1H-indol-6-ylamino]-phenyl}-3-trifluoromethyl-benzamide;
4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide;
4-(4-Ethyl-piperazin-1-ylmethyl)-N-{3-[3-(3H-imidazol-4-ylmethylene)-2-oxo-2,3-dihydro-1H-indol-6-ylamino]-phenyl}-3-trifluoromethyl-benzamide;
3-Chloro-4-(4-ethyl-piperazin-1-ylmethyl)-N-{3-[3-(3H-imidazol-4-ylmethylene)-2-oxo-2,3-dihydro-1H-indol-6-ylamino]-phenyl}-benzamide;
N-{3-[3-(1H-Indol-3-ylmethylene)-2-oxo-2,3-dihydro-1H-indol-6-ylamino]-phenyl}-3-(4-methyl-imidazol-1-yl)-5-trifluoromethyl-benzamide;
N-[3-(3-Furan-3-ylmethylene-2-oxo-2,3-dihydro-1H-indol-6-ylamino)-phenyl]-3-(4-methyl-imidazol-1-yl)-5-trifluoromethyl-benzamide;
N-{3-[3-(3H-Imidazol-4-ylmethylene)-2-oxo-2,3-dihydro-1H-indol-6-ylamino]-phenyl}-3-(4-methyl-imidazol-1-yl)-5-trifluoromethyl-benzamide;
N-{3-[3-(1H-Indol-2-ylmethylene)-2-oxo-2,3-dihydro-1H-indol-6-ylamino]-phenyl}-3-(4-methyl-imidazol-1-yl)-5-trifluoromethyl-benzamide;

N-{3-[3-(5-Methyl-3H-imidazol-4-ylmethylene)-2-oxo-2,3-dihydro-1H-indol-6-ylamino]-phenyl}-3-(4-methyl-piperazin-1-yl)-5-trifluoromethyl-benzamide;

3-(4-Methyl-piperazin-1-yl)-N-{3-[2-oxo-3-(1H-pyrrol-2-ylmethylene)-2,3-dihydro-1H-indol-6-ylamino]-phenyl}-5-trifluoromethyl-benzamide;

N-{3-Methoxy-5-[2-oxo-3-(1H-pyrrol-2-ylmethylene)-2,3-dihydro-1H-indol-6-ylamino]-phenyl}-3-(4-methyl-piperazin-1-yl)-5-trifluoromethyl-benzamide;

N-{4-Methyl-3-[2-oxo-3-(1H-pyrrol-2-ylmethylene)-2,3-dihydro-1H-indol-6-ylamino]-phenyl}-3-(4-Methyl-piperazin-1-yl)-5-trifluoromethyl-benzamide;

3-(4-Hydroxy-piperidin-1-yl)-N-{3-[2-oxo-3-(1H-pyrrol-2-ylmethylene)-2,3-dihydro-1H-indol-6-ylamino]-phenyl}-5-trifluoromethyl-benzamide;

4-Trifluoromethyl-1H-indole-6-carboxylic acid {3-methoxy-5-[2-oxo-3-(1H-pyrrol-2-ylmethylene)-2,3-dihydro-1H-indol-6-ylamino]-phenyl}-amide;

3-[2-Oxo-3-(1H-pyrrol-2-ylmethylene)-2,3-dihydro-1H-pyrrolo[2,3-b]pyridin-6-yloxy]-N-(3-trifluoromethyl-phenyl)-benzamide; and 3-(1H-Pyrrol-2-ylmethylene)-6-{3-[3-(3-trifluoromethyl-phenyl)-[1,2,4]oxadiazol-5-yl]-phenylamino}-1,3-dihydro-indol-2-one;

or the pharmaceutically acceptable salts thereof.

10. A pharmaceutical composition comprising a therapeutically effective amount of a compound of claim 9 in combination with a pharmaceutically acceptable excipient.

* * * * *